(12) United States Patent
Orth et al.

(10) Patent No.: US 11,421,235 B2
(45) Date of Patent: Aug. 23, 2022

(54) METHODS AND MICROORGANISMS FOR THE FERMENTATION OF METHANE TO MULTI-CARBON COMPOUNDS

(71) Applicant: PRECIGEN, INC., Blacksburg, VA (US)

(72) Inventors: Jeffrey David Orth, Alameda, CA (US); Louis A. Clark, San Francisco, CA (US); Lily Yuin Chao, San Francisco, CA (US); Na My Trinh, Walnut Creek, CA (US); Christopher Cheyney Farwell, South San Francisco, CA (US); Xinhua Zhao, Dublin, CA (US); Matthias Helmut Schmalisch, South San Francisco, CA (US); Grayson Thomas Wawrzyn, Oakland, CA (US); Xuezhi Li, Hayward, CA (US); Mark Anton Held, Emeryville, CA (US); Kevin Lee Dietzel, Pacifica, CA (US); James Kealey, Sebastopol, CA (US)

(73) Assignee: PRECIGEN, INC., Germantown, MD (US)

( * ) Notice: Subject to any disclaimer, the term of this patent is extended or adjusted under 35 U.S.C. 154(b) by 0 days.

(21) Appl. No.: 16/604,425

(22) PCT Filed: Apr. 27, 2018

(86) PCT No.: PCT/US2018/029688
§ 371 (c)(1),
(2) Date: Oct. 10, 2019

(87) PCT Pub. No.: WO2018/200894
PCT Pub. Date: Nov. 1, 2018

(65) Prior Publication Data
US 2021/0115452 A1  Apr. 22, 2021

Related U.S. Application Data

(60) Provisional application No. 62/491,683, filed on Apr. 28, 2017, provisional application No. 62/512,315, filed on May 30, 2017.

(51) Int. Cl.
*C12N 1/20* (2006.01)
*C12N 9/10* (2006.01)
(Continued)

(52) U.S. Cl.
CPC .......... *C12N 15/52* (2013.01); *C12N 9/0006* (2013.01); *C12N 9/1022* (2013.01);
(Continued)

(58) Field of Classification Search
CPC ...... C12N 9/1022; C12N 9/0006; C12N 9/88; C12N 15/74
See application file for complete search history.

(56) References Cited

U.S. PATENT DOCUMENTS 7,851,188 B2 * 12/2010 Donaldson ........... C12N 9/1022
435/160
9,267,158 B2 * 2/2016 Coleman ................ C12N 15/52
(Continued)

FOREIGN PATENT DOCUMENTS

WO  2010051527 A2  5/2010
WO  2014/092562 A1  6/2014
(Continued)

OTHER PUBLICATIONS

Studer. Residue mutations and their impact on protein structure and function: detecting beneficial and pathogenic changes. Biochem. J. (2013) 449, 581-594.*
(Continued)

*Primary Examiner* — Yong D Pak
(74) *Attorney, Agent, or Firm* — Gene J. Yao; Barnes & Thornburg LLP

(57) ABSTRACT

Genetically modified microorganisms that have the ability to convert carbon substrates into multicarbon products. Methods of making these genetically modified microorganisms and methods of using them. Vectors encoding enzymes for use in converting carbon substrates into multicarbon products.

11 Claims, 18 Drawing Sheets

Specification includes a Sequence Listing.

(51) Int. Cl.
- *C12N 9/04* (2006.01)
- *C12N 9/12* (2006.01)
- *C12N 9/88* (2006.01)
- *C12P 7/00* (2006.01)
- *C12N 15/52* (2006.01)
- *C12N 15/70* (2006.01)
- *C12P 7/16* (2006.01)
- *C12P 7/24* (2006.01)

(52) U.S. Cl.
CPC ............ *C12N 9/1205* (2013.01); *C12N 9/88* (2013.01); *C12N 15/70* (2013.01); *C12P 7/16* (2013.01); *C12P 7/24* (2013.01); *C12Y 101/01001* (2013.01); *C12Y 101/01086* (2013.01); *C12Y 202/01006* (2013.01); *C12Y 401/01072* (2013.01); *C12Y 402/01009* (2013.01)

(56) References Cited

U.S. PATENT DOCUMENTS

| | | | |
|---|---|---|---|
| 9,399,783 B2* | 7/2016 | Coleman | C12Y 203/03006 |
| 9,745,603 B2* | 8/2017 | Coleman | C12N 9/0006 |
| 10,858,661 B2 | 12/2020 | Lee et al. | |
| 10,876,137 B2* | 12/2020 | Coleman | C12N 9/1025 |
| 2007/0092957 A1 | 4/2007 | Donaldson et al. | |
| 2007/0292927 A1 | 12/2007 | Donaldson et al. | |
| 2008/0014619 A1 | 1/2008 | Huang et al. | |
| 2011/0014669 A1 | 1/2011 | Madden et al. | |
| 2014/0004526 A1 | 1/2014 | Dauner et al. | |
| 2014/0273128 A1 | 9/2014 | Coleman et al. | |
| 2015/0064759 A1 | 3/2015 | Perez et al. | |
| 2015/0240247 A1 | 8/2015 | Atsumi et al. | |
| 2015/0259389 A9 | 9/2015 | Berka et al. | |
| 2016/0160243 A1 | 6/2016 | Coleman et al. | |

FOREIGN PATENT DOCUMENTS

| | | |
|---|---|---|
| WO | 2018/140928 A1 | 8/2018 |
| WO | 2019/075159 A1 | 4/2019 |

OTHER PUBLICATIONS

KRN57005.1. GenBank Database. Nov. 6, 2015.*
A0A0B5HLI4_BACLI. UniProtKB/TrEMBL Database. Mar. 16, 2016.*
Chu et al., Journal of Bacteriology, 198:1317-1325 (2016).
International Search Report issued in PCT/US2018/029688.
Written Opinion issued in PCT/US2018/029688.
Kopke et al., Applied and Environmental Microbiology, 77:5467-5475 (2011).
Campbell et al., Cell Calcium, 41:97-106 (2006).
Cui et al., Journal of Applied Microbiology, 117:690-698 (2014).
Zhang et al., Green Chemistry, 14:3441-3450 (2012).
EC 4.1.1.5-Acetolactate Decarboxylase, IntEz, 2015.

* cited by examiner

SEQUENCE LISTING

<160> NUMBER OF SEQ ID NOS: 100

<210> SEQ ID NO 1
<211> LENGTH: 1713
<212> TYPE: DNA
<213> ORGANISM: Bacillus subtilis

<400> SEQUENCE: 1

```
atgaccaagg ccaccaagga acagaaaagc ctggtcaaga accgcggtgc tgaactggtt      60
gtggactgcc tcgtggaaca gggcgtgacc catgtcttcg gcatcccggg cgccaagatc     120
gacgccgtct tcgacgccct gcaggataaa ggtccggaaa tcatcgtggc acgccatgag     180
cagaacgcag ccttcatggc ccaggccgtc ggtcggctga cgggtaagcc cggcgtggtg     240
ctggtcacct ccggtccggg agcctcgaac ctggccacgg gactgctcac cgccaacacc     300
gaaggcgacc cggtggtcgc cctggccggt aatgtcatcc gggcggatcg cctgaagcgc     360
acccatcagt ccctggataa cgcggccctg ttccagccaa tcaccaaata tagtgtcgaa     420
gtgcaggatg tgaagaacat cccggaagcc gtcaccaatg cgttccgaat cgcgtccgcc     480
ggccaagcag gggcagcatt cgtgagcttc ccccaggacg tggtcaatga agtgaccaac     540
accaaaaacg tcagagccgt agccgccccg aagctgggcc ctgcagcaga tgacgccatc     600
tccgctgcca tcgcgaagat ccagaccgca aagctgccgg tcgtgctggt cggaatgaag     660
ggcggacgcc cggaggccat caaggccgtg cgtaaactgc tgaagaaggt gcagctaccg     720
ttcgtggaaa cctaccaggc cgccggcacc ctgagtcggg acttggaaga ccagtatttc     780
ggccgtatcg gcctgttccg caaccagccg ggcgacctgc tcctggaaca gccgatgtg      840
gtgctgacca tcggctacga cccgatcgaa tatgacccga agttctggaa catcaatggc     900
gaccgcacga tcatccatct ggacgaaatc atcgccgaca tcgaccatgc ctatcagccg     960
gacctggaac tgatcggcga catcccgagc accatcaacc acatcgaaca cgatgccgtg    1020
aaggtggaat ttgccgaacg cgaacagaag atcctgtcgg acctgaagca gtatatgcat    1080
gagggcgaac aggtgcctgc cgactggaag tcggacagag cccatccgct ggaaatcgtg    1140
aaggaactgc gtaacgccgt cgacgaccat gtcaccgtca cctgcgatat cggcagccat    1200
gccatttgga tgagccgcta cttccggagc tatgaaccgc tgaccctgat gatctccaac    1260
ggtatgcaga ccctcggcgt cgccctcccg tgggccatcg gcgcaagtct ggtgaagccg    1320
ggcgaaaaag tggtcagcgt gtccggcgac ggcggcttcc tgttctccgc tatggaactg    1380
gaaaccgcgg tccgcctgaa ggccccgatc gtgcatatcg tgtggaacga cagcacctac    1440
gacatggtcg ccttccagca gctgaaaaag tacaaccgca ccagcgccgt ggacttcggc    1500
aatatcgaca tcgtgaagta tgccgaatcc ttcggagcca ccggactgcg cgtggaatcc    1560
ccggaccagc tggcggacgt tctgcgtcag ggcatgaatg ccgaaggtcc cgtgattatc    1620
gatgtgcccg tcgactacag cgacaacatc aacctggcct cggacaaatt gccgaaggag    1680
ttcggcgaac tgatgaaaac aaaagcacta taa                                 1713
```

<210> SEQ ID NO 2
<211> LENGTH: 570
<212> TYPE: PRT
<213> ORGANISM: Bacillus subtilis

<400> SEQUENCE: 2

```
Met Thr Lys Ala Thr Lys Glu Gln Lys Ser Leu Val Lys Asn Arg Gly
1               5                   10                  15
```

```
Ala Glu Leu Val Val Asp Cys Leu Val Glu Gln Gly Val Thr His Val
             20                  25                  30

Phe Gly Ile Pro Gly Ala Lys Ile Asp Ala Val Phe Asp Ala Leu Gln
         35                  40                  45

Asp Lys Gly Pro Glu Ile Ile Val Ala Arg His Glu Gln Asn Ala Ala
 50                  55                  60

Phe Met Ala Gln Ala Val Gly Arg Leu Thr Gly Lys Pro Gly Val Val
 65                  70                  75                  80

Leu Val Thr Ser Gly Pro Gly Ala Ser Asn Leu Ala Thr Gly Leu Leu
                 85                  90                  95

Thr Ala Asn Thr Glu Gly Asp Pro Val Val Ala Leu Ala Gly Asn Val
             100                 105                 110

Ile Arg Ala Asp Arg Leu Lys Arg Thr His Gln Ser Leu Asp Asn Ala
         115                 120                 125

Ala Leu Phe Gln Pro Ile Thr Lys Tyr Ser Val Glu Val Gln Asp Val
     130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                 165                 170                 175

Glu Val Thr Asn Thr Lys Asn Val Arg Ala Val Ala Ala Pro Lys Leu
             180                 185                 190

Gly Pro Ala Ala Asp Asp Ala Ile Ser Ala Ala Ile Ala Lys Ile Gln
         195                 200                 205

Thr Ala Lys Leu Pro Val Val Leu Val Gly Met Lys Gly Gly Arg Pro
     210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                 245                 250                 255

Asp Gln Tyr Phe Gly Arg Ile Gly Leu Phe Arg Asn Gln Pro Gly Asp
             260                 265                 270

Leu Leu Leu Glu Gln Ala Asp Val Val Leu Thr Ile Gly Tyr Asp Pro
         275                 280                 285

Ile Glu Tyr Asp Pro Lys Phe Trp Asn Ile Asn Gly Asp Arg Thr Ile
     290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                 325                 330                 335

His Asp Ala Val Lys Val Glu Phe Ala Glu Arg Glu Gln Lys Ile Leu
             340                 345                 350

Ser Asp Leu Lys Gln Tyr Met His Glu Gly Glu Gln Val Pro Ala Asp
         355                 360                 365

Trp Lys Ser Asp Arg Ala His Pro Leu Glu Ile Val Lys Glu Leu Arg
     370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                 405                 410                 415

Met Ile Ser Asn Gly Met Gln Thr Leu Gly Val Ala Leu Pro Trp Ala
             420                 425                 430

Ile Gly Ala Ser Leu Val Lys Pro Gly Glu Lys Val Val Ser Val Ser
```

```
            435                 440                 445
Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 3
<211> LENGTH: 1476
<212> TYPE: DNA
<213> ORGANISM: Escherichia coli

<400> SEQUENCE: 3
atggctaact acttcaacac cctgaacttg cgtcagcagc tggcccagct gggtaagtgc        60
cggttcatgg ccgtgatga gttcgccgat ggcgccagct acctgcaggg caaaaaggtg       120
gtgatcgtgg gctgcggagc ccagggcctg aaccagggcc tgaatatgcg cgatagcggc       180
ctggacatct cctatgctct gcgcaaggaa gcgatcgcgg aaaagcgggc atcctggcgc       240
aaggccaccg aaaacggttt caaagtgggc acctacgaag aactgatccc gcaggccgat       300
ttggtcataa acctgacccc ggacaagcag cattccgatg tggttcgcac cgtccagccg       360
ctgatgaagg acggggcagc cctgggttac tcccacggct tcaacatcgt ggaagtcggc       420
gaacagatcc gcaaggacat caccgtcgtc atggtcgcac cgaagtgtcc gggcaccgaa       480
gtccgggaag aatataagcg cggattcggc gtaccgaccc tgatcgccgt ccatcccgaa       540
aacgacccga agggcgaagg catggccatc gccaaggcct gggctgccgc caccggaggc       600
catcgcgctg gcgtgctgga agctcgttc gtcgccgaag tgaagagcga cctgatgggc       660
gaacagacca tcctgtgcgg catgctgcag gccgtagcc tgctgtgttt cgacaagctg       720
gtcgaagaag gcaccgaccc tgcgtatgcc gaaaagctga tccagttcgg ctgggaaacc       780
atcaccgaag cgctgaaaca gggcggtatc accctgatga tggaccgcct gtcgaaccct       840
gccaagttac gtgcctatgc cctgagcgaa cagctgaagg aaatcatggc gcctctgttc       900
cagaaacata tggacgatat catcagcggc gagttcagct ccggcatgat ggcggactgg       960
gcgaatgacg acaagaagct gctgacctgg cgggaagaaa ccggcaagac ggccttcgaa      1020
accgcaccgc agtacgaagg caaaatcggc gaacaggagt acttcgacaa aggcgtcctg      1080
atgatcgcga tggtcaaggc gggagtcgaa ctggccttcg aaacaatggt cgatagcggc      1140
atcatcgagg aatccgccta ctacgaaagc ctgcatgaac tcccgctgat cgccaatacc      1200
atagcccgca gcggctgta cgaaatgaac gtcgtgatct ccgacactgc cgaatacggc      1260
aattatctct ctcctatgc ctgcgtgccg ctcctgaagc ccttcatggc cgaactgcag      1320
ccaggcgacc tggggaaggc gatccccgaa ggcgctgtcg acaacggcca gctgcgcgat      1380
```

```
gtcaacgaag ccattcgctc ccatgccatc gagcaggtcg gcaagaagct gcgtggctat    1440
atgacggaca tgaagcgcat cgcagtagcc ggataa                              1476
```

<210> SEQ ID NO 4
<211> LENGTH: 491
<212> TYPE: PRT
<213> ORGANISM: Escherichia coli

<400> SEQUENCE: 4

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350
```

```
Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 5
<211> LENGTH: 1851
<212> TYPE: DNA
<213> ORGANISM: Escherichia coli

<400> SEQUENCE: 5
atgccgaagt atcggtcagc caccactaca catggccgca acatggcagg cgctcgtgcc      60
ctgtggcgtg ctaccggcat gaccgatgcc gacttcggca agccgatcat cgccgtggtc     120
aactctttca cccagttcgt cccagggcac gttcatctgc gcgacctggg caagctggtg     180
gccgaacaga tcgaggccgc aggtggcgtc gcgaaagagt tcaacaccat cgccgtcgac     240
gatggcatcg ctatgggcca cggtggcatg ctgtatagcc tgccgtcccg cgaactgatc     300
gccgatagcg tcgaatatat ggtgaacgcc cattgcgccg atgctatggt gtgcatcagc     360
aactgcgaca agatcacacc ggggatgctg atgccagcc tgcggctgaa catcccggtg     420
atcttcgtga gcggtggccc gatggaagcc ggcaagacca gctgtcgga tcagatcatc     480 aagctggatc tggtcgacgc catgatccaa ggtgccgatc gaaggtgag cgactcccag     540 tccgatcagg tggaacggag cgcctgcccg acttgcggct catgcagcgg catgttcacc     600
gccaactcca tgaattgcct gacggaagcc ctgggcctgt cccagcccgg taacgggagc     660
ctgttggcga cccatgccga ccgcaagcag ctgttcctga tgccggcaa cgcatcgtg     720 gaactgacca gcgctatta tgaacagaac gacgaatccg ccctgcccg taatatcgcc     780 tcaaaagccg ccttcgaaaa cgccatgacc ctggacatcg ctatgggtgg cagcaccaac     840
accgtgctgc acctgctggc tgccgctcag gaagccgaga tcgacttcac catgtccgac     900
atcgacaagc tgagtcggaa ggtgccgcag ctgtgcaagg tggcaccgtc cacccagaag     960
tatcatatgg aagacgtgca tcgcgcaggc ggtgtgatcg gcatcctggg cgaactggat    1020
cgcgctggcc tgctgaatcg cgatgtgaag aacgtcctgg gcctgaccct gccgcagacc    1080
ctggaacagt acgacgttat gctgacccag gatgatgccg tcaagaatat gttccgcgca    1140
ggccctgccg gcattcgcac cacccaagcc ttcagccagg actgccggtg ggataccctg    1200
gatgacgatc gcgccaatgg ctgcatccgt agcctggaac atgcctattc caaggatggc    1260
ggtctggccg ttctgtatgg caacttcgcg gaaaacggct gcatcgtcaa gaccgctggc    1320
```

```
gtggatgatt cgatcctgaa gttcaccgga ccggccaaag tctacgaaag ccaggacgat    1380
gccgtcgaag ccatcctggg aggcaaggtc gtcgccggag atgtcgtggt gatccgctat    1440
gaaggcccga aaggcggtcc gggcatgcag agatgctgt atccgacctc cttcttaaag     1500
agcatgggct tgggcaaagc gtgtgcgctc atcaccgatg ccgcttcag tggcggcacc     1560 agcggcctgt ccatcggcca tgtctcgccg gaagccgcca gtggcggcag catcggcctc    1620
atcgaagacg gcgatctgat cgccatcgat atcccgaatc gtggcatcca gctgcaggtg    1680
tccgacgccg aactagccgc acggagggaa gcgcaggatg cccgaggcga caaggcctgg    1740
accccgaaga accgtgaacg tcaggtgtcc ttcgcgcttc gcgcctatgc cagcctggcc    1800
accagcgccg ataagggtgc cgtgcgcgac aagagcaaac taggaggata a              1851
```

<210> SEQ ID NO 6
<211> LENGTH: 616
<212> TYPE: PRT
<213> ORGANISM: Escherichia coli

<400> SEQUENCE: 6

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
    275                 280                 285
```

Ala Gln Glu Ala Glu Ile Asp Phe Thr Met Ser Asp Ile Asp Lys Leu
            290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
610                 615

<210> SEQ ID NO 7
<211> LENGTH: 1689
<212> TYPE: DNA
<213> ORGANISM: Methylococcus capsulatus

<400> SEQUENCE: 7
atgaccgaca agcacccccg tccccattcg tcccaggtcg tcgacggcat ggagcgggcc     60
ccgagccgcg cgatgctgca cgccgtcggc ttcgccgatg ccgacttcgc caaaccgcag    120
atcggcatcg cttccaccct ggcgatggtg acgccgtgca acatgcacat caacaagctc    180
gccgaggacg cagcacgcgg cgtcgacggc ggcggcggca aggcagtgat cttcaacacc    240

```
atcaccattt ccgacggcat ctcgatgggc accgaaggaa tgaaatactc cctcgtgtcg    300
cgggaagtca tcgccgactc gatcgaaacc gtggtggcct gtcagggtta tgacggcgtg    360
gtcgccatcg gcggctgcga caagaacatg cccggctgcc tgatcgccct cgcccgcctc    420
aaccgtccgg cggtgttcgt ctatggcggc accatcctgc cgggctgcca cgacggcaag    480
aagctggacg tggtgtcggt gttcgaagcg gtcggcgccc gcgccaacca ccgcatcgac    540
gatgccgaac tgcacgccat cgaatccaat gccatccccg gtccgggctc ctgcggtggc    600
atgtataccg cgaacacgat ggcctccgcc atcgaggcat agggatgag cctgccgggc     660
agttcggccc aggtggccat tcccgcgcc aaggaactgg attgcgagcg ggccggcgcc     720
caggtcctca agctcctgga cctggggctc aaaccccgcg acatcatgac caagaaggcg    780
ttcgagaacg ccatcacggt ggtgatcgcc ctgggcggct ccaccaacgc cgtgctgcac    840
ctcctggcca tggccaacgc ctgcggcgtc gacctgaagc tcgacgattt cacccgcatc    900
gggcgcaaag tgccgatgct ggcggatctg aaacccagcg gcagatactc gatggccgaa    960
ctggtggaaa tcggcggcat ccagccgctg atgaagacct tgctggacgc gggactcctg   1020
cacggcgact gcatgaccgt aaccggcaag accctggaag aaaacctggc cgacgcgccc   1080
gactacccgg ccggacaaga catgatccgg tcgctggaca accccatcaa aaaggacagc   1140
catctggtga tcctcaaggg caacctggcc cggaaggcg cggtcgccaa gatcaccggc    1200
aaggaaggac tgagcttcac cggcaccgcc cgcgtattcg actgcgagga agcggcgctc   1260
acggccatcc tcgacggcac gatcgtgaaa ggcgacgtaa tcgtcatccg ctatgaaggc   1320
cccaagggcg ccccggcat gcgcgagatg ctctcgccga cctcggcggt catgggcaag   1380
ggattgggca aggaggtcgc cctcatcacc gacggccgct tttccggcgg cacccacggc   1440
ttcgtggtcg gccacatcac gccggaagcc tacaccggcg gcccctggc gatcgtccgg    1500
gacggcgata ccatcaccat cgacgccgaa acccgcgaat tgagcctgca cgtcaccgac   1560
gatgaaatcg gccggcgcct ggcgcagtgg actcaaccgg cgccgcgcta caccaagggc   1620
gtgctggcca aatacgccag gttggtgagc ccggcctcgg aaggcgccgt caccgacgac   1680
ggcctctga                                                             1689
```

<210> SEQ ID NO 8
<211> LENGTH: 562
<212> TYPE: PRT
<213> ORGANISM: Methylococcus capsulatus

<400> SEQUENCE: 8

```
Met Thr Asp Lys His Pro Arg Pro His Ser Ser Gln Val Val Asp Gly
1               5                   10                  15

Met Glu Arg Ala Pro Ser Arg Ala Met Leu His Ala Val Gly Phe Ala
                20                  25                  30

Asp Ala Asp Phe Ala Lys Pro Gln Ile Gly Ile Ala Ser Thr Trp Ala
            35                  40                  45

Met Val Thr Pro Cys Asn Met His Ile Asn Lys Leu Ala Glu Asp Ala
        50                  55                  60

Ala Arg Gly Val Asp Gly Gly Gly Lys Ala Val Ile Phe Asn Thr
65                  70                  75                  80

Ile Thr Ile Ser Asp Gly Ile Ser Met Gly Thr Glu Gly Met Lys Tyr
                85                  90                  95

Ser Leu Val Ser Arg Glu Val Ile Ala Asp Ser Ile Glu Thr Val Val
                100                 105                 110
```

```
Ala Cys Gln Gly Tyr Asp Gly Val Ala Ile Gly Cys Asp Lys
        115                 120                 125

Asn Met Pro Gly Cys Leu Ile Ala Leu Ala Arg Leu Asn Arg Pro Ala
    130                 135                 140

Val Phe Val Tyr Gly Gly Thr Ile Leu Pro Gly Cys His Asp Gly Lys
145                 150                 155                 160

Lys Leu Asp Val Val Ser Val Phe Glu Ala Val Gly Ala Arg Ala Asn
                165                 170                 175

His Arg Ile Asp Asp Ala Glu Leu His Ala Ile Glu Ser Asn Ala Ile
            180                 185                 190

Pro Gly Pro Gly Ser Cys Gly Gly Met Tyr Thr Ala Asn Thr Met Ala
        195                 200                 205

Ser Ala Ile Glu Ala Leu Gly Met Ser Leu Pro Gly Ser Ser Ala Gln
    210                 215                 220

Val Ala Ile Ser Arg Ala Lys Glu Leu Asp Cys Glu Arg Ala Gly Ala
225                 230                 235                 240

Gln Val Leu Lys Leu Leu Asp Leu Gly Leu Lys Pro Arg Asp Ile Met
                245                 250                 255

Thr Lys Lys Ala Phe Glu Asn Ala Ile Thr Val Val Ile Ala Leu Gly
            260                 265                 270

Gly Ser Thr Asn Ala Val Leu His Leu Leu Ala Met Ala Asn Ala Cys
        275                 280                 285

Gly Val Asp Leu Lys Leu Asp Asp Phe Thr Arg Ile Gly Arg Lys Val
    290                 295                 300

Pro Met Leu Ala Asp Leu Lys Pro Ser Gly Arg Tyr Ser Met Ala Glu
305                 310                 315                 320

Leu Val Glu Ile Gly Gly Ile Gln Pro Leu Met Lys Thr Leu Leu Asp
                325                 330                 335

Ala Gly Leu Leu His Gly Asp Cys Met Thr Val Thr Gly Lys Thr Leu
            340                 345                 350

Glu Glu Asn Leu Ala Asp Ala Pro Asp Tyr Pro Ala Gly Gln Asp Met
        355                 360                 365

Ile Arg Ser Leu Asp Asn Pro Ile Lys Lys Asp Ser His Leu Val Ile
    370                 375                 380

Leu Lys Gly Asn Leu Ala Pro Glu Gly Ala Val Ala Lys Ile Thr Gly
385                 390                 395                 400

Lys Glu Gly Leu Ser Phe Thr Gly Thr Ala Arg Val Phe Asp Cys Glu
                405                 410                 415

Glu Ala Ala Leu Thr Ala Ile Leu Asp Gly Thr Ile Val Lys Gly Asp
            420                 425                 430

Val Ile Val Ile Arg Tyr Glu Gly Pro Lys Gly Gly Pro Gly Met Arg
        435                 440                 445

Glu Met Leu Ser Pro Thr Ser Ala Val Met Gly Lys Gly Leu Gly Lys
    450                 455                 460

Glu Val Ala Leu Ile Thr Asp Gly Arg Phe Ser Gly Gly Thr His Gly
465                 470                 475                 480

Phe Val Val Gly His Ile Thr Pro Glu Ala Tyr Thr Gly Gly Pro Leu
                485                 490                 495

Ala Ile Val Arg Asp Gly Asp Thr Ile Thr Ile Asp Ala Glu Thr Arg
            500                 505                 510

Glu Leu Ser Leu His Val Thr Asp Asp Glu Ile Gly Arg Arg Leu Ala
        515                 520                 525
```

Gln Trp Thr Gln Pro Ala Pro Arg Tyr Thr Lys Gly Val Leu Ala Lys
        530                 535                 540

Tyr Ala Arg Leu Val Ser Pro Ala Ser Glu Gly Ala Val Thr Asp Asp
545                 550                 555                 560

Gly Leu

<210> SEQ ID NO 9
<211> LENGTH: 1647
<212> TYPE: DNA
<213> ORGANISM: Carnobacterium divergens

<400> SEQUENCE: 9

| | | | | |
|---|---|---|---|---|
| atgtataccg | tgggcgacta | tctcctggag | cggctctcgg | aactgggcat caaagagatc | 60 |
| ttcggcgtgc | cgggcgacta | caacctgaag | ttcctggatc | acatcgtgga gcatccgaac | 120 |
| ctgaagtgga | tcggcaacgc | gaatgaactc | aacgcggcgt | atgccgccga cggctacgcc | 180 |
| cgcacgaagg | cgtctccgc | gctggtgacc | accttcggcg | tcggcgagct ctccgccatc | 240 |
| aacggcatcg | ccgctcgta | tgccgagaaa | gtcccggtca | tccagatcgt gggcagcccc | 300 |
| acgatggcgg | tgcagaatgc | ccataagctg | gtgcatcata | ccctgggcga tggcaaattc | 360 |
| gaccacttcg | agaacatgca | tgagtccgtc | accgaagcca | tcggcagcct caccaaggag | 420 |
| aacgcggtga | ccgagatcga | tcgcgtgctg | cgggccgccg | tgctcaaacg cgcccggtg | 480 |
| tatctgaacc | tcccgatcga | cgtggccgaa | atggtcgtcg | aaaaaccgtc gggccccctg | 540 |
| ctgcccaagc | aggcgagcct | gagcgcccgc | gaggtcgaac | tcgtgcatga gctggagaag | 600 |
| gccctgcagc | aggcgaagaa | cccggtggtc | ctggcgggca | acgagctggc gtcgttccac | 660 |
| ctcgaaacgt | acctcgccga | cttcatccac | aagttcaacc | tccccatcac gaccctcccc | 720 |
| ttcggcaagg | gcgtcttcaa | cgaggaagac | gagcattatc | tgggcgtcta tgcgggctcg | 780 |
| ccgaccgaag | aaggcctgcg | gaagcgcgtc | gatacggcgg | acctggtcgt ggcgctgggc | 840 |
| gcgaagctga | cggactccgc | cacctccggc | ttctcgtacg | acttctccga aaaacagctc | 900 |
| ttcagcctgg | cgtccgacga | agtcatcgtc | aaagaggaac | acctcgaagg catccatctg | 960 |
| ccggccgtca | tgaaggcgct | gacgagcatc | gactaccagg | gctaccaggg cgacatccag | 1020 |
| ccgatggccc | ggctgaagag | catcaaaccc | accaaccagg | tgctgaccca gcgccacttc | 1080 |
| tgggaggcca | tcgaaggctt | cctggaaaag | ggcgacaccg | ccgtcgcgga gcagggcacg | 1140 |
| agcttcttcg | gcctctcgac | cgtgccgctg | aagagcgaaa | tgtcgttcat cggccagccg | 1200 |
| ctgtggggct | ccatcggcta | tacgttcccg | gcgatgctgg | gcagccagct cgccaacccg | 1260 |
| tccagccggc | acctcctgtt | catcggcgac | ggcagcctgc | agctgacgat ccaggagctc | 1320 |
| ggcatggccc | tccgcgaaaa | actcaccccg | atcgtgttcg | tcatcaacaa taacggctat | 1380 |
| acggtcgaac | gggaaatcca | cggcccgaat | gaaatctata | cgacatccc gatgtgggac | 1440 |
| taccagaaac | tcccgctcgt | cttcggcggc | tccgagcagt | cggtcatcac ctataaagtg | 1500 |
| acgaccgaac | tggaactggc | gaacgcgctc | aaggcggccc | ggctggacaa caaccgcctg | 1560 |
| cagtggatcg | aagtggtgat | ggaccagacc | gatgcgccgg | agctcctcat gaagctgggc | 1620 |
| aagatcttcg | cgaagcagaa | tagctga | | | 1647 |

<210> SEQ ID NO 10
<211> LENGTH: 548
<212> TYPE: PRT
<213> ORGANISM: Carnobacterium divergens

<400> SEQUENCE: 10

-continued

```
Met Tyr Thr Val Gly Asp Tyr Leu Leu Glu Arg Leu Ser Glu Leu Gly
 1               5                  10                  15

Ile Lys Glu Ile Phe Gly Val Pro Gly Asp Tyr Asn Leu Lys Phe Leu
             20                  25                  30

Asp His Ile Val Glu His Pro Asn Leu Lys Trp Ile Gly Asn Ala Asn
             35                  40                  45

Glu Leu Asn Ala Ala Tyr Ala Ala Asp Gly Tyr Ala Arg Thr Lys Gly
 50                  55                  60

Val Ser Ala Leu Val Thr Thr Phe Gly Val Gly Glu Leu Ser Ala Ile
 65                  70                  75                  80

Asn Gly Ile Ala Gly Ser Tyr Ala Glu Lys Val Pro Val Ile Gln Ile
             85                  90                  95

Val Gly Ser Pro Thr Met Ala Val Gln Asn Ala His Lys Leu Val His
             100                 105                 110

His Thr Leu Gly Asp Gly Lys Phe Asp His Phe Glu Asn Met His Glu
             115                 120                 125

Ser Val Thr Glu Ala Ile Gly Ser Leu Thr Lys Glu Asn Ala Val Thr
             130                 135                 140

Glu Ile Asp Arg Val Leu Arg Ala Ala Val Leu Lys Arg Arg Pro Val
145                 150                 155                 160

Tyr Leu Asn Leu Pro Ile Asp Val Ala Glu Met Val Val Glu Lys Pro
             165                 170                 175

Ser Gly Pro Leu Leu Pro Lys Gln Ala Ser Leu Ser Ala Arg Glu Val
             180                 185                 190

Glu Leu Val His Glu Leu Glu Lys Ala Leu Gln Gln Ala Lys Asn Pro
             195                 200                 205

Val Val Leu Ala Gly Asn Glu Leu Ala Ser Phe His Leu Glu Thr Tyr
             210                 215                 220

Leu Ala Asp Phe Ile His Lys Phe Asn Leu Pro Ile Thr Thr Leu Pro
225                 230                 235                 240

Phe Gly Lys Gly Val Phe Asn Glu Glu Asp Glu His Tyr Leu Gly Val
             245                 250                 255

Tyr Ala Gly Ser Pro Thr Glu Glu Gly Leu Arg Lys Arg Val Asp Thr
             260                 265                 270

Ala Asp Leu Val Val Ala Leu Gly Ala Lys Leu Thr Asp Ser Ala Thr
             275                 280                 285

Ser Gly Phe Ser Tyr Asp Phe Ser Glu Lys Gln Leu Phe Ser Leu Ala
             290                 295                 300

Ser Asp Glu Val Ile Val Lys Glu Glu His Leu Glu Gly Ile His Leu
305                 310                 315                 320

Pro Ala Val Met Lys Ala Leu Thr Ser Ile Asp Tyr Gln Gly Tyr Gln
             325                 330                 335

Gly Asp Ile Gln Pro Met Ala Arg Leu Lys Ser Ile Lys Pro Thr Asn
             340                 345                 350

Gln Val Leu Thr Gln Arg His Phe Trp Glu Ala Ile Glu Gly Phe Leu
             355                 360                 365

Glu Lys Gly Asp Thr Ala Val Ala Glu Gln Gly Thr Ser Phe Phe Gly
             370                 375                 380

Leu Ser Thr Val Pro Leu Lys Ser Glu Met Ser Phe Ile Gly Gln Pro
385                 390                 395                 400

Leu Trp Gly Ser Ile Gly Tyr Thr Phe Pro Ala Met Leu Gly Ser Gln
             405                 410                 415
```

```
Leu Ala Asn Pro Ser Ser Arg His Leu Leu Phe Ile Gly Asp Gly Ser
            420                 425                 430

Leu Gln Leu Thr Ile Gln Glu Leu Gly Met Ala Leu Arg Glu Lys Leu
        435                 440                 445

Thr Pro Ile Val Phe Val Ile Asn Asn Asn Gly Tyr Thr Val Glu Arg
    450                 455                 460

Glu Ile His Gly Pro Asn Glu Ile Tyr Asn Asp Ile Pro Met Trp Asp
465                 470                 475                 480

Tyr Gln Lys Leu Pro Leu Val Phe Gly Gly Ser Glu Gln Ser Val Ile
                485                 490                 495

Thr Tyr Lys Val Thr Thr Glu Leu Glu Leu Ala Asn Ala Leu Lys Ala
            500                 505                 510

Ala Arg Leu Asp Asn Asn Arg Leu Gln Trp Ile Glu Val Val Met Asp
        515                 520                 525

Gln Thr Asp Ala Pro Glu Leu Leu Met Lys Leu Gly Lys Ile Phe Ala
    530                 535                 540

Lys Gln Asn Ser
545

<210> SEQ ID NO 11
<211> LENGTH: 1650
<212> TYPE: DNA
<213> ORGANISM: Methylococcus capsulatus

<400> SEQUENCE: 11
atgggcacgg ttgagcctgg cgctatcgga caacatctgc tcgcctgcct ttaccaggcg      60
ggcgtcgggc acatcttcgg cgttccggc gattacgtgc tgggcttcta tgatctgatg     120
gccaaaggtc ccgtccggca tatcgggacc acgcgggagg acaccgccgc cttcgccgcc     180
gacggctatg cccgctgccg gggcatgggc gccctggcgg tgacttacgg ggtcggtgcg     240
ctcaacaccg tcaacgccgt cgccggcgcc tatgcggaat cctcgccggt ggtggtcatc     300
agcggtgcgc gggggtgcg cgagcaaagg gaagacccgt tgatccacca ccgcttcggg      360
ccgttccggt tccagcgcga gatattcgaa cggatcacct cgccgccgt ggtgctggac      420 gatccggtga tcgccttccg gcaggtggag cgtgcgctcg cagccgcccg tcagcactgc     480
aagccggtgt acatcgagat tcccgccgac cgggtgatgg cgccgggata tccgattcca     540
caggaaaccc cggaaacgcc ttccagcgac gattcggccc tggcggaggc ggtcgccgag     600
gccgcggagc tcctgggccg tgcggtgtcg ccggtgatcc ttgcaggcgt cgagttgcac     660
cggcgagggc tccaggacgc cctcgtcggc ctcgtcgagc aggcccgcct gccggtggcg     720
gcgaccttga ccggcaagtc ggtgttcgcc gagcgccatc ccgcctatct gggggtgtac     780
gagggtgcga tgagcacgga aaacgcccgc tacatggtcg agcagtccga cctcctgctg     840
atgctcgggg tcacgctgaa cgatgtcgac acgggcatct acacggcgcg tctcgatccg     900
cagcgcatcg tccgcgcagc ccagaacgag gtcgtgattc gccatcaccg ctatccccgc     960
gtcctgctcg cggacttcgt cacggccctg gcgcggtccg tcaaggcccg gggcgaggcg    1020
tttccgatgc cggcgggcc ggaaccgtgg gactttcccg cgccggaccg gccgatgacg     1080
atcgcccggc tggtggagcg gctcgaccgc gccctgacct ccgacatgat cgtagtgtgc    1140
gatgtcggcg actgcctgtt cgcagccacc gacctgcgcg tgcacgagcg cagcgaattt    1200
ctggcgtccg ccttctatac ctcgatgggg ttcgcggtgc ccgccgccct cggggcccag    1260
atcgcccgtc cggaccaccg ggcgctgatc ctggtcggcg acggtgcctt ccagatgacc    1320
```

-continued

```
ggaacggagc tgtcgaccca tgcccgtctc ggcctggcgc ccatcgtggt ggtgctcgac    1380
aatcgcggtt acagcaccga gcgcttcatc ctcgacggag ccttcaacga catcgccgac    1440
tggcgcttcc accggctggg cgaggtgttc ggcccctac agggctacga cgcgcccgac     1500
gaagcggcgt tcgaaaacgc gctcagcgaa gcgctggtca accgaaacat gccgagcctc    1560
atcaacgtcc gtcttcccc cggcgatgcc tcgatagcca tgaagcgtct cgccgggcat     1620
ctgcagtgcc gggtcaaggg cgagggctaa                                     1650
```

<210> SEQ ID NO 12
<211> LENGTH: 549
<212> TYPE: PRT
<213> ORGANISM: Methylococcus capsulatus

<400> SEQUENCE: 12

```
Met Gly Thr Val Glu Pro Gly Ala Ile Gly Gln His Leu Leu Ala Cys
1               5                   10                  15

Leu Tyr Gln Ala Gly Val Gly His Ile Phe Gly Val Pro Gly Asp Tyr
            20                  25                  30

Val Leu Gly Phe Tyr Asp Leu Met Ala Lys Gly Pro Val Arg His Ile
        35                  40                  45

Gly Thr Thr Arg Glu Asp Thr Ala Ala Phe Ala Ala Asp Gly Tyr Ala
    50                  55                  60

Arg Cys Arg Gly Met Gly Ala Leu Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Val Val Ile Ser Gly Ala Pro Gly Val Arg Glu Gln Arg Glu Asp
            100                 105                 110

Pro Leu Ile His His Arg Phe Gly Pro Phe Arg Phe Gln Arg Glu Ile
        115                 120                 125

Phe Glu Arg Ile Thr Cys Ala Ala Val Val Leu Asp Asp Pro Val Ile
    130                 135                 140

Ala Phe Arg Gln Val Glu Arg Ala Leu Ala Ala Arg Gln His Cys
145                 150                 155                 160

Lys Pro Val Tyr Ile Glu Ile Pro Ala Asp Arg Val Met Ala Pro Gly
                165                 170                 175

Tyr Pro Ile Pro Gln Glu Thr Pro Glu Thr Pro Ser Ser Asp Asp Ser
            180                 185                 190

Ala Leu Ala Glu Ala Val Ala Glu Ala Ala Glu Leu Leu Gly Arg Ala
        195                 200                 205

Val Ser Pro Val Ile Leu Ala Gly Val Glu Leu His Arg Arg Gly Leu
    210                 215                 220

Gln Asp Ala Leu Val Gly Leu Val Glu Gln Ala Arg Leu Pro Val Ala
225                 230                 235                 240

Ala Thr Leu Thr Gly Lys Ser Val Phe Ala Glu Arg His Pro Ala Tyr
                245                 250                 255

Leu Gly Val Tyr Glu Gly Ala Met Ser Thr Glu Asn Ala Arg Tyr Met
            260                 265                 270

Val Glu Gln Ser Asp Leu Leu Met Leu Gly Val Thr Leu Asn Asp
        275                 280                 285

Val Asp Thr Gly Ile Tyr Thr Ala Arg Leu Asp Pro Gln Arg Ile Val
    290                 295                 300

Arg Ala Ala Gln Asn Glu Val Val Ile Arg His His Arg Tyr Pro Arg
305                 310                 315                 320
```

Val Leu Leu Ala Asp Phe Val Thr Ala Leu Ala Arg Ser Val Lys Ala
            325                 330                 335

Arg Gly Glu Ala Phe Pro Met Pro Ala Gly Pro Glu Pro Trp Asp Phe
            340                 345                 350

Pro Ala Pro Asp Arg Pro Met Thr Ile Ala Arg Leu Val Glu Arg Leu
            355                 360                 365

Asp Arg Ala Leu Thr Ser Asp Met Ile Val Val Cys Asp Val Gly Asp
            370                 375                 380

Cys Leu Phe Ala Ala Thr Asp Leu Arg Val His Glu Arg Ser Glu Phe
385                 390                 395                 400

Leu Ala Ser Ala Phe Tyr Thr Ser Met Gly Phe Ala Val Pro Ala Ala
            405                 410                 415

Leu Gly Ala Gln Ile Ala Arg Pro Asp His Arg Ala Leu Ile Leu Val
            420                 425                 430

Gly Asp Gly Ala Phe Gln Met Thr Gly Thr Glu Leu Ser Thr His Ala
            435                 440                 445

Arg Leu Gly Leu Ala Pro Ile Val Val Leu Asp Asn Arg Gly Tyr
            450                 455                 460

Ser Thr Glu Arg Phe Ile Leu Asp Gly Ala Phe Asn Asp Ile Ala Asp
465                 470                 475                 480

Trp Arg Phe His Arg Leu Gly Glu Val Phe Gly Pro Leu Gln Gly Tyr
            485                 490                 495

Asp Ala Pro Asp Glu Ala Ala Phe Glu Asn Ala Leu Ser Glu Ala Leu
            500                 505                 510

Val Asn Arg Asn Met Pro Ser Leu Ile Asn Val Arg Leu Ser Pro Gly
            515                 520                 525

Asp Ala Ser Ile Ala Met Lys Arg Leu Ala Gly His Leu Gln Cys Arg
            530                 535                 540

Val Lys Gly Glu Gly
545

<210> SEQ ID NO 13
<211> LENGTH: 1083
<212> TYPE: DNA
<213> ORGANISM: Saccharomyces cerevisiae

<400> SEQUENCE: 13
atgagctatc ccgagaagtt cgagggggatc gccatccaga gccacgagga ctggaagaac     60
ccgaaaaaga ccaagtatga tccgaagccc ttctacgatc acgacatcga catcaagatc    120
gaggcctgcg gcgtctgcgg cagcgatatc cattgtgcgg ctggccactg gggcaacatg    180
aagatgccgt tggtcgtcgg ccacgagatc gtgggcaagg tcgtgaagtt aggcccgaaa    240
agcaacagcg gcttgaaggt gggccagcgc gtgggtgtgg gtgcgcaggt cttcagctgt    300
ctggagtgcg accgttgcaa gaacgacaac gaaccgtact gcaccaagtt cgtcaccacc    360
tactcgcagc cctacgagga cggctacgtc tcgcagggcg gttacgccaa ctatgtccga    420
gtccacgaac acttcgtggt gcccatcccg gaaaatatcc ccagccatct ggcggctccc    480
ctgctgtgcg gtggcttgac cgtctacagc cccctcgtcc gcaatggctg cggtcccggc    540
aagaaggtgg gtatcgtggg cctcggcggt ataggctcta tgggcacgct gatctcgaaa    600
gcgatgggcg cagaaacgta cgtgatctcg cgttcctcgc gcaagcgcga ggatgcgatg    660
aagatgggtg cggaccacta catcgccacg ctggaggagg tgactgggg tgagaagtac    720 ttcgacacgt tcgacctcat cgtggtgtgc gcgagttccc tgacggacat cgacttcaat    780

```
atcatgccca aggcgatgaa ggtcggaggg cgcatcgtct ccatctcgat cccggagcag    840
cacgaaatgc tgtcgctgaa gccctacggc ctgaaagccg tctccattag ctactcggcg    900
ctcggtagta tcaaggagct caaccagctg ttgaagttgg tttccgaaaa ggacatcaag    960
atctgggtgg aaacgctccc ggtgggcgaa gccggtgtgc acgaggcctt tgagcggatg   1020 gagaagggggg atgtccgtta tcggtttaca ctcgtcggct acgataaaga gttctcggat   1080
taa                                                                 1083
```

<210> SEQ ID NO 14
<211> LENGTH: 360
<212> TYPE: PRT
<213> ORGANISM: Saccharomyces cerevisiae
<400> SEQUENCE: 14

```
Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
```

```
305                 310                 315                 320
Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
                340                 345                 350

Gly Tyr Asp Lys Glu Phe Ser Asp
                355                 360

<210> SEQ ID NO 15
<211> LENGTH: 1164
<212> TYPE: DNA
<213> ORGANISM: Escherichia coli

<400> SEQUENCE: 15
atgaacaact taatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc acgaactga ctgcgatgca cggtctggat    840
cacgcgcaaa cactggctat cgtcctgcct gcactgtgga tgaaaaacg cgataccaag    900 cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa atcatgaca ttacgttgga tgtcagccgc   1140
cgtatatacg aagccgcccg ctaa                                          1164

<210> SEQ ID NO 16
<211> LENGTH: 387
<212> TYPE: PRT
<213> ORGANISM: Escherichia coli

<400> SEQUENCE: 16

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
                35                  40                  45

Gln Val Leu Asp Ala Leu Lys Gly Met Asp Val Leu Glu Phe Gly Gly
                50                  55                  60
```

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 17
<211> LENGTH: 1149
<212> TYPE: DNA
<213> ORGANISM: Escherichia coli

<400> SEQUENCE: 17
atggcgaatc ggatgatcct caatgaaacg gcctggttcg ccgcggcgc ggtcggcgcc     60 ctcaccgatg aggtcaagcg gcggggctac cagaaggccc tgatcgtcac ggataaaacc    120
ctggtgcagt gcggcgtcgt cgccaaggtg accgacaaga tggatgcggc cggcctggcc    180
tgggcgatct acgacggcgt ggtgcccaac cccaccatca ccgtggtgaa ggaaggcctg    240

```
ggcgtgttcc agaactcggg cgcggattat ctcatcgcga tcggcggcgg cagcccccag    300
gacacctgca aggccatcgg catcatctcg aacaaccccg agttcgcgga cgtgcgctcc    360
ctggagggcc tgtcgccgac gaacaagccc tccgtcccga tcctcgccat cccgacgacg    420
gccggcaccg cggccgaggt gaccatcaat tacgtcatca ccgacgagga aaagcggcgc    480
aagttcgtgt gtgtggaccc ccatgacatc ccccaggtcg ccttcatcga cgccgacatg    540
atggatggca tgcccccccgc cctcaaggcc gcgacgggcg tggacgcgct gacgcatgcc    600
atcgaaggct acatcacccg gggcgcctgg gccctgacgg atgccctgca tatcaaggcc    660
atcgaaatca tcgccggcgc cctgcgcggg tccgtggccg cgacaaggga tgcgggcgag    720
gagatggcgc tgggccagta cgtggccggc atgggcttct ccaatgtggg cctgggcctg    780
gtgcatggca tggcccatcc gctcggcgcc ttctacaaca cgccgcatgg cgtcgcgaac    840
gcgatcctcc tgccgcatgt catgcgctac aatgcggact tcacgggcga gaataccgc     900 gatatcgccc gggtcatggg cgtgaaggtc gagggcatgt cgctggaaga ggcgcggaac    960
gccgcggtcg aagccgtctt cgccctgaac cgggatgtgg gcatcccgcc gcacctgcgc   1020
gatgtcggcg tccgcaagga agacatcccc gcgctggcgc aggccgccct ggacgatgtg   1080
tgcaccggcg caaccccccg cgaggcgacg ctggaagaca tcgtcgaact ctaccatacc   1140
gcgtggtga                                                            1149

<210> SEQ ID NO 18
<211> LENGTH: 382
<212> TYPE: PRT
<213> ORGANISM: Escherichia coli

<400> SEQUENCE: 18

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
    50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205
```

```
Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
            245                 250                 255

Gly Leu Gly Leu Val His Gly Met Ala His Pro Leu Gly Ala Phe Tyr
        260                 265                 270

Asn Thr Pro His Gly Val Ala Asn Ala Ile Leu Leu Pro His Val Met
    275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
370                 375                 380

<210> SEQ ID NO 19
<211> LENGTH: 1254
<212> TYPE: DNA
<213> ORGANISM: Escherichia coli

<400> SEQUENCE: 19
atgtactacc tgaagaacac caatttctgg atgttcggcc tgttcttctt cttctatttc      60
ttcatcatgg gcgcctactt cccgttcttc ccgatctggc tgcacgatat caatcacatc     120
agcaagtcgg ataccggcat catcttcgcc gccatcagcc tgttcagcct gctgttccag     180
ccgctcttcg gcctcctgag cgacaagctc ggcctgcgga agtacctgct gtggatcatc     240
acgggcatgc tggtgatgtt cgccccccttc ttcatcttca tcttcggccc gctcctgcag     300
tacaacatcc tcgtgggcag catcgtgggc ggcatctacc tgggcttctg cttcaatgcg     360 ggcgccccg ccgtcgaggc cttcatcgag aaagtgagcc ggcgctccaa cttcgagttc     420
ggccgggccc ggatgttcgg ctgcgtcggc tgggcgctgt gcgcgagcat cgtgggcatc     480
atgttcacga tcaacaacca gttcgtgttc tggctgggct ccggctgttg tctcatcctg     540
gccgtcctgc tgttcttcgc caagacggac gccccgagct ccgcgaccgt cgccaacgcg     600
gtcggcgcca atcactccgc gttctcgctg aagctggcgc tggagctgtt ccgccagccg     660
aagctgtggt tcctgagcct ctacgtgatc ggcgtctcgt gcacgtacga tgtcttcgat     720
cagcagttcg ccaacttctt cacctcgttc ttcgccaccg cgagcaggg cacgcgcgtc     780 ttcggctatg tgacgacgat gggcgagctg ctgaacgcca gcatcatgtt cttcgccccg     840
ctcatcatca accgcatcgg cggcaaaaac gcgctgctgc tcgccggcac catcatgtcg     900
gtgcggatca tcggctcctc cttcgccacc tcggccctgg aagtcgtcat cctgaagacc     960
ctgcacatgt tcgaagtccc gttcctgctc gtcggctgtt tcaagtacat cacctcccag    1020
ttcgaggtgc gcttcagcgc cacgatctac tggtgtgct tctgcttctt caagcagctg    1080
gcgatgatct tcatgtccgt gctggcgggc aatatgtatg agtcgatcgg cttccagggc    1140
```

```
gcgtatctgg tcctgggcct cgtggccctg ggcttcaccc tgatctccgt gttcacgctg      1200
agcggcccgg gcccgctgtc gctgctgcgg cgccaggtga atgaggtcgc ctga            1254
```

<210> SEQ ID NO 20
<211> LENGTH: 417
<212> TYPE: PRT
<213> ORGANISM: Escherichia coli

<400> SEQUENCE: 20

| | | | | | | | | | | | | | | |
|---|---|---|---|---|---|---|---|---|---|---|---|---|---|---|
| Met | Tyr | Tyr | Leu | Lys | Asn | Thr | Asn | Phe | Trp | Met | Phe | Gly | Leu | Phe | Phe |
| 1 | | | | 5 | | | | | 10 | | | | | 15 | |
| Phe | Phe | Tyr | Phe | Phe | Ile | Met | Gly | Ala | Tyr | Phe | Pro | Phe | Phe | Pro | Ile |
| | | | 20 | | | | | 25 | | | | | 30 | | |
| Trp | Leu | His | Asp | Ile | Asn | His | Ile | Ser | Lys | Ser | Asp | Thr | Gly | Ile | Ile |
| | | | | 35 | | | | | 40 | | | | | 45 | |
| Phe | Ala | Ala | Ile | Ser | Leu | Phe | Ser | Leu | Leu | Phe | Gln | Pro | Leu | Phe | Gly |
| | | 50 | | | | | 55 | | | | | 60 | | | |
| Leu | Leu | Ser | Asp | Lys | Leu | Gly | Leu | Arg | Lys | Tyr | Leu | Leu | Trp | Ile | Ile |
| 65 | | | | | 70 | | | | | 75 | | | | | 80 |
| Thr | Gly | Met | Leu | Val | Met | Phe | Ala | Pro | Phe | Phe | Ile | Phe | Ile | Phe | Gly |
| | | | | 85 | | | | | 90 | | | | | 95 | |
| Pro | Leu | Leu | Gln | Tyr | Asn | Ile | Leu | Val | Gly | Ser | Ile | Val | Gly | Gly | Ile |
| | | | 100 | | | | | 105 | | | | | 110 | | |
| Tyr | Leu | Gly | Phe | Cys | Phe | Asn | Ala | Gly | Ala | Pro | Ala | Val | Glu | Ala | Phe |
| | | | | 115 | | | | | 120 | | | | | 125 | |
| Ile | Glu | Lys | Val | Ser | Arg | Arg | Ser | Asn | Phe | Glu | Phe | Gly | Arg | Ala | Arg |
| 130 | | | | | 135 | | | | | 140 | | | | | |
| Met | Phe | Gly | Cys | Val | Gly | Trp | Ala | Leu | Cys | Ala | Ser | Ile | Val | Gly | Ile |
| 145 | | | | | 150 | | | | | 155 | | | | | 160 |
| Met | Phe | Thr | Ile | Asn | Asn | Gln | Phe | Val | Phe | Trp | Leu | Gly | Ser | Gly | Cys |
| | | | | 165 | | | | | 170 | | | | | 175 | |
| Cys | Leu | Ile | Leu | Ala | Val | Leu | Leu | Phe | Phe | Ala | Lys | Thr | Asp | Ala | Pro |
| | | | | 180 | | | | | 185 | | | | | 190 | |
| Ser | Ser | Ala | Thr | Val | Ala | Asn | Ala | Val | Gly | Ala | Asn | His | Ser | Ala | Phe |
| | | | 195 | | | | | 200 | | | | | 205 | | |
| Ser | Leu | Lys | Leu | Ala | Leu | Glu | Leu | Phe | Arg | Gln | Pro | Lys | Leu | Trp | Phe |
| | 210 | | | | | 215 | | | | | 220 | | | | |
| Leu | Ser | Leu | Tyr | Val | Ile | Gly | Val | Ser | Cys | Thr | Tyr | Asp | Val | Phe | Asp |
| 225 | | | | | 230 | | | | | 235 | | | | | 240 |
| Gln | Gln | Phe | Ala | Asn | Phe | Phe | Thr | Ser | Phe | Phe | Ala | Thr | Gly | Glu | Gln |
| | | | | 245 | | | | | 250 | | | | | 255 | |
| Gly | Thr | Arg | Val | Phe | Gly | Tyr | Val | Thr | Thr | Met | Gly | Glu | Leu | Leu | Asn |
| | | | 260 | | | | | 265 | | | | | 270 | | |
| Ala | Ser | Ile | Met | Phe | Phe | Ala | Pro | Leu | Ile | Ile | Asn | Arg | Ile | Gly | Gly |
| | | | 275 | | | | | 280 | | | | | 285 | | |
| Lys | Asn | Ala | Leu | Leu | Leu | Ala | Gly | Thr | Ile | Met | Ser | Val | Arg | Ile | Ile |
| | 290 | | | | | 295 | | | | | 300 | | | | |
| Gly | Ser | Ser | Phe | Ala | Thr | Ser | Ala | Leu | Glu | Val | Val | Ile | Leu | Lys | Thr |
| 305 | | | | | 310 | | | | | 315 | | | | | 320 |
| Leu | His | Met | Phe | Glu | Val | Pro | Phe | Leu | Leu | Val | Gly | Cys | Phe | Lys | Tyr |
| | | | | 325 | | | | | 330 | | | | | 335 | |
| Ile | Thr | Ser | Gln | Phe | Glu | Val | Arg | Phe | Ser | Ala | Thr | Ile | Tyr | Leu | Val |
| | | | 340 | | | | | 345 | | | | | 350 | | |
| Cys | Phe | Cys | Phe | Phe | Lys | Gln | Leu | Ala | Met | Ile | Phe | Met | Ser | Val | Leu |

```
            355                 360                 365
Ala Gly Asn Met Tyr Glu Ser Ile Gly Phe Gln Gly Ala Tyr Leu Val
            370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala
```

<210> SEQ ID NO 21
<211> LENGTH: 879
<212> TYPE: DNA
<213> ORGANISM: Escherichia coli

<400> SEQUENCE: 21

```
atggccgagg cgcagaacga tccgctcctg ccgggctata gcttcaatgc ccatctggtc      60
gcgggcctga ccccgatcga ggcgaatggc tacctggact tcttcatcga ccgcccgctg     120
ggcatgaagg gctacatcct caatctgacc atccggggcc agggcgtcgt gaagaatcag     180
ggccgcgagt tcgtgtgccg ccccggcgac atcctcctgt tcccgcccgg cgaaatccat     240
cattatggcc gccatccgga agcccgcgag tggtatcatc agtgggtcta tttccggccc     300
cgcgcgtatt ggcatgagtg gctgaactgg ccctcgatct cgccaacac cggcttcttc      360
cggccggacg aggcccacca gccccatttc tccgacctgt tcggccagat catcaacgcc     420
ggccagggcg aaggccgcta ttcggaactg ctggccatca acctgctcga acagctcctc     480
ctgcggcgga tggaagccat caacgaatcc ctgcatcccc gatggacaa ccgcgtgcgg      540
gaagcgtgcc agtacatcag cgaccacctg gcggactcga atttcgatat cgcgtccgtg     600
gcccagcatg tctgcctgag cccgagccgg ctgtcccatc tcttccgcca gcagctgggc     660
atctccgtgc tctcgtggcg cgaagaccag cggatctccc aggccaagct gctgctctcc     720
accacccgca tgcccatcgc caccgtcggc cgcaacgtcg gcttcgacga ccagctgtat     780
ttctcgcggg tgttcaagaa gtgtacgggc gcctcgccct cggagttccg cgccggctgc     840
gaggagaaag tcaacgacgt ggccgtcaaa ctcagctga                            879
```

<210> SEQ ID NO 22
<211> LENGTH: 292
<212> TYPE: PRT
<213> ORGANISM: Escherichia coli

<400> SEQUENCE: 22

```
Met Ala Glu Ala Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
                20                  25                  30

Asp Phe Phe Ile Asp Arg Pro Leu Gly Met Lys Gly Tyr Ile Leu Asn
            35                  40                  45

Leu Thr Ile Arg Gly Gln Gly Val Val Lys Asn Gln Gly Arg Glu Phe
        50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
                100                 105                 110
```

Ile Phe Ala Asn Thr Gly Phe Arg Pro Asp Glu Ala His Gln Pro
            115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
    195                 200                 205

Ser Arg Leu Ser His Leu Phe Arg Gln Gln Leu Gly Ile Ser Val Leu
210                 215                 220

Ser Trp Arg Glu Asp Gln Arg Ile Ser Gln Ala Lys Leu Leu Leu Ser
225                 230                 235                 240

Thr Thr Arg Met Pro Ile Ala Thr Val Gly Arg Asn Val Gly Phe Asp
                245                 250                 255

Asp Gln Leu Tyr Phe Ser Arg Val Phe Lys Lys Cys Thr Gly Ala Ser
            260                 265                 270

Pro Ser Glu Phe Arg Ala Gly Cys Glu Glu Lys Val Asn Asp Val Ala
    275                 280                 285

Val Lys Leu Ser
    290

<210> SEQ ID NO 23
<211> LENGTH: 389
<212> TYPE: PRT
<213> ORGANISM: Clostridium acetobutylicum

<400> SEQUENCE: 23

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr

```
                180                 185                 190
Ala Asp Ile Met Ser His Thr Phe Glu Ser Tyr Phe Ser Gly Val Glu
            195                 200                 205
Gly Ala Tyr Val Gln Asp Gly Ile Ala Glu Ala Ile Leu Arg Thr Cys
            210                 215                 220
Ile Lys Tyr Gly Lys Ile Ala Met Glu Lys Thr Asp Asp Tyr Glu Ala
225                 230                 235                 240
Arg Ala Asn Leu Met Trp Ala Ser Ser Leu Ala Ile Asn Gly Leu Leu
            245                 250                 255
Ser Leu Gly Lys Asp Arg Lys Trp Ser Cys His Pro Met Glu His Glu
            260                 265                 270
Leu Ser Ala Tyr Tyr Asp Ile Thr His Gly Val Gly Leu Ala Ile Leu
            275                 280                 285
Thr Pro Asn Trp Met Glu Tyr Ile Leu Asn Asp Thr Leu His Lys
            290                 295                 300
Phe Val Ser Tyr Gly Ile Asn Val Trp Gly Ile Asp Lys Asn Lys Asp
305                 310                 315                 320
Asn Tyr Glu Ile Ala Arg Glu Ala Ile Lys Asn Thr Arg Glu Tyr Phe
            325                 330                 335
Asn Ser Leu Gly Ile Pro Ser Lys Leu Arg Glu Val Gly Ile Gly Lys
            340                 345                 350
Asp Lys Leu Glu Leu Met Ala Lys Gln Ala Val Arg Asn Ser Gly Gly
            355                 360                 365
Thr Ile Gly Ser Leu Arg Pro Ile Asn Ala Glu Asp Val Leu Glu Ile
            370                 375                 380
Phe Lys Lys Ser Tyr
385

<210> SEQ ID NO 24
<211> LENGTH: 1170
<212> TYPE: DNA
<213> ORGANISM: Clostridium acetobutylicum

<400> SEQUENCE: 24
atgctctcgt tcgactacag catccccacc aaggtcttct tcggcaaagg caagatcgac        60
gtgatcggcg aagagatcaa aaagtacggc tcccgcgtgc tgatcgtcta cggcggcggc       120
tcgatcaaac gcaacggcat ctatgaccgg gccacggcga tcctgaagga aaacaacatc       180
gccttctacg agctgtccgg cgtggagccc aacccgcgga tcaccacggt caagaagggc       240
atcgaaatct gtcgcgaaaa caacgtcgac ctggtgctgg ccatcggcgg cggcagcgcg       300
atcgattgct ccaaggtgat cgccgccggc gtctattatg acggcgacac ctgggacatg       360
gtcaaagacc ccagcaagat caccaaagtg ctgccgatcg cctccatcct caccctgagc       420
gcgacgggca gcgaaatgga tcagatcgcc gtgatctcga catggagac gaacgaaaag       480 ctcggcgtgg ccacgacga tatgcggccg aagttctcgg tcctcgatcc gacgtatacc       540
ttcacggtgc cgaagaacca gaccgccgcc ggcacggcgg acatcatgtc gcataccttc       600
gaatcgtatt tcagcggcgt cgaaggcgcg tatgtccagg acggcatcgc ggaagccatc       660
ctccgcacct gcatcaagta tggcaagatc gcgatggaaa agaccgacga ctacgaggcc       720
cgcgcgaatc tgatgtgggc ctcgtccctg gccatcaatg gcctgctgag cctcggcaag       780
gatcggaaat ggtcgtgcca cccgatggag cacgagctga cgcctatta cgacatcacc       840 cacggcgtgg gcctggccat cctgaccccc aactggatgg aatatatcct gaacgacgac       900
```

```
acgctgcata aattcgtgtc gtacggcatc aacgtctggg gcatcgataa gaacaaggac    960
aactacgaga tcgcccgcga agccatcaaa aatacgcggg agtacttcaa cagcctgggc   1020
atcccgtcga agctgcgcga ggtcggcatc ggcaaagata aactggagct gatggccaag   1080
caggcggtgc gcaactcggg cggcacgatc ggcagcctcc gccccatcaa cgcggaggat   1140
gtgctggaga tcttcaagaa gagctattga                                   1170
```

<210> SEQ ID NO 25
<211> LENGTH: 390
<212> TYPE: PRT
<213> ORGANISM: Clostridium acetobutylicum

<400> SEQUENCE: 25

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
```

```
                325                 330                 335
Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 26
<211> LENGTH: 1173
<212> TYPE: DNA
<213> ORGANISM: Clostridium acetobutylicum

<400> SEQUENCE: 26
atggtcgatt tcgagtattc gatcccgacg cggatcttct tcggcaagga caaaatcaac      60
gtcctgggcc gcgaactcaa gaaatacggc agcaaagtgc tgatcgtcta cggcggcggc     120
tcgatcaagc ggaacggcat ctacgataag gccgtgtcga tcctggaaaa gaatagcatc     180
aagttctatg aactggcggg cgtcgaaccg aaccccgcg tgaccaccgt cgagaagggc     240
gtcaagatct gccgggaaaa cggcgtggaa gtcgtgctgg cgatcggcgg cggctccgcg     300
atcgactgcg ccaaggtgat cgcggcggcc tgcgagtacg acggcaatcc ctgggacatc     360
gtcctggacg gctccaagat caagcgcgtc ctcccgatcg ccagcatcct gaccatcgcc     420
gcgacgggct cggaaatgga cacctgggcc gtcatcaaca tatggatac caacgaaaag     480
ctcatcgcgg cccacccgga catggccccg aagttctcga tcctcgatcc cacctacacc     540
tacaccgtcc cgacgaacca gaccgcgcc ggcaccgccg atatcatgtc ccatatcttc     600
gaggtgtatt tctccaacac caagacggcg tacctccagg accgcatggc ggaggcgctc     660
ctccggaccct gcatcaagta cggcggcatc gccctggaga agccggacga ctatgaggcc     720
cgcgccaacc tcatgtgggc cgtcctcctg gcgatcaatg gcctgctgac gtacggcaaa     780
gacacgaact tggtccgtgca tctcatggag cacgagctgt cggcctatta tgatatcacc     840
cacggcgtgg gcctcgcgat cctcacgccc aactggatgg aatacatcct caacaatgat     900
acggtgtaca gttcgtcga gtacggcgtc aatgtctggg catcgataaa ggaaaaaaat     960
cactatgaca tcgcgcatca ggcgatccag aagacgcgcg actacttcgt caacgtgctc    1020
ggcctgccct cccgcctccg cgacgtgggc atcgaagagg aaaagctgga tatcatggcc    1080
aaggagagcg tgaagctgac cggcggcacc atcggcaacc tgcgccccgt gaacgcctcc    1140
gaggtcctcc agatcttcaa aaagtcggtg tga                                 1173

<210> SEQ ID NO 27
<211> LENGTH: 336
<212> TYPE: PRT
<213> ORGANISM: Escherichia coli

<400> SEQUENCE: 27

Met Lys Ala Ala Val Val Thr Lys Asp His Val Asp Val Thr Tyr
1               5                   10                  15

Lys Thr Leu Arg Ser Leu Lys His Gly Glu Ala Leu Leu Lys Met Glu
            20                  25                  30

Cys Cys Gly Val Cys His Thr Asp Leu His Val Lys Asn Gly Asp Phe
        35                  40                  45
```

```
Gly Asp Lys Thr Gly Val Ile Leu Gly His Glu Gly Ile Gly Val Val
 50                  55                  60

Ala Glu Val Gly Pro Gly Val Thr Ser Leu Lys Pro Gly Asp Arg Ala
 65                  70                  75                  80

Ser Val Ala Trp Phe Tyr Glu Gly Cys Gly His Cys Glu Tyr Cys Asn
                 85                  90                  95

Ser Gly Asn Glu Thr Leu Cys Arg Ser Val Lys Asn Ala Gly Tyr Ser
                100                 105                 110

Val Asp Gly Gly Met Ala Glu Cys Ile Val Val Ala Asp Tyr Ala
                115                 120                 125

Val Lys Val Pro Asp Gly Leu Asp Ser Ala Ala Ala Ser Ser Ile Thr
130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Glu Met Gly Ala Asp
                195                 200                 205

Leu Ala Ile Asn Ser His Thr Glu Asp Ala Ala Lys Ile Val Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
                260                 265                 270

Val Leu Asp Gly Ile Glu Val Val Gly Ser Leu Val Gly Thr Arg Gln
                275                 280                 285

Asp Leu Thr Glu Ala Phe Gln Phe Ala Ala Glu Gly Lys Val Val Pro
290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

<210> SEQ ID NO 28
<211> LENGTH: 1011
<212> TYPE: DNA
<213> ORGANISM: Escherichia coli

<400> SEQUENCE: 28
atgaaggccg cggtcgtgac caaggaccat cacgtcgatg tcacgtacaa gacgctgcgc      60
tccctgaagc atggcgaagc gctgctgaag atggagtgct gtggcgtctg ccacacggac     120
ctgcatgtga aaacggcga cttcggcgac aagaccggcg tcatcctcgg ccacgaaggc      180
atcggcgtcg tggccgaggt gggccccggc gtcacgtccc tcaagccggg cgatcgggcc     240
tcggtggcgt ggttctatga gggctgcggc cactgcgaat attgcaactc gggcaacgaa     300
accctgtgtc ggtcggtgaa aaatgcgggc tactccgtcg acggcggcat ggcggaagaa     360
tgtatcgtgg tggccgacta cgccgtgaag gtcccggatg gcctggacag cgccgccgcc     420
tcgtcgatca cctgcgccgg cgtcaccacc tataaggcgg tgaaactgag caaaatccgc     480
ccgggccagt ggatcgccat ctacggcctg gcggcctgg gcaacctggc cctgcagtac     540
```

```
gccaagaatg tcttcaacgc gaaggtcatc gccatcgatg tcaatgatga acagctgaag    600
ctggccacgg agatgggcgc ggacctggcg atcaacagcc acaccgaaga cgcggccaag    660
atcgtccagg agaagaccgg cggcgcccat gccgccgtgg tgaccgccgt ggccaaagcc    720
gccttcaatt ccgccgtcga cgccgtccgg gccggcggcc gggtcgtcgc ggtgggcctg    780
ccgccggagt cgatgtccct cgacatcccg cgcctggtgc tggatggcat cgaggtggtg    840
ggctccctgg tcggcacccg ccaggacctg accgaagcct tccagttcgc cgccgaaggc    900
aaggtcgtgc ccaaggtcgc cctgcggccc ctcgccgaca tcaacaccat cttcacggag    960
atggaggaag gcaagatccg gggccgcatg gtcatcgatt ccgccactg a              1011
```

<210> SEQ ID NO 29
<211> LENGTH: 339
<212> TYPE: PRT
<213> ORGANISM: Escherichia coli

<400> SEQUENCE: 29

```
Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285
```

```
Thr Pro Tyr Glu Leu Arg Lys Leu Met Arg Phe Ala Ala Arg Ser Lys
    290                 295                 300
Val Ala Pro Thr Thr Glu Leu Phe Pro Met Ser Lys Ile Asn Asp Ala
305                 310                 315                 320
Ile Gln His Val Arg Asp Gly Lys Ala Arg Tyr Arg Val Val Leu Lys
                325                 330                 335
Ala Asp Phe

<210> SEQ ID NO 30
<211> LENGTH: 1020
<212> TYPE: DNA
<213> ORGANISM: Escherichia coli

<400> SEQUENCE: 30
atgtccatga tcaaaagcta cgccgcgaaa gaggcgggcg gcgagctgga ggtgtatgag      60
tatgacccgg gcgagctgcg gccccaggac gtggaagtgc aggtcgacta ctgcggcatc     120
tgccattcgg acctctcgat gatcgataac gagtggggct tcagccagta ccccctggtg     180
gccggccacg aggtgatcgg ccgcgtggtc gccctgggct cggccgcgca ggataaaggc     240
ctgcaggtcg gccagcgcgt cggcatcggc tggacggccc gcagctgcgg ccattgcgat     300
gcctgcatca gcggcaatca gatcaattgc gaacagggcg cggtcccgac catcatgaac     360
cggggcggct cgccgaaaa gctgcgggcc gattggcagt gggtgatccc gctgccggag     420
aacatcgata tcgagtcggc cggccccctg ctgtgcggcg catcaccgt cttcaagccg      480 ctcctgatgc atcatatcac ggcgaccagc cgggtcggcg tgatcggcat cggcggcctc     540
ggccacatcg cgatcaaact gctgcacgcg atgggctgcg aggtcaccgc gttctcctcg     600
aaccccgcca aggagcagga agtgctggcg atgggcgccg ataaagtcgt gaactcgcgc     660 gaccccagg ccctcaaagc cctggccggc cagttcgatc tcatcatcaa cacggtgaac      720
gtgtcgctgg actggcagcc ctacttcgaa gccctgacct atggcggcaa cttccatacc     780
gtcggcgccg tgctgacccc gctgtccgtc ccggccttca ccctgatcgc cggcgaccgc     840
agcgtgtccg gcagcgccac cggcacgccg tatgagctgc gcaagctgat gcgcttcgcc     900 gccccgcagca aggtcgcccc gaccaccgag ctgttcccca tgtccaagat caatgacgcg     960
atccagcatg tccgggacgg caaggcccgc tatcgcgtcg tcctcaaggc ggacttctga    1020

<210> SEQ ID NO 31
<211> LENGTH: 382
<212> TYPE: PRT
<213> ORGANISM: Escherichia coli

<400> SEQUENCE: 31

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
                20                  25                  30

Ala Leu Ile Val Thr Asp Lys Thr Leu Val Gln Cys Gly Val Val Ala
            35                  40                  45

Lys Val Thr Asp Lys Met Asp Ala Ala Gly Leu Ala Trp Ala Ile Tyr
        50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95
```

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
    370                 375                 380

<210> SEQ ID NO 32
<211> LENGTH: 1149
<212> TYPE: DNA
<213> ORGANISM: Escherichia coli

<400> SEQUENCE: 32
atggcgaatc ggatgatcct caatgaaacg gcctggttcg ccgcggcgc ggtcggcgcc         60 ctcaccgatg aggtcaagcg gcggggctac cagaaggccc tgatcgtcac ggataaaacc       120
ctggtgcagt gcggcgtcgt cgccaaggtg accgacaaga tggatgcggc cggcctggcc      180
tgggcgatct acgacggcgt ggtgcccaac cccaccatca ccgtggtgaa ggaaggcctg      240
ggcgtgttcc agaactcggg cgcggattat ctcatcgcga tcggcggcgg cagcccccag      300
gacacctgca aggccatcgg catcatctcg aacaaccccg agttcgcgga cgtgcgctcc      360
ctggagggcc tgtcgccgac gaacaagccc tccgtcccga tcctcgccat cccgacgacg      420
gccggcaccg cggccgaggt gaccatcaat tacgtcatca ccgacgagga aaagcggcgc      480
aagttcgtgt gtgtggaccc ccatgacatc ccccaggtcg ccttcatcga cgccgacatg      540

-continued

```
atggatggca tgccccccgc cctcaaggcc gcgacgggcg tggacgcgct gacgcatgcc      600
atcgaaggct acatcacccg gggcgcctgg gccctgacgg atgccctgca tatcaaggcc      660
atcgaaatca tcgccggcgc cctgcgcggc tccgtggccg gcgacaagga tgcgggcgag      720
gagatggcgc tgggccagta cgtggccggc atgggcttct ccaatgtggg cctgggcctg      780
gtgcatggca tggcccatcc gctcggcgcc ttctacaaca cgccgcatgg cgtcgcgaac      840
gcgatcctcc tgccgcatgt catgcgctac aatgcggact tcacgggcga gaaataccgc      900
gatatcgccc gggtcatggg cgtgaaggtc gagggcatgt cgctggaaga ggcgcggaac      960
gccgcggtcg aagccgtctt cgccctgaac cgggatgtgg gcatcccgcc gcacctgcgc     1020
gatgtcggcg tccgcaagga agacatcccc gcgctggcgc aggccgccct ggacgatgtg     1080
tgcaccggcg caacccccg cgaggcgacg ctggaagaca tcgtcgaact ctaccatacc     1140
gcgtggtga                                                            1149
```

<210> SEQ ID NO 33
<211> LENGTH: 339
<212> TYPE: PRT
<213> ORGANISM: Escherichia coli

<400> SEQUENCE: 33

```
Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255
```

```
Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala
305                 310                 315                 320

Ile Gln His Val Arg Asp Gly Lys Ala Arg Tyr Arg Val Val Leu Lys
                325                 330                 335

Ala Asp Phe

<210> SEQ ID NO 34
<211> LENGTH: 1020
<212> TYPE: DNA
<213> ORGANISM: Escherichia coli

<400> SEQUENCE: 34
atgtccatga tcaaaagcta tgccgcgaag gaagccggcg gcgagctgga ggtctacgag     60
tacgaccccg cgaactccg cccgcaggac gtggaggtgc aggtggatta ctgcggcatc    120
tgccacagcg acctgtcgat gatcgacaac gagtggggct cagccagta cccgctggtg    180 gccggccatg aagtgatcgg ccgcgtcgtc gcgctgggct ccgccgccca ggataaaggc    240
ctgcaggtcg gccagcgcgt gggcatcggc tggaccgccc ggtcgtgcgg ccactgcgac    300
gcctgcatct cgggcaacca gatcaattgc gagcagggcg ccgtcccac catcatgaac    360 cgcggcggct tcgcggagaa gctccgcgcg gactggcagt gggtgatccc gctgccggaa    420
aatatcgata tcgaatccgc cggccccctg ctgtgcggcg catcaccgt cttcaagccg    480 ctcctgatgc atcatatcac cgccacctcc cgcgtcggcg tcatcggcat cggcggcctc    540
ggccacatcg ccatcaaact cctgcatgcg atgggctgtg aagtgaccgc cttcagcagc    600
aaccccgcga agagcagga agtgctcgcg atgggcgcgg acaaggtcgt gaacagccgc    660 gatcccagg ccctcaaagc gctggccggc cagttcgatc tcatcatcaa caccgtcaac    720
gtctcgctcg actggcagcc gtacttcgaa gcgctgacgt acggcggcaa cttccacacc    780
gtgggcgcgg tcctgacgcc cctgtcggtg ccggcgttca ccctgatcgc cggcgatcgg    840
agcgtgtcgg gctccgccac cggcaccccg tatgagctgc ggaagctgat gcggttcgcg    900
gcccgcagca aggtcgcccc gacgaccgag ctgttcccca tgagcaagat caacgacgcc    960
atccagcatg tgcgcgatgg caaagcccgg tatcgcgtgg tcctgaaagc ggatttctga   1020

<210> SEQ ID NO 35
<211> LENGTH: 387
<212> TYPE: PRT
<213> ORGANISM: Escherichia coli

<400> SEQUENCE: 35

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60
```

```
Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
             85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 36
<211> LENGTH: 1164
<212> TYPE: DNA
<213> ORGANISM: Escherichia coli

<400> SEQUENCE: 36
atgaacaatt tcaacctcca caccccgacc cgcatcctct cggcaagggg cgccatcgcc     60
ggcctgcgcg agcagatccc gcacgacgcc cgcgtcctca tcacctatgg cggcggctcc    120
gtcaaaaaga ccggcgtgct cgatcaggtc ctggacgccc tgaagggcat ggacgtgctg    180
gagttcggcg gcatcgagcc gaacccggcc tacgagacgc tgatgaatgc ggtgaagctg    240
```

```
gtgcgcgagc agaaggtcac gttcctgctc gcggtcggcg gcggctcggt gctggacggc    300
accaagttca tcgccgccgc ggcgaattat cccgagaaca tcgatccctg cacatcctg     360 cagacgggcg gcaaggagat caagtcggcc atcccgatgg gctgcgtcct gaccctcccc    420
gccaccggct cggagagcaa cgccggcgcc gtgatctcgc gcaaaaccac cggcgacaaa    480
caggcgttcc actccgccca tgtgcagccg gtcttcgcgg tgctggaccc cgtctacacg    540 tacacccctcc cgccgcggca ggtcgccaac ggcgtggtcg atgccttcgt gcatacggtg    600
gagcagtacg tcaccaagcc ggtggatgcc aagatccagg accgcttcgc ggagggcatc    660
ctgctgacgc tgatcgagga cggcccgaaa gccctcaagg aaccggaaaa ctacgatgtg    720
cgggcgaacg tcatgtgggc gcgacccag gccctgaacg gcctgatcgg cgccggcgtg     780
ccccaggatt gggcgacgca catgctgggc acgaactca ccgcgatgca cggcctcgac     840
cacgcccaga cgctcgccat cgtcctgccg gccctgtgga atgagaagcg ggacaccaag    900
cgggcgaagc tcctgcagta tgccgaacgg gtgtggaaca tcaccgaagg ctcggacgat    960
gaacgcatcg atgccgccat cgcggccacg cggaacttct tcgagcagct gggcgtcccg   1020
acccatctct ccgactacgg cctggatggc tcctccatcc ccgcgctgct gaaaaaactg   1080
gaagaacacg gcatgaccca gctgggcgaa accacgaca tcaccctgga tgtctcgcgc     1140
cgcatctacg aagccgcccg gtga                                            1164
```

<210> SEQ ID NO 37
<211> LENGTH: 336
<212> TYPE: PRT
<213> ORGANISM: Bacillus stearothermophilus

<400> SEQUENCE: 37

Met Arg Ala Ala Val Val Thr Lys Asp His Lys Val Ser Ile Glu Asp
1               5                   10                  15

Lys Lys Leu Arg Ala Leu Lys Pro Gly Glu Ala Leu Val Gln Thr Glu
                20                  25                  30

Tyr Cys Gly Val Cys His Thr Asp Leu His Val Lys Asn Ala Asp Phe
            35                  40                  45

Gly Asp Val Thr Gly Val Thr Leu Gly His Glu Gly Ile Gly Lys Val
        50                  55                  60

Ile Glu Val Ala Glu Asp Val Glu Ser Leu Lys Ile Gly Asp Arg Val
65                  70                  75                  80

Ser Ile Ala Trp Met Phe Glu Ser Cys Gly Arg Cys Glu Tyr Cys Thr
                85                  90                  95

Thr Gly Arg Glu Thr Leu Cys Arg Ser Val Lys Asn Ala Gly Tyr Thr
            100                 105                 110

Val Asp Gly Ala Met Ala Glu Gln Val Ile Val Thr Ala Asp Tyr Ala
        115                 120                 125

Val Lys Val Pro Glu Lys Leu Asp Pro Ala Ala Ser Ser Ile Thr
    130                 135                 140

Cys Ala Gly Val Thr Thr Tyr Lys Ala Val Lys Val Ser Asn Val Lys
145                 150                 155                 160

Pro Gly Gln Trp Leu Gly Val Phe Gly Ile Gly Gly Leu Gly Asn Leu
                165                 170                 175

Ala Leu Gln Tyr Ala Lys Asn Val Met Gly Ala Lys Ile Val Ala Phe
            180                 185                 190

Asp Ile Asn Asp Asp Lys Leu Ala Phe Ala Lys Glu Leu Gly Ala Asp
        195                 200                 205

```
Ala Ile Ile Asn Ser Lys Asp Val Asp Pro Val Ala Glu Val Met Lys
    210                 215                 220

Leu Thr Asp Asn Lys Gly Leu Asp Ala Thr Val Val Thr Ser Val Ala
225                 230                 235                 240

Lys Thr Pro Phe Asn Gln Ala Val Asp Val Lys Ala Gly Ala Arg
                245                 250                 255

Val Val Ala Val Gly Leu Pro Val Asp Lys Met Asn Leu Asp Ile Pro
                260                 265                 270

Arg Leu Val Leu Asp Gly Ile Glu Val Val Gly Ser Leu Val Gly Thr
            275                 280                 285

Arg Gln Asp Leu Arg Glu Ala Phe Glu Phe Ala Ala Glu Asn Lys Val
    290                 295                 300

Thr Pro Lys Val Gln Leu Arg Lys Leu Glu Glu Ile Asn Asp Ile Phe
305                 310                 315                 320

Glu Glu Met Glu Asn Gly Thr Ile Thr Gly Arg Met Val Ile Lys Phe
                325                 330                 335
```

<210> SEQ ID NO 38
<211> LENGTH: 1011
<212> TYPE: DNA
<213> ORGANISM: Bacillus stearothermophilus

<400> SEQUENCE: 38

```
atgcgggcgg ccgtggtgac caaggaccac aaggtcagca tcgaagataa gaaactgcgg     60
gccctgaaac cggcgaggc gctggtgcag accgaatatt gtggcgtgtg tcatacggat    120
ctccatgtca aaaacgccga tttcggcgat gtgaccggcg tgacgctcgg ccatgagggc    180
atcggcaagg tgatcgaagt cgccgaagac gtggaaagcc tcaagatcgg cgatcgcgtg    240
tccatcgcct ggatgttcga gtcgtgtggc cgctgcgagt attgcacgac cggccgggaa    300
accctgtgtc ggagcgtcaa gaatgccggc tacaccgtgg acggcgcgat ggccgaacag    360
gtcatcgtga cggccgacta tgcggtcaag gtcccggaaa agctggaccc ggccgcgggcg    420
tcgtcgatca cctgcgcggg cgtcaccacc tataaggccg tcaaggtgag caatgtcaaa    480
ccgggccagt ggctgggcgt cttcggcatc ggcggcctgg caacctggcc ctgcagtac    540
gcgaagaatg tcatgggcgc caaaatcgtg gccttcgata tcaacgatga caagctggcg    600
ttcgccaaag aactcggcgc ggatgcgatc atcaactcga aggacgtgga cccggtggcc    660
gaggtgatga aactgacgga caacaagggc ctggacgcga cggtcgtcac cagcgtcgcg    720
aagaccccct tcaatcaggc ggtcgacgtg gtcaaggcgg gcgcccgcgt ggtggccgtg    780
ggcctgccgg tcgacaaaat gaacctggat atcccgcgcc tcgtgctgga cggcatcgag    840
gtggtgggca gcctggtcgg cacccgccag gacctgcggg aggccttcga gttcgcggcc    900
gagaataaag tgacgcccaa ggtccagctc cggaagctcg aagaaatcaa cgatatcttc    960
gaggagatgg aaaacggcac gatcaccggc cggatggtca tcaagttctg a          1011
```

<210> SEQ ID NO 39
<211> LENGTH: 339
<212> TYPE: PRT
<213> ORGANISM: Bacillus stearothermophilus

<400> SEQUENCE: 39

```
Met Lys Ala Ala Val Val Asn Glu Phe Lys Lys Ala Leu Glu Ile Lys
1               5                   10                  15

Glu Val Glu Arg Pro Lys Leu Glu Glu Gly Glu Val Leu Val Lys Ile
                20                  25                  30
```

```
Glu Ala Cys Gly Val Cys His Thr Asp Leu His Ala Ala His Gly Asp
         35                  40                  45

Trp Pro Ile Lys Pro Lys Leu Pro Leu Ile Pro Gly His Glu Gly Val
 50                  55                  60

Gly Ile Val Val Glu Val Ala Lys Gly Val Lys Ser Ile Lys Val Gly
 65                  70                  75                  80

Asp Arg Val Gly Ile Pro Trp Leu Tyr Ser Ala Cys Gly Glu Cys Glu
                 85                  90                  95

Tyr Cys Leu Thr Gly Gln Glu Thr Leu Cys Pro His Gln Leu Asn Gly
             100                 105                 110

Gly Tyr Ser Val Asp Gly Tyr Ala Glu Tyr Cys Lys Ala Pro Ala
         115                 120                 125

Asp Tyr Val Ala Lys Ile Pro Asp Asn Leu Asp Pro Val Glu Val Ala
         130                 135                 140

Pro Ile Leu Cys Ala Gly Val Thr Thr Tyr Lys Ala Leu Lys Val Ser
145                 150                 155                 160

Gly Ala Arg Pro Gly Glu Trp Val Ala Ile Tyr Gly Ile Gly Gly Leu
                 165                 170                 175

Gly His Ile Ala Leu Gln Tyr Ala Lys Ala Met Gly Leu Asn Val Val
         180                 185                 190

Ala Val Asp Ile Ser Asp Glu Lys Ser Lys Leu Ala Lys Asp Leu Gly
         195                 200                 205

Ala Asp Ile Ala Ile Asn Gly Leu Lys Glu Asp Pro Val Lys Ala Ile
         210                 215                 220

His Asp Gln Val Gly Val His Ala Ala Ile Ser Val Ala Val Asn
225                 230                 235                 240

Lys Lys Ala Phe Glu Gln Ala Tyr Gln Ser Val Lys Arg Gly Gly Thr
                 245                 250                 255

Leu Val Val Val Gly Leu Pro Asn Ala Asp Leu Pro Ile Pro Ile Phe
         260                 265                 270

Asp Thr Val Leu Asn Gly Val Ser Val Lys Gly Ser Ile Val Gly Thr
         275                 280                 285

Arg Lys Asp Met Gln Glu Ala Leu Asp Phe Ala Ala Arg Gly Lys Val
         290                 295                 300

Arg Pro Ile Val Glu Thr Ala Glu Leu Glu Glu Ile Asn Glu Val Phe
305                 310                 315                 320

Glu Arg Met Glu Lys Gly Lys Ile Asn Gly Arg Ile Val Leu Lys Leu
                 325                 330                 335

Lys Glu Asp

<210> SEQ ID NO 40
<211> LENGTH: 1020
<212> TYPE: DNA
<213> ORGANISM: Bacillus stearothermophilus

<400> SEQUENCE: 40
atgaaggcgg ccgtcgtgaa cgagttcaag aaggcgctgg aaatcaagga ggtcgagcgg      60
cccaaactcg aagagggcga ggtcctggtg aagatcgagg cctgcggcgt gtgccatacc     120
gacctgcacg ccgcccacgg cgactggccg atcaagccga actgcccct gatcccgggc     180 cacgagggcg tgggcatcgt cgtggaagtg gcgaagggcg tgaaaagcat caaagtgggc     240
gatcgcgtcg gcatcccgtg gctgtacagc gcgtgcggcg agtgcgagta ctgcctgacg     300
ggccaggaaa cgctctgccc gcatcagctg aatggcggct attccgtgga cggcggctat     360
```

-continued

```
gccgagtatt gcaaagcccc ggccgactat gtcgccaaga tcccggacaa tctggacccc    420
gtcgaggtcg cccccatcct gtgcgccggc gtgaccacct ataaggcgct gaaagtctcg    480
ggcgcccggc cgggcgagtg ggtcgcgatc tacggcatcg gcggcctggg ccacatcgcc    540
ctgcagtacg ccaaggcgat gggcctgaac gtggtcgcgg tcgacatctc cgacgagaaa    600
tcgaagctgg cgaaagatct cggcgcggac atcgccatca atggcctgaa ggaagacccg    660
gtcaaggcga tccatgacca ggtcggcggc gtccatgccg ccatctccgt cgcggtgaat    720
aagaaagcct tcgagcaggc ctatcagtcc gtcaagcgcg gcggcaccct ggtcgtggtg    780
ggcctcccga tgcggacct gccgatcccc atcttcgata cggtgctcaa cggcgtgtcg    840
gtgaagggca gcatcgtcgg cacccgcaag acatgcagg aagccctgga tttcgccgcg    900
cggggcaagg tccgccccat cgtggaaacg gccgagctgg aggaaatcaa cgaagtgttc    960
gagcgcatgg aaaaaggcaa atcaacggc cgcatcgtcc tgaagctgaa ggaggattga   1020
```

<210> SEQ ID NO 41
<211> LENGTH: 346
<212> TYPE: PRT
<213> ORGANISM: Geobacillus thermoglucosidas

<400> SEQUENCE: 41

```
Met Lys Ala Leu Thr Tyr Leu Gly Pro Gly Lys Lys Glu Leu Met Glu
1               5                   10                  15

Lys Pro Lys Pro Lys Ile Glu Lys Glu Thr Asp Ala Ile Val Lys Met
                20                  25                  30

Ile Lys Thr Thr Ile Cys Gly Thr Asp Leu His Ile Leu Ser Gly Asp
            35                  40                  45

Val Pro Thr Val Glu Glu Gly Arg Ile Leu Gly His Glu Gly Val Gly
        50                  55                  60

Ile Ile Glu Glu Val Gly Ser Ala Val Lys Asn Phe Lys Lys Gly Asp
65                  70                  75                  80

Arg Val Leu Ile Ser Cys Ile Thr Ser Cys Gly Lys Cys Glu Asn Cys
                85                  90                  95

Lys Lys Gly Leu Tyr Ala His Cys Glu Asp Gly Gly Trp Ile Leu Gly
                100                 105                 110

His Leu Ile Asp Gly Thr Gln Ala Glu Tyr Val Arg Ile Pro His Ala
            115                 120                 125

Asp Asn Ser Leu Tyr Pro Ile Pro Glu Gly Val Asp Glu Glu Ala Leu
        130                 135                 140

Val Met Leu Ser Asp Ile Leu Pro Thr Gly Phe Glu Ile Gly Val Leu
145                 150                 155                 160

Asn Gly Lys Val Gln Pro Gly Gln Thr Val Ala Ile Ile Gly Ala Gly
                165                 170                 175

Pro Val Gly Met Ala Ala Leu Leu Thr Ala Gln Phe Tyr Ser Pro Ala
            180                 185                 190

Glu Ile Ile Met Val Asp Leu Asp Asp Asn Arg Leu Glu Val Ala Lys
        195                 200                 205

Lys Phe Gly Ala Thr Gln Val Val Asn Ser Ala Asp Gly Lys Ala Val
    210                 215                 220

Glu Lys Ile Met Glu Leu Thr Gly Gly Lys Gly Val Asp Val Ala Met
225                 230                 235                 240

Glu Ala Val Gly Ile Pro Ala Thr Phe Asp Ile Cys Gln Glu Ile Val
                245                 250                 255
```

Lys Pro Gly Gly Tyr Ile Ala Asn Ile Gly Val His Gly Lys Ser Val
              260                 265                 270

Glu Phe His Ile Glu Lys Leu Trp Ile Arg Asn Ile Thr Leu Thr Thr
          275                 280                 285

Gly Leu Val Asn Thr Thr Ser Thr Pro Met Leu Leu Lys Thr Val Gln
          290                 295                 300

Ser Lys Lys Leu Lys Pro Glu Gln Leu Ile Thr His Arg Phe Ala Phe
305                 310                 315                 320

Ser Asp Ile Met Lys Ala Tyr Glu Val Phe Gly Asn Ala Ala Lys Glu
              325                 330                 335

Lys Ala Leu Lys Val Ile Ile Ser Asn Ser
              340                 345

<210> SEQ ID NO 42
<211> LENGTH: 1041
<212> TYPE: DNA
<213> ORGANISM: Geobacillus thermoglucosidas

<400> SEQUENCE: 42

```
atgaaagccc tgacctatct gggcccgggc aaaaagaac tgatggaaaa accgaagccg    60
aagatcgaaa aagagacgga tgccatcgtc aagatgatca aaaccaccat ctgcggcacc   120
gacctccata tcctgtcggg cgacgtgccc accgtggaag agggccgcat cctgggccac   180
gagggcgtcg gcatcatcga ggaagtgggc tccgccgtca gaacttcaa gaaaggcgac   240
cgggtgctga tctcgtgcat caccagctgt ggcaagtgcg agaattgcaa gaagggcctg   300
tacgcccact gcgaggacgg cggctggatc ctgggccatc tgatcgacgg cacccaggcc   360
gagtacgtgc gcatccccca tgcggacaac agcctgtacc cgatccccga gggcgtcgac   420
gaggaagccc tggtcatgct gtcggatatc ctgcccaccg gcttcgagat cggcgtgctg   480
aacggcaagg tccagcccgg ccagaccgtg gcgatcatcg gcgccggccc ggtgggcatg   540
gccgcgctgc tgaccgccca gttctacagc ccggccgaga tcatcatggt ggacctggac   600
gataaccgcc tcgaagtggc gaagaagttc ggcgcgaccc aggtcgtcaa cagcgcggat   660
ggcaaggcgg tggagaagat catggaactc accggcggca agggcgtgga cgtggcgatg   720
gaagccgtcg gcatcccggc caccttcgat atctgccagg agatcgtgaa gccgggcggc   780
tacatcgcca catcggcgt gcatggcaag tccgtggagt tccatatcga aaaactgtgg   840
atccgcaaca tcaccctgac gacgggcctg gtgaacacca cgagcacgcc catgctgctg   900
aagacggtgc agtcgaagaa gctcaagccc gaacagctca tcacccaccg cttcgccttc   960
agcgatatca tgaaagcgta cgaagtcttc ggcaacgccg ccaaggagaa ggcgctgaaa  1020
gtcatcatca gcaattcgtg a                                             1041
```

<210> SEQ ID NO 43
<211> LENGTH: 340
<212> TYPE: PRT
<213> ORGANISM: Geobacillus thermoglucosidas

<400> SEQUENCE: 43

Met Lys Ala Ala Val Val Asn Glu Phe Lys Gln Lys Leu Glu Ile Lys
1               5                   10                  15

Glu Val Glu Lys Pro Lys Leu Asn Tyr Gly Glu Val Leu Val Lys Ile
              20                  25                  30

Glu Ala Cys Gly Val Cys His Thr Asp Leu His Ala Ala His Gly Asp
          35                  40                  45

Trp Pro Val Lys Pro Lys Leu Pro Leu Ile Pro Gly His Glu Gly Val
    50                  55                  60

Gly Ile Val Val Glu Val Ala Glu Gly Val Lys Ser Val Lys Val Gly
65                  70                  75                  80

Asp Arg Val Gly Ile Pro Trp Leu Tyr Ser Ala Cys Gly Glu Cys Glu
                85                  90                  95

Tyr Cys Leu Ser Gly Gln Glu Thr Leu Cys Pro His Gln Leu Asn Gly
            100                 105                 110

Gly Tyr Ser Ala Asp Gly Gly Tyr Ala Glu Tyr Cys Lys Ala Pro Ala
        115                 120                 125

Asn Tyr Val Ala Lys Ile Pro Glu His Leu Asp Pro Val Glu Val Ala
    130                 135                 140

Pro Ile Leu Cys Ala Gly Val Thr Thr Tyr Lys Ala Leu Lys Val Ser
145                 150                 155                 160

Asn Ala Lys Pro Gly Glu Trp Val Ala Ile Tyr Gly Ile Gly Gly Leu
                165                 170                 175

Gly His Ile Ala Leu Gln Tyr Ala Lys Ala Met Gly Leu Asn Val Ile
            180                 185                 190

Ala Val Asp Ile Ser Asp Glu Lys Ile Glu Leu Ala Lys Gln Leu Gly
        195                 200                 205

Ala Asp Ile Ala Ile Asn Gly Leu Lys Glu Asp Pro Val Glu Ala Ile
    210                 215                 220

Gln Gln Asn Val Gly Gly Ala His Ala Ala Ile Ser Val Ala Val Thr
225                 230                 235                 240

Lys Lys Ala Phe Glu Gln Ala Tyr Gln Ser Val Arg Arg Gly Gly Cys
                245                 250                 255

Leu Val Val Val Gly Leu Pro Asn Glu Asp Leu Pro Ile Pro Ile Phe
            260                 265                 270

Asn Thr Val Leu Asn Gly Ile Thr Val Lys Gly Ser Ile Val Gly Thr
        275                 280                 285

Arg Lys Asp Met Gln Glu Ala Leu Asp Phe Ala Ala Arg Gly Lys Val
    290                 295                 300

Arg Pro Ile Val Glu Thr Ala Pro Leu Glu Lys Ile Asn Glu Val Phe
305                 310                 315                 320

Glu Arg Met Glu Lys Gly Lys Ile Asn Gly Arg Val Val Leu Thr Ile
                325                 330                 335

Gly Val Asn Arg
        340

<210> SEQ ID NO 44
<211> LENGTH: 1023
<212> TYPE: DNA
<213> ORGANISM: Geobacillus thermoglucosidas

<400> SEQUENCE: 44
atgaaagccg cggtggtcaa tgagttcaag cagaaactcg aaatcaagga agtcgaaaag    60
ccgaagctca actacggcga agtgctggtg aaaatcgagg cctgcggcgt ctgccacacc   120
gacctccatg cggcccacgg cgactggccc gtcaagccga agctgcccct gatcccgggc   180
catgagggcg tgggcatcgt cgtggaagtc gcggagggcg tcaagagcgt caaggtcggc   240
gaccgggtgg gcatcccctg gctgtattcc gcctgcggcg aatgcgaata ctgcctgagc   300
ggccaggaaa ccctgtgccc ccaccagctg aacggcggct atagcgcgga tggcggctat   360
gccgagtact gtaaagcccc cgccaactac gtggcgaaga tcccggaaca tctggacccc   420

```
gtggaagtgg cgcccatcct ctgcgcgggc gtgaccacct ataaagccct caaggtgtcc    480
aacgccaaac ccggcgagtg ggtcgccatc tacggcatcg gcggcctcgg ccatatcgcg    540
ctgcagtacg ccaaggcgat gggcctcaac gtcatcgccg tggatatcag cgacgagaaa    600
atcgaactgg cgaaacagct cggcgcggac atcgcgatca acggcctgaa agaagatccg    660
gtggaagcca tccagcagaa cgtcggcggc gcccacgccg cgatcagcgt cgccgtgacc    720
aagaaggcgt tcgaacaggc ctatcagagc gtccggcggg cggctgcct ggtcgtggtc    780 ggcctgccca acgaggacct gcccatcccg atcttcaaca ccgtcctgaa tggcatcacc    840
gtcaagggct ccatcgtggg cacgcggaag gatatgcagg aagcgctgga tttcgcggcg    900
cggggcaagg tgcggccgat cgtcgagacg gccccgctgg agaagatcaa tgaggtcttc    960
gaacgcatgg agaagggcaa gatcaatggc cgcgtcgtgc tcaccatcgg cgtcaaccgc    1020
tga                                                                 1023
```

<210> SEQ ID NO 45
<211> LENGTH: 340
<212> TYPE: PRT
<213> ORGANISM: Lactococcus lactis

<400> SEQUENCE: 45

Met Lys Ala Ala Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Phe Gly Asn Lys Ala Gly Thr Val Leu Gly His Glu Gly Ile Gly
    50                  55                  60

Ile Val Lys Glu Ile Gly Thr Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Ser Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Thr Ile Asn Ser Gly Asp Val Asn Pro Val Asp Glu Ile
    210                 215                 220

Lys Lys Ile Thr Gly Gly Leu Gly Ala Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser

```
                260                 265                 270
Val Pro Thr Val Val Phe Asp Gly Val Glu Val Ala Gly Ser Leu Val
            275                 280                 285

Gly Thr Arg Leu Asp Leu Ala Glu Ala Phe Gln Phe Gly Ala Glu Gly
            290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 46
<211> LENGTH: 1023
<212> TYPE: DNA
<213> ORGANISM: Lactococcus lactis

<400> SEQUENCE: 46
atgaaggcgg ccgtcgtgcg gcacaacccg gacggctatg ccgatctggt ggagaaggag      60
ctccgcgcga tcaagccgaa cgaggccctc ctggacatgg agtactgcgg cgtgtgccac     120
accgacctgc acgtcgccgc cggcgatttc ggcaacaaag ccggcaccgt cctgggccat     180
gagggcatcg gcatcgtgaa ggaaatcggc accgatgtgt cgtccctcca ggtgggcgac     240
cgggtcagcg tcgcctggtt cttcgaaggc tgcggccact gcgagtactg cgtgtccggc     300
aacgagacgt tctgccggga agtcaagagc gcgggctaca cgtcgatgg cggcatggcc     360 gaggaagcca tcgtcgtcgc cgactacgcc gtgaaggtcc cggatggcct cgatcccatc     420
gaggccagca gcatcacctg cgcgggcgtg accacctaca aggccatcaa ggtgtccggc     480
gtcaaaccgg gcgattggca ggtgatcttc ggcgccggcg gcctgggcaa cctcgcgatc     540
cagtacgcca aaaacgtctt cggcgcgaag gtcatcgcgg tggacatcaa ccaggacaag     600
ctgaacctcg cgaagaagat cggcgccgat gtcaccatca actcgggcga tgtcaacccg     660
gtcgacgaga tcaagaaaat caccggcggc ctgggcgccc agtcggccat cgtgtgcgcg     720
gtcgcccgca tcgcgttcga acaggcggtg gccagcctca aaccgatggg caaaatggtg     780
gcggtggccg tcccgaacac cgagatgacc ctgagcgtgc cgaccgtggt cttcgacggc     840
gtcgaggtcg cgggctcgct cgtcggcacc cggctggacc tcgccgaggc cttccagttc     900
ggcgcggagg gcaaagtcaa gccgatcgtc gcgacccgga agctggagga gatcaatgac     960
atcatcgatg agatgaaggc cggcaagatc gaaggccgga tggtcatcga tttcaccaag    1020
tga                                                                  1023

<210> SEQ ID NO 47
<211> LENGTH: 340
<212> TYPE: PRT
<213> ORGANISM: Lactococcus lactis

<400> SEQUENCE: 47

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
```

```
                    50                  55                  60
Ile Val Lys Glu Ile Gly Thr Asp Val Ser Ser Leu Gln Val Gly Asp
 65                  70                  75                  80

Arg Val Ser Val Ala Trp Phe Phe Glu Gly Cys Gly His Cys Glu Tyr
                     85                  90                  95

Cys Val Ser Gly Asn Glu Thr Phe Cys Arg Glu Val Lys Asn Ala Gly
                    100                 105                 110

Tyr Ser Val Asp Gly Gly Met Ala Glu Glu Ala Ile Val Val Ala Asp
            115                 120                 125

Tyr Ala Val Lys Val Pro Asp Gly Leu Asp Pro Ile Glu Ala Ser Ser
            130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                    165                 170                 175

Asn Leu Ala Ile Gln Tyr Ala Lys Asn Val Phe Gly Ala Lys Val Ile
                180                 185                 190

Ala Val Asp Ile Asn Gln Asp Lys Leu Asn Leu Ala Lys Lys Ile Gly
            195                 200                 205

Ala Asp Val Ile Ile Asn Ser Gly Asp Val Asn Pro Val Asp Glu Ile
210                 215                 220

Lys Lys Ile Thr Gly Gly Leu Gly Ala Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
                260                 265                 270

Val Pro Thr Val Val Phe Asp Gly Val Glu Val Ala Gly Ser Leu Val
            275                 280                 285

Gly Thr Arg Leu Asp Leu Ala Glu Ala Phe Gln Phe Gly Ala Glu Gly
            290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 48
<211> LENGTH: 1023
<212> TYPE: DNA
<213> ORGANISM: Lactococcus lactis

<400> SEQUENCE: 48
atgaaggcgg cggtcgtgcg ccataacccg gacggctacg ccgacctggt ggaaaaggag      60
ctgcgggcca tcaagccgaa cgaggcgctg ctcgacatgg agtactgcgg cgtctgccat     120
acggacctcc acgtcgccgc cggcgactac ggcaacaagg cgggcacggt gctgggccat     180
gagggcatcg gcatcgtgaa ggaaatcggc accgacgtgt cctccctgca ggtcggcgac     240
cgggtcagcg tcgcctggtt cttcgagggc tgtggccact gcgagtattg tgtcagcggc     300
aatgaaacgt tctgtcgcga agtcaaaaac gccggctact cggtcgatgg cggcatggcg     360
gaagaagcca tcgtggtcgc ggactatgcc gtgaaggtgc cggacggcct ggaccccatc     420
gaagcgtcct cgatcacctg cgcgggcgtc acgacctaca aggcgatcaa agtgtcgggc     480
```

-continued

```
gtcaagccgg gcgactggca ggtgatcttc ggcgcgggcg gcctcggcaa cctcgccatc    540
cagtacgcca agaacgtctt cggcgccaaa gtgatcgccg tcgacatcaa tcaggacaaa    600
ctgaatctgg cgaaaaagat cggcgccgat gtcatcatca acagcggcga tgtgaacccg    660
gtggacgaga tcaaaaagat cacgggcggc tcggcgccc agagcgcgat cgtgtgcgcc     720
gtggcccgca tcgccttcga acaggccgtc gcgtccctga agccgatggg caagatggtc    780
gccgtcgccc tcccgaacac ggaaatgacg ctgtccgtcc cgaccgtggt cttcgacggc    840
gtggaagtgg ccggctcgct ggtcggcacc cggctggacc tcgccgaggc cttccagttc    900
ggcgcggaag gcaaggtcaa gccgatcgtg gccacgcgca agctcgaaga gatcaatgat    960
atcatcgatg agatgaaggc gggcaagatc gaaggccgca tggtcatcga tttcaccaag   1020
tga                                                                  1023
```

<210> SEQ ID NO 49
<211> LENGTH: 401
<212> TYPE: PRT
<213> ORGANISM: Oenococcus oeni

<400> SEQUENCE: 49

```
Met Arg Gly Ser His His His His His Gly Ser Ala Glu Arg Ala
1               5                   10                  15

Tyr Asp Phe Leu Met Pro Ser Val Asn Phe Gly Pro Gly Val Ile
            20                  25                  30

Ser Lys Ile Gly Glu Arg Ala Lys Met Leu Gly Met Lys Lys Pro Val
        35                  40                  45

Ile Val Thr Asp Lys Phe Leu Glu Asn Leu Lys Asn Gly Ala Val Ala
    50                  55                  60

Gln Thr Leu Ala Ser Leu Lys Lys Ser Gly Val Asp Tyr Val Val Tyr
65                  70                  75                  80

Asn Gly Val Glu Pro Asn Pro Lys Ile His Asn Ile Lys Glu Val Lys
                85                  90                  95

Thr Leu Tyr Glu Lys Glu Asp Ala Asp Ser Ile Ile Thr Val Gly Gly
            100                 105                 110

Gly Ser Ala His Asp Thr Gly Lys Gly Ala Gly Ile Ile Met Thr Asn
        115                 120                 125

Gly Asp Asp Ile Thr Lys Leu Ala Gly Ile Glu Thr Leu Lys Asn Pro
    130                 135                 140

Leu Pro Pro Leu Ile Ala Val Asn Thr Thr Ala Gly Thr Gly Ser Glu
145                 150                 155                 160

Leu Thr Arg His Ala Val Ile Thr Asn Glu Glu Thr His Leu Lys Phe
                165                 170                 175

Val Val Val Ser Trp Arg Asn Ile Pro Leu Val Ser Phe Asn Asp Pro
            180                 185                 190

Thr Leu Met Leu Asp Ile Pro Lys Gly Leu Thr Ala Ala Thr Gly Met
        195                 200                 205

Asp Ala Phe Val Gln Ala Val Glu Pro Tyr Val Ser Val Asp His Asn
    210                 215                 220

Pro Ile Thr Asp Ser Gln Cys Ile Gln Ala Ile Lys Leu Ile Glu Ser
225                 230                 235                 240

Ser Leu Arg Glu Ala Val Ala Asn Gly His Asn Leu Gln Ala Arg Thr
                245                 250                 255

Lys Met Val Glu Ala Glu Met Leu Ala Gly Met Ala Phe Asn Asn Ala
            260                 265                 270
```

```
Asn Leu Gly Tyr Val His Ala Met Ala His Gln Leu Gly Gly Gln Tyr
            275                 280                 285

Asp Ala Pro His Gly Val Cys Cys Ala Leu Leu Pro Tyr Ala Glu
        290                 295                 300

Glu Tyr Asn Leu Ile Ala Asp Pro Glu Arg Phe Ala Glu Leu Ala Arg
305                 310                 315                 320

Ile Met Gly Glu Asn Thr Asp Gly Leu Ser Thr Arg Asp Ala Ala Glu
                325                 330                 335

Leu Ser Ile Lys Ala Met Lys Gln Leu Ser Glu Asp Val Gly Ile Pro
            340                 345                 350

His Ser Ile Lys Asp Ile Gly Ala Lys Pro Glu Asp Phe Asp Leu Met
        355                 360                 365

Ala Glu Asn Ala Leu Lys Asp Gly Asn Ala Phe Ser Asn Pro Arg Lys
    370                 375                 380

Gly Thr Lys Glu Asp Ile Val Lys Ile Phe Gln Glu Ala Tyr Asp Ala
385                 390                 395                 400

Lys

<210> SEQ ID NO 50
<211> LENGTH: 1206
<212> TYPE: DNA
<213> ORGANISM: Oenococcus oeni

<400> SEQUENCE: 50
```

| | | | | |
|---|---|---|---|---|
| atgcgcggca | gccatcatca | ccatcaccac | ggcagcgccg | aacgggccta cgatttcctg | 60 |
| atgccctccg | tcaacttctt | cggcccgggc | gtgatctcca | agatcggcga acgggcgaaa | 120 |
| atgctcggca | tgaagaagcc | ggtgatcgtc | accgataagt | tcctggagaa tctgaaaaat | 180 |
| ggcgccgtgg | cccagaccct | ggccagcctc | aagaagagcg | gcgtcgatta cgtcgtgtat | 240 |
| aacggcgtgg | agcccaaccc | caaaatccac | aacatcaagg | aggtgaaaac cctgtacgaa | 300 |
| aaggaagacg | ccgacagcat | catcaccgtg | gcggcgggct | cggcccacga tacgggcaag | 360 |
| ggcgccggca | tcatcatgac | gaacggcgat | gacatcacca | gctggccgg catcgaaacc | 420 |
| ctgaagaatc | ccctcccccc | cctgatcgcc | gtgaatacca | ccgcgggcac cggctcggaa | 480 |
| ctcacgcggc | acgccgtcat | cacgaacgag | gaaacccatc | tgaagttcgt cgtggtgtcc | 540 |
| tggcgcaaca | tcccgctggt | cagcttcaat | gaccccaccc | tgatgctgga catccccaag | 600 |
| ggcctcaccg | cggccacggg | catggacgcc | ttcgtccagg | cggtcgaacc gtacgtgagc | 660 |
| gtggatcaca | tcccatcac | cgactcccag | tgtatccagg | ccatcaagct gatcgaatcg | 720 |
| tcgctgcggg | aggccgtggc | gaacggccat | aacctgcagg | cccgcaccaa aatggtggaa | 780 |
| gccgaaatgc | tcgcgggcat | ggcgttcaat | aacgccaacc | tgggctacgt ccacgcgatg | 840 |
| gcccatcagc | tgggcggcca | gtacgacgcc | ccgcatggcg | tctgctgcgc cctgctcctg | 900 |
| ccgtatgcgg | aggagtacaa | cctgatcgcc | gacccggaac | gcttcgcgga actggcccgc | 960 |
| atcatgggcg | agaacaccga | cggcctctcg | acccgcgacg | cggccgaact gtccatcaag | 1020 |
| gcgatgaaac | agctgtcgga | ggacgtgggc | atcccgcact | cgatcaagga catcggcgcc | 1080 |
| aagccggagg | acttcgacct | gatggccgaa | atgcgctga | aggacggcaa tgccttctcc | 1140 |
| aacccgcgca | aggcaccaa | ggaggatatc | gtcaagatct | tccaggaggc ctatgacgcc | 1200 |
| aaatga | | | | | 1206 |

```
<210> SEQ ID NO 51
```

<211> LENGTH: 333
<212> TYPE: PRT
<213> ORGANISM: Pectobacterium atrosepticum

<400> SEQUENCE: 51

```
Met Leu Asn Phe Thr Leu His Thr Pro Thr Lys Ile Leu Phe Gly Glu
1               5                   10                  15

Gly Gln Ile Ala Glu Leu Gly Lys Glu Ile Pro Ala Asp Ala Arg Ile
            20                  25                  30

Leu Ile Thr Tyr Gly Gly Ser Val Lys His Asn Gly Val Leu Asp
        35                  40                  45

Gln Val Tyr Arg Ala Leu Glu Gly Arg Asn Val Arg Glu Phe Ser Gly
    50                  55                  60

Ile Glu Pro Asn Pro Thr Tyr Glu Thr Leu Met Lys Ala Val Glu Val
65                  70                  75                  80

Val Arg Ala Glu Lys Ile Asp Phe Leu Leu Ala Val Gly Gly Gly Ser
                85                  90                  95

Val Val Asp Gly Thr Lys Phe Ile Ala Ala Ala Asp Tyr Gln Ala
            100                 105                 110

Ala Gln Asp Pro Trp His Ile Leu Gln Thr Gly Gly Ala Glu Ile Asp
        115                 120                 125

Arg Gly Val Ala Leu Ala Ala Val Leu Thr Leu Pro Ala Thr Gly Ser
    130                 135                 140

Glu Ser Asn Asn Gly Ala Val Ile Thr Arg Lys Ser Thr Asn Asp Lys
145                 150                 155                 160

Leu Ala Phe Arg Ser Pro His Thr Gln Pro Leu Phe Ala Val Leu Asp
                165                 170                 175

Pro Val Val Thr Tyr Thr Leu Pro Ala Arg Gln Ile Ala Asn Gly Val
            180                 185                 190

Val Asp Ala Phe Val His Thr Val Glu Gln Tyr Leu Thr Tyr Ser Val
        195                 200                 205

Asp Ala Lys Val Gln Asp Arg Phe Ala Glu Gly Leu Leu Leu Thr Leu
    210                 215                 220

Val Glu Glu Gly Pro Arg Ala Leu Ala Glu Pro Glu Asn Tyr Lys Val
225                 230                 235                 240

Arg Ala Asn Val Met Trp Ser Ala Thr Met Ala Leu Asn Gly Leu Ile
                245                 250                 255

Gly Ala Gly Val Pro Gln Asp Trp Ser Thr His Met Leu Gly His Glu
            260                 265                 270

Leu Thr Ala Leu His Gly Leu Asp His Ala Gln Thr Leu Ala Ile Val
        275                 280                 285

Leu Pro Ala Met Leu Ala Ala Arg Lys Ser Gln Lys Arg Asp Lys Leu
    290                 295                 300

Leu Gln Tyr Ala Glu Arg Val Trp Asn Leu Arg Asp Gly Ser Glu Asp
305                 310                 315                 320

Gln Arg Ile Asp Gly Ala Ile Ala Ala Thr Arg Asp Phe
                325                 330
```

<210> SEQ ID NO 52
<211> LENGTH: 1002
<212> TYPE: DNA
<213> ORGANISM: Pectobacterium atrosepticum

<400> SEQUENCE: 52

```
atgctgaatt tcaccctcca taccccgacg aagatcctgt tcggcgaggg ccagatcgcg    60
```

```
gagctgggca aggagatccc ggccgacgcc cgcatcctca tcacctacgg cggcggctcg   120
gtcaaacaca acggcgtgct ggatcaggtg taccgggcgc tggaaggccg aacgtgcgg    180 gagttctccg gcatcgagcc aacccgacc tacgaaacgc tcatgaaggc cgtggaggtg    240
gtccgggcgg aaaagatcga tttcctgctc gccgtgggcg gcggcagcgt cgtcgacggc   300
accaagttca tcgccgcggc ggccgactac caggccgcgc aggacccgtg gcacatcctc   360
cagaccggcg gcgccgaaat cgaccggggc gtggccctcg ccgcggtgct gaccctgccc   420
gccacgggca gcgaatccaa taacggcgcc gtcatcaccc gcaaaagcac caatgacaag   480
ctcgcgttcc ggtccccgca tacgcagccc ctcttcgccg tcctcgaccc ggtggtcacg   540
tacaccctgc cggcccggca gatcgcgaat ggcgtcgtcg acgccttcgt ccacaccgtc   600
gagcagtacc tgacctactc cgtcgacgcg aaagtccagg atcgcttcgc cgagggcctg   660
ctgctcaccc tggtcgaaga gggcccccgg gccctggccg aacccgaaaa ctacaaagtg   720
cgggcgaatg tcatgtggag cgccacgatg gcgctgaacg gcctcatcgg cgccggcgtc   780
ccccaggatt ggtcgaccca catgctgggc cacgaactca cggccctgca cggcctcgac   840
cacgcgcaga cgctggccat cgtcctgccg gccatgctgg cggcccggaa atcccagaaa   900
cgggataaac tcctgcagta cgccgagcgc gtctggaacc tccgcgacgg ctcggaagat   960
cagcggatcg acggcgccat cgccgccacg cgcgatttct ga                    1002

<210> SEQ ID NO 53
<211> LENGTH: 351
<212> TYPE: PRT
<213> ORGANISM: Psychrobacter cryohalolentis

<400> SEQUENCE: 53

Met Ala Asn Thr Lys Ala Tyr Ala Ala Thr Ala Pro Asp Ser Gly Leu
1               5                   10                  15

Ala Pro Tyr Ala Ile Asp Arg Arg Glu Leu Arg Ala Asp Asp Val Ala
            20                  25                  30

Ile Glu Ile Asp Tyr Cys Gly Val Cys His Ser Asp Leu His Thr Val
        35                  40                  45

Glu Asn Asp Trp Gly Gly Ser Lys Tyr Pro Val Ile Pro Gly His Glu
    50                  55                  60

Ile Val Gly Arg Val Thr Ala Val Gly Pro Glu Val Ser His Phe Lys
65                  70                  75                  80

Ala Gly Asp Leu Val Gly Val Gly Cys Met Val Asp Ser Cys Arg Ser
                85                  90                  95

Cys Ser Ala Cys Asp Ser Gly Leu Glu Gln Tyr Cys Ile Glu Gly Ser
            100                 105                 110

Thr Met Thr Tyr Gly Ser Leu Asp Arg His Asp Gly Ser Val Thr His
        115                 120                 125

Gly Gly Tyr Ser Glu Arg Ile Val Val Ser Glu Arg Phe Val Val Arg
    130                 135                 140

Val Pro Glu Lys Leu Asp Pro Ala Ser Ala Ala Pro Ile Leu Cys Ala
145                 150                 155                 160

Gly Ile Thr Thr Tyr Ser Pro Leu Lys His Phe Lys Val Gly Lys Gly
                165                 170                 175

His Lys Val Gly Val Leu Gly Met Gly Gly Leu Gly His Met Gly Val
            180                 185                 190

Lys Phe Ala Lys Ala Leu Gly Ala Glu Val Thr Ile Phe Thr Arg Ser
        195                 200                 205
```

```
Glu Ala Lys Val Ala Glu Ala Lys Lys Gln Gly Ala Asp His Val Ile
    210                 215                 220

Ile Ser Thr Asp Lys Glu Gln Met Lys Ala Ala Ala Asp Ser Phe Asp
225                 230                 235                 240

Phe Leu Leu Asp Thr Ile Pro Val Ala His Asp Leu Asn Pro Tyr Leu
                245                 250                 255

Lys Cys Leu Lys Tyr Asp Gly Thr His Ile Leu Val Gly Leu Leu Thr
                260                 265                 270

Pro Ile Glu Pro Ala Leu Gln Ala Gly Leu Leu Val Thr Lys Arg Arg
            275                 280                 285

Val Val Ala Gly Ser Leu Ile Gly Gly Met Pro Glu Thr Gln Glu Val
    290                 295                 300

Leu Asp Phe Cys Ala Glu His Asp Ile Thr Cys Asp Ile Glu Met Leu
305                 310                 315                 320

Asp Ile Arg Asn Ile Asn Glu Ala Tyr Val Arg Met Lys Lys Gly Asp
                325                 330                 335

Val Lys Tyr Arg Phe Val Ile Asp Met Lys Thr Leu Lys Glu Gly
            340                 345                 350

<210> SEQ ID NO 54
<211> LENGTH: 1056
<212> TYPE: DNA
<213> ORGANISM: Psychrobacter cryohalolentis

<400> SEQUENCE: 54
atggccaata ccaaggccta cgccgccacg gcgccggatt cgggcctggc cccgtacgcg      60
atcgaccggc gggaactgcg ggccgatgac gtggcgatcg aaatcgacta ctgtggcgtg     120
tgccatagcg atctccatac cgtggaaaac gactgggggcg gctcgaagta cccggtgatc     180
ccgggccatg agatcgtcgg ccgggtgacg gcggtgggcc ccgaggtcag ccatttcaag     240
gccggcgacc tcgtgggcgt gggctgcatg gtggattcgt gtcgctcgtg cagcgcctgc     300
gacagcggcc tcaacagta ttgcatcgag ggcagcacga tgacctacgg cagcctggac     360
cgccacgatg gctccgtcac ccacggcggc tacagcgaac gcatcgtcgt ctcggaacgg     420
ttcgtcgtgc gggtgcccga aaaactggac ccggcctcgg ccgccccgat cctgtgcgcc     480
ggcatcacga cgtacagccc gctgaagcac ttcaaggtgg gcaagggcca taaagtcggc     540
gtcctgggca tgggcggcct gggccatatg ggcgtgaagt tcgccaaggc cctgggcgcc     600
gaggtgacga tcttcacccg gtccgaggcg aaagtggccg aagcgaagaa cagggcgcc     660 gaccatgtca tcatctcgac cgataaggag cagatgaagg ccgccgccga cagcttcgat     720
ttcctcctcg acaccatccc ggtggcgcac gacctgaatc cgtatctgaa gtgtctgaaa     780
tacgatggca cccacatcct cgtgggcctg ctgacccca tcgaaccggc gctgcaggcc     840
ggcctcctgg tcaccaagcg cgcgtcgtg gcgggcagcc tgatcggcgg catgcccgag     900
acgcaggaag tcctggactt ctgcgccgaa catgacatca cctgtgatat cgagatgctc     960
gacatccgca acatcaacga agcgtacgtc cgcatgaaaa agggcgatgt caagtaccgc    1020
ttcgtgatcg atatgaagac gctgaaggaa ggctga                              1056

<210> SEQ ID NO 55
<211> LENGTH: 548
<212> TYPE: PRT
<213> ORGANISM: Methylocaldus szegediense

<400> SEQUENCE: 55
```

```
Met Gly Thr Ala Lys Ala Asp Ser Ile Gly Gln Tyr Leu Leu Lys Arg
1               5                   10                  15

Leu Tyr Glu Ala Gly Val Lys His Ile Phe Gly Val Pro Gly Asp Tyr
            20                  25                  30

Val Leu Gly Phe Tyr Asp Leu Met Ala Lys Ser Pro Ile Gln His Val
        35                  40                  45

Gly Thr Thr Arg Glu Asp Thr Ala Ala Phe Ala Ala Asp Gly Tyr Ala
    50                  55                  60

Arg Cys Arg Gly Leu Gly Ala Leu Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Ile Val Ile Ser Gly Ala Pro Gly Val Arg Glu Gln Lys Glu Asp
            100                 105                 110

Pro Met Ile His His Arg Phe Gly Pro Phe Thr Phe Gln Arg Glu Ile
        115                 120                 125

Phe Asp Arg Ile Thr Cys Ala Ala Val Thr Leu Asp Asp Pro Ile Ile
    130                 135                 140

Ala Phe Arg Gln Ile Asp Arg Val Ile Ala Ala Arg His Ser Cys
145                 150                 155                 160

Lys Pro Val Tyr Ile Glu Leu Pro Arg Asp Leu Val Met Ala Glu Gly
                165                 170                 175

His Pro Val Pro Thr Glu Pro Pro Glu Pro Ala Ser Asp Glu Ala
                180                 185                 190

Ala Leu Ser Glu Ala Val Ala Glu Thr Ala Glu Leu Met Ser Lys Ser
            195                 200                 205

Val Ser Pro Thr Val Leu Ala Gly Val Glu Leu His Arg Arg Gly Leu
        210                 215                 220

Gln Asp Ala Leu Val Glu Leu Val Glu Arg Ala Arg Leu Pro Val Ala
225                 230                 235                 240

Ala Thr Leu Thr Gly Lys Ser Val Ile Ala Glu Arg His Pro Ala Tyr
                245                 250                 255

Leu Gly Val Tyr Glu Gly Ala Met Ser Ser Glu Asn Ala Arg Tyr Met
            260                 265                 270

Val Glu Gln Ser Asp Leu Leu Leu Met Leu Gly Val Thr Leu Asn Asp
        275                 280                 285

Ile Asp Thr Gly Val Tyr Thr Ala Arg Leu Asp Pro His Arg Ile Val
    290                 295                 300

Arg Ala Ala Gln Asn Glu Val Val Ile Arg Tyr His Arg Tyr Pro Arg
305                 310                 315                 320

Val Thr Leu Ser Asp Phe Val Leu Ser Leu Ala Arg Thr Val Lys Ala
                325                 330                 335

Lys His Glu Thr Phe Pro Ala Pro Val Thr Thr Pro Glu Ala Thr Glu
            340                 345                 350

Phe Pro Met Pro Glu Arg Pro Met Thr Ile Ala Arg Leu Ile Glu Arg
        355                 360                 365

Leu Asp Arg Ala Leu Thr Pro Asp Met Ile Val Ser Asp Val Gly
    370                 375                 380

Asp Cys Leu Phe Ala Ala Ile Asp Leu Arg Val Tyr Glu Arg Ser Glu
385                 390                 395                 400

Phe Leu Ser Ser Ala Phe Tyr Thr Thr Met Gly Phe Ala Val Pro Ala
                405                 410                 415

Ala Leu Gly Ala Gln Ile Ala Arg Pro Asp His Arg Ala Leu Ile Leu
```

-continued

```
                  420                 425                 430
Val Gly Asp Gly Ala Phe Gln Met Thr Gly Thr Glu Leu Ser Thr His
                435                 440                 445

Ile Arg Phe Gly Leu Ala Pro Ile Val Val Val Phe Asn Asn Cys Gly
            450                 455                 460

Tyr Ser Thr Glu Arg Tyr Ile Leu Asp Gly Pro Phe Asn Asp Ile Ser
465                 470                 475                 480

Cys Trp Asn Phe Asp Arg Leu Gly Glu Leu Phe Gly Pro Leu Asn Gly
                485                 490                 495

Tyr Asp Ala Pro Asp Glu Glu Ser Phe Glu Lys Ala Leu Val Glu Ala
            500                 505                 510

Leu Ala Asn His Ala Thr Pro Ser Ile Ile Asn Val His Ile Ser Arg
            515                 520                 525

Asp Asp Ser Ser Ser Ala Met Arg Arg Leu Ala Glu Val Leu Lys Ser
            530                 535                 540

Arg Val Arg Gly
545
```

<210> SEQ ID NO 56
<211> LENGTH: 1647
<212> TYPE: DNA
<213> ORGANISM: Methylocaldus szegediense

<400> SEQUENCE: 56

```
atgggcaccg ccaaggcgga tagcatcggc cagtacctcc tgaaacgcct gtacgaggcc      60
ggcgtgaaac atatcttcgg cgtgcccggc gattacgtgc tgggcttcta cgatctgatg     120
gcgaagagcc cgatccagca cgtcggcacg acccgcgagg acaccgcggc cttcgccgcc     180
gacggctacg cccgctgtcg cggcctcggc gccctggcgg tcacctatgg cgtcggcgcc     240
ctgaacaccg tgaatgccgt cgcgggcgcc tatgccgaat cgagcccggt gatcgtcatc     300
agcggcgccc cgggcgtgcg cgaacagaag gaagacccga tgatccatca tcggttcggc     360
ccgttcacct tccagcggga aatcttcgac cggatcacct cgccgcgggt cacgctggac     420
gatcccatca tcgccttccg ccagatcgac cgggtgatcg cggcggcccg ccactcgtgc     480
aaaccgtgt atatcgaact gccccgcgac ctggtgatgg ccgaaggcca tccggtcccg     540
acggagcccc cggaagagcc cgcctccgat gaggcggccc tgagcgaagc ggtgccgaa      600
accgcggaac tgatgtccaa gtcggtgagc cccaccgtcc tggcgggcgt cgaactgcac     660
cggcgcggcc tgcaggacgc cctggtggaa ctggtggaac gcgcccggct gccggtggcc     720
gccacccttca ccggcaagag cgtgatcgcc gaacgccacc ccgcctatct gggcgtctac    780
gaaggcgcca tgtcctcgga aaacgcccgc tacatggtgg aacagtccga tctcctgctc     840
atgctgggcg tgacgctgaa cgacatcgac accggcgtct ataccgcccg cctcgacccg     900
catcgcatcg tgcgggcggc ccagaacgag gtggtgatcc gctaccatcg ctatccgcgg     960
gtcaccctgt cggacttcgt cctgagcctg ccccgcaccg tgaaagcgaa gcatgaaacc    1020
ttccccgccc cggtcacgac ccccgaagcc acggagttcc ccatgcccga cgcccgatg     1080
acgatcgccc gcctcatcga acgcctggac cgcgccctga ccccgacat gatcgtcgtg     1140
agcgatgtgg cgattgcct gttcgcggcc atcgatctcc gggtctacga gcggagcgag    1200
ttcctctcgt cggccttcta caccacgatg ggcttcgccg tcccggccgc cctgggcgcc    1260
cagatcgcgc ggccggacca ccgggccctg atcctggtgg cgatggcgc gttccagatg    1320
acgggcaccg agctcagcac gcacatccgc ttcggcctcg cgcccatcgt ggtcgtgttc    1380
```

```
aacaactgtg gctattcgac cgaacggtac atcctggacg gcccgttcaa cgacatctcg    1440
tgctggaact tcgaccggct gggcgaactg ttcggcccgc tgaacggcta tgacgcgccg    1500
gacgaggaga gcttcgagaa ggccctcgtc gaggccctgg ccaaccatgc cacgcccagc    1560
atcatcaacg tccacatcag ccgcgacgac agctccagcg cgatgcggcg gctggccgaa    1620
gtcctgaaga gccgcgtccg gggctga                                        1647
```

<210> SEQ ID NO 57
<211> LENGTH: 550
<212> TYPE: PRT
<213> ORGANISM: Methylosarcina lacus

<400> SEQUENCE: 57

```
Met Asn Thr Ala Lys Phe Asp Thr Ile Gly Gln Tyr Leu Leu Lys Arg
1               5                   10                  15

Leu Tyr Asp Ala Gly Val Lys His Ile Phe Gly Val Pro Gly Asp Tyr
                20                  25                  30

Ile Leu Gly Phe Tyr Asp Leu Met Val Asn Ser Pro Val Gln His Ile
            35                  40                  45

Gly Thr Thr Arg Glu Asp Thr Ala Ala Phe Ala Ala Asp Ala Tyr Ala
        50                  55                  60

Arg Cys Leu Gly Leu Gly Ala Met Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Ile Val Ile Ser Gly Ala Pro Gly Ile Arg Glu Gln Arg Glu Asp
            100                 105                 110

Pro Leu Ile His His Arg Phe Gly Pro Phe Thr Phe Gln Arg Glu Ile
        115                 120                 125

Phe Glu Arg Ile Thr Cys Ala Thr Glu Val Leu Asn Asp Pro Val Ile
130                 135                 140

Ala Phe Arg Gln Ile Asp Arg Ala Ile Ala Thr Ala Arg Arg Leu Cys
145                 150                 155                 160

Lys Pro Val Tyr Ile Glu Ile Pro Arg Asp Leu Val Met Ala Glu Gly
                165                 170                 175

Tyr Pro Met Pro Asp Glu Ala Leu Glu Pro Leu Glu Ser Asp Glu Thr
            180                 185                 190

Ala Leu Ser Glu Ala Leu Ala Glu Thr Met Glu Leu Met Ala Lys Ser
        195                 200                 205

Val Ser Pro Met Ile Ile Ala Gly Val Glu Leu His Arg Arg Gly Leu
    210                 215                 220

Gln Ser Ala Leu Val Asn Leu Val Glu Arg Ala His Leu Pro Val Val
225                 230                 235                 240

Ala Thr Leu Ser Gly Lys Ser Val Met Ala Glu Arg His Pro Ala Tyr
                245                 250                 255

Leu Gly Ile Tyr Glu Gly Ala Met Ser Ser Glu Asn Ala Arg Tyr Met
            260                 265                 270

Val Glu Gln Ser Asp Leu Leu Leu Met Leu Gly Val Thr Leu Asn Asp
        275                 280                 285

Ile Asp Thr Gly Ile Tyr Thr Ala Lys Leu Asp Pro His His Met Ile
    290                 295                 300

Arg Ala Ala Gln Asn Glu Val Val Ile Ser Ser His Arg Tyr Pro Arg
305                 310                 315                 320
```

| | | | | | | | | | | | |
|---|---|---|---|---|---|---|---|---|---|---|---|
| Val | Thr | Leu | Ser | Asp | Phe | Leu | Thr | Ala | Leu | Val | Gly | Leu | Val | Lys | Thr |
| | | | | 325 | | | | 330 | | | | 335 | |

Val Thr Leu Ser Asp Phe Leu Thr Ala Leu Val Gly Leu Val Lys Thr
                     325                     330                   335

Arg Ser Glu Gly Phe Ser Ser Pro Pro Ala Ala Tyr Glu Ala Ser Ala
        340                     345                 350

Phe Pro Glu Pro Lys Arg Pro Ile Thr Thr Ala Arg Met Ile Gly Arg
        355                     360                 365

Leu Asn Gln Ala Leu Ser Pro Glu Met Ile Val Val Cys Asp Val Gly
        370                     375                 380

Asp Cys Leu Phe Ala Ala Ile Asp Leu Gln Val His Glu Gln Ser Glu
385                     390                     395                 400

Phe Leu Ala Ser Cys Tyr Tyr Ala Thr Met Gly Phe Ala Val Pro Ala
                 405                     410                 415

Ala Leu Gly Ala Gln Ile Ala Arg Pro Asp His Arg Leu Leu Val Leu
        420                     425                 430

Val Gly Asp Gly Ala Phe Gln Met Thr Gly Thr Glu Leu Ser Thr His
               435                     440                 445

Ala Tyr Leu Gly Leu Asn Pro Ile Val Val Phe Asn Asn Ser Gly
        450                     455                 460

Tyr Gly Thr Glu Arg Gly Ile Leu Gly Pro Phe Asn Asp Ile Ser
465                     470                     475                 480

Ser Trp Arg Phe Asp Arg Leu Gly Glu Val Phe Gly Pro Leu Lys Gly
               485                     490                 495

Tyr Asp Ala Ala Thr Glu Glu Ala Phe Glu Ala Ala Leu Ile Asn Ser
             500                     505                 510

Leu Asn Asn Arg Thr Met Pro Ser Ile Ile Asn Val His Leu Ser Ala
        515                     520                 525

Asp Asp Ala Ser Ser Ala Met Lys Arg Leu Ala Glu His Leu Lys Ser
530                     535                     540

Arg Val Lys Gly Gly Ser
545                     550

<210> SEQ ID NO 58
<211> LENGTH: 1653
<212> TYPE: DNA
<213> ORGANISM: Methylosarcina lacus

<400> SEQUENCE: 58

```
atgaacaccg ccaagttcga caccatcggc cagtacctgc tcaagcggct gtacgacgcg    60
ggcgtgaaac acatcttcgg cgtgccgggc gattatatcc tgggcttcta tgacctgatg   120
gtgaacagcc cggtccagca catcggcacc acgcgcgagg acaccgcggc cttcgcggcg   180
gacgcctacg cccgctgcct gggcctcggc gcgatggcgg tcacgtacgg cgtgggcgcc   240
ctgaatacct gaatgccgt cgccggcgcg tatgccgaaa gctcgccggt gatcgtcatc   300
tccggcgccc ccggcatccg cgagcagcgg gaggacccgc tgatccatca tcggttcggc   360
ccgttcacct tccagcggga gatcttcgag cgcatcacct gcgcgaccga agtgctcaac   420
gacccggtga tcgccttccg ccagatcgat cgcgcgatcg ccaccgcccg cggctgtgc    480 aagccggtgt acatcgagat cccgcgcgat ctggtgatgg cggaaggcta ccccatgccg   540
gacgaggccc tcgaacccct ggagagcgat gaaaccgccc tgagcgaggc gctggcggaa   600
acgatggaac tgatggcgaa aagcgtctcc ccgatgatca tcgccggcgt cgaactgcat   660
cggcggggcc tgcagagcgc cctcgtcaac ctggtggaac gcgcccatct cccggtggtc   720 gccacccctgt cgggcaaaag cgtcatggcg aacggcacc cggcctacct gggcatctac   780
```

```
gaaggcgcga tgtcctcgga aaatgcccgg tacatggtcg aacagagcga cctcctcctc    840
atgctgggcg tcaccctcaa cgacatcgat accggcatct atacggccaa gctcgacccg    900
catcatatga tccgggcggc ccagaacgag gtggtgatct cctcgcatcg ctacccgcgg    960
gtcaccctct cggacttcct gacggcgctg gtgggcctgg tcaagacccg gagcgaaggc   1020
ttcagctcgc cgccggccgc ctacgaggcc agcgccttcc cggaaccgaa gcggccgatc   1080
accacggcgc ggatgatcgg ccggctgaac caggcgctgt cgccggaaat gatcgtggtg   1140
tgcgacgtgg gcgactgcct cttcgccgcc atcgatctgc aggtgcacga gcagtccgag   1200
ttcctcgcca gctgctacta tgccacgatg ggcttcgccg tgcccgcggc gctcggcgcc   1260
cagatcgcgc ggcccgatca ccggctgctc gtgctggtgg gcgacggcgc cttccagatg   1320
acgggcaccg aactgagcac ccatgcctat ctgggcctca cccgatcgt cgtggtgttc   1380
aacaactccg gctacggcac cgaacgcggc atcctggaag gccccttcaa cgacatcagc   1440
agctggcggt tcgaccgcct cggcgaagtg ttcggcccgc tgaagggcta tgacgccgcc   1500
accgaggagg ccttcgaagc ggcgctcatc aactccctca caaccggac gatgccgagc   1560
atcatcaacg tccatctctc cgccgacgac gcctcctccg ccatgaagcg cctcgccgag   1620
cacctgaaga gccgcgtgaa gggcggctcg tga                                1653
```

<210> SEQ ID NO 59
<211> LENGTH: 550
<212> TYPE: PRT
<213> ORGANISM: Methylomonas denitrificans

<400> SEQUENCE: 59

```
Met Ser Thr Ala Lys Phe Asp Thr Ile Gly Gln Tyr Leu Leu Lys Arg
1               5                   10                  15

Leu Tyr Gln Ala Gly Val Lys Asp Ile Phe Gly Val Pro Gly Asp Tyr
            20                  25                  30

Val Leu Gly Phe Tyr Asp Leu Met Ile Lys Ser Gln Val Arg His Ile
        35                  40                  45

Gly Thr Thr Arg Glu Asp Ser Ala Ala Phe Ala Ala Asp Gly Tyr Ala
    50                  55                  60

Arg Cys Val Gly Met Gly Ala Leu Ala Val Thr Tyr Gly Val Gly Ala
65                  70                  75                  80

Leu Asn Thr Val Asn Ala Ile Ala Gly Ala Tyr Ala Glu Ser Ser Pro
                85                  90                  95

Val Val Leu Ile Ser Gly Ala Pro Gly Val Ser Glu Gln Lys Asp Asp
            100                 105                 110

Pro Leu Ile His His Arg Phe Gly Pro Phe Thr Phe Gln Arg Glu Ile
        115                 120                 125

Phe Glu Arg Ile Ser Cys Ala Ser Val Val Leu Asn Asp Pro Val Ile
    130                 135                 140

Ala Phe Arg Gln Ile Asp His Ala Ile Glu Ala Ala Arg Arg Phe Cys
145                 150                 155                 160

Lys Pro Val Tyr Ile Glu Leu Pro Arg Asp Leu Val Met Ala Glu Gly
                165                 170                 175

Tyr Pro Met Pro Thr Glu Thr Val Glu Lys Phe Thr Ser Asp Glu Ala
            180                 185                 190

Ala Leu Ser Glu Ala Ile Ala Glu Thr Met Thr Leu Leu Ser Lys Ala
        195                 200                 205

Val Ser Pro Met Ile Val Ala Gly Val Glu Leu His Arg Arg Gly Leu
    210                 215                 220
```

```
Gln Gly Ala Leu Ala Asp Phe Val Glu Arg Thr Cys Leu Pro Val Val
225                 230                 235                 240

Ala Thr Leu Thr Gly Lys Ser Val Met Ser Glu Arg His Pro Ala Tyr
            245                 250                 255

Leu Gly Ile Tyr Glu Gly Ala Met Ser Ser Glu Ala Val Arg Asp Arg
        260                 265                 270

Val Glu Lys Ser Asp Leu Leu Met Leu Gly Val Thr Leu Asn Glu
            275                 280                 285

Ile Asp Thr Gly Ile Tyr Thr Ala Lys Leu Asn Ser His Ser Thr Ile
        290                 295                 300

Arg Ala Ala Leu Asn Glu Val Val Ile Ser Ala His Arg Tyr Pro Gly
305                 310                 315                 320

Ile Ala Leu Glu Asp Phe Leu Gly Ala Leu Ala Ser Ser Val Ser Leu
                325                 330                 335

Ser Ser Arg Glu Val Val Ser Ser Pro Lys Pro Pro Glu Ser Ile Ala
            340                 345                 350

Phe Pro Glu Pro Asp Arg Pro Ile Thr Thr Ala Arg Leu Val Glu Arg
                355                 360                 365

Leu Asn Ser Ala Leu Ser Asn Asp Met Ile Val Cys Asp Val Gly
370                 375                 380

Asp Cys Leu Phe Ala Ala Ile Asp Leu Arg Val His Glu Gln Ser Glu
385                 390                 395                 400

Phe Leu Ala Ser Ala Phe Tyr Thr Thr Met Gly Phe Ala Val Pro Ala
                405                 410                 415

Ala Leu Gly Ala Gln Ile Ala Arg Pro Asp Arg Arg Ala Leu Ile Leu
            420                 425                 430

Val Gly Asp Gly Ala Phe Gln Met Thr Gly Thr Glu Leu Ser Thr His
        435                 440                 445

Ala Arg Leu Gly Leu Asn Pro Ile Val Val Phe Asn Asn Gly Gly
450                 455                 460

Tyr Ser Thr Glu Arg Cys Ile Leu Glu Gly Pro Phe Asn Asp Ile Asn
465                 470                 475                 480

Pro Trp Arg Phe Asp Arg Leu Gly Glu Leu Phe Gly Pro Leu Ala Gly
                485                 490                 495

Tyr Glu Ala Ala Thr Glu Ala Glu Phe Glu Glu Ala Leu Leu Asn Ala
            500                 505                 510

Leu Asp Asn His Gly Met Pro Ser Ile Ile Asn Val His Leu Ala Ala
            515                 520                 525

Asp Asp Ser Ser Glu Ala Met Lys Arg Leu Ala Glu His Leu Gln Ser
530                 535                 540

Lys Ile Lys Arg Asp Ala
545                 550

<210> SEQ ID NO 60
<211> LENGTH: 1653
<212> TYPE: DNA
<213> ORGANISM: Methylomonas denitrificans

<400> SEQUENCE: 60
atgtcgaccg cgaagttcga caccatcggc cagtatctgc tgaagcggct gtatcaggcc     60
ggcgtcaagg atatcttcgg cgtccccggc gactacgtgc tgggcttcta tgacctgatg    120
atcaagtcgc aggtgcgcca tatcggcacc acgcgggagg acagcgcggc cttcgcggcc    180
gacggctacg cccggtgtgt gggcatgggc gccctggcgg tgacgtacgg cgtcggcgcc    240
```

```
ctgaacacgg tgaacgccat cgccggcgcg tacgccgaat cgtcccccgt cgtcctcatc    300
agcggcgccc cgggcgtgtc cgagcagaag gacgatccgc tgatccatca tcgcttcggc    360
cccttcacgt tccagcgcga aatcttcgaa cggatcagct gtgcctccgt cgtcctgaat    420
gacccggtca tcgcgttccg gcagatcgac catgccatcg aggccgcccg cgcttctgc     480 aagccggtgt atatcgaact gccgcgggac ctcgtgatgg cggagggcta ccccatgccc    540
accgagacgg tcgaaaagtt cacctccgat gaggccgcgc tgtccgaagc gatcgcggaa    600
accatgaccc tgctcagcaa ggcggtcagc ccgatgatcg tggcgggcgt ggagctgcat    660
cggcgcggcc tgcagggcgc cctggccgac ttcgtggaac ggacctgtct gcccgtggtg    720
gccaccctga cgggcaagtc ggtgatgtcg gagcgccatc ccgcctacct gggcatctac    780
gaaggcgcca tgtcctcgga agcggtgcgc gatcgggtgg agaagagcga tctgctcctg    840
atgctgggcg tgaccctcaa cgaaatcgac accggcatct acacggccaa actgaacagc    900
catagcacga tccgcgccgc gctgaacgag gtcgtgatct ccgcccaccg ctatcccggc    960
atcgcgctgg aagatttcct gggcgccctg gcctcgtcgg tgtccctcag ctcgcgcgag   1020
gtggtcagca gcccgaaacc cccggagtcg atcgccttcc cggaaccgga ccggccgatc   1080
acgacggccc gcctggtcga acggctcaac tccgccctca gcaatgacat gatcgtcgtg   1140
tgtgacgtgg cgactgcct gttcgcggcc atcgacctcc gcgtgcatga gcagagcgag    1200
ttcctggcct ccgccttcta caccacgatg ggcttcgcgg tgcccgcggc cctcggcgcc   1260
cagatcgccc gccccgaccg gcgggcgctg atcctggtcg cgacggcgc gttccagatg    1320 accggcaccg aactgtccac gcacgcgcgg ctgggcctga cccgatcgt cgtcgtgttc    1380 aataatggcg gctactcgac cgaacgctgc atcctggaag gcccgttcaa tgatatcaac    1440
ccctggcgct tcgaccgcct gggcgagctg ttcggccccc tggccggcta tgaggccgcc    1500
acggaagccg agttcgagga agccctgctg aacgcgctgg acaaccacgg catgccgtcc    1560
atcatcaatg tgcatctcgc cgccgacgat agctccgagg cgatgaaacg cctggccgag    1620
cacctgcaga gcaaaatcaa gcgggacgcc tga                                1653
```

<210> SEQ ID NO 61
<211> LENGTH: 553
<212> TYPE: PRT
<213> ORGANISM: Methylomonas methanica

<400> SEQUENCE: 61

```
Met Asn Thr Val Lys Leu Glu Thr Met Gly Gln Tyr Leu Leu Asn Arg
1               5                   10                  15

Leu Tyr Glu Ala Gly Val Lys His Val Phe Gly Val Pro Gly Asp Tyr
            20                  25                  30

Val Leu Gly Phe Tyr Asp Leu Met Glu Lys Ser Pro Ile Gln His Ile
        35                  40                  45

Gly Thr Thr Arg Glu Asp Thr Ala Ala Phe Ala Ala Asp Gly Tyr Ala
    50                  55                  60

Arg Cys Arg Gly Leu Gly Ala Leu Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Ile Val Ile Ser Gly Ala Pro Gly Val Cys Glu Gln Arg Asp Asp
            100                 105                 110

Pro Leu Ile His His Arg Phe Gly Pro Phe Thr Phe Gln Arg Glu Ile
```

```
              115                 120                 125
Phe Glu Arg Ile Thr Cys Ala Thr Ala Val Leu Asn Asp Pro Val Ile
    130                 135                 140
Ala Phe Arg Gln Ile Asp His Ala Ile Ala Ser Ala Arg His Tyr Cys
145                 150                 155                 160
Lys Pro Val Tyr Ile Glu Ile Pro Arg Asp Leu Val Ser Val Glu Gly
                165                 170                 175
Tyr Pro Met Pro Ala Ile Ala Ala Met Glu Pro Ser Gly Ser Asp Lys
            180                 185                 190
Ser Ala Leu Ser Glu Ala Val Ala Glu Thr Met Ser Leu Leu Glu Lys
        195                 200                 205
Ser Val Ser Pro Met Val Ile Ala Gly Ile Glu Leu His Arg Arg Gly
    210                 215                 220
Leu Gln Asn Arg Leu Leu Glu Leu Ile Glu Arg Ala Arg Leu Pro Val
225                 230                 235                 240
Thr Ala Thr Leu Thr Gly Lys Ser Val Ile Ala Glu Arg His Pro Ala
                245                 250                 255
Tyr Leu Gly Ile Tyr Glu Gly Ala Met Ser Ser Glu His Ala Arg Tyr
            260                 265                 270
Met Val Glu Gln Ser Asp Leu Leu Leu Met Leu Gly Val Thr Leu Asn
        275                 280                 285
Glu Val Asp Thr Gly Ile Tyr Thr Ala Lys Leu Asp Pro Gln His Thr
    290                 295                 300
Ile Arg Ala Ala Leu Asn Glu Val Val Ile Ser Ala His Arg Tyr Pro
305                 310                 315                 320
Asn Ile Ala Leu Ala Asp Tyr Leu Asn Ala Leu Val Asp Ala Val Lys
                325                 330                 335
Pro Ser Glu Ala Gly Phe Ser Ala Lys Pro Gly Lys Pro Val Ala Arg
            340                 345                 350
Ala Phe Pro Glu Pro Asp Arg Pro Ile Ser Ile Asn Arg Leu Ile Glu
        355                 360                 365
Arg Ile Asn Gln Ala Leu Glu Pro Glu Thr Ile Val Val Cys Asp Val
    370                 375                 380
Gly Asp Cys Leu Phe Ala Ala Ile Asp Leu Glu Val His Glu Gln Ser
385                 390                 395                 400
Glu Phe Leu Ala Ser Gly Phe Tyr Thr Thr Met Gly Phe Ala Val Pro
                405                 410                 415
Ala Ala Leu Gly Ala Gln Val Ala Arg Pro Gly His Arg Ala Leu Ile
            420                 425                 430
Leu Val Gly Asp Gly Ala Phe Gln Met Thr Gly Thr Glu Leu Ser Thr
        435                 440                 445
Gln Ala Arg Leu Gly Leu Asp Ser Ile Val Ile Val Phe Asn Asn Ser
    450                 455                 460
Gly Tyr Ser Thr Glu Arg Cys Ile Leu Glu Gly Pro Phe Asn Asp Ile
465                 470                 475                 480
Ala Arg Trp Arg Phe Asp Arg Leu Gly Glu Val Phe Gly Pro Leu Gln
                485                 490                 495
Gly Phe Asp Ala Ala Thr Glu Glu Ser Phe Glu Ser Ala Leu Ile Gln
            500                 505                 510
Ala Leu Asn Asn Arg Ser Met Pro Ser Ile Ile Asn Val His Leu Ala
        515                 520                 525
Ser Asp Asp Thr Ser Ser Ala Met Arg Arg Leu Ala Glu His Leu Lys
    530                 535                 540
```

Ser Lys Val Gln Gly Glu Arg Pro Ala
545             550

<210> SEQ ID NO 62
<211> LENGTH: 1662
<212> TYPE: DNA
<213> ORGANISM: Methylomonas methanica

<400> SEQUENCE: 62

```
atgaacacgg tcaaactgga aacgatgggc cagtacctgc tgaaccgcct ctatgaggcg      60
ggcgtgaaac atgtcttcgg cgtcccgggc gactatgtcc tgggcttcta cgacctgatg     120
gagaagtccc ccatccagca tatcggcacc acccgcgaag ataccgcggc cttcgccgcc     180
gacggctacg cccgctgccg cggcctgggc gccctggccg tcacgtacgg cgtcggcgcc     240
ctcaacacgg tgaatgcggt ggcgggcgcc tacgcggagt cgtcgcccgt gatcgtcatc     300
agcggcgccc cgggcgtctg tgagcagcgc gatgacccgc tgatccacca ccgcttcggc     360
cccttcacct tccagcgcga gatcttcgaa cggatcacct gcgccaccgc ggtgctgaac     420
gacccggtga tcgcgttccg gcagatcgat cacgccatcg cctccgcccg ccattattgc     480
aagccggtct atatcgaaat cccgcgggac ctcgtgtccg tggaaggcta cccgatgccc     540
gccatcgccg cgatggagcc gtcgggctcc gacaagtccg ccctcagcga ggccgtggcg     600
gaaaccatgt cgctgctgga aaagtccgtg tccccgatgg tcatcgccgg catcgagctc     660
caccgccgcg gcctgcagaa ccgcctcctc gaactgatcg aacgcgcccg cctgcccgtg     720
acggccaccc tcaccggcaa aagcgtgatc gcggagcggc accccgcgta cctgggcatc     780
tatgagggcg cgatgtccag cgaacacgcc cgctatatgg tcgagcagtc cgacctcctc     840
ctcatgctgg gcgtgaccct gaacgaggtc gacacgggca tctacaccgc gaagctggac     900
ccccagcata ccatccgggc ggcgctgaac gaggtggtga tctcggccca ccgctatccg     960
aatatcgccc tggccgacta tctgaacgcc tggtggacg cggtgaagcc gtcggaggcg    1020
ggcttctccg ccaaaccggg caaacccgtc gcgcgggcgt tcccggagcc cgaccgcccg    1080
atctcgatca accgcctgat cgaacgcatc aatcaggcgc tggaaccgga cgcgatcgtg    1140
gtgtgcgacg tgggcgactg tctcttcgcc gccatcgatc tggaggtcca cgagcagtcg    1200
gagttcctgg cctcgggctt ctataccacg atgggcttcg ccgtgcccgc cgccctgggc    1260
gcccaggtcg cccggcccgg ccaccgcgcc ctgatcctgg tgggcgacgg cgcgttccag    1320
atgaccggca cggaactctc cacccaggcc cggctgggcc tggactcgat cgtgatcgtc    1380
ttcaacaatt cgggctattc cacggagcgg tgcatcctgg agggcccgtt caacgatatc    1440
gcccgctggc gcttcgaccg cctcggcgaa gtcttcggcc cgctgcaggg cttcgacgcg    1500
gcgaccgagg agtccttcga gtcggcgctg atccaggccc tgaacaaccg cagcatgccc    1560
agcatcatca cgtccacct cgcgagcgac gacacgagca gcgcgatgcg gcgcctggcg    1620
gaacacctga agtcgaaggt gcagggcgaa cgccccgcct ga                      1662
```

<210> SEQ ID NO 63
<211> LENGTH: 552
<212> TYPE: PRT
<213> ORGANISM: Methylohalobius crimeensis

<400> SEQUENCE: 63

Met Ala Thr Arg Asn Ser Thr Thr Ser Ile Gly Glu Tyr Leu Leu Gln
1               5                   10                  15

```
Arg Leu His Glu Ala Gly Ala His His Ile Phe Gly Val Pro Gly Asp
            20                  25                  30

Tyr Ile Leu Lys Phe Tyr Glu Gln Ile Ser Gln Gly Pro Val Arg His
        35                  40                  45

Ile Gly Thr Thr Arg Glu Asp Thr Ala Ala Phe Ala Ala Asp Gly Tyr
50                      55                  60

Ala Arg Cys Gln Gly Ile Gly Ala Met Ala Ile Thr Tyr Gly Val Gly
65                      70                  75                  80

Ala Leu Asn Val Val Asn Ala Val Ala Gly Ala Tyr Ala Glu Ser Ser
                85                  90                  95

Pro Val Val Ile Ser Gly Ala Pro Gly Val Trp Glu Gln Arg Glu
                100                 105                 110

Asp Pro Leu Leu His His Arg Phe Gly Pro Tyr Thr Phe Gln Arg Glu
            115                 120                 125

Ile Phe Asp Arg Ile Thr Cys Ala Thr Thr Val Leu Asp Asp Pro Ile
        130                 135                 140

Thr Ala Phe Arg Gln Ile Asp Arg Thr Ile Ala Ala Gln Arg Glu
145                 150                 155                 160

His Lys Pro Val Tyr Ile Glu Leu Pro Arg Asp Arg Val Thr Val Ala
                165                 170                 175

Gly Val Pro Leu Pro Ala Val Ala Glu Ala Thr Pro Gln Glu Thr Ser
            180                 185                 190

Asp Ala Ala Thr Leu Asp Glu Ala Val Ala Glu Thr Leu Ala Leu Leu
        195                 200                 205

Ala Gln Ala Lys Ser Pro Val Leu Ile Ala Gly Val Glu Val His Arg
210                 215                 220

Cys Gly Leu Gln Asp Ala Leu Val Asp Leu Val Val Arg Ala Gly Leu
225                 230                 235                 240

Pro Val Ala Ala Thr Leu Thr Gly Lys Ser Val Val Gly Glu Arg His
                245                 250                 255

Pro Ala Tyr Ile Gly Val Tyr Glu Gly Ala Ala Ser Ser Glu His Thr
            260                 265                 270

Arg Gln Met Val Glu Arg Ala Asp Val Leu Ile Met Leu Gly Val Thr
        275                 280                 285

Leu Asn Asp Val Asp Thr Gly Val Tyr Thr Ala Asn Leu Asp Pro His
290                 295                 300

Arg Leu Val Arg Ala Ser Gln Gly Glu Val Asn Ile Arg Tyr His Arg
305                 310                 315                 320

Tyr Pro Arg Val Gln Leu Gln Asp Phe Ile Gly Ala Leu Ala Arg Gln
                325                 330                 335

Val Ser Pro Arg Arg Glu Ala Leu Pro Ser Gln Pro Phe Val Asp Ser
            340                 345                 350

Gly Pro Ala Phe Pro Val Pro Gly Gln Ala Met Thr Ala Arg Leu
        355                 360                 365

Ile Ala Arg Leu Asn Cys Ala Leu Thr Pro Glu Met Ile Val Val Ser
370                 375                 380

Asp Val Gly Asp Cys Leu Phe Ala Ala Ile Glu Leu Arg Val Cys Glu
385                 390                 395                 400

Arg Ser Glu Phe Leu Ala Ser Ala Tyr Tyr Thr Thr Met Gly Phe Ala
                405                 410                 415

Val Pro Ala Ala Leu Gly Ala Gln Val Ala Arg Pro Asp Arg Arg Ala
            420                 425                 430

Leu Ile Leu Val Gly Asp Gly Ala Phe Gln Met Thr Gly Thr Glu Leu
```

```
                 435                 440                 445
Ser Thr His Ala Arg Leu Asn Leu Ala Pro Ile Ile Val Phe Asn
    450                 455                 460

Asn Ala Gly Tyr Ser Thr Glu Arg Asn Ile Leu Glu Gly Pro Phe Asn
465                 470                 475                 480

Asp Ile Ala Ala Trp Arg Phe Asp Arg Leu Gly Glu Val Phe Gly Pro
                485                 490                 495

Leu His Gly Tyr Asp Ala Lys Thr Glu Asp Ala Phe Glu Thr Ala Leu
            500                 505                 510

Ala Arg Ala Leu Ala Glu Thr Gly Cys Pro Ser Leu Ile Asn Val His
        515                 520                 525

Leu Ser Pro Asp Asp Ala Ser Pro Ala Met Arg Arg Leu Thr Glu Arg
    530                 535                 540

Leu Ser His Arg Val Gly Asn Gln
545                 550

<210> SEQ ID NO 64
<211> LENGTH: 1659
<212> TYPE: DNA
<213> ORGANISM: Methylohalobius crimeensis

<400> SEQUENCE: 64
atggccacgc gcaactcgac gacctcgatc ggcgagtatc tcctccagcg cctgcacgag      60
gccggcgccc accacatctt cggcgtcccg ggcgattata tcctgaaatt ctatgaacag     120
atctcgcagg gccggtccg ccacatcggc accgcgcg aagacaccgc ggcgttcgcg     180
gcggacggct atgcccggtg ccagggcatc ggcgcgatgg ccatcaccta cggcgtgggc     240
gccctcaacg tggtgaatgc cgtcgcgggc gcgtacgccg aaagctcgcc ggtggtcgtg     300
atctcgggcg ccccggcgt gtgggaacag cgcgaggacc cgctgctgca ccaccgcttc     360
ggcccctaca cgttccagcg ggagatcttc gaccggatca cctgtgccac cacggtcctg     420
gacgatccga tcacggcgtt ccgccagatc gatcgcacga tcgccgcggc gcagcgcgaa     480
cataagccgg tctacatcga actgccgcgc gatcgggtca cggtggccgg cgtgccgctc     540
ccggccgtcg cggaggcgac gccccaggaa acgtccgacg ccgccaccct ggacgaggcc     600
gtggccgaaa cgctggccct cctcgcccag gccaagagcc ccgtgctgat cgcgggcgtg     660
gaggtccacc gctgcggcct ccaggatgcg ctcgtcgacc tggtcgtccg cgcgggcctg     720
ccggtcgcgg ccacccctgac gggcaaatcc gtcgtgggcg aacgccaccc ggcgtatatc     780
ggcgtctacg agggcgccgc gtcgtccgaa cacacccgcc agatggtgga acgcgcggac     840
gtgctcatca tgctcggcgt gacgctgaac gacgtggaca ccggcgtcta cggcgaaac     900 ctggaccccc atcgcctggt ccgcgcgtcc cagggcgagg tgaacatccg ctaccatcgg     960
tatccgcgcg tccagctgca ggacttcatc ggcgccctcg cccgccaggt cagccccgc    1020 cgcgaggccc tgccgtccca gcccttcgtc gatagcggcc ccgccttccc cgtcccgggc    1080
caggcgatga ccacggcgcg gctcatcgcc cgcctgaact gcgccctcac ccccgaaatg    1140
atcgtggtgt ccgatgtggg cgattgcctg ttcgccgcca tcgaactccg ggtctgcgaa    1200
cggagcgagt tcctggcctc cgcctactat cgacgatgg gcttcgcggt gccggccgcc    1260
ctgggcgccc aggtcgcgcg gccggatcgg cgggccctga tcctggtggg cgacggcgcc    1320
ttccagatga cgggcaccga gctgagcacc cacgcccgcc tgaacctggc cgcgatcatc    1380
atcgtcttca caacgccgg ctacagcacg gagcgcaata tcctggaggg cccgttcaat    1440
```

-continued

```
gacatcgcgg cctggcggtt cgaccgcctc ggcgaagtgt tcggcccct gcatggctac    1500 gacgccaaga cggaagatgc gttcgagacg gcgctcgccc gcgccctggc cgagacgggc    1560
tgcccgtcgc tcatcaatgt gcatctgtcc ccggacgacg cctcgccggc catgcgccgc    1620
ctgacggagc ggctgtccca tcgcgtgggc aatcagtga                          1659
```

<210> SEQ ID NO 65
<211> LENGTH: 544
<212> TYPE: PRT
<213> ORGANISM: Methylobacter marinus

<400> SEQUENCE: 65

```
Met Ser Ser Asn Pro Ser Ile Gly His Tyr Leu Leu Thr Arg Leu Tyr
1               5                   10                  15

Glu Ser Gly Val His His Ile Phe Gly Val Pro Gly Asp Tyr Ile Leu
            20                  25                  30

Arg Phe Tyr Gln Gln Leu Ser Glu Ser Pro Val Gln His Ile Gly Thr
        35                  40                  45

Thr Arg Glu Asp Thr Ala Ala Phe Ala Thr Asp Ala Tyr Ala Arg Cys
    50                  55                  60

Arg Gly Leu Gly Ala Met Ala Val Thr Tyr Gly Val Gly Ala Leu Asn
65                  70                  75                  80

Val Val Asn Ala Val Ala Gly Ala His Ala Glu Ser Ser Pro Ile Val
                85                  90                  95

Val Ile Ser Gly Ala Pro Gly Ile Lys Glu Arg Arg Glu His Pro Leu
            100                 105                 110

Leu His His Arg Phe Gly Pro Phe Arg Leu Gln Arg Glu Ile Phe Glu
        115                 120                 125

Arg Ile Thr Cys Ala Val Ala Val Leu Asp Asp Pro Tyr Thr Ala Phe
    130                 135                 140

Arg Gln Ile Asp Arg Val Leu Ala Ala Ala Arg Glu His Cys Lys Pro
145                 150                 155                 160

Val Tyr Ile Glu Leu Pro Arg Asp Arg Val Asp Thr Glu Gly Tyr Pro
                165                 170                 175

Ile Pro Ser Glu Ser Leu Pro Ala Pro Ala Ser Asp Ala Ala Ser Leu
            180                 185                 190

Asn Glu Ala Val Glu Glu Ala Leu Gln Leu Leu Asp Glu Ala Ala Ser
        195                 200                 205

Pro Val Leu Val Ala Gly Val Glu Leu His Arg Arg Gly Leu Gln Asp
    210                 215                 220

Gln Leu Leu Ser Leu Val Asp Lys Thr His Leu Pro Val Ala Ala Thr
225                 230                 235                 240

Leu Thr Gly Lys Ser Val Leu Gly Glu Arg His Pro Cys Tyr Leu Gly
                245                 250                 255

Ile Tyr Glu Gly Ala Met Gly Ser Pro Leu Ala Arg Asp Arg Val Glu
            260                 265                 270

Gln Ala Asp Phe Leu Leu Met Leu Gly Val Thr Leu Asn Asp Val Asp
        275                 280                 285

Leu Gly Ile Phe Thr Ala Arg Leu Asp Ala Asn Arg Ile Ile Arg Ala
    290                 295                 300

Ser Gln Asp Glu Val Ile Ile His His Arg Tyr Pro Gln Val Leu
305                 310                 315                 320

Leu Arg Asp Phe Val Ser Met Leu Asn Glu Arg Met Thr Pro Arg Pro
                325                 330                 335
```

| | | | | | | | | | | | |
|---|---|---|---|---|---|---|---|---|---|---|---|
|Gln|Thr|Gly|Pro|Ala|Val|Ala|Ala|Lys|Pro|Ala|Ala|Phe|Asp|Phe|Pro|
| | |340| | | |345| | | |350| |

Val Lys Gly Gln Pro Met Lys Ile Ile Arg Leu Ile Ala Arg Leu Asn
    355                 360                 365

Arg Phe Leu Thr Pro Asp Met Val Val Ser Asp Val Gly Asp Cys
370                 375                 380

Leu Phe Ser Ala Ile Asp Leu Arg Val His Glu Asn Ser Glu Phe Leu
385                 390                 395                 400

Ala Ser Ala Tyr Tyr Thr Ser Met Gly Phe Ala Val Pro Ala Ala Leu
                405                 410                 415

Gly Ala Gln Ile Ala Arg Pro Thr Arg Arg Thr Leu Val Leu Val Gly
            420                 425                 430

Asp Gly Ala Phe Gln Met Thr Gly Thr Glu Leu Ser Thr Ile Ala His
            435                 440                 445

Leu Gly Leu Asn Pro Ile Val Ile Val Phe Asn Asn Lys Gly Tyr Ser
    450                 455                 460

Thr Glu Arg Tyr Ile Leu Asp Gly Pro Phe Asn Asp Ile Pro Ala Trp
465                 470                 475                 480

Gln Phe Glu Arg Leu Gly Glu Leu Phe Gly Pro Leu Thr Gly Tyr Ala
                485                 490                 495

Ala Ser Thr Glu Asp Glu Phe Glu Asp Cys Leu Asn Gln Ala Leu Ala
            500                 505                 510

Gln Arg Ser Ser Pro Ser Leu Ile Asn Val His Leu Ser Pro Asp Asp
        515                 520                 525

Pro Ser Ala Ala Met Arg Gly Leu Ala Glu His Leu Gly Lys Arg Val
    530                 535                 540

<210> SEQ ID NO 66
<211> LENGTH: 1635
<212> TYPE: DNA
<213> ORGANISM: Methylobacter marinus

<400> SEQUENCE: 66

```
atgagcagca acccgtcgat cggccactac ctgctcacgc ggctgtacga atccggcgtg      60
caccacatct tcggcgtccc gggcgactac atcctccgct tctaccagca gctgagcgag     120
agcccggtgc agcatatcgg caccacgcgc gaagacacgg ccgccttcgc gaccgatgcg     180
tatgcccgct gtcggggcct gggcgcgatg gccgtgacct acggcgtcgg cgccctcaat     240
gtggtcaacg ccgtggcggg cgcccatgcc gagtcgagcc catcgtggt catctccggc      300
gcccccggca tcaaggaacg ccgggaacac cccctgctgc atcaccgctt cggcccgttc     360
cgcctgcagc gcgagatctt cgaacggatc acctgcgccg tcgcggtgct ggatgacccc     420
tataccgcct tccggcagat cgaccgggtc ctggcggcgg cgcgggagca ctgcaagccc     480
gtctacatcg agctgccgcg cgatcgcgtg gataccgagg gctatccgat cccgtcggag     540
tccctgccgg cccccgcctc cgacgccgcg agcctcaacg aagccgtgga ggaagccctg     600
cagctcctcg atgaggccgc gtcgccggtg ctggtcgccg gcgtggaact gcaccgccgg     660
ggcctccagg atcagctcct ctcgctggtg gataaaaccc atctgccggt cgccgccacg     720
ctcaccggca gtccgtcct gggcgagcgg cacccgtgtt atctgggcat ctacgagggc     780
gcgatgggct cccccctggc gcgggaccgc gtcgagcagg ccgatttcct gctgatgctg     840
ggcgtcacgc tgaacgatgt ggacctcggc atcttcaccg cccgcctcga cgccaatcgc     900
atcatccggg cctcccagga cgaagtcatc atccaccacc accgctatcc gcaggtcctc     960
```

```
ctgcgggact tcgtgtccat gctgaacgaa cggatgaccc cgcgccccca gacgggcccg    1020
gccgtcgccg cgaagccggc cgccttcgat ttcccggtca aaggccagcc gatgaagatc    1080
atccggctga tcgcccggct gaatcggttc ctcaccccgg acatggtcgt ggtcagcgac    1140
gtgggcgatt gcctgttcag cgcgatcgac ctgcgggtgc acgaaaacag cgagttcctc    1200
gcctcggcct actacaccag catgggcttc gcggtcccgg ccgcgctggg cgcccagatc    1260
gcccgcccca cccggcgcac gctggtcctc gtgggcgacg gcgcgttcca gatgaccggc    1320
accgagctct cgaccatcgc gcacctcggc ctgaacccga tcgtgatcgt cttcaataac    1380
aagggctact cgaccgaacg ctatatcctg gatgggcccgt tcaatgatat cccggcctgg    1440
cagttcgagc gcctgggcga actcttcggc ccgctgaccg gctatgccgc cagcaccgag    1500
gacgagttcg aagattgtct gaaccaggcc ctggcccagc ggtcgagccc ctccctcatc    1560
aacgtccacc tctccccgga cgatccgagc gccgccatgc ggggcctcgc cgaacatctg    1620
ggcaagcgcg tctga                                                     1635
```

<210> SEQ ID NO 67
<211> LENGTH: 549
<212> TYPE: PRT
<213> ORGANISM: Methylobacter luteus

<400> SEQUENCE: 67

```
Met Glu Val His Leu Met Ser Ser Asn Pro Ser Ile Gly His Tyr Leu
1               5                   10                  15

Leu Ala Arg Leu Tyr Glu Ser Gly Val His His Ile Phe Gly Val Pro
            20                  25                  30

Gly Asp Tyr Ile Leu Arg Phe Tyr Gln Gln Leu Ser Glu Ser Pro Ile
        35                  40                  45

Gln His Ile Gly Thr Thr Arg Glu Asp Thr Ala Ala Phe Ala Thr Asp
    50                  55                  60

Ala Tyr Ala Arg Cys Arg Gly Leu Gly Ala Met Ala Val Thr Tyr Gly
65                  70                  75                  80

Val Gly Ala Leu Asn Val Val Asn Gly Val Ala Gly Ala Tyr Ala Glu
                85                  90                  95

Ser Ser Pro Val Val Ile Ser Gly Ala Pro Gly Ile Lys Glu Arg
            100                 105                 110

His Glu His Pro Leu Leu His Arg Phe Gly Pro Phe Arg Leu Gln
        115                 120                 125

His Glu Ile Phe Glu Arg Ile Thr Cys Ala Thr Ala Val Leu Asp Asp
    130                 135                 140

Pro Tyr Met Ala Phe Arg Gln Ile Asp Arg Val Leu Ala Ala Ala Arg
145                 150                 155                 160

Glu His Cys Lys Pro Val Tyr Ile Glu Leu Pro Arg Asp Arg Val Asp
                165                 170                 175

Val Glu Gly Tyr Pro Met Pro Ser Glu Ser Met Pro Ala Pro Ala Ser
            180                 185                 190

Asp Ala Glu Ser Leu Asn Glu Ala Val Glu Glu Thr Leu Gln Leu Leu
        195                 200                 205

Gly Lys Ala Ala Ser Pro Val Leu Ile Ala Gly Val Glu Leu His Arg
    210                 215                 220

Arg Gly Leu Gln Asp Lys Leu Leu Ser Leu Val Asp Lys Thr His Leu
225                 230                 235                 240

Pro Val Ala Ala Ser Leu Thr Gly Lys Ser Val Leu Gly Glu Arg His
                245                 250                 255
```

```
Pro Cys Tyr Leu Gly Ile Tyr Glu Gly Ala Met Gly Ser Ser Leu Ala
            260                 265                 270

Arg Asp Ser Val Glu Gln Ser Asp Phe Leu Leu Met Leu Gly Val Thr
        275                 280                 285

Met Asn Asp Ile Asp Leu Gly Ile Phe Thr Ala Lys Leu Asp Ala Asn
    290                 295                 300

Arg Ile Ile Arg Ala Thr Gln Asp Glu Val Ile Ile His His His Arg
305                 310                 315                 320

Tyr Pro His Val Leu Leu Arg Asp Phe Val Thr Val Leu Asn Glu Arg
            325                 330                 335

Ile Thr Pro Arg Pro Gly Ile Arg Pro Ala Val Ala Ala Glu Pro Ala
            340                 345                 350

Ala Phe Asp Phe Pro Val Lys Asp Gln Pro Met Lys Ile Leu Arg Leu
            355                 360                 365

Ile Glu Arg Leu Asn Arg Phe Leu Thr Pro Asp Met Ala Val Val Ser
            370                 375                 380

Asp Val Gly Asp Cys Leu Phe Ala Ala Ile Asp Leu Arg Val His Glu
385                 390                 395                 400

Asn Ser Glu Phe Leu Ala Ser Ala Tyr Tyr Thr Ser Met Gly Phe Ala
            405                 410                 415

Val Pro Ala Ala Leu Gly Ala Gln Ile Ala Asn Pro Thr Arg Arg Thr
            420                 425                 430

Leu Val Leu Val Gly Asp Gly Ala Phe Gln Met Thr Gly Thr Glu Leu
            435                 440                 445

Ser Thr Ile Ala Arg Phe Gly Leu Asn Pro Ile Val Ile Val Phe Asn
            450                 455                 460

Asn Cys Gly Tyr Ser Thr Glu Arg Tyr Ile Leu Asp Gly Pro Phe Asn
465                 470                 475                 480

Asp Ile Ala Cys Trp Gln Phe Glu Arg Leu Ser Glu Val Phe Gly Pro
            485                 490                 495

Leu Ser Gly Tyr Ser Ala Arg Thr Glu Asp Glu Phe Glu Asn Cys Leu
            500                 505                 510

Thr Gln Ala Phe Ala Gln Gln Ser Ser Pro Ser Leu Ile Asn Val His
            515                 520                 525

Leu Pro Pro Asp Asp Pro Ser Ala Ala Met Arg Gly Leu Ala Glu His
            530                 535                 540

Leu Gly Lys Arg Val
545

<210> SEQ ID NO 68
<211> LENGTH: 1650
<212> TYPE: DNA
<213> ORGANISM: Methylobacter luteus

<400> SEQUENCE: 68
atggaggtgc atctgatgtc ctccaacccg tccatcggcc attatctgct cgcccgcctg     60
tacgagtccg gcgtgcatca catcttcggc gtccccggcg actacatcct gcgcttctac    120
cagcagctca gcgagtcccc gatccagcac atcggcacca cgcgcgagga caccgccgcc    180
ttcgcgaccg acgcctacgc cgctgccgg ggcctgggcg cgatggccgt gacctacggc    240
gtgggcgccc tgaacgtcgt gaacggcgtg gccggcgcgt acgcggaatc ctcgccggtc    300
gtggtgatct ccggcgcccc gggcatcaag gaacgccatg aacatccgct gctgcatcat    360
cgcttcggcc cgttccgcct gcagcatgaa atcttcgaac gcatcacctg cgcgacggcg    420
```

```
gtcctggacg atccctacat ggcgttccgg cagatcgacc gggtgctggc cgccgcccgc      480
gagcactgca agcccgtgta tatcgagctg ccgcgcgacc gggtggatgt cgaaggctat      540
ccgatgccga gcgagagcat gccggccccg gcctccgacg cggaaagcct gaacgaagcg      600
gtcgaagaaa cgctgcagct gctgggcaag gccgcgtcgc ccgtgctgat cgcgggcgtc      660
gaactgcacc gccgcggcct ccaggacaaa ctgctctccc tggtcgacaa gacccatctc      720
ccggtggccg cctcgctgac cggcaaatcg gtcctgggcg aacgccaccc gtgctatctg      780
ggcatctatg aaggcgcgat gggctcgtcc ctggcccggg actccgtgga gcagtcggac      840
ttcctcctga tgctgggcgt caccatgaac gacatcgatc tgggcatctt caccgcgaag      900
ctggacgcga accgcatcat ccgcgccacg caggatgagg tcatcatcca ccatcatcgc      960
tatccccacg tcctgctgcg ggacttcgtc accgtcctga atgagcgcat cacgccccgc     1020
ccgggcatcc gcccggccgt cgcggcggag ccggccgcct tcgacttccc ggtcaaggac     1080
cagcccatga aaatcctccg gctgatcgaa cggctcaacc gcttcctgac ccccgacatg     1140
gccgtcgtct ccgatgtcgg cgattgcctc ttcgcggcga tcgacctccg ggtgcacgag     1200
aactcggagt tcctggcgtc ggcgtattat accagcatgg gcttcgccgt gcccgcggcg     1260
ctcggcgccc agatcgcgaa cccgacccgc cgcacgctgg tgctggtcgg cgacggcgcc     1320
ttccagatga ccggcaccga actgtccacc atcgcccggt tcggcctgaa cccgatcgtg     1380
atcgtcttca ataactgtgg ctattcgacc gagcggtaca tcctggatgg ccccttcaac     1440
gatatcgcct gctggcagtt cgaacggctg agcgaggtgt tcggcccgct ctcgggctat     1500
tcggcccgga cggaggatga gttcgaaaac tgcctgaccc aggccttcgc ccagcagtcc     1560
tcgccgtccc tcatcaacgt ccacctcccc ccggatgacc cgagcgcggc catgcgcggc     1620
ctcgcggaac acctcggcaa gcgcgtctga                                     1650
```

<210> SEQ ID NO 69
<211> LENGTH: 542
<212> TYPE: PRT
<213> ORGANISM: Lamprocystis purpurea

<400> SEQUENCE: 69

```
Met Gly Asp Tyr Leu Leu Arg Leu Lys Glu Ala Gly Val Asp His
1               5                  10                  15

Cys Phe Gly Val Pro Gly Asp Tyr Val Leu Arg Phe Tyr Asp Arg Leu
                20                  25                  30

Cys Arg Ser Asp Ile Arg His Ile Gly Thr Thr Arg Glu Asp Thr Ala
            35                  40                  45

Ala Phe Ala Ala Asp Gly Tyr Ala Arg Ser Arg Gly Leu Gly Ala Leu
        50                  55                  60

Ala Val Thr Tyr Gly Val Gly Ala Leu Asn Val Val Asn Ala Val Ala
65                  70                  75                  80

Gly Ala Asn Ala Glu Ser Ser Pro Val Val Ile Ser Gly Ala Pro
                85                  90                  95

Gly Val Ala Glu Gln Arg Asp Asp Pro Gln Leu His His Arg Phe Gly
            100                 105                 110

Pro Phe Arg Phe Gln Arg Glu Ile Phe Glu Arg Ile Thr Cys Ala Cys
        115                 120                 125

Ala Val Leu Asp Asp Pro Tyr Thr Ala Leu Arg Glu Ile Asp Arg Thr
    130                 135                 140

Leu Asp Ala Ala Arg Arg Tyr Ser Arg Pro Val Tyr Ile Glu Leu Pro
```

```
            145                 150                 155                 160
Arg Asp Arg Val Asp Thr Pro Ala Phe Pro Ile Pro His Glu Pro Glu
                165                 170                 175

Glu Glu Ala Gly Ser Asp Pro Glu Ala Leu Ala Glu Ala Val Ala Glu
                180                 185                 190

Thr Leu Ala Leu Val Gly Arg Ala Gln Ala Pro Val Ile Leu Ala Gly
                195                 200                 205

Val Glu Leu His Arg Arg Gly Leu Gln Asp Leu Leu Ala Gly Phe Val
210                 215                 220

Leu Lys Ala His Leu Pro Val Ala Ala Thr Leu Thr Gly Lys Ser Val
225                 230                 235                 240

Val Ala Glu Arg Gln Pro Gly Tyr Leu Gly Val Tyr Glu Gly Ala Met
                245                 250                 255

Gly Pro Glu Gly Ala Arg Arg Val Val Glu Glu Ala Asp Leu Leu Leu
                260                 265                 270

Leu Leu Gly Val Thr Pro Asn Asp Ile Asp Leu Gly Ile Asn Thr Ala
                275                 280                 285

Arg Leu Asp Pro Ala Arg Thr Val Arg Ala Gly Gln Glu Glu Ile Trp
                290                 295                 300

Val His Arg His Arg Tyr Pro His Val His Leu Arg Asp Phe Leu Ala
305                 310                 315                 320

Ala Leu Thr Asp Ala Val Val Pro His Pro Gly Pro Leu Pro Asp Val
                325                 330                 335

Pro Gly Pro Val Gly Ala Pro Asp Phe Pro Gln Pro Gly Gln Pro Met
                340                 345                 350

Thr Met Ala Arg Met Met Ala Arg Leu Asn Asp Phe Leu Thr Pro Asp
                355                 360                 365

Met Gln Val Val Ala Asp Ser Gly Asp Cys Leu Phe Ala Ser Val Asp
                370                 375                 380

Leu Arg Val His Ala Arg Ser Glu Phe Leu Ala Ser Ala Tyr Tyr Thr
385                 390                 395                 400

Thr Met Gly Phe Ala Val Pro Ala Ala Leu Gly Ala Gln Val Ala Asn
                405                 410                 415

Pro Gly Arg Arg Pro Leu Val Leu Val Gly Asp Gly Ala Phe Gln Met
                420                 425                 430

Thr Gly Thr Glu Leu Ser Thr Ala Ala Arg Leu Gly Leu Asp Pro Ile
                435                 440                 445

Val Ile Ile Gly Asn Asn Arg Gly Tyr Thr Thr Glu Arg Phe Ile Leu
450                 455                 460

Glu Gly Pro Phe Asn Asp Ile Ala Asp Trp Arg Phe His Arg Leu Gly
465                 470                 475                 480

Glu Leu Phe Gly Pro Leu Arg Gly Phe Ser Ala Pro Thr Glu Asp Ala
                485                 490                 495

Phe Asp Ala Ala Leu Gly Ala Ala Leu Ala Phe Arg Asp Gly Pro Ser
                500                 505                 510

Val Ile Glu Val Ala Leu Arg Pro Asp Asp Cys Ser Ala Ala Leu Thr
                515                 520                 525

Arg Leu Ser Glu Arg Leu Arg Asp Val Val Gln Gln Ser Ala
530                 535                 540

<210> SEQ ID NO 70
<211> LENGTH: 1629
<212> TYPE: DNA
<213> ORGANISM: Lamprocystis purpurea
```

<400> SEQUENCE: 70

```
atgggcgact acctcctgct ccgcctgaag gaagcgggcg tcgaccactg cttcggcgtc    60
cccggcgact acgtcctgcg gttctacgat cggctctgcc ggtcggacat ccggcacatc   120
ggcaccaccc gcgaggacac cgcggccttc gcggccgacg gctacgcccg gtcccgcggc   180
ctgggcgccc tggccgtgac gtatggcgtg ggcgccctca acgtggtcaa cgcggtcgcc   240
ggcgccaacg cggagtcctc cccggtcgtc gtgatctccg cgcccccggg cgtcgcggaa   300
cagcgcgacg atccccagct gcaccatcgg ttcggcccgt ccggttccaa gcgcgagatc   360
ttcgaacgca tcacctgcgc gtgtgccgtg ctcgacgacc cgtacaccgc cctgcgcgag   420
atcgaccgca cgctcgacgc ggcgcggcgg tacagccggc ccgtgtatat cgaactcccg   480
cgcgaccggg tcgacacgcc cgccttcccc atcccccacg agccggaaga ggaagccggc   540
agcgacccgg aggccctggc cgaggcggtc gccgaaaccc tggcgctcgt cggccgcgcc   600
caggcccccg tcatcctggc cggcgtggag ctgaccgcc gcggcctgca ggacctcctg    660
gccggcttcg tgctgaaggc ccacctcccg gtggccgcga cgctgacggg caagtcggtg   720
gtcgccgagc gccagccggg ctacctgggc gtgtacgagg cgcgatggg cccggaaggc    780
gcccgccgcg tcgtggaaga agccgacctg ctgctcctgc tgggcgtgac cccgaacgac   840
atcgacctgg gcatcaacac cgccggctg accccgccc ggaccgtccg ggccggccag     900
gaagaaatct gggtccatcg gcaccgctac ccgcatgtgc acctgcggga tttcctggcc   960
gcgctgacgg atgccgtggt gccccacccc ggccccctgc cggatgtccc cggcccggtc  1020
ggcgccccgg acttcccccca gccgggccag cccatgacga tggcccgcat gatggcccgc  1080
ctgaacgact tcctgacccc cgacatgcag gtggtggccg actccggcga ctgtctgttc  1140
gcgtccgtcg acctgcgcgt ccatgcccgc agcgagttcc tggcctcggc ctattacacg  1200
acgatgggct cgccgtccc ggccgcgctc ggcgcccagg tcgccaaccc cggccgccgc   1260
ccgctcgtgc tggtgggcga cggcgccttc cagatgaccg gcacggagct gtcgaccgcc  1320
gcccgcctgg gcctcgatcc gatcgtcatc atcggcaata atcgcggcta caccaccgaa  1380
cgcttcatcc tggaaggccc gttcaacgac atcgccgact ggcggttcca tcgcctgggc  1440
gaactgttcg gcccgctgcg gggcttctcg gcccccacgg aagacgcctt cgacgccgcc  1500
ctgggcgccg cctggccttt ccgggacggc ccctccgtca tcgaggtggc gctgcgcccg  1560
gacgactgct ccgcggccct gacccggctc tccgaacgcc tgcgcgatgt ggtgcagcag  1620
agcgcctga                                                          1629
```

<210> SEQ ID NO 71
<211> LENGTH: 551
<212> TYPE: PRT
<213> ORGANISM: Andreprevotia chitinilytica

<400> SEQUENCE: 71

```
Met His Met Arg Glu Thr Asp Met Asp Thr Met Gly Gly Tyr Leu Leu
1               5                   10                  15

Gln Ala Leu His Arg Glu Gly Val Arg His Val Phe Gly Val Pro Gly
            20                  25                  30

Asp Tyr Ile Leu Arg Trp Tyr Gln Leu Leu Ser Gln Ser Asn Leu Lys
        35                  40                  45

His Val Gly Thr Ser Arg Glu Asp Cys Ala Ala Phe Ala Ala Asp Gly
    50                  55                  60
```

-continued

```
Tyr Ala Arg Cys His Gly Leu Gly Ala Leu Ala Val Thr Tyr Gly Val
 65                  70                  75                  80

Gly Ala Leu Asn Val Val Asn Ala Val Ala Gly Ala Asn Ala Glu Ser
                 85                  90                  95

Ser Pro Val Val Val Ile Ser Gly Ala Pro Gly Val Ala Glu Gln Arg
            100                 105                 110

Gln Asn Pro Leu Leu His His Arg Phe Gly Pro Phe Cys Phe Gln Arg
            115                 120                 125

Glu Ile Phe Glu Arg Met Thr Cys Tyr Ala Ala Leu Asp Asp Pro
130                 135                 140

Leu Leu Ala Arg Arg Gln Ile Asp Arg Ala Leu Glu Leu Ala Gln Leu
145                 150                 155                 160

His His Lys Pro Val Tyr Leu Glu Leu Pro Arg Asp Leu Val Asp Ala
            165                 170                 175

Glu Leu Pro Pro Ala Leu Ser Pro Pro Thr Ser Ser Ala Pro Ile Ser
            180                 185                 190

Asp Trp Asp Ala Leu Glu Glu Ala Val Ala Glu Thr Leu Ser Leu Leu
            195                 200                 205

Ala Lys Ala Lys Ser Ala Ala Val Leu Ala Gly Ser Glu Leu His Arg
210                 215                 220

Tyr Gln Leu Gln Asp Glu Leu Thr Gln Leu Val Glu Arg Gly Ala Leu
225                 230                 235                 240

Pro Val Ala Ala Thr Leu Thr Gly Lys Ser Val Ile Ala Glu Arg His
                245                 250                 255

Pro Ala Tyr Met Gly Ile Tyr Glu Gly Ala Met Gly Gly Ala Arg Thr
            260                 265                 270

Arg Glu Leu Ile Glu Arg Ala Asp Val Leu Leu Leu Gly Ala Thr
            275                 280                 285

Leu Asn Asp Val Asp Leu Gly Ile Phe Thr Ala Lys Leu Asp Val Gln
290                 295                 300

His Met Val Gln Ala Thr Ala Asp Gly Val Gln Ile His His His Arg
305                 310                 315                 320

Tyr Thr Gly Val Pro Leu Gly Asp Tyr Val Arg Ala Leu Thr Ala Gly
                325                 330                 335

Ile Glu Arg Ser Gly Arg Ser Leu Pro Val Val Glu Pro Pro Leu Ala
            340                 345                 350

Ala Ile Gly Phe Pro Ile Thr Ser Gln Pro Met Thr Val Ala Arg Leu
            355                 360                 365

Ile Gly Arg Leu Asn Asp Thr Leu Pro Gln Asp Met Ile Val Val Cys
370                 375                 380

Asp Thr Gly Asp Cys Leu Phe Ala Ser Leu Glu Leu Arg Val His Ala
385                 390                 395                 400

Arg Thr Ala Phe Leu Ala Ser Ala Phe Tyr Thr Thr Met Gly Phe Ala
                405                 410                 415

Val Pro Ala Ser Leu Gly Ala Gln Leu Gly Ser Gly Arg Arg Pro Leu
            420                 425                 430

Val Leu Val Gly Asp Gly Ala Phe Gln Met Thr Gly Thr Glu Leu Ala
            435                 440                 445

Thr Ala Ala Trp Lys Gly Leu Asn Pro Ile Val Ile Val Phe Asn Asn
            450                 455                 460

Ala Gly Tyr Ser Thr Glu Arg Phe Ile Leu Asp Gly Pro Phe Asn Asp
465                 470                 475                 480

Ile Pro Ser Trp Gln Phe His Arg Leu Gly Glu Leu Phe Gly Pro Leu
```

485                 490                 495
Ala Gly Phe Asp Val His Asp Glu Glu Ser Phe Asp Ser Ala Trp Arg
            500                 505                 510

Ser Ala Leu Ala Gln Thr Asp Arg Pro Ser Leu Leu Asn Val His Leu
        515                 520                 525

Ala Pro Asp Asp Pro Ser Pro Ala Met Arg Arg Leu Gly Glu His Leu
    530                 535                 540

Gly Lys Arg Val Arg Ala Gly
545                 550

<210> SEQ ID NO 72
<211> LENGTH: 1656
<212> TYPE: DNA
<213> ORGANISM: Andreprevotia chitinilytica

<400> SEQUENCE: 72

| | | | | | |
|---|---|---|---|---|---|
| atgcacatgc | gggagacgga | catggatacg | atgggcggct | acctgctgca | ggccctgcat | 60 |
| cgcgagggcg | tccggcatgt | gttcggcgtg | ccgggcgact | acatcctgcg | ctggtatcag | 120 |
| ctgctctcgc | agagcaacct | gaagcacgtc | ggcacctcgc | gcgaagactg | cgccgcgttc | 180 |
| gccgccgacg | gctacgcgcg | gtgccacggc | ctgggcgccc | tggccgtcac | ctacggcgtc | 240 |
| ggcgccctga | acgtggtgaa | cgcggtggcc | ggcgcgaacg | cggagtccag | ccccgtggtg | 300 |
| gtcatcagcg | cgcccgggc | cgtcgcgaaa | cagcgccaga | cccgctgct | ccaccaccgc | 360 |
| ttcggcccgt | tctgcttcca | gcgcgaaatc | ttcgaacgca | tgacgtgcta | cgcggcggcg | 420 |
| ctcgacgatc | cctcctggc | gcggcgccag | atcgaccgcg | ccctggagct | ggcccagctc | 480 |
| catcacaagc | cggtctacct | cgaactgccg | cgggatctcg | tggatgcgga | actgccgccg | 540 |
| gccctctcgc | cgcccacctc | ctcggcgccc | atctcggatt | gggacgcgct | cgaagaagcg | 600 |
| gtcgcggaaa | ccctcagcct | cctggcgaag | gcgaaaagcg | ccgcggtcct | cgccggctcg | 660 |
| gagctgcacc | gctaccagct | gcaggacgag | ctgacgcagc | tcgtggaacg | ggcgcccctc | 720 |
| cccgtggccg | ccaccctgac | cggcaagtcc | gtgatcgccg | agcgccaccc | ggcctacatg | 780 |
| ggcatctacg | aaggcgcgat | gggcggcgcc | cgcacgcggg | aactgatcga | gcgggcggac | 840 |
| gtgctgctgc | tgctgggcgc | caccctcaat | gatgtggatc | tgggcatctt | caccgccaag | 900 |
| ctggatgtcc | agcacatggt | gcaggcgacc | gccgatggcg | tccagatcca | ccaccaccgc | 960 |
| tacaccggcg | tccccctcgg | cgactatgtg | cgggccctga | cggcgggcat | cgaacgctcg | 1020 |
| ggccgctccc | tccggtggt | ggaaccccc | ctggcggcca | tcggcttccc | gatcacctcg | 1080 |
| cagcccatga | ccgtggcccg | cctgatcggc | cgcctcaatg | ataccctgcc | gcaggacatg | 1140 |
| atcgtcgtct | gtgacaccgg | cgactgcctc | ttcgcctccc | tggagctccg | cgtccatgcc | 1200 |
| cgcaccgcct | tcctggcctc | ggcgttctac | acgacgatgg | gcttcgccgt | gcccgcctcg | 1260 |
| ctgggcgccc | agctcggctc | gggcggcgc | ccctggtgc | tggtgggcga | tggcgccttc | 1320 |
| cagatgacgg | gcaccgagct | ggccaccgcc | gcgtggaagg | cctgaaccc | catcgtcatc | 1380 |
| gtcttcaaca | cgccggcta | ctccaccgag | cgcttcatcc | tggacggccc | cttcaacgac | 1440 |
| atcccgtcgt | ggcagttcca | tcgcctgggc | gaactgttcg | gccgctggc | cggcttcgat | 1500 |
| gtccacgacg | aagagtcgtt | cgactccgcc | tggcgctcgg | ccctcgccca | gaccgatcgc | 1560 |
| ccgtcgctgc | tgaacgtgca | tctggccccc | gacgacccct | cgcccgcgat | gcggcggctg | 1620 |
| ggcgaacatc | tgggcaagcg | ggtgcgggcg | ggctga | | | 1656 |

<210> SEQ ID NO 73
<211> LENGTH: 548
<212> TYPE: PRT
<213> ORGANISM: Lactococcus lactis

<400> SEQUENCE: 73

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380
```

```
Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
        500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
        530                 535                 540

Gln Asn Lys Ser
545
```

<210> SEQ ID NO 74
<211> LENGTH: 1647
<212> TYPE: DNA
<213> ORGANISM: Lactococcus lactis

<400> SEQUENCE: 74

```
atgtacaccg taggagacta cctacttgac agactccatg agctgggcat agaggaaatc      60
ttcggagtcc cgggtgatta caacctgcag ttcctggacc agatcatcag ccacaaggac     120
atgaagtggg tgggcaacgc gaacgaactg aacgcgagct atatggcgga cggttatgcc     180
cgcaccaaga aggcagccgc gttcctcacc actttcggcg tgggcgaact cagcgccgtg     240
aacggcttgg caggcagcta tgcggaaaac ctgccggtgg tggaaatcgt cggctccccg     300
acctcgaagg tgcagaacga gggcaagttc gtgcatcata ccctggcgga cggggacttc     360
aagcatttca tgaagatgca cgaacccgtc accgctgccc gcacgctgct gaccgcggaa     420
aacgcgaccg tggagatcga ccgggtcctc tccgccctgc tgaaggaacg aagcccgtg      480
tacatcaatc tacccgtcga cgtagcagcc gccaaggccg aaaagccctc gctcccgctg     540
aagaaggaga actcgacgag caacacgagt gaccaggaaa tcctgaacaa gatccaggag     600
tcgttaaaga acgcgaagaa gccgatcgtc atcaccggcc atgagatcat cagcttcggc     660
cttgagaaga ccgtgacaca gttcatctcc aagaccaagc tgcccatcac caccctcaac     720
ttcggcaagt ccagcgtgga cgaagccctg ccgagcttcc tgggcatcta aacggcacc     780
ctgtcggaac ccaacctgaa ggagttcgtc gaaagcgcgg acttcatcct gatgctgggc     840
gtgaagctga ccgactcctc gacgggagcc ttcacccatc acctgaacga aaacaagatg     900
atctccctca catcgatga aggcaagatc ttcaacgagc gcatccaaaa cttcgacttc     960
gaaagcctga tctcctcgct gctggacctg tccgagatcg agtacaaggg caagtacatc    1020
gacaagaagc aggaagactt cgtgccgtcg aacgcgctgc tgtcgcagga ccgcctgtgg    1080
caggcggtcg aaaacctgac gcagtcaaac gaaaccatcg tcgccgaaca gggaacctcg    1140
```

```
ttcttcggtg cctcaagtat cttcctgaag tccaagtccc acttcatcgg ccagcccctg    1200
tggggctcga tcggctatac cttcccggca gcgctaggct cccagatcgc ggacaaggaa    1260
tcgcggcacc tgctcttcat cggcgacggc tccctgcagc tgaccgtcca ggagctgggc    1320
ctcgccatcc gggaaaagat caacccgatc tgcttcatca ttaacaacga cggctacacc    1380
gtggagcgcg agattcatgg cccgaaccag agctacaacg acatccccat gtggaactac    1440
tctaagctgc cggaatcgtt tggcgccacg gaggaccggg tggtcagcaa gatcgtccgg    1500
acggagaacg agttcgtctc ggtgatgaag gaagcgcagg cggaccccaa ccggatgtat    1560
tggatcgagc tcatcttggc caaggagggc gctccgaagg tcctgaagaa gatgggcaag    1620
ctcttcgccg aacagaacaa gtcgtaa                                        1647
```

<210> SEQ ID NO 75
<211> LENGTH: 570
<212> TYPE: PRT
<213> ORGANISM: Lactococcus lactis

<400> SEQUENCE: 75

```
Met Gly Ser Ser His His His His His His Ser Ser Gly Leu Val Pro
1               5                   10                  15

Arg Gly Ser His Met Ala Ser Met Tyr Thr Val Gly Asp Tyr Leu Leu
            20                  25                  30

Asp Arg Leu His Glu Leu Gly Ile Glu Glu Ile Phe Gly Val Pro Gly
        35                  40                  45

Asp Tyr Asn Leu Gln Phe Leu Asp Gln Ile Ile Ser Arg Glu Asp Met
    50                  55                  60

Lys Trp Ile Gly Asn Ala Asn Glu Leu Asn Ala Ser Tyr Met Ala Asp
65                  70                  75                  80

Gly Tyr Ala Arg Thr Lys Lys Ala Ala Ala Phe Leu Thr Thr Phe Gly
                85                  90                  95

Val Gly Glu Leu Ser Ala Ile Asn Gly Leu Ala Gly Ser Tyr Ala Glu
            100                 105                 110

Asn Leu Pro Val Val Glu Ile Val Gly Ser Pro Thr Ser Lys Val Gln
        115                 120                 125

Asn Asp Gly Lys Phe Val His His Thr Leu Ala Asp Gly Asp Phe Lys
    130                 135                 140

His Phe Met Lys Met His Glu Pro Val Thr Ala Ala Arg Thr Leu Leu
145                 150                 155                 160

Thr Ala Glu Asn Ala Thr Tyr Glu Ile Asp Arg Val Leu Ser Gln Leu
                165                 170                 175

Leu Lys Glu Arg Lys Pro Val Tyr Ile Asn Leu Pro Val Asp Val Ala
            180                 185                 190

Ala Ala Lys Ala Glu Lys Pro Ala Leu Ser Leu Glu Lys Glu Ser Ser
        195                 200                 205

Thr Thr Asn Thr Thr Glu Gln Val Ile Leu Ser Lys Ile Glu Glu Ser
    210                 215                 220

Leu Lys Asn Ala Gln Lys Pro Val Val Ile Ala Gly His Glu Val Ile
225                 230                 235                 240

Ser Phe Gly Leu Glu Lys Thr Val Thr Gln Phe Val Ser Glu Thr Lys
                245                 250                 255

Leu Pro Ile Thr Thr Leu Asn Phe Gly Lys Ser Ala Val Asp Glu Ser
            260                 265                 270

Leu Pro Ser Phe Leu Gly Ile Tyr Asn Gly Lys Leu Ser Glu Ile Ser
        275                 280                 285
```

```
Leu Lys Asn Phe Val Glu Ser Ala Asp Phe Ile Leu Met Leu Gly Val
    290                 295                 300

Lys Leu Thr Asp Ser Ser Thr Gly Ala Phe Thr His His Leu Asp Glu
305                 310                 315                 320

Asn Lys Met Ile Ser Leu Asn Ile Asp Glu Gly Ile Ile Phe Asn Lys
                    325                 330                 335

Val Val Glu Asp Phe Asp Phe Arg Ala Val Val Ser Ser Leu Ser Glu
                340                 345                 350

Leu Lys Gly Ile Glu Tyr Glu Gly Gln Tyr Ile Asp Lys Gln Tyr Glu
                355                 360                 365

Glu Phe Ile Pro Ser Ser Ala Pro Leu Ser Gln Asp Arg Leu Trp Gln
    370                 375                 380

Ala Val Glu Ser Leu Thr Gln Ser Asn Glu Thr Ile Val Ala Glu Gln
385                 390                 395                 400

Gly Thr Ser Phe Phe Gly Ala Ser Thr Ile Phe Leu Lys Ser Asn Ser
                    405                 410                 415

Arg Phe Ile Gly Gln Pro Leu Trp Gly Ser Ile Gly Tyr Thr Phe Pro
                420                 425                 430

Ala Ala Leu Gly Ser Gln Ile Ala Asp Lys Glu Ser Arg His Leu Leu
                435                 440                 445

Phe Ile Gly Asp Gly Ser Leu Gln Leu Thr Val Gln Glu Leu Gly Leu
    450                 455                 460

Ser Ile Arg Glu Lys Leu Asn Pro Ile Cys Phe Ile Ile Asn Asn Asp
465                 470                 475                 480

Gly Tyr Thr Val Glu Arg Glu Ile His Gly Pro Thr Gln Ser Tyr Asn
                    485                 490                 495

Asp Ile Pro Met Trp Asn Tyr Ser Lys Leu Pro Glu Thr Phe Gly Ala
                500                 505                 510

Thr Glu Asp Arg Val Val Ser Lys Ile Val Arg Thr Glu Asn Glu Phe
                515                 520                 525

Val Ser Val Met Lys Glu Ala Gln Ala Asp Val Asn Arg Met Tyr Trp
    530                 535                 540

Ile Glu Leu Val Leu Glu Lys Glu Asp Ala Pro Lys Leu Leu Lys Lys
545                 550                 555                 560

Met Gly Lys Leu Phe Ala Glu Gln Asn Lys
                565                 570

<210> SEQ ID NO 76
<211> LENGTH: 1713
<212> TYPE: DNA
<213> ORGANISM: Lactococcus lactis

<400> SEQUENCE: 76
atgggctcgt cccatcatca tcaccaccat tccagcggcc tggtcccgcg cggcagccac      60
atggcctcga tgtacaccgt gggcgattac ctgctggacc ggctccacga actgggcatc     120
gaagagatct tcggcgtccc gggcgactat aacctccagt cctggatca gatcatctcc      180 cgcgaggaca tgaaatggat cggcaatgcg aacgagctga cgcctccta tatggccgac     240 ggctatgccc gcaccaaaaa agccgccgcc ttcctgacca cgttcggcgt gggcgaactg     300
tcggccatca acggcctggc cggctcctac gccgagaacc tgcccgtggt ggaaatcgtg     360
ggctcgccga cctcgaaggt ccagaacgac ggcaagttcg tgcaccacac gctcgcggac     420
ggcgacttca gcacttcat gaagatgcac gagccggtca ccgccgcccg cacccctgctg    480
```

```
acggccgaga acgcgaccta tgaaatcgac cgggtgctct cccagctcct gaaggagcgg    540
aagccggtgt acatcaacct ccccgtcgat gtggccgccg ccaaggccga gaaacccgcg    600
ctgagcctgg agaaggagtc ctccacgacc aacaccaccg aacaggtgat cctcagcaag    660
atcgaagaat ccctcaagaa cgcccagaaa cccgtggtga tcgcgggcca tgaggtgatc    720
tcgttcggcc tggagaaaac cgtcacccag ttcgtgagcg aaaccaagct ccccatcacc    780
accctcaact tcggcaagtc ggccgtggac gagtccctgc cgtccttcct gggcatctat    840
aatggcaaac tgtcggaaat cagcctgaaa aatttcgtcg aaagcgccga cttcatcctc    900
atgctgggcg tgaagctgac cgactcctcg accggcgcct tcacccacca cctcgatgaa    960
aacaagatga tctccctgaa catcgacgaa ggcatcatct tcaacaaggt ggtcgaagac    1020
ttcgacttcc gggccgtcgt gtcgagcctg tccgaactga aaggcatcga atatgaaggc    1080
cagtacatcg acaagcagta tgaagagttc atcccgtcgt cggcgccgct cagccaggat    1140
cgcctctggc aggccgtgga aagcctgacc cagtccaacg aaacgatcgt cgccgaacag    1200
ggcacctcgt tcttcggcgc cagcacgatc ttcctgaagt ccaactcccg gttcatcggc    1260
cagccgctgt ggggctcgat cggctacacg ttcccggccg cgctgggcag ccagatcgcc    1320
gacaaggaat cccgccacct cctgttcatc ggcgacggct ccctccagct gaccgtgcag    1380
gagctgggcc tgtcgatccg cgaaaagctg aatccgatct gcttcatcat caacaacgac    1440
ggctacacgg tcgaacggga gatccacggc ccgacgcagt cctacaacga catccccatg    1500
tggaactaca gcaaactccc ggaaaccttc ggcgccaccg aagaccgcgt cgtctcgaag    1560
atcgtgcgga ccgaaaacga gttcgtgtcc gtgatgaaag aggcgcaggc ggatgtgaac    1620
cggatgtact ggatcgaact ggtcctggag aaagaggacg ccccgaagct cctgaagaag    1680
atgggcaagc tcttcgccga gcagaacaaa tga                                1713
```

<210> SEQ ID NO 77
<211> LENGTH: 549
<212> TYPE: PRT
<213> ORGANISM: Streptococcus didelphis

<400> SEQUENCE: 77

```
Met Tyr Thr Val Gly Asp Tyr Leu Leu Asp Arg Leu Lys Glu Ile Gly
1               5                  10                  15

Ile Asp His Ile Phe Gly Val Pro Gly Asp Tyr Asn Leu Gln Phe Leu
            20                  25                  30

Asp Gln Ile Thr Ala Arg Asp Asp Leu Lys Trp Val Gly Asn Ala Asn
        35                  40                  45

Glu Leu Asn Ala Ser Tyr Met Ser Asp Gly Tyr Ala Arg Thr Lys Lys
    50                  55                  60

Ala Ala Ala Phe Val Thr Thr Phe Gly Val Gly Glu Leu Ser Ala Ile
65                  70                  75                  80

Asn Gly Leu Ala Gly Ser Phe Ala Glu Asn Val Pro Val Ile Glu Ile
                85                  90                  95

Val Gly Ser Pro Thr Thr Lys Val Gln Glu Ala Gly Lys Leu Val His
            100                 105                 110

His Thr Leu Gly Asp Gly Asn Phe Asn His Phe Gln Glu Met His Lys
        115                 120                 125

Ser Val Thr Val Ala Gln Val Lys Val Ser Ala Glu His Ala Gln Thr
    130                 135                 140

Asp Ile Asp Gln Val Leu Leu Ser Leu Leu Lys Glu Arg Lys Pro Val
145                 150                 155                 160
```

Tyr Ile Asn Leu Pro Ile Asp Val Ala Gln Met Pro Ala Gln Lys Pro
                165                 170                 175

Glu Ser Ala Leu Leu Val Glu Lys Val Ile Ser Glu Gln Asp Lys Ile
            180                 185                 190

Ile Leu Gln Ala Ile Glu Lys Gly Leu Lys Thr Ala Lys Gln Pro Leu
        195                 200                 205

Ile Met Val Gly His Glu Val Ala Ser Phe Gly Leu Glu Ala Thr Ile
    210                 215                 220

Asn Asn Phe Ile Lys Lys Lys Tyr Pro Val Thr Ser Leu Ser Leu
225                 230                 235                 240

Gly Lys Gly Ile Val Asn Glu Ser Pro Glu Thr Phe Leu Gly Ile Tyr
                245                 250                 255

Ser Gly Ala Leu Ser Pro Gln Ala Leu Lys Asp Tyr Val Asp Gln Ala
            260                 265                 270

Asp Phe Ile Leu Thr Leu Gly Val Lys Leu Thr Asp Ser Val Thr Gly
        275                 280                 285

Gly Phe Ser Gln Gly Phe Asp Ala Lys Gln Val Leu Ser Leu Ala Ala
    290                 295                 300

Asn Gln Ala Ser Leu Phe Gly Glu Asn Tyr Gln Gly Tyr His Phe Ser
305                 310                 315                 320

Asp Val Ile Arg Glu Ile Glu Asn Leu Asp Ile Pro Ser Tyr Ser Gly
                325                 330                 335

Ser Tyr Ile Ala Lys Thr Lys Val Ala Asp Phe Glu Ala Glu Lys Gly
            340                 345                 350

Gln Val Leu Ser Gln Lys Arg Phe Trp Gln Ala Met Glu Ser Phe Val
        355                 360                 365

Gln Ala Gly Asp Thr Ile Phe Ala Glu Gln Gly Thr Ser Tyr Phe Gly
    370                 375                 380

Ala Ser Gln Leu Asn Leu Lys Glu Asn Val Ala Tyr Gln Gly Gln Pro
385                 390                 395                 400

Leu Trp Gly Ser Ile Gly Tyr Thr Phe Pro Ala Val Phe Gly Ser Gln
                405                 410                 415

Leu Ala Asn Pro Asp Ser Arg His Ile Leu Phe Val Gly Asp Gly Ser
            420                 425                 430

Leu Gln Leu Thr Val Gln Asp Ile Gly Leu Ala Leu Arg Glu Gln Leu
        435                 440                 445

Asn Thr Ile Val Phe Val Ile Asn Asn Asp Gly Tyr Thr Val Glu Arg
    450                 455                 460

Lys Ile His Gly Pro Glu Val Tyr Asn Asp Ile Pro Gln Trp Gln
465                 470                 475                 480

Tyr Ser Gln Leu Pro Ala Ser Phe Gly Gly Asn Asp Ser Gln Val Leu
                485                 490                 495

Ala Arg Lys Val Ser Thr Glu Glu Leu Val Glu Ile Leu Glu Lys
            500                 505                 510

Ala Arg Ala Asp Val Ser Arg Met Tyr Trp Ile Glu Leu Met Leu Pro
        515                 520                 525

Lys Met Asp Ala Pro Glu Tyr Leu Glu Lys Leu Gly Lys Leu Phe Ala
    530                 535                 540

Gln Gln Asn Lys Ala
545

<210> SEQ ID NO 78
<211> LENGTH: 1650

<212> TYPE: DNA
<213> ORGANISM: Streptococcus didelphis

<400> SEQUENCE: 78

```
atgtataccg tcggcgatta tctgctggat cggctcaagg aaatcggcat cgaccatatc     60
ttcggcgtcc cgggcgacta caacctccag ttcctggatc agatcaccgc cgcgacgac    120
ctcaaatggg tgggcaacgc caacgaactc aacgcgagct acatgtccga cggctatgcc    180
cgcaccaaga aggccgccgc cttcgtcacc accttcggcg tgggcgaact gtcggcgatc    240
aacggcctgg ccggctcgtt cgcggaaaac gtccccgtga tcgagatcgt cggctcgccg    300
acgaccaagg tgcaggaagc cggcaaactg gtgcaccata cgctcggcga cggcaacttc    360
aatcacttcc aggagatgca caaatcggtc accgtggccc aggtcaaagt cagcgccgaa    420
catgcccaga ccgacatcga ccaggtgctc ctgtccctgc tgaaggagcg gaagccggtg    480
tatatcaacc tgcccatcga tgtggcccag atgcccgccc agaagccgga tcggccctc    540
ctggtcgaga aggtcatctc cgagcaggac aagatcatcc tgcaggcgat cgagaaaggc    600
ctgaagaccg ccaagcagcc cctcatcatg gtcggccatg aagtcgccag cttcggcctg    660
gaagccacca tcaacaactt catcaaaaag aagaagtacc ccgtgacctc gctcagcctg    720
ggcaaaggca tcgtcaacga gtcgccggaa accttcctgg gcatctactc cggcgccctg    780
tccccgcagg ccctgaaaga ctacgtcgat caggcggact tcatcctcac cctcggcgtc    840
aagctgaccg actccgtgac gggcggcttc agccagggct tcgatgcgaa gcaggtgctg    900
agcctggccg ccaaccaggc gtcgctcttc ggcgaaaaact accagggcta tcacttctcc    960
gacgtgatcc gcgaaatcga aaatctggac atccccagct attcgggctc ctatatcgcc   1020
aagaccaagg tcgccgattt cgaagcgag aagggccagg tcctgtccca gaagcgcttc   1080
tggcaggcga tggaatcgtt cgtccaggcc ggcgacacca tcttcgccga gcagggcacc   1140
tcgtacttcg cgcgcagcca gctcaacctg aaagagaacg tggcctacca gggccagccg   1200
ctctggggca gcatcggcta ccttcccg gccgtcttcg gcagccagct cgcgaacccc   1260
gattcgcggc atatcctgtt cgtcggcgac ggcagcctgc agctgaccgt ccaggacatc   1320
ggcctggcgc tgcgcgagca gctgaacacg atcgtgttcg tcatcaacaa cgacggctat   1380
accgtggagc gcaagatcca cggcccggaa gaggtctata tgacatccc gcagtggcag   1440
tacagccagc tccccgcctc cttcggcggc aacgactcgc aggtcctggc ccggaaagtg   1500
agcaccgaag aggagctggt cgaaatcctg gaaaaggcgc gggccgacgt gtcccggatg   1560
tattggatcg agctcatgct cccccaaaatg gacgcgccgg agtatctgga aaagctgggc   1620
aagctgttcg cccagcagaa taaagcctga                                   1650
```

<210> SEQ ID NO 79
<211> LENGTH: 548
<212> TYPE: PRT
<213> ORGANISM: Enterococcus caccae

<400> SEQUENCE: 79

```
Met Tyr Thr Val Ala Asp Tyr Leu Leu Asp Arg Leu Lys Glu Leu Gly
1               5                   10                  15

Ile Asp Glu Leu Phe Gly Val Pro Gly Asp Tyr Asn Leu Gln Phe Leu
            20                  25                  30

Asp His Ile Thr Ala Arg Gln Asp Leu Glu Trp Ile Gly Asn Ala Asn
        35                  40                  45

Glu Leu Asn Ala Ala Tyr Met Ala Asp Gly Tyr Ala Arg Thr Lys Gly
```

```
            50                  55                  60
Ile Ser Ala Phe Val Thr Thr Phe Gly Val Gly Glu Leu Ser Ala Ile
 65                  70                  75                  80

Asn Gly Leu Ala Gly Ser Phe Ala Glu Asn Val Pro Val Val Glu Ile
                 85                  90                  95

Val Gly Ser Pro Thr Thr Thr Val Gln Asn Asp Lys Lys Leu Val His
                100                 105                 110

His Thr Leu Gly Asp Gly Asn Phe Leu His Phe Glu Lys Met His Glu
            115                 120                 125

Glu Val Thr Ala Ala Ile Ala His Leu Thr Ala Glu Asn Ala Leu Thr
        130                 135                 140

Glu Ile Asp Arg Val Leu Ile Ile Ala Met Ile Glu Lys Arg Pro Val
145                 150                 155                 160

Tyr Ile Asn Leu Pro Ile Asp Ile Ala Glu Phe Lys Ala Thr Pro Pro
                165                 170                 175

Leu Ser Pro Leu Ser Arg Ser Ala Glu Lys Leu Thr Asp Val Glu Ile
            180                 185                 190

Ala Ile Leu Asp Lys Val Glu Lys Ala Leu Ser Gln Ala Lys Asn Pro
        195                 200                 205

Val Val Ile Ala Gly His Glu Ile Leu Ser Tyr His Ile Glu His Gln
    210                 215                 220

Leu Asp Glu Phe Ile Gln Lys Phe Asn Leu Pro Ile Thr Thr Leu Pro
225                 230                 235                 240

Leu Gly Lys Arg Ala Phe Asn Glu Glu Asp Pro His Tyr Leu Gly Thr
                245                 250                 255

Tyr Ser Gly Ser Thr Thr Glu Glu Pro Leu Lys Thr Arg Val Asp Thr
            260                 265                 270

Ala Asp Leu Val Leu Leu Gly Ala Lys Leu Thr Asp Ser Ala Thr
        275                 280                 285

Ser Gly Phe Ser Phe Gly Phe Thr Asp Gln Gln Ile Ile Ser Ile Gly
    290                 295                 300

Ser Thr Glu Val Leu Phe Tyr Gly Glu Thr Phe Lys Ala Val Gln Leu
305                 310                 315                 320

Asp Arg Phe Val Ser Ala Leu Thr Thr Leu Ser Phe Ser Arg Tyr Glu
                325                 330                 335

Asp Glu Ile Gln Pro Val Thr Arg Ile Ser Asn Gln Ala Ile Lys Asp
            340                 345                 350

Glu Lys Leu Ser Gln Lys Gln Phe Trp Glu Met Val Glu Thr Phe Leu
        355                 360                 365

Ile Pro Gly Asp Thr Val Ile Gly Glu Gln Gly Thr Ser Phe Phe Gly
370                 375                 380

Leu Thr Asn Val Ala Leu Lys Arg Asn Met His Phe Ile Gly Gln Pro
                390                 395                 400
385

Leu Trp Gly Ser Ile Gly Tyr Thr Phe Pro Ser Ala Leu Gly Ser Gln
            405                 410                 415

Ile Ala Asn Lys Glu Ser Arg His Leu Leu Phe Ile Gly Asp Gly Ser
        420                 425                 430

Leu Gln Leu Thr Val Gln Glu Leu Gly Thr Ala Leu Arg Glu Lys Leu
    435                 440                 445

Thr Pro Ile Val Phe Val Ile Asn Asn Asn Gly Tyr Thr Val Glu Arg
450                 455                 460

Glu Ile His Gly Ala Thr Glu Gln Tyr Asn Asp Ile Pro Met Trp Asp
465                 470                 475                 480
```

Tyr Gln Asn Leu Pro Leu Val Phe Gly Gly Asn Asn Gln Thr Val Ala
            485                 490                 495

Thr Tyr Lys Val Thr Thr Ala Ile Glu Leu Asp Glu Val Met Lys Thr
            500                 505                 510

Ala Arg Lys Asp Thr Lys Arg Leu Gln Trp Ile Glu Val Val Met Ala
            515                 520                 525

Gln Asp Asp Ala Pro Glu Leu Leu Lys Lys Leu Ala Lys Ile Phe Ala
    530                 535                 540

Lys Gln Asn Ser
545

<210> SEQ ID NO 80
<211> LENGTH: 1647
<212> TYPE: DNA
<213> ORGANISM: Enterococcus caccae

<400> SEQUENCE: 80

| | |
|---|---|
| atgtacaccg tcgccgatta cctgctggat cgcctgaagg agctgggcat cgatgagctg | 60 |
| ttcggcgtgc cgggcgacta caacctgcag ttcctcgacc acatcaccgc ccgccaggac | 120 |
| ctggagtgga tcgcaacgc caacgaactg aacgccgcgt atatggccga cggctacgcc | 180 |
| cggaccaagg gcatctcggc gttcgtgacc accttcggcg tgggcgagct gtccgccatc | 240 |
| aatggcctcg ccggcagctt cgcggagaac gtcccggtcg tcgagatcgt gggctccccg | 300 |
| accaccacgg tccagaacga caagaagctg gtgcatcaca cgctgggcga cggcaatttc | 360 |
| ctgcatttcg agaagatgca tgaagaggtc accgccgcca tcgcgcacct caccgccgaa | 420 |
| aacgcgctga ccgaaatcga ccgggtgctc atcatcgcca tgatcgagaa cgcccggtc | 480 |
| tatatcaacc tcccgatcga catcgccgag ttcaaagcca cccgccgct cagcccctg | 540 |
| agccggtcgg ccgaaaagct gacggatgtc gaaatcgcca tcctcgacaa ggtggaaaag | 600 |
| gcgctgtcgc aggcgaagaa ccccgtcgtg atcgccggcc acgaaatcct cagctaccat | 660 |
| atcgaacatc agctggacga gttcatccag aagttcaacc tcccgatcac cacgctgccc | 720 |
| ctgggcaaac gcgcgttcaa tgaggaagac ccgcactatc tcggcaccta cagcggctcc | 780 |
| accaccgagg agccgctgaa gacccgcgtg gataccgcgg atctggtcct gctgctgggc | 840 |
| gcgaagctga cggactcggc cacctcgggc ttctccttcg gcttcaccga ccagcagatc | 900 |
| atcagcatcg gctccacgga ggtcctcttc tacggcgaaa ccttcaaagc cgtgcagctc | 960 |
| gaccgcttcg tctcggcgct caccaccctg agcttctccc ggtacgaaga tgaaatccag | 1020 |
| ccggtgaccc ggatcagcaa ccaggcgatc aaggacgaga agctgtcgca gaagcagttc | 1080 |
| tgggagatgg tcgagacgtt cctgatcccg ggcgacaccg tgatcggcga gcagggcacc | 1140 |
| tcgttcttcg gcctgaccaa cgtcgccctg aagcggaata tgcacttcat cggccagccg | 1200 |
| ctgtggggca gcatcggcta cgttcccgtc tcggccctcg gctcgcagat cgccaacaag | 1260 |
| gaaagccggc atctgctgtt catcggcgat ggctccctcc agctgaccgt gcaggaactg | 1320 |
| ggcaccgccc tgcgcgagaa gctgacgccg atcgtcttcg tcatcaacaa caatggctat | 1380 |
| accgtggaac gggagatcca cggcgccacc gagcagtaca cgacatccc catgtgggat | 1440 |
| tatcagaacc tgccgctcgt gttcggcggc aacaaccaga ccgtcgccac ctacaaggtc | 1500 |
| accaccgcga tcgaactgga tgaggtcatg aaaaccgccc gcaaggacac caagcgcctg | 1560 |
| cagtggatca agtggtcat ggcgcaggat gacgcgccgg aactgctcaa gaaactcgcc | 1620 |
| aaaatcttcg ccaaacagaa cagctga | 1647 |

<210> SEQ ID NO 81
<211> LENGTH: 548
<212> TYPE: PRT
<213> ORGANISM: Enterococcus haemoperoxidus

<400> SEQUENCE: 81

```
Met Tyr Thr Ile Ser Asp Tyr Leu Leu Asp Arg Leu Lys Glu Leu Gly
1               5                   10                  15

Ile Asp Glu Val Phe Gly Val Pro Gly Asp Tyr Asn Leu Gln Phe Leu
            20                  25                  30

Asp His Ile Thr Ala Arg Glu Asp Leu Lys Trp Ile Gly Asn Ala Asn
        35                  40                  45

Glu Leu Asn Ala Ala Tyr Met Ala Asp Gly Tyr Ala Arg Thr Lys Gly
    50                  55                  60

Ile Ser Ala Phe Val Thr Thr Phe Gly Val Gly Glu Leu Ser Ala Val
65                  70                  75                  80

Asn Gly Leu Ala Gly Ser Tyr Ala Glu Asn Val Pro Val Val Glu Ile
                85                  90                  95

Ile Gly Ser Pro Thr Thr Thr Val Gln Asn Asn Lys Lys Leu Val His
            100                 105                 110

His Thr Leu Gly Asp Gly Asp Phe Leu Arg Phe Glu Lys Met His Glu
        115                 120                 125

Glu Val Thr Ala Ala Ile Ala His Leu Thr Ile Glu Asn Ala Thr Ser
    130                 135                 140

Glu Ile Asp Arg Val Leu Thr Ile Ala Met Thr Glu Lys Arg Pro Val
145                 150                 155                 160

Tyr Ile Asn Leu Pro Ile Asp Ile Ala Glu Thr Lys Thr Asn Lys Pro
                165                 170                 175

Asn Lys Pro Leu Gln Lys Met Thr Glu Arg Leu Thr Glu Ala Glu Ala
            180                 185                 190

Thr Ile Leu Ser Lys Val Glu Lys Ala Leu Gln Ala Glu Asn Pro
    195                 200                 205

Val Ile Ile Ala Gly His Glu Ile Leu Ser Tyr His Ile Glu His Gln
    210                 215                 220

Leu Asn Glu Phe Ile Gln Lys Phe Asn Leu Pro Ile Thr Thr Leu Pro
225                 230                 235                 240

Leu Gly Lys Gly Ala Phe Asp Glu Glu Asp Ser His Tyr Met Gly Thr
                245                 250                 255

Tyr Ser Gly Ser Pro Thr Glu Glu Pro Leu Lys Ser Arg Val Asp Asn
            260                 265                 270

Ala Asp Leu Val Leu Leu Leu Gly Ala Lys Leu Thr Asp Ser Ala Thr
        275                 280                 285

Ser Gly Phe Ser Phe Gly Phe Thr Asp Lys Gln Ile Ile Ser Ile Gly
    290                 295                 300

Ala Thr Glu Val Leu Phe Tyr Gly Glu Lys His Glu Ala Ile Gln Leu
305                 310                 315                 320

Asp Arg Phe Val Ser Ala Leu Ser Thr Leu Ser Phe Ser Arg Phe Thr
                325                 330                 335

Gly Asp Leu Leu Pro Val Lys Arg Ile Ser Lys Val Glu Phe Lys Asp
            340                 345                 350

Glu Gln Leu Thr Gln Lys Arg Phe Trp Lys Met Val Glu Thr Phe Leu
        355                 360                 365

Leu Gln Gly Asp Thr Val Val Gly Glu Gln Gly Thr Ser Phe Phe Gly
```

```
                370                375                380
Leu Thr Asn Val Pro Leu Lys Lys Asp Met His Phe Ile Gly Gln Pro
385                390                395                400

Leu Trp Gly Ser Ile Gly Tyr Thr Phe Pro Ser Thr Leu Gly Ser Gln
            405                410                415

Ile Ala Asn Lys Asp Ser Arg His Leu Leu Phe Ile Gly Asp Gly Ser
            420                425                430

Leu Gln Leu Thr Val Gln Glu Leu Gly Thr Ala Ile Arg Glu Lys Leu
            435                440                445

Thr Pro Ile Val Phe Val Ile Asn Asn Asn Gly Tyr Thr Val Glu Arg
450                455                460

Glu Ile His Gly Ala Thr Glu Gln Tyr Asn Asp Ile Pro Met Trp Asp
465                470                475                480

Tyr Gln Asn Leu Pro Leu Val Phe Gly Gly Thr Ser Gln Thr Val Ala
            485                490                495

Thr Tyr Lys Ala Thr Thr Glu Ala Glu Leu Ala Glu Val Met Lys Ser
            500                505                510

Ala Arg Lys Asp Thr Glu Arg Leu Gln Trp Ile Glu Val Val Met Asp
            515                520                525

Gln Glu Asp Ala Pro Leu Leu Leu Gln Lys Leu Ala Lys Ile Phe Ala
            530                535                540

Lys Gln Asn Ser
545
```

<210> SEQ ID NO 82
<211> LENGTH: 1647
<212> TYPE: DNA
<213> ORGANISM: Enterococcus haemoperoxidus

<400> SEQUENCE: 82

```
atgtacacca tcagcgacta cctcctggac cggctgaagg aactcggcat cgacgaagtc    60
ttcggcgtcc cgggcgacta caacctccag ttcctcgatc atatcaccgc ccgcgaagac   120
ctgaaatgga tcggcaacgc gaatgaactc aatgccgcct acatggcgga cggctatgcc   180
cgcaccaagg gcatcagcgc cttcgtgacc accttcggcg tcggcgaact gagcgcggtg   240
aacggcctgg ccggctcgta cgccgagaac gtgccggtgg tcgagatcat cggcagcccc   300
accaccaccg tgcagaacaa caagaaactg gtccaccaca cgctgggcga tggcgacttc   360
ctgcggttcg aaaagatgca cgaggaagtc accgccgcga tcgcccatct gaccatcgag   420
aatgccacga gcgaaatcga ccgcgtcctg acgatcgcca tgaccgagaa cgccccgtg   480
tatatcaacc tgccgatcga tatcgcggaa accaagacga acaagccgaa caaaccgctg   540
cagaagatga ccgagcggct cacgaagcc gaagcgacca tcctgtcgaa ggtcgagaag   600
gccctccagc aggcggagaa cccggtcatc atcgccggcc atgagatcct gtcctaccac   660
atcgagcacc agctgaatga gttcatccag aagttcaatc tccccatcac cacgctgccg   720
ctgggcaagg gcgccttcga cgaggaagac tcgcactaca tgggcacgta ttccggctcc   780
cccacggaag agccccctgaa gagccgcgtg ataacgccg atctggtcct gctgctcggc   840
gccaagctga ccgattccgc gacctccggc ttctcgttcg gcttcaccga caagcagatc   900
atcagcatcg gcgcgaccga agtcctgttc tacggcgaga acacgaggc catccagctc   960
gatcgcttcg tgtccgccct gtccacgctc tccttctccc gcttcaccgg cgatctgctc  1020
ccggtgaaac ggatcagcaa ggtcgagttc aaggacgagc agctcaccca gaagcgcttc  1080
```

```
tggaagatgg tcgaaacgtt cctgctccag ggcgacaccg tcgtgggcga acagggcacc   1140
agcttcttcg gcctgaccaa tgtgcccctg aagaaggata tgcacttcat cggccagccg   1200
ctctggggca gcatcggcta ccttccccc agcaccctgg gctcgcagat cgccaacaag   1260
gactcccgcc acctgctgtt catcggcgat ggctcgctgc agctgaccgt gcaggagctc   1320
ggcacggcca tccgggagaa gctcacgccg atcgtcttcg tcatcaacaa caacggctac   1380
accgtggaac gcaaaatcca cggcgccacc gagcagtaca cgacatccc gatgtgggac   1440 taccagaacc tccccctggt cttcggcggc acgagccaga ccgtggcgac gtataaagcc   1500
acgaccgaag cggagctggc cgaggtcatg aagtccgccc ggaaggatac ggagcggctg   1560
cagtggatcg aggtggtgat ggaccaggaa gacgcgcccc tgctgctgca gaagctggcc   1620
aagatcttcg ccaagcagaa ctcgtga                                       1647
```

<210> SEQ ID NO 83
<211> LENGTH: 548
<212> TYPE: PRT
<213> ORGANISM: Enterococcus moraviensis

<400> SEQUENCE: 83

```
Met Tyr Thr Val Ala Asp Tyr Leu Leu Asp Arg Leu Lys Glu Leu Gly
 1               5                  10                  15

Ile Asp Glu Val Phe Gly Val Pro Gly Asp Tyr Asn Leu Gln Phe Leu
            20                  25                  30

Asp His Ile Thr Ala Arg Lys Asp Leu Glu Trp Ile Gly Asn Ala Asn
        35                  40                  45

Glu Leu Asn Ala Ala Tyr Met Ala Asp Gly Tyr Ala Arg Thr Lys Gly
    50                  55                  60

Ile Ser Ala Leu Val Thr Thr Phe Gly Val Gly Glu Leu Ser Ala Ile
65                  70                  75                  80

Asn Gly Leu Ala Gly Ser Tyr Ala Glu Ser Ile Pro Val Ile Glu Ile
                85                  90                  95

Val Gly Ser Pro Thr Thr Thr Val Gln Gln Asn Lys Lys Leu Val His
            100                 105                 110

His Thr Leu Gly Asp Gly Asp Phe Leu Arg Phe Glu Arg Ile His Glu
        115                 120                 125

Glu Val Ser Ala Ala Ile Ala His Leu Ser Thr Glu Asn Ala Pro Ser
    130                 135                 140

Glu Ile Asp Arg Val Leu Thr Val Ala Met Thr Glu Lys Arg Pro Val
145                 150                 155                 160

Tyr Ile Asn Leu Pro Ile Asp Ile Ala Glu Met Lys Ala Ser Ala Pro
                165                 170                 175

Thr Thr Pro Leu Asn His Thr Thr Asp Gln Leu Thr Thr Val Glu Thr
            180                 185                 190

Ala Ile Leu Thr Lys Val Glu Asp Ala Leu Lys Gln Ser Lys Asn Pro
        195                 200                 205

Val Val Ile Ala Gly His Glu Ile Leu Ser Tyr His Ile Glu Asn Gln
    210                 215                 220

Leu Glu Gln Phe Ile Gln Lys Phe Asn Leu Pro Ile Thr Val Leu Pro
225                 230                 235                 240

Phe Gly Lys Gly Ala Phe Asn Glu Glu Asp Ala His Tyr Leu Gly Thr
                245                 250                 255

Tyr Thr Gly Ser Thr Thr Asp Glu Ser Met Lys Asn Arg Val Asp His
            260                 265                 270
```

Ala Asp Leu Val Leu Leu Leu Gly Ala Lys Leu Thr Asp Ser Ala Thr
            275                 280                 285

Ser Gly Phe Ser Phe Gly Phe Thr Glu Lys Gln Met Ile Ser Ile Gly
        290                 295                 300

Ser Thr Glu Val Leu Phe Tyr Gly Glu Lys Gln Glu Thr Val Gln Leu
305                 310                 315                 320

Asp Arg Phe Val Ser Ala Leu Ser Thr Leu Ser Phe Ser Arg Phe Thr
                325                 330                 335

Asp Glu Met Pro Ser Val Lys Arg Leu Ala Thr Pro Lys Val Arg Asp
            340                 345                 350

Glu Lys Leu Thr Gln Lys Gln Phe Trp Gln Met Val Glu Ser Phe Leu
        355                 360                 365

Leu Gln Gly Asp Thr Val Val Gly Glu Gln Gly Thr Ser Phe Phe Gly
    370                 375                 380

Leu Thr Asn Val Pro Leu Lys Lys Asp Met His Phe Ile Gly Gln Pro
385                 390                 395                 400

Leu Trp Gly Ser Ile Gly Tyr Thr Phe Pro Ser Ala Leu Gly Ser Gln
                405                 410                 415

Ile Ala Asn Lys Glu Ser Arg His Leu Leu Phe Ile Gly Asp Gly Ser
            420                 425                 430

Leu Gln Leu Thr Val Gln Glu Leu Gly Thr Ala Ile Arg Glu Lys Leu
        435                 440                 445

Thr Pro Ile Val Phe Val Ile Asn Asn Asn Gly Tyr Thr Val Glu Arg
    450                 455                 460

Glu Ile His Gly Ala Thr Glu Gln Tyr Asn Asp Ile Pro Met Trp Asp
465                 470                 475                 480

Tyr Gln Lys Leu Pro Phe Val Phe Gly Gly Thr Asp Gln Thr Val Ala
                485                 490                 495

Thr Tyr Lys Val Ser Thr Glu Ile Glu Leu Asp Asn Ala Met Thr Arg
            500                 505                 510

Ala Arg Thr Asp Val Asp Arg Leu Gln Trp Ile Glu Val Val Met Asp
        515                 520                 525

Gln Asn Asp Ala Pro Val Leu Leu Lys Lys Leu Ala Lys Ile Phe Ala
    530                 535                 540

Lys Gln Asn Ser
545

<210> SEQ ID NO 84
<211> LENGTH: 1647
<212> TYPE: DNA
<213> ORGANISM: Enterococcus moraviensis

<400> SEQUENCE: 84
atgtacacgg tggcggacta tctgctggac cggctgaaag agctgggcat cgacgaagtg      60
ttcggcgtgc ccggcgacta caacctgcag ttcctcgacc acatcacggc ccggaaggac     120
ctcgaatgga tcggcaatgc caacgaactg aacgccgcct acatgccgac ggctacgcc      180 cgcaccaagg gcatctccgc gctggtcacc accttcggcg tcggcgaact gtcggccatc     240
aatggcctgg ccggctcgta cgcggaaagc atcccggtga tcgaaatcgt gggctccccg     300
acgacgacgg tgcagcagaa caagaagctc gtgcatcata cgctgggcga cggcgatttc     360
ctgcggttcg agcgcatcca cgaggaggtg tcggcggcca tcgcgcacct gtccaccgag     420
aacgccccct ccgagatcga ccgcgtgctg acggtggcca tgaccgaaaa agcgcccggtc    480 tatatcaacc tcccgatcga tatcgcggag atgaaagcgt cggcccccac cacgcccctg    540

```
aaccacacca cggatcagct gacgaccgtc gagacggcca tcctcaccaa ggtcgaggat    600
gcgctgaagc agtccaagaa tcccgtcgtc atcgccggcc acgagatcct gagctaccac    660
atcgaaaatc agctggaaca gttcatccag aagttcaacc tgccgatcac cgtgctcccg    720
ttcggcaagg gcgccttcaa cgaagaggac gcgcattacc tgggcaccta cgggcagc     780 acgaccgacg agtccatgaa gaatcgcgtc gaccatgcgg acctggtcct gctgctcggc    840
gccaagctca ccgactcggc cacctcgggc ttcagcttcg gcttcacgga gaagcagatg    900
atctcgatcg gctcgaccga agtgctgttc tatggcgaga agcaggagac ggtgcagctc    960
gaccgcttcg tgagcgccct gtcgaccctg tccttctccc gcttcaccga cgagatgccg   1020
agcgtgaaac gcctggccac cccgaaggtg cgcgatgaga gctgaccca aagcagttc    1080 tggcagatgg tcgagagctt cctgctccag ggcgacaccg tcgtgggcga gcagggcacg   1140
agcttcttcg gcctgacgaa tgtgcccctg aaaaaggaca tgcacttcat cggccagccg   1200
ctgtggggca gcatcggcta tacgttcccc agcgccctgg gcagccagat cgccaacaaa   1260
gagtcccgcc acctgctgtt catcggcgac ggctcgctcc agctgacggt ccaggagctg   1320
ggcaccgcga tccgcgaaaa gctgaccccc atcgtgttcg tcatcaacaa caacggctat   1380
accgtggaac gcgagatcca cggcgcgacc gagcagtaca cgacatcccc catgtgggac   1440
taccagaaac tgccgttcgt gttcggcggc accgatcaga cggtggccac ctataaggtg   1500
tccaccgaaa tcgaactcga taacgcgatg acccgggccc ggacggacgt ggaccgcctc   1560
cagtggatcg aagtcgtgat ggaccagaac gacgccccgg tcctgctgaa gaagctcgcc   1620
aagatcttcg cgaaacagaa ctcctga                                       1647

<210> SEQ ID NO 85
<211> LENGTH: 548
<212> TYPE: PRT
<213> ORGANISM: Carnobacterium maltaromaticum

<400> SEQUENCE: 85

Met Tyr Thr Val Gly Asn Tyr Leu Leu Asp Arg Leu Thr Glu Leu Gly
1               5                   10                  15

Ile Arg Asp Ile Phe Gly Val Pro Gly Asp Tyr Asn Leu Lys Phe Leu
            20                  25                  30

Asp His Val Met Thr His Lys Glu Leu Asn Trp Ile Gly Asn Ala Asn
        35                  40                  45

Glu Leu Asn Ala Ala Tyr Ala Ala Asp Gly Tyr Ala Arg Thr Lys Gly
    50                  55                  60

Ile Ala Ala Leu Val Thr Thr Phe Gly Val Gly Glu Leu Ser Ala Ala
65                  70                  75                  80

Asn Gly Thr Ala Gly Ser Tyr Ala Glu Lys Val Pro Val Val Gln Ile
                85                  90                  95

Val Gly Thr Pro Thr Thr Ala Val Gln Asn Ser His Lys Leu Val His
            100                 105                 110

His Thr Leu Gly Asp Gly Arg Phe Asp His Phe Glu Lys Met Gln Thr
        115                 120                 125

Glu Ile Asn Gly Ala Ile Ala His Leu Thr Ala Asp Asn Ala Leu Ala
    130                 135                 140

Glu Ile Asp Arg Val Leu Arg Ile Ala Val Thr Glu Arg Cys Pro Val
145                 150                 155                 160

Tyr Ile Asn Leu Ala Ile Asp Val Ala Glu Val Ala Glu Lys Pro
                165                 170                 175
```

Leu Lys Pro Leu Met Glu Glu Ser Lys Lys Val Glu Glu Thr Ala
            180                 185                 190

Leu Val Leu Asn Lys Ile Glu Lys Ala Leu Gln Asp Ser Lys Asn Pro
        195                 200                 205

Val Val Leu Ile Gly Asn Glu Ile Ala Ser Phe His Leu Glu Ser Ala
    210                 215                 220

Leu Ala Asp Phe Val Lys Lys Phe Asn Leu Pro Val Thr Val Leu Pro
225                 230                 235                 240

Phe Gly Lys Gly Gly Phe Asp Glu Glu Asp Ala His Phe Ile Gly Val
                245                 250                 255

Tyr Thr Gly Ala Pro Thr Ala Glu Ser Ile Lys Glu Arg Val Glu Lys
            260                 265                 270

Ala Asp Leu Ile Leu Ile Gly Ala Lys Leu Thr Asp Ser Ala Thr
        275                 280                 285

Ala Gly Phe Ser Tyr Asp Phe Glu Asp Arg Gln Val Ile Ser Val Gly
    290                 295                 300

Ser Asp Glu Val Ser Phe Tyr Gly Glu Ile Met Lys Pro Val Ala Phe
305                 310                 315                 320

Ala Gln Phe Val Asn Gly Leu Asn Ser Leu Asn Tyr Leu Gly Tyr Thr
                325                 330                 335

Gly Glu Ile Lys Gln Val Glu Arg Val Ala Asp Ile Glu Ala Lys Ala
            340                 345                 350

Ser Asn Leu Thr Gln Asn Asn Phe Trp Lys Phe Val Glu Lys Tyr Leu
        355                 360                 365

Ser Asn Gly Asp Thr Leu Val Ala Glu Gln Gly Thr Ser Phe Phe Gly
    370                 375                 380

Ala Ser Leu Val Pro Leu Lys Ser Lys Met Lys Phe Ile Gly Gln Pro
385                 390                 395                 400

Leu Trp Gly Ser Ile Gly Tyr Thr Phe Pro Ala Met Leu Gly Ser Gln
                405                 410                 415

Ile Ala Asn Pro Ala Ser Arg His Leu Leu Phe Ile Gly Asp Gly Ser
            420                 425                 430

Leu Gln Leu Thr Ile Gln Glu Leu Gly Met Thr Phe Arg Glu Lys Leu
        435                 440                 445

Thr Pro Ile Val Phe Val Ile Asn Asn Asp Gly Tyr Thr Val Glu Arg
    450                 455                 460

Glu Ile His Gly Pro Asn Glu Leu Tyr Asn Asp Ile Pro Met Trp Asp
465                 470                 475                 480

Tyr Gln Asn Leu Pro Tyr Val Phe Gly Gly Asn Lys Gly Asn Val Ala
                485                 490                 495

Thr Tyr Lys Val Thr Thr Glu Glu Leu Val Ala Ala Met Ser Gln
            500                 505                 510

Ala Arg Gln Asp Thr Thr Arg Leu Gln Trp Ile Glu Val Val Met Gly
        515                 520                 525

Lys Gln Asp Ser Pro Asp Leu Leu Val Gln Leu Gly Lys Val Phe Ala
    530                 535                 540

Lys Gln Asn Ser
545

<210> SEQ ID NO 86
<211> LENGTH: 1647
<212> TYPE: DNA
<213> ORGANISM: Carnobacterium maltaromaticum

<400> SEQUENCE: 86

```
atgtataccg tgggcaacta cctgctggac cgcctcaccg aactgggcat ccgggatatc      60
ttcggcgtcc cggcgatta taacctcaag ttcctggacc atgtcatgac ccataaggaa     120
ctgaattgga tcggcaacgc caacgagctg aatgcggcct atgccgccga cggctacgcg     180
cggaccaagg gcatcgcggc cctggtcacc accttcggcg tgggcgaact gagcgcggcc     240
aatggcaccg cgggctccta tgccgaaaag gtgcccgtgg tgcagatcgt gggcacgccc     300
acgacggcgg tgcagaactc ccacaaactg gtgcaccata ccctgggcga cggccgcttc     360
gatcacttcg aaaagatgca gaccgagatc aatggcgcca tcgcgcatct gaccgcggac     420
aacgccctgg cggagatcga tcgcgtgctg cggatcgccg tgaccgaacg gtgcccggtc     480
tatatcaacc tggccatcga tgtcgcggag gtggtggccg aaaaaccgct gaagcccctg     540
atggaggaat cgaagaaagt cgaggaggag acggccctcg tcctcaacaa gatcgaaaag     600
gcgctccagg actccaaaaa cccggtggtc ctgatcggca cgagatcgc cagcttccat     660
ctggaatcgg cgctggccga tttcgtcaag aagttcaacc tcccggtcac ggtgctgccc     720
ttcggcaagg gcggcttcga cgaggaggat gcgcacttca tcggcgtcta taccggcgcc     780
ccgaccgccg aaagcatcaa ggagcgggtg aaaaaggccg acctcatcct catcatcggc     840
gcgaagctga ccgatagcgc caccgcgggc ttctcctacg acttcgagga ccgccaggtc     900
atcagcgtcg gcagcgacga agtgtccttc tatggcgaga tcatgaaacc cgtggcgttc     960
gcccagttcg tgaacggcct gaactccctg aattacctgg gctacaccgg cgaaatcaag    1020
caggtggagc gggtggcgga catcgaggcg aaggcgtcga atctcaccca gaacaacttc    1080
tggaagttcg tggaaaagta cctgtcgaac ggcgacaccc tggtggccga gcagggcacc    1140
agcttcttcg gcgcctcgct cgtgccgctg aaatcgaaga tgaagttcat cggccagccg    1200
ctgtggggca gcatcggcta cgttcccc gccatgctgg gcagccagat cgcgaatccc    1260
gcgagccggc atctgctctt catcggcgac ggctccctgc agctgaccat ccaggagctc    1320
ggcatgacct tccgggagaa actgaccccg atcgtgttcg tcatcaacaa cgatggctac    1380
accgtcgagg gggaaatcca cggcccgaac gagctctaca cgatatccc gatgtgggat    1440
tatcagaacc tcccgtacgt gttcggcggc aacaagggca cgtcgccac ctataaggtc    1500
accaccgaga agaactggt ggccgccatg tcccaggccc ggcaggacac cacccggctg    1560
cagtggatcg aggtcgtgat gggcaaacag gattcgccgg acctcctggt ccagctgggc    1620
aaggtgttcg ccaagcagaa cagctga                                        1647
```

<210> SEQ ID NO 87
<211> LENGTH: 548
<212> TYPE: PRT
<213> ORGANISM: Brochothrix thermosphacta

<400> SEQUENCE: 87

```
Met Tyr Thr Ile Gly Asp Tyr Leu Leu Asp Arg Leu Asn Glu Leu Gly
  1               5                  10                  15

Val Glu Asp Ile Phe Gly Val Pro Gly Asp Tyr Asn Leu Thr Phe Leu
             20                  25                  30

Asp His Ile Thr Ala His Pro Gln Leu Ser Trp Val Gly Asn Ala Asn
         35                  40                  45

Glu Leu Asn Ala Ala Tyr Ala Ala Asp Gly Tyr Ala Arg Thr Lys Gly
     50                  55                  60

Phe Ala Ala Leu Val Thr Thr Phe Gly Val Gly Glu Leu Ser Ala Ile
```

```
                65                  70                  75                  80
Asn Gly Leu Ala Gly Ser Phe Ala Glu Arg Val Pro Val Ile Glu Ile
                        85                  90                  95

Val Gly Ser Pro Val Ser Thr Val Gln Thr Asp Lys Lys Leu Val His
                100                 105                 110

His Thr Leu Gly Asp Gly Asp Phe Leu His Phe Glu Lys Met His Asp
            115                 120                 125

Ala Val Thr Val Ala Ser Ala His Leu Thr Ile Gln Asn Ala Thr Ser
        130                 135                 140

Glu Ile Asp Arg Val Leu Thr Thr Ala Leu Ser Leu Arg Arg Pro Gly
145                 150                 155                 160

Tyr Ile Asn Leu Pro Ile Asp Val Ala Ala Pro Ala Glu Lys Ala
                165                 170                 175

Gln Lys Lys Leu Gln Leu Lys Val Thr Ser Pro Ile Asp Ser Thr Leu
                180                 185                 190

Leu Glu Lys Ile Gln Thr Ala Phe Ser Ser Ala Lys Gln Pro Val Phe
            195                 200                 205

Ile Thr Gly His Glu Ile Gln Ser Tyr His Leu Glu Asp Thr Val Ala
        210                 215                 220

Lys Ile Ala Ala His Thr Thr Val Pro Val Ala Ala Leu Ser Leu Gly
225                 230                 235                 240

Lys Ser Ser Ile Asp Glu Thr His Pro Gln Phe Val Gly Ile Tyr Ser
                245                 250                 255

Gly Ala Leu Thr Ala Glu Pro Leu Lys Thr Tyr Val Asp Asn Ala Asp
                260                 265                 270

Leu Val Ile Leu Leu Gly Ala Gln Leu Thr Asp Thr Ala Thr Ser Gly
            275                 280                 285

Phe Ser Gln Ser Phe Ser Ala Ser Lys Ile Ile Ala Ile His Pro Glu
        290                 295                 300

Thr Thr Thr Val Phe Gly Gln Asp Tyr Pro Ser Asn Asp Phe Lys Glu
305                 310                 315                 320

Leu Ile Glu Ala Leu Thr Thr Ile Asp Tyr Arg Met Glu Thr Ser Ala
                325                 330                 335

Ala Leu Lys Thr Met Pro Ser Thr Lys Glu Phe Ile Ala Thr Asp Thr
                340                 345                 350

Leu Leu Thr Gln Asn Arg Phe Trp Glu Ala Ile Glu Thr Asn Phe Lys
            355                 360                 365

Gln Asn Asp Thr Ile Val Ala Glu Gln Gly Thr Ser Phe Phe Gly Ile
        370                 375                 380

Thr Asn Thr Gln Phe Lys Lys Asp Met Arg Leu Ile Gly Gln Pro Leu
385                 390                 395                 400

Trp Gly Ser Ile Gly Tyr Thr Phe Pro Ala Ala Leu Gly Ser Gln Leu
                405                 410                 415

Ala Ala Arg Ser Lys Arg His Leu Leu Phe Ile Gly Asp Gly Ser Leu
                420                 425                 430

Gln Leu Thr Ile Gln Glu Leu Gly Met Ala Leu Arg Ala Lys Leu Thr
            435                 440                 445

Pro Leu Ile Phe Val Ile Asn Asn Gly Tyr Thr Val Glu Arg Glu
        450                 455                 460

Ile His Gly Pro Asn Glu Arg Tyr Asn Asp Ile Pro Thr Trp Asp Tyr
465                 470                 475                 480

Ala Gln Leu Pro Thr Val Phe Gly Gly Thr Asp Gln Asn Val Ala Thr
                485                 490                 495
```

Tyr Lys Val Thr Thr Glu Thr Glu Leu Ala Glu Ala Leu Val Thr Ala
        500                 505                 510

Lys Ala Asp Thr Thr Arg Leu Gln Trp Ile Glu Val Val Met Asp Gln
        515                 520                 525

Thr Asp Ala Pro Glu Leu Leu Lys Glu Met Gly Arg Ile Phe Ala Lys
        530                 535                 540

Gln Asn Thr His
545

<210> SEQ ID NO 88
<211> LENGTH: 1647
<212> TYPE: DNA
<213> ORGANISM: Brochothrix thermosphacta

<400> SEQUENCE: 88

| | | | | | |
|---|---|---|---|---|---|
| atgtatacga | tcggcgacta | cctcctcgac | cggctgaacg | agctgggcgt | ggaagacatc | 60 |
| ttcggcgtgc | cgggcgacta | caacctgacg | ttcctcgatc | atatcaccgc | gcatccgcag | 120 |
| ctctcctggg | tcggcaatgc | caacgaactc | aacgccgcct | acgccgccga | tggctatgcg | 180 |
| cggacgaaag | gcttcgccgc | gctggtgacg | accttcggcg | tcggcgagct | gtcggccatc | 240 |
| aacggcctcg | ccggctcctt | cgccgaacgg | gtgccggtca | tcgagatcgt | cggcagcccg | 300 |
| gtcagcaccg | tgcagaccga | caagaagctg | gtgcaccaca | ccctgggcga | cggcgacttc | 360 |
| ctgcacttcg | agaagatgca | tgacgccgtc | acggtggcct | cggcgcacct | cacgatccag | 420 |
| aacgccacca | cgcgaaatcga | ccgggtcctg | acgaccgccc | tctcgctgcg | gcgccccggc | 480 |
| tatatcaacc | tgcccatcga | cgtggcggcg | ccccggccg | aaaaagccca | gaaaaagctc | 540 |
| cagctgaaag | tgaccagccc | gatcgacagc | acgctgctgg | aaaagatcca | gacggccttc | 600 |
| tcctcggcca | gcagcccgt | cttcatcacg | ggccatgaaa | tccagtccta | ccacctggag | 660 |
| gataccgtgg | cgaagatcgc | cgcgcacacg | accgtgccgg | tcgcggccct | ctcgctgggc | 720 |
| aagagctcca | tcgatgaaac | ccatccccag | ttcgtcggca | tctactccgg | cgccctgacg | 780 |
| gcggagcccc | tgaaaaccta | cgtcgataac | gccgatctgg | tgatcctgct | cggcgcccag | 840 |
| ctgaccgaca | cggccaccct | gggcttcagc | cagtccttct | cggccagcaa | aatcatcgcc | 900 |
| atccacccgg | aaacgaccac | cgtgttcggc | caggattacc | cgtcgaacga | tttcaaggaa | 960 |
| ctgatcgagg | ccctcacgac | catcgattac | cgcatgaaaa | cctccgcggc | cctgaagacg | 1020 |
| atgccgtcca | ccaaggagtt | catcgccacc | gacacgctgc | tcacccagaa | tcgcttctgg | 1080 |
| gaagccatcg | aaaccaactt | caagcagaac | gataccatcg | tggcggaaca | gggcacgtcg | 1140 |
| ttcttcggca | tcaccaatac | ccagttcaag | aaagatatgc | gcctgatcgg | ccagcccctg | 1200 |
| tggggctcga | tcggctatac | gttccccgcc | gccctgggct | cgcagctggc | cgcccgctcc | 1260 |
| aagcggcatc | tgctcttcat | cggcgatggc | tcgctgcagc | tgaccatcca | ggaactgggc | 1320 |
| atggcgctcc | gcgccaaact | caccccctg | atcttcgtca | tcaacaacaa | cggctacacc | 1380 |
| gtggaacgcg | agatccacgg | cccgaacgaa | cggtataatg | catcccgac | ctgggactat | 1440 |
| gcgcagctgc | cgaccgtgtt | cggcggcacg | gaccagaacg | tggccacgta | taaggtgacg | 1500 |
| accgaaaccg | aactggcgga | ggcgctcgtc | accgccaagg | cggacaccac | ccgcctgcag | 1560 |
| tggatcgagg | tggtgatgga | ccagacggac | gccccggaac | tgctgaaaga | gatgggccgc | 1620 |
| atcttcgcca | agcagaacac | ccattga | | | | 1647 |

<210> SEQ ID NO 89

<211> LENGTH: 548
<212> TYPE: PRT
<213> ORGANISM: Carnobacterium gallinarum

<400> SEQUENCE: 89

```
Met Tyr Thr Val Ala Asp Tyr Leu Leu Asp Arg Leu Lys Glu Leu Gly
1               5                   10                  15

Ile Asn Asp Ile Phe Gly Val Pro Gly Asp Tyr Asn Leu Lys Phe Leu
            20                  25                  30

Asp His Ile Thr Ala Arg Asp Asp Leu Lys Trp Ile Gly Asn Ala Asn
        35                  40                  45

Glu Leu Asn Ala Ala Tyr Met Ala Asp Gly Tyr Ala Arg Thr Lys Gly
    50                  55                  60

Met Ala Ala Leu Val Thr Thr Phe Gly Val Gly Glu Leu Ser Ala Met
65                  70                  75                  80

Asn Gly Ile Gly Gly Ser Phe Ala Glu Lys Val Pro Val Ile Glu Ile
                85                  90                  95

Val Gly Ser Pro Thr Thr Ala Val Gln Asn Ala Gln Lys Leu Val His
            100                 105                 110

His Thr Leu Gly Asp Gly Arg Phe Asn His Phe Glu Lys Met His Glu
        115                 120                 125

Ala Ile Thr Val Gly Ile Gly Ser Leu Thr Lys Glu Asn Ala Ile Thr
    130                 135                 140

Glu Ile Asp Arg Ile Leu Gly Leu Ala Ser Glu Lys Arg Gln Pro Gly
145                 150                 155                 160

Tyr Leu Asn Leu Pro Ile Asp Val Ala Glu Met Glu Val Glu Lys Pro
                165                 170                 175

Asn Lys Pro Leu Phe Asp Thr Lys Val Met Glu Ile Lys Met Glu Gln
            180                 185                 190

Glu Leu Ile Lys Ser Ile Glu Lys Val Leu Asn Ser Val Lys His Pro
        195                 200                 205

Val Ile Ile Ala Gly Asn Glu Ile Ala Ser Phe His Leu Glu Ala Lys
    210                 215                 220

Leu Ala Glu Phe Ile Glu Lys Phe Asn Leu Pro Val Thr Thr Leu Pro
225                 230                 235                 240

Phe Gly Lys Gly Val Phe Asn Glu Glu Asp Lys His Tyr Leu Gly Val
                245                 250                 255

Tyr Thr Gly Thr Pro Thr Thr Glu Pro Leu Lys Ser Tyr Val Asp Gln
            260                 265                 270

Ala Asp Leu Val Leu Leu Leu Gly Ala Lys Leu Thr Asp Ser Ala Thr
        275                 280                 285

Ser Gly Phe Ser Gln Gly Phe Thr Glu Lys Gln Met Ile Ser Leu Ala
    290                 295                 300

Ser Asp Glu Val Ile Phe Gln Gly Glu His Leu Ala Gly Ile Gln Leu
305                 310                 315                 320

Pro Thr Val Leu Asp Glu Leu Leu Met Ile Asn Tyr Pro Gly Tyr His
                325                 330                 335

Gly Glu Ile Gln Pro Met Ser Arg Leu Ala Glu Val Lys Ser Ser Ser
            340                 345                 350

Ser Leu Val Thr Gln Ala Tyr Phe Trp Glu Ala Val Glu Ser Tyr Leu
        355                 360                 365

Glu Glu Gly Asp Thr Leu Val Ala Glu Gln Gly Thr Ser Phe Phe Gly
    370                 375                 380

Ala Ser Thr Val Pro Met Lys Lys Gly Met Ser Phe Ile Gly Gln Pro
```

```
            385                 390                 395                 400
Leu Trp Gly Ser Ile Gly Tyr Thr Phe Pro Ala Met Leu Gly Ser Gln
                405                 410                 415
Ile Ala Lys Lys Gly Ser Arg His Leu Leu Phe Ile Gly Asp Gly Ser
                420                 425                 430
Leu Gln Leu Thr Val Gln Glu Leu Gly Met Thr Leu Arg Glu Lys Leu
            435                 440                 445
Ala Pro Ile Val Phe Ile Asn Asn Asn Gly Tyr Thr Val Glu Arg
        450                 455                 460
Glu Ile His Gly Pro Glu Glu Ile Tyr Asn Asp Ile Pro Met Trp Asp
465                 470                 475                 480
Tyr Gln Lys Leu Pro Ser Val Phe Gly Gly Thr Ala Glu Asn Val Val
                485                 490                 495
Thr Tyr Lys Val Gln Thr Glu Ala Glu Leu Ala Thr Ala Met Arg Lys
                500                 505                 510
Ala Arg Leu Asp Ser Lys Arg Leu Gln Trp Ile Glu Val Val Met Asn
            515                 520                 525
Gln Lys Asp Ala Pro Asp Leu Leu Val Gln Met Gly Lys Ile Phe Ala
        530                 535                 540
Lys Gln Asn Ser
545

<210> SEQ ID NO 90
<211> LENGTH: 1647
<212> TYPE: DNA
<213> ORGANISM: Carnobacterium gallinarum

<400> SEQUENCE: 90
atgtacacgg tcgccgatta cctgctcgat cggctgaagg aactgggcat caatgacatc      60
ttcggcgtcc cgggcgatta taacctcaag ttcctggacc acatcacggc ccgcgacgac     120
ctgaaatgga tcggcaacgc gaacgagctg aacgcggcgt atatggccga tggctacgcc     180
cgcaccaaag gcatggccgc gctggtcacg accttcggcg tcggcgaact ctcggccatg     240
aacggcatcg gcggctcgtt cgccgagaaa gtcccggtca tcgagatcgt gggctccccc     300
accaccgccg tccagaatgc ccagaaactg gtccatcata cgctgggcga cggccgcttc     360
aaccatttcg agaagatgca tgaggcgatc accgtgggca tcggctcgct gaccaaggag     420
aatgccatca ccgaaatcga tcgcatcctg ggcctggcgt ccgagaagcg gcagcccggc     480
tacctgaacc tgccgatcga tgtggccgaa atggaagtgg agaaaccgaa caagccgctc     540
ttcgatacca aggtcatgga aatcaaaatg gaacaggagc tcatcaagag catcgagaaa     600
gtgctcaact cggtcaagca tccggtcatc atcgccggca acgagatcgc cagcttccat     660
ctggaggcca agctggccga gttcatcgag aagttcaatc tccccgtcac cacgctgccg     720
ttcggcaagg gcgtcttcaa cgaagaagat aagcattatc tgggcgtgta tacgggcacc     780
cccacgacgg aaccctgaa gtcctacgtc gaccaggcgg atctggtcct cctgctgggc     840
gccaagctga ccgactccgc caccagcggc ttcagccagg gcttcaccga gaagcagatg     900
atctcgctgg cctcggacga ggtcatcttc cagggcgagc acctcgccgg catccagctc     960
cccaccgtcc tggatgagct gctgatgatc aactatccgg gctaccacgg cgagatccag    1020
ccgatgtcgc ggctggcgga agtgaagtcg tcctccagcc tcgtcaccca ggcgtacttc    1080
tgggaggccc tcgagtcgta cctggaagaa ggcgatacgc tcgtcgccga acagggcacc    1140
agcttcttcg gcgcctccac cgtccccatg aagaagggca tgagcttcat cggccagccg    1200
```
ctgtggggct ccatcggcta cacgttcccg gccatgctcg gctcgcagat cgccaagaag    1260
ggctcgcgcc atctgctgtt catcggcgac ggctcgctcc agctgaccgt ccaggaactg    1320
ggcatgacgc tccgggaaaa gctggcgccg atcgtgttca tcatcaacaa taacggctac    1380
accgtggaac gggaaatcca cggccccgaa gaaatctata cgacatccc gatgtgggac    1440 taccagaagc tcccgtccgt cttcggcggc accgccgaaa acgtggtgac ctataaggtc    1500
cagaccgagg cggagctggc caccgccatg cgcaaggccc gcctggactc gaagcggctg    1560
cagtggatcg aagtggtgat gaaccagaag gacgccccgg acctcctggt gcagatgggc    1620
aagatcttcg ccaagcagaa tagctga                                        1647

<210> SEQ ID NO 91
<211> LENGTH: 548
<212> TYPE: PRT
<213> ORGANISM: Carnobacterium divergens

<400> SEQUENCE: 91

Met Tyr Thr Val Gly Asp Tyr Leu Leu Glu Arg Leu Ser Glu Leu Gly
1               5                   10                  15

Ile Lys Glu Ile Phe Gly Val Pro Gly Asp Tyr Asn Leu Lys Phe Leu
            20                  25                  30

Asp His Ile Val Glu His Pro Asn Leu Lys Trp Ile Gly Asn Ala Asn
        35                  40                  45

Glu Leu Asn Ala Ala Tyr Ala Ala Asp Gly Tyr Ala Arg Thr Lys Gly
    50                  55                  60

Val Ser Ala Leu Val Thr Thr Phe Gly Val Gly Glu Leu Ser Ala Ile
65                  70                  75                  80

Asn Gly Ile Ala Gly Ser Tyr Ala Glu Lys Val Pro Val Ile Gln Ile
                85                  90                  95

Val Gly Ser Pro Thr Met Ala Val Gln Asn Ala His Lys Leu Val His
            100                 105                 110

His Thr Leu Gly Asp Gly Lys Phe Asp His Phe Glu Asn Met His Glu
        115                 120                 125

Ser Val Thr Glu Ala Ile Gly Ser Leu Thr Lys Glu Asn Ala Val Thr
    130                 135                 140

Glu Ile Asp Arg Val Leu Arg Ala Ala Val Leu Lys Arg Arg Pro Val
145                 150                 155                 160

Tyr Leu Asn Leu Pro Ile Asp Val Ala Glu Met Val Val Glu Lys Pro
                165                 170                 175

Ser Gly Pro Leu Leu Pro Lys Gln Ala Ser Leu Ser Ala Arg Glu Val
            180                 185                 190

Glu Leu Val His Glu Leu Glu Lys Ala Leu Gln Gln Ala Lys Asn Pro
        195                 200                 205

Val Val Leu Ala Gly Asn Glu Leu Ala Ser Phe His Leu Glu Thr Tyr
    210                 215                 220

Leu Ala Asp Phe Ile His Lys Phe Asn Leu Pro Ile Thr Thr Leu Pro
225                 230                 235                 240

Phe Gly Lys Gly Val Phe Asn Glu Glu Asp Glu His Tyr Leu Gly Val
                245                 250                 255

Tyr Ala Gly Ser Pro Thr Glu Glu Gly Leu Arg Lys Arg Val Asp Thr
            260                 265                 270

Ala Asp Leu Val Val Ala Leu Gly Ala Lys Leu Thr Asp Ser Ala Thr
        275                 280                 285

Ser Gly Phe Ser Tyr Asp Phe Ser Glu Lys Gln Leu Phe Ser Leu Ala
    290                 295                 300

Ser Asp Glu Val Ile Val Lys Glu His Leu Glu Gly Ile His Leu
305                 310                 315                 320

Pro Ala Val Met Lys Ala Leu Thr Ser Ile Asp Tyr Gln Gly Tyr Gln
                325                 330                 335

Gly Asp Ile Gln Pro Met Ala Arg Leu Lys Ser Ile Lys Pro Thr Asn
            340                 345                 350

Gln Val Leu Thr Gln Arg His Phe Trp Glu Ala Ile Glu Gly Phe Leu
        355                 360                 365

Glu Lys Gly Asp Thr Ala Val Ala Glu Gln Gly Thr Ser Phe Phe Gly
    370                 375                 380

Leu Ser Thr Val Pro Leu Lys Ser Glu Met Ser Phe Ile Gly Gln Pro
385                 390                 395                 400

Leu Trp Gly Ser Ile Gly Tyr Thr Phe Pro Ala Met Leu Gly Ser Gln
                405                 410                 415

Leu Ala Asn Pro Ser Ser Arg His Leu Leu Phe Ile Gly Asp Gly Ser
            420                 425                 430

Leu Gln Leu Thr Ile Gln Glu Leu Gly Met Ala Leu Arg Glu Lys Leu
        435                 440                 445

Thr Pro Ile Val Phe Val Ile Asn Asn Asn Gly Tyr Thr Val Glu Arg
    450                 455                 460

Glu Ile His Gly Pro Asn Glu Ile Tyr Asn Asp Ile Pro Met Trp Asp
465                 470                 475                 480

Tyr Gln Lys Leu Pro Leu Val Phe Gly Gly Ser Glu Gln Ser Val Ile
                485                 490                 495

Thr Tyr Lys Val Thr Thr Glu Leu Glu Leu Ala Asn Ala Leu Lys Ala
            500                 505                 510

Ala Arg Leu Asp Asn Asn Arg Leu Gln Trp Ile Glu Val Val Met Asp
        515                 520                 525

Gln Thr Asp Ala Pro Glu Leu Leu Met Lys Leu Gly Lys Ile Phe Ala
    530                 535                 540

Lys Gln Asn Ser
545

<210> SEQ ID NO 92
<211> LENGTH: 1647
<212> TYPE: DNA
<213> ORGANISM: Carnobacterium divergens

<400> SEQUENCE: 92
atgtataccg tgggcgacta tctcctggag cggctctcgg aactgggcat caaagagatc      60
ttcggcgtgc cgggcgacta caacctgaag ttcctggatc acatcgtgga gcatccgaac     120
ctgaagtgga tcggcaacgc gaatgaactc aacgcggcgt atgccgccga cggctacgcc     180
cgcacgaagg cgtctccgc gctggtgacc accttcggcg tcggcgagct ctccgccatc     240
aacggcatcg ccggctcgta tgccgagaaa gtcccggtca tccagatcgt gggcagcccc     300
acgatggcgg tgcagaatgc ccataagctg gtgcatcata ccctgggcga tgcaaattc     360 gaccacttcg agaacatgca tgagtccgtc accgaagcca tcggcagcct caccaaggag     420
aacgcggtga ccgagatcga tcgcgtgctg cgggccgccg tgctcaaacg cgcccggtg      480 tatctgaacc tccgatcga cgtggccgaa atgtcgtcg aaaaaccgtc gggcccctg       540 ctgcccaagc aggcgagcct gagcgcccgc gaggtcgaac tcgtgcatga gctggagaag     600

```
gccctgcagc aggcgaagaa cccggtggtc ctggcgggca acgagctggc gtcgttccac      660
ctcgaaacgt acctcgccga cttcatccac aagttcaacc tccccatcac gaccctcccc      720
ttcggcaagg gcgtcttcaa cgaggaagac gagcattatc tgggcgtcta tgcgggctcg      780
ccgaccgaag aaggcctgcg gaagcgcgtc gatacggcgg acctggtcgt ggcgctgggc      840
gcgaagctga cggactccgc cacctccggc ttctcgtacg acttctccga aaacagctc       900 ttcagcctgg cgtccgacga agtcatcgtc aaagaggaac acctcgaagg catccatctg      960
ccggccgtca tgaaggcgct gacgagcatc gactaccagg gctaccaggg cgacatccag     1020
ccgatggccc ggctgaagag catcaaaccc accaaccagg tgctgaccca gcgccacttc     1080
tgggaggcca tcgaaggctt cctggaaaag ggcgacaccg ccgtcgcgga gcagggcacg     1140
agcttcttcg gcctctcgac cgtgccgctg aagagcgaaa tgtcgttcat cggccagccg     1200
ctgtggggct ccatcggcta tacgttcccg gcgatgctgg gcagccagct cgccaacccg     1260
tccagccggc acctcctgtt catcggcgac ggcagcctgc agctgacgat ccaggagctc     1320
ggcatggccc tccgcgaaaa actcaccccg atcgtgttcg tcatcaacaa taacggctat     1380
acggtcgaac gggaaatcca cggcccgaat gaaatctata cgacatccc gatgtgggac     1440 taccagaaac tcccgctcgt cttcggcggc tccgagcagt cggtcatcac ctataaagtg     1500
acgaccgaac tggaactggc gaacgcgctc aaggcggccc ggctggacaa caaccgcctg     1560
cagtggatcg aagtggtgat ggaccagacc gatgcgccgg agctcctcat gaagctgggc     1620
aagatcttcg cgaagcagaa tagctga                                         1647
```

<210> SEQ ID NO 93
<211> LENGTH: 174
<212> TYPE: PRT
<213> ORGANISM: Helicobacter bizzozeronii

<400> SEQUENCE: 93

```
Met Ile Ala Glu Gln Gly Thr Ser Phe Phe Gly Ala Ile Ser Met Val
1               5                   10                  15

Leu Pro Ser Gly Val Ser Phe Ile Gly Gln Pro Leu Trp Gly Ser Ile
            20                  25                  30

Gly Tyr Thr Phe Gly Ala Leu Leu Gly Thr Ala Leu Ala Ser Pro Asp
        35                  40                  45

Arg Arg His Ile Leu Leu Ile Gly Asp Gly Ser Phe Gln Leu Val Ala
    50                  55                  60

Gln Glu Leu Ser Thr Met Leu Arg Glu Asn Ile Thr Pro Ile Ile Ile
65                  70                  75                  80

Val Ile Asn Asn Asp Gly Tyr Thr Val Glu Arg Cys Ile His Gly Pro
                85                  90                  95

Thr Arg Gln Tyr Asn His Ile Asn Met Trp His Tyr Ser Lys Leu Ala
            100                 105                 110

Ser Phe Phe Asp Val His Leu Ala Arg Glu Val Val Ser Phe Gln Val
        115                 120                 125

Ser Ser Val Ala Gly Leu Arg Glu Ala Leu Cys Val Ala Gln Gln Asn
    130                 135                 140

Ser Lys Leu Ala Leu Ile Glu Ala Cys Met Asp Lys Asn Asp Ala Pro
145                 150                 155                 160

Ile Leu Leu Lys Lys Leu Gly Ala Leu Phe Gly Ala Gln Ile
                165                 170
```

<210> SEQ ID NO 94

<211> LENGTH: 1104
<212> TYPE: DNA
<213> ORGANISM: Helicobacter bizzozeronii

<400> SEQUENCE: 94

```
atgcagacga cgatcggcca gtatctcctg gaccggctga agtcctacgg cgtgcagcat      60
ctcttcggcg tgcccggcga ctataacctg gccttcctcg acctgatcga agacgatccg     120
cacatccagt gggtcggcaa ctgcaacgaa ctgaatgcgt cctacgccgc cgacggctac     180
gcgcggctca agagcatggg cgccctcctg acgaccttcg gcgtcggcga gctgagcgcc     240
atcaacggca tcgccggctc gtacgcggaa tccgtgccgg tcgtgaagat cgtcggcatg     300
ccctcccgcg gcgtggtcca ttcccgcaag ctggtgcacc acaccctggg cgacggcgag     360
ttcctcaagt tctacaacat cgtatgccga agtgagcgtcg cccagacgat cctcaacaaa     420
cagaacgccc agagcgaaat cgaccgcgtc ctgggcgaat gcttcctgca taaaaagccg     480
gtctacatcg gcctcccggt ggacgtgacg cacatcccga tcgaaacgta cgcccccctcc     540
cccctggtgg ccaagagcga cccgaaaatc ctcaacgcct tcctgaagga cgcccaggag     600
ctgctgtcga gagcaaatc ccaggtggtc atggcggatt atgaagtgaa ccgctaccag      660
ttcaaccagg agctgacgcg cttcatcgaa gccgtgaacc tgcccatcgt gtcgctggcg     720
atgggcaagg gcgtcttcga tgaaacgcac ccgaacttca tcggcgtgta acggcatc      780
ctctcggacg cccgggtgag ctcgctgatg aagcacgccg actgcgcgat cctggtgggc     840
gtgaagctga cggactcgct gacggccggc ttccactata tccgcgaaca tcacctgtcc     900
atccagatcc acccctttcta ctcccagatc ggcgaaaaga cgtacgacga tatcctcatg     960
caggacgtgc tgaaagcgct cgcccagctg aagttccagg cctcgttccc gaaggagacg    1020
caccccaaaa cgccgcacct gaacggcaag ctgacccagg acaagttctt caagatcgac    1080
tcgcgcatcc tgaccccccc gtga                                           1104
```

<210> SEQ ID NO 95
<211> LENGTH: 273
<212> TYPE: PRT
<213> ORGANISM: Staphylococcus aureus

<400> SEQUENCE: 95

```
Met Lys Gln Arg Ile Gly Ala Tyr Leu Ile Asp Ala Ile His Arg Ala
 1               5                  10                  15

Gly Val Asp Lys Ile Phe Gly Val Pro Gly Asp Phe Asn Leu Ala Phe
            20                  25                  30

Leu Asp Asp Ile Ile Ser Asn Pro Asn Val Asp Trp Val Gly Asn Thr
        35                  40                  45

Asn Glu Leu Asn Ala Ser Tyr Ala Ala Asp Gly Tyr Ala Arg Leu Asn
    50                  55                  60

Gly Leu Ala Ala Leu Val Thr Thr Phe Gly Val Gly Glu Leu Ser Ala
65                  70                  75                  80

Val Asn Gly Ile Ala Gly Ser Tyr Ala Glu Arg Ile Pro Val Ile Ala
                85                  90                  95

Ile Thr Gly Ala Pro Thr Arg Ala Val Glu Gln Ala Gly Lys Tyr Val
            100                 105                 110

His His Ser Leu Gly Glu Gly Thr Phe Asp Asp Tyr Arg Lys Met Phe
        115                 120                 125

Ala His Ile Thr Val Ala Gln Gly Tyr Ile Thr Pro Glu Asn Ala Thr
    130                 135                 140
```

```
Thr Glu Ile Pro Arg Leu Ile Asn Thr Ala Ile Ala Glu Arg Arg Pro
145                 150                 155                 160

Val His Leu His Leu Pro Ile Asp Val Ala Ile Ser Glu Ile Glu Ile
                165                 170                 175

Pro Thr Pro Phe Glu Val Thr Ala Ala Lys Asp Thr Asp Ala Ser Thr
            180                 185                 190

Tyr Ile Glu Leu Leu Ala Ser Lys Leu His Gln Ser Lys Gln Pro Ile
        195                 200                 205

Ile Ile Thr Gly His Glu Ile Asn Ser Phe His Leu His Gln Glu Leu
    210                 215                 220

Glu Asp Phe Val Asn Gln Thr Gln Ile Pro Val Ala Gln Leu Ser Leu
225                 230                 235                 240

Gly Lys Gly Ala Phe Asn Glu Glu Asn Pro Tyr Tyr Met Gly Ile Tyr
                245                 250                 255

Asp Gly Lys Leu Pro Lys Ile Lys Tyr Ala Ile Met Trp Thr Thr Ala
            260                 265                 270

Ile
```

<210> SEQ ID NO 96
<211> LENGTH: 822
<212> TYPE: DNA
<213> ORGANISM: Staphylococcus aureus

<400> SEQUENCE: 96

```
atgaaacagc gcatcggcgc ctacctgatc gatgccatcc accgcgccgg cgtggacaag    60
atcttcggcg tcccgggcga tttcaacctc gccttcctgg acgatatcat cagcaacccg   120
aacgtggatt gggtcggcaa caccaacgag ctgaacgcct cgtatgcggc cgatggctat   180
gcccgcctca acggcctggc ggccctggtc accaccttcg gcgtgggcga actgtcggcg   240
gtgaatggca tcgcgggcag ctatgccgag cgcatcccgg tgatcgccat caccggcgcc   300
cccacccgcg ccgtcgagca ggccggcaag tatgtgcatc atagcctggg cgaaggcacg   360
ttcgatgact accggaagat gttcgcccat atcaccgtgg cccagggcta catcacgccc   420
gagaatgcga cgaccgaaat ccccgcctc atcaacacgg ccatcgccga cgccgcccg    480
gtgcatctcc acctgcccat cgatgtggcg atctcggaga tcgagatccc caccccgttc   540
gaggtgacgg cggcgaaaga cacggacgcc tcgacctata tcgagctgct ggccagcaaa   600
ctgcaccaga gcaagcagcc catcatcatc acgggccatg agatcaactc cttccatctg   660
caccaggaac tggaagattt cgtcaatcag acccagatcc ccgtggcgca gctctcgctg   720
ggcaaaggcg ccttcaacga ggaaaacccg tactatatgg gcatctacga tggcaagctg   780
cccaaaatca gtatgcgat catgtggacc acggcgatct ga                       822
```

<210> SEQ ID NO 97
<211> LENGTH: 554
<212> TYPE: PRT
<213> ORGANISM: Fictibacillus macauensis

<400> SEQUENCE: 97

```
Met Asn Asn His Tyr Thr Val Gly Thr Tyr Leu Leu His Arg Leu Ser
1               5                   10                  15

Glu Leu Gly Val Arg His Met Phe Gly Val Pro Gly Asp Tyr Asn Leu
            20                  25                  30

Thr Phe Leu Asp Asp Val Ile Asp Phe Glu Gly Met Glu Trp Ile Gly
        35                  40                  45
```

```
Asn Cys Asn Glu Leu Asn Ala Ala Tyr Ala Ala Asp Gly Tyr Ala Arg
 50                  55                  60

Ile Asn Gly Met Ala Ala Leu Val Thr Thr Phe Gly Val Gly Glu Leu
 65                  70                  75                  80

Ser Ala Ile Asn Gly Ile Ala Gly Ser Tyr Ala Glu Lys Val Pro Val
                 85                  90                  95

Val Lys Ile Thr Gly Met Pro Thr Thr Asn Val Met Asn Gln Asn Leu
            100                 105                 110

Tyr Val His His Thr Leu Gly Asp Gly Asn Phe Gln His Phe Gly Asn
            115                 120                 125

Met Phe Gln Glu Val Thr Ala Ala Gln Thr Met Leu Thr Gln Glu Asn
130                 135                 140

Ala Ala Gln Glu Ile Asp Arg Val Leu Leu Ala Cys Trp His Glu Lys
145                 150                 155                 160

Arg Pro Val His Ile Asn Leu Pro Ile Asp Val Tyr Asn Lys Pro Val
                165                 170                 175

Asn Pro Pro Glu His Ser Leu Leu Glu Arg Gly Ile Ser Ser Asn Ala
            180                 185                 190

Thr Ala Leu Glu Gln Met Leu Thr Thr Val Ile Pro Thr Ile Lys Glu
            195                 200                 205

Ala Thr Ser Pro Val Ile Leu Ala Asp Tyr Glu Val Tyr Arg Tyr Gln
210                 215                 220

Ala Gln Glu Ala Leu Met Leu Leu Ala Glu Lys Thr Gly Phe Pro Val
225                 230                 235                 240

Ala Thr Leu Ser Met Gly Lys Gly Val Phe Asn Glu Thr His Pro Gln
                245                 250                 255

Phe Ile Gly Val Tyr Asn Gly Asp Leu Ser Ser Asp Tyr Val Lys Asn
            260                 265                 270

Met Val Asp His Ala Asp Cys Ile Leu Ser Ile Gly Val Lys Leu Thr
            275                 280                 285

Asp Ser Ile Thr Gly Gly Phe Ser His Glu Phe Thr Glu Glu Gln Val
290                 295                 300

Ile Asp Ile Ser Pro Tyr Ser Val Ser Lys Lys Ala Leu Lys Trp Ala
305                 310                 315                 320

Pro Ile Thr Met Leu Asp Ala Leu Gly Ala Ile Thr Asp Ala Leu Glu
                325                 330                 335

Gln Lys Pro Thr Pro Ala Thr Ala Arg Leu Ala Ala Tyr Ser Asn
            340                 345                 350

Glu Ser Ser Phe Thr Ala Thr Asn Thr Thr Leu Thr Gln Glu Arg Phe
            355                 360                 365

Phe Asp Gln Val Ser His Phe Leu Gln Glu Gly Asp Val Ile Leu Ala
370                 375                 380

Glu Gln Gly Thr Ser Phe Phe Gly Ala Ala Thr Met Pro Leu Pro Lys
385                 390                 395                 400

Gly Ala Thr Phe Ile Gly Gln Pro Leu Trp Gly Ser Ile Gly Tyr Thr
                405                 410                 415

Leu Pro Ala Leu Leu Gly Ser Gln Leu Ala Asp Glu Ser Arg Arg Asn
            420                 425                 430

Leu Leu Leu Ile Gly Asp Gly Ser Phe Gln Leu Thr Ala Gln Glu Leu
            435                 440                 445

Ser Thr Met Leu Arg Gln Arg Ile Ala Pro Ile Phe Leu Ile Asn
450                 455                 460

Asn Asp Gly Tyr Thr Val Glu Arg Ala Ile His Gly Glu Asn Gln Val
```

| | | 465 | | | 470 | | | | 475 | | | 480 | |
|---|---|---|---|---|---|---|---|---|---|---|---|---|---|

Tyr Asn Asp Ile Gln Met Trp Asp Tyr Ser Lys Leu Pro Ala Val Phe
                485                 490                 495

Gly Ala Ala Asp Ala Ser Val Thr Tyr Lys Val Arg Thr Glu Glu Glu
            500                 505                 510

Leu Glu Ala Ala Leu His Ser Ala Gln Asn Ser Ser Gln Leu Val Phe
        515                 520                 525

Ile Glu Val Met Met Glu Lys Asn Asp Thr Pro Glu Leu Leu Thr Ala
530                 535                 540

Leu Ser Lys Arg Phe Ala Asn Gln Asn Asn
545                 550

<210> SEQ ID NO 98
<211> LENGTH: 1665
<212> TYPE: DNA
<213> ORGANISM: Fictibacillus macauensis

<400> SEQUENCE: 98

```
atgaacaacc attataccgt cggcacctat ctgctgcatc gcctgtccga gctgggcgtc      60
cgccatatgt tcggcgtgcc cggcgactat aatctgacgt tcctggacga tgtcatcgac     120
ttcgaaggca tggaatggat cggcaactgt aacgagctca cgccgccta cgcggccgac     180
ggctatgccc gcatcaacgg catggccgcc ctggtgacca cttcggcgt cggcgagctg     240
tcggccatca cggcatcgc cggctcgtac gccgaaaaag tgccggtcgt caaaatcacg     300
ggcatgccca ccaccaacgt gatgaaccag aatctgtacg tccatcacac gctgggcgac     360
ggcaacttcc agcacttcgg caacatgttc caggaggtca ccgccgcgca gacgatgctg     420
acccaggaaa acgcggcgca ggagatcgat gcgtgctgc tcgcctgctg gcacgaaaag     480
cgcccggtgc acatcaacct cccgatcgat gtctacaaca agccggtcaa ccccccccgag     540
cattcgctcc tggaacgggg catctcgtcg aacgcgaccg cgctcgaaca gatgctgacc     600
accgtgatcc cgacgatcaa ggaggccacc tcgcccgtga tcctggcgga ttatgaggtg     660
tatcgctacc aggcccagga agccctgatg ctgctggcgg aaaagaccgg cttcccggtg     720
gccaccctga gcatgggcaa gggcgtgttc aacgaaaccc atccccagtt catcggcgtg     780
tacaacggcg acctgtcgtc cgactacgtg aagaatatgg tcgaccatgc cgactgtatc     840
ctctccatcg gcgtcaagct gaccgacagc atcacgggcg gcttcagcca tgagttcacc     900
gaggagcagg tcatcgacat ctccccgtat agcgtgagca aaaagcccct caaatgggcg     960
cccatcacga tgctggatgc gctgggcgcc atcacggatg ccctggagca agagccgacc    1020
cccgccacca ccgcgcggct cgccgcctac tcgaacgaga gctccttcac cgcgacgaac    1080
acgacgctga cccaggagcg cttcttcgac caggtgtccc acttcctcca ggagggcgac    1140
gtgatcctgg cggaacaggg caccagcttc ttcggcgcgg ccacgatgcc gctcccgaag    1200
ggcgccacgt tcatcggcca gccgctgtgg ggcagcatcg gctacaccct gccggccctg    1260
ctgggcagcc agctggccga cgaatcccgc cgcaatctcc tgctcatcgg cgatggctcg    1320
ttccagctca ccgcccagga gctgtcgacg atgctgcgcc agcggatcgc gccgatcatc    1380
ttcctcatca caacgacgg ctacaccgtg aacgggcga tccacggcga gaatcaggtg    1440
tataacgaca tccagatgtg ggactattcg aagctgccgg cggtcttcgg cgcggcggac    1500
gccagcgtca cctacaaggt ccggaccgaa gaggagctgg aggcggccct gcatagcgcc    1560
cagaactcgt cccagctggt cttcatcgaa gtgatgatgg agaagaatga cacccccgaa    1620
```
ctgctgacgg ccctgagcaa gcgcttcgcg aatcagaaca actga        1665

<210> SEQ ID NO 99
<211> LENGTH: 572
<212> TYPE: PRT
<213> ORGANISM: Bacillus licheniformis

<400> SEQUENCE: 99

```
Met Asn Asn Val Ala Ala Lys Asn Glu Thr Leu Thr Val Arg Gly Ala
1               5                   10                  15

Glu Leu Val Val Asp Ser Leu Ile Gln Gln Gly Val Thr His Val Phe
            20                  25                  30

Gly Ile Pro Gly Ala Lys Ile Asp Ala Val Phe Asp Val Leu Lys Asp
        35                  40                  45

Lys Gly Pro Glu Leu Ile Val Cys Arg His Glu Gln Asn Ala Ala Phe
    50                  55                  60

Met Ala Ala Val Gly Arg Leu Thr Gly Lys Pro Gly Val Cys Leu
65                  70                  75                  80

Val Thr Ser Gly Pro Gly Ala Ser Asn Leu Ala Thr Gly Leu Val Thr
            85                  90                  95

Ala Asn Thr Glu Gly Asp Pro Val Ala Leu Ala Gly Ala Val Lys
            100                 105                 110

Arg Ala Asp Arg Leu Lys Lys Thr His Gln Ser Met Asp Asn Ala Ala
        115                 120                 125

Leu Phe Gln Pro Ile Thr Lys Tyr Ser Ala Glu Val Glu Asp Ala Asn
130                 135                 140

Asn Ile Pro Glu Ala Val Thr Asn Ala Phe Arg Ala Ala Ser Gly
145                 150                 155                 160

Gln Ala Gly Ala Ala Phe Leu Ser Phe Pro Gln Asp Val Thr Ala Gly
                165                 170                 175

Pro Ala Thr Ala Lys Pro Val Lys Thr Met Pro Ala Pro Lys Leu Gly
            180                 185                 190

Ala Ala Ser Asp Glu Gln Ile Ser Ala Ala Ile Ala Lys Ile His Asn
        195                 200                 205

Ala Asn Leu Pro Val Val Leu Val Gly Met Lys Gly Gly Arg Pro Glu
    210                 215                 220

Ala Ile Glu Ala Val Arg Arg Leu Leu Arg Lys Val Lys Leu Pro Phe
225                 230                 235                 240

Val Glu Thr Tyr Gln Ala Ala Gly Thr Leu Ser His Asp Leu Glu Asp
                245                 250                 255

Gln Tyr Phe Gly Arg Ile Gly Leu Phe Arg Asn Gln Pro Gly Asp Met
            260                 265                 270

Leu Leu Glu Lys Ala Asp Val Val Leu Thr Val Gly Tyr Asp Pro Ile
        275                 280                 285

Glu Tyr Asp Pro Val Phe Trp Asn Gly Lys Gly Glu Arg Ser Val Ile
    290                 295                 300

His Leu Asp Glu Ile Gln Ala Ile Asp His Asp Tyr Gln Pro Glu
305                 310                 315                 320

Ile Glu Leu Ile Gly Asp Ile Ala Glu Thr Leu Asn His Ile Glu His
                325                 330                 335

Asp Ser Leu Pro Val Ser Ile Asp Glu Ser Phe Ala Pro Val Leu Asp
            340                 345                 350

Tyr Leu Lys Lys Ala Leu Glu Glu Gln Ser Glu Pro Pro Lys Glu Thr
        355                 360                 365
```

```
Lys Thr Asp Leu Val His Pro Leu Gln Ile Val Arg Asp Leu Arg Glu
370                 375                 380
Leu Leu Ser Asp Asp Ile Thr Val Thr Cys Asp Ile Gly Ser His Ala
385                 390                 395                 400
Ile Trp Met Ser Arg Tyr Phe Arg Thr Tyr Arg Pro His Gly Leu Leu
                405                 410                 415
Ile Ser Asn Gly Met Gln Thr Leu Gly Val Ala Leu Pro Trp Ala Ile
            420                 425                 430
Ala Ala Thr Leu Val Asn Pro Gly Gln Lys Val Val Ser Val Ser Gly
        435                 440                 445
Asp Gly Gly Phe Leu Phe Ser Ala Met Glu Leu Glu Thr Ala Val Arg
    450                 455                 460
Leu Lys Ala Pro Ile Val His Ile Val Trp Asn Asp Ser Thr Tyr Asp
465                 470                 475                 480
Met Val Ala Phe Gln Gln Glu Met Lys Tyr Lys Arg Thr Ser Gly Val
                485                 490                 495
Asp Phe Gly Gly Ile Asp Ile Val Lys Tyr Ala Glu Ser Phe Gly Ala
            500                 505                 510
Lys Gly Leu Arg Val Asn Ser Pro Asp Glu Leu Ala Glu Val Leu Lys
        515                 520                 525
Ala Gly Leu Asp Ala Glu Gly Pro Val Val Ile Asp Ile Pro Val Asp
    530                 535                 540
Tyr Ser Asp Asn Ile His Leu Ala Asp Gln Arg Phe Pro Lys Lys Phe
545                 550                 555                 560
Glu Glu His Phe Asn Lys Glu Ala Ser Lys Gln Ser
                565                 570
```

<210> SEQ ID NO 100
<211> LENGTH: 1719
<212> TYPE: DNA
<213> ORGANISM: Bacillus licheniformis

<400> SEQUENCE: 100

```
atgaataacg tcgcggccaa gaacgaaacc ctgaccgtcc ggggcgccga actcgtggtg      60
gatagcctga tccagcaggg cgtgacccat gtcttcggca tcccgggcgc caaaatcgac     120
gcggtcttcg acgtgctgaa ggataagggc cccgaactga tcgtctgccg ccatgagcag     180
aacgcggcct tcatggccgc cgccgtcggc cgcctgacgg gcaagccggg cgtctgcctg     240
gtcacctccg gcccgggcgc ctcgaatctc gcgaccggcc tggtcaccgc gaacacggaa     300
ggcgacccgg tggtcgccct ggcgggcgcc gtgaagcggg cggatcggct gaagaagacg     360
caccagtcga tggataacgc cgccctgttc cagcccatca cgaagtacag cgcggaggtg     420
gaagacgcga caacatcccc ggaggccgtg acgaacgcct tccgcgccgc gggcgtccggc    480
caggccggcg cggccttcct cagcttcccc caggatgtca ccgccggccc ggccaccgcc     540
aagccggtca aaaccatgcc cgccccgaag ctgggcgccg cgagcgatga acagatctcc     600
gccgcgatcg cgaagatcca caacgcgaat ctgccggtgg tcctcgtggg catgaagggc     660
ggccggccgg aagccatcga agccgtcgcg cgcctgctcc gcaaggtcaa gctcccgttc     720
gtggaaacct accaggcggc cggcacgctg tcgcacgatc tggaggatca gtacttcggc     780
cggatcggcc tgttccggaa ccagccgggc gacatgctcc tggaaaaggc cgacgtggtc     840
ctgaccgtgg gctacgaccc gatcgagtac atccgggtgt tctggaatgg caaaggcgaa     900
cgctcggtca tccacctcga cgaaatccag gccgatatcg atcacgacta ccagcccgag     960
```

-continued

```
atcgaactca tcggcgacat cgcggaaacc ctcaatcaca tcgagcatga ctcgctgccg    1020
gtgtccatcg acgaatcctt cgcgcccgtg ctcgactatc tcaagaaggc gctcgaagaa    1080
cagtcggagc ccccgaagga aacgaagacc gatctggtcc acccgctcca gatcgtgcgc    1140
gacctgcgcg agctgctctc cgatgacatc accgtcacct gcgacatcgg cagccacgcc    1200
atctggatgt cccgctattt ccgcacctat cgcccgcatg gcctcctgat ctccaacggc    1260
atgcagacgc tgggcgtcgc cctgccgtgg gcgatcgccg cgaccctggt gaacccgggc    1320
cagaaggtgg tgtcggtcag cggcgatggc ggcttcctct tctccgcgat ggaactcgaa    1380
accgccgtcc gcctcaaggc gccgatcgtg cacatcgtgt ggaacgactc cacgtacgac    1440
atggtcgcgt tccagcagga aatgaagtac aagcgcacct ccggcgtcga tttcggcggc    1500
atcgacatcg tcaagtatgc ggaatccttc ggcgccaaag gcctccgcgt gaatagcccc    1560
gatgaactgg ccgaggtcct gaaggccggc ctcgacgcgg agggcccggt ggtcatcgac    1620
atccccgtcg actactcgga taacatccac ctggccgacc agcgcttccc gaagaagttc    1680
gaggagcact tcaacaagga agcgtcgaag cagtcctga                          1719
```

METHODS AND MICROORGANISMS FOR THE FERMENTATION OF METHANE TO MULTI-CARBON COMPOUNDS

CROSS-REFERENCE

This application claims priority benefit of U.S. Provisional Application Nos. 62/491,683, filed Apr. 28, 2017; and 62/512,315, filed May 30, 2017, which are hereby incorporated by reference in their entireties.

SEQUENCE LISTING

The instant application contains a Sequence Listing which has been submitted electronically in ASCII format and is hereby incorporated by reference in its entirety. The ASCII copy was created on Feb. 23, 2021, is named 16604425SeqList.txt and is 295,325 bytes in size.

BACKGROUND OF THE DISCLOSURE

As crude oil becomes very expensive, there has been a push to use alternative methods to produce fuels and fuel additives. Alternative methods, including fermentation, have been pursued in recent years; however, most of these methods require a feedstock that consumes our food supply. For example, sugar (usually in the form of corn) is used to produce ethanol and isobutanol.

A feedstock that is relatively cheap and does not decrease overall food supply is natural gas. The methane ($CH_4$) contained in natural gas has great value as a chemical feedstock for the production of chemicals and food additives. Methane can be obtained from shale gas, oil drilling, municipal solid waste, biomass gasification/conversion, and methanogenic archaea. Wellhead natural gas varies in composition from 40% to 95% methane, wherein the other components include ethane, propane, butane, pentane, and heavier hydrocarbons, along with hydrogen sulfide, carbon dioxide, helium and nitrogen.

One chemical that has recently received a great deal of attention is isobutanol. Isobutanol (also known as 2-methylpropan-1-ol) is an organic compound with the formula $(CH_3)_2CHCH_2OH$. Since isobutanol is a higher-chain alcohol, it has an energy density that is close to gasoline. Currently, ethanol is used to supplement gasoline, and is added up to 10%. However, isobutanol has several advantageous properties that make it an attractive alternative to ethanol as a gasoline additive or biofuel. For example, isobutanol is not as volatile or corrosive as ethanol, and does not readily absorb water. Furthermore, branched-chain alcohols, such as isobutanol, have higher-octane numbers, resulting in less knocking in engines. Thus, isobutanol is fully compatible with gasoline combusting engines as well as in jet engines.

Other uses of isobutanol include, but are not limited to, its use as: a feedstock chemical in the manufacture of isobutyl acetate (which is used in the production of lacquer and similar coatings, and in the food industry as a flavoring agent); a precursor of derivative esters-isobutyl esters such as diisobutyl phthalate (DIBP) (used as plasticizers in plastics, rubbers, and other dispersions); a precursor of p-xylene (a building block for plastic bottles, textiles and clothing); a paint solvent; a varnish remover; an ink ingredient; a paint additive (to reduce viscosity, improve brush flow, and retard formation of oil residues (blush) on painted surfaces); a gasoline additive (to reduce carburetor icing); an automotive polish additive; an automotive paint cleaner additive; a chemical extractant in production of organic compounds; and a mobile phase in thin layer chromatography.

The present inventors have developed a way of using genetically modified microorganisms, such as methanotrophs, bacteria, or yeast, in order to dramatically improve the production of multi-carbon compounds, such as isobutyraldehyde and isobutanol, from cheap carbon compounds, such as methane.

INCORPORATION BY REFERENCE

All publications, patents, and patent applications cited herein are hereby incorporated by reference in their entirety and to the same extent as if each individual publication, patent, or patent application was specifically and individually indicated to be incorporated by reference. In the event of a conflict between a term herein and a term in an incorporated reference, the term herein controls.

SUMMARY

Isobutanol and other alcohols are valuable chemicals that can be used in a variety of ways, such as for fuels and solvents. Disclosed herein are methods and microorganisms that can be used to generate valuable alcohols such as isobutanol.

Aldehydes, such as isobutyraldehyde and isovaleraldehyde, can also be produced by the methods and microorganisms disclosed herein. These aldehydes can be used to generate alcohols and can be converted into different useful polymers.

Disclosed herein are genetically modified microorganisms capable of converting a $C_1$ carbon to a multicarbon product. These microorganisms can comprise a gene encoding an acetolactate synthase (AlsS); a ketol-acid reductoisomerase; a dihydroxy-acid dehydratase (DHAD); and/or a 2-keto acid decarboxylase (KDC). In some cases, the genes encoding for the acetolactate synthase (AlsS); ketol-acid reductoisomerase (KARI); dihydroxy-acid dehydratase (DHAD); and/or 2-keto acid decarboxylase (KDC) is under the control of a rare earth metal switch. In some cases, the rare earth metal switch can be a lanthanum switch.

In one example, disclosed herein is a genetically modified microorganism capable of converting a $C_1$ carbon to a multicarbon product comprising a gene encoding: an acetolactate synthase (AlsS); a ketol-acid reductoisomerase (KARI); a dihydroxy-acid dehydratase (DHAD); and a 2-keto acid decarboxylase (KDC), where the gene encoding the 2-keto acid decarboxylase (KDC) comprises a polynucleotide that is at least 60% identical to SEQ ID NO: 9.

In another example, disclosed herein is a genetically modified microorganism capable of converting a $C_1$ carbon to a multicarbon product comprising a gene encoding for an acetolactate synthase (AlsS); a ketol-acid reductoisomerase (KARI); a dihydroxy-acid dehydratase (DHAD); a 2-keto acid decarboxylase (KDC); and an alcohol dehydrogenase (ADH), where the gene encoding the alcohol dehydrogenase (ADH) comprises a polynucleotide that is at least 60% identical to SEQ ID NO: 17.

The genetically modified microorganism can produce multicarbon products such as aldehydes. For example, the aldehyde can be isobutyraldehyde. In some cases, the genetically modified microorganism can produce an alcohol as a multicarbon product. The alcohol can be ethanol, methanol, and/or isobutanol. In some cases, isobutanol is produced.

The acetolactate synthase (AlsS) gene used can be a gram positive bacterial AlsS gene. In some cases, the AlsS gene can comprise a polynucleotide that is at least 60% identical SEQ ID NO: 1. In some cases, the AlsS gene can encode for a polypeptide that comprises an amino acid sequence that is at least 90% identical to SEQ ID NO: 2. In some cases, the AlsS gene can comprise a polynucleotide that is at least 60% identical SEQ ID NO: 100. In some cases, the AlsS gene can encode for a polypeptide that comprises an amino acid sequence that is at least 90% identical to SEQ ID NOs: 99.

The ketol-acid reductoisomerase (KARI) gene can be from a gram negative bacterial ketol-acid reductoisomerase gene. In some cases, the gene encoding for a ketol-acid reductoisomerase (KARI) comprises a polynucleotide that is at least 85% identical to SEQ ID NO: 3. In some cases, the ketol-acid reductoisomerase gene can encode for a polypeptide that comprises an amino acid sequence that is at least 90% identical to SEQ ID NO: 4.

The dihydroxy-acid dehydratase (DHAD) gene can be a gram negative bacterial dihydroxy-acid dehydratase (DHAD) gene or a methanotrophic dihydroxy-acid dehydratase (DHAD) gene. In some cases, the gene encoding a dihydroxy-acid dehydratase (DHAD) can comprise a polynucleotide that is at least 82% identical to SEQ ID NO: 5 or can comprise a polynucleotide that is 90% identical to SEQ ID NO: 7. In some cases, the gene encoding for a dihydroxy-acid dehydratase (DHAD) can encode for a polypeptide that comprises an amino acid sequence that is at least 90% identical to SEQ ID NOs: 6 or 8.

The KDC gene used in these microorganisms can comprise a polynucleotide that is at least 60% identical to SEQ ID NO: 9. In some cases, the genetically modified microorganism can further comprise one or more additional genes encoding for a 2-keto acid decarboxylase (KDC), e.g., a second KDC gene. In some cases, the 2-keto acid decarboxylase (KDC) (e.g., the second KDC) can be from a microorganism that is capable of converting a $C_1$ carbon to a multicarbon product. In some cases, the additional gene encoding for a 2-keto acid decarboxylase (KDC) can be a methanotroph KDC gene. In some cases, the additional gene encoding for a 2-keto acid decarboxylase (KDC) can be a *Methylococcus capsulatus* KDC gene. In some cases, the additional gene encoding for a 2-keto acid decarboxylase (KDC) can comprise a polynucleotide that is at least 60% identical to SEQ ID NO: 9. In some cases, the additional gene encoding for a 2-keto acid decarboxylase (KDC) can comprise a polynucleotide that is at least 60% identical to SEQ ID NO: 11. In some cases, the additional gene encoding for a 2-keto acid decarboxylase (KDC) can encode for a polypeptide comprising an amino acid sequence at least 90% identical to the amino acid sequence of any one of SEQ ID NOs: 10, 12, 55, 57, 59, 61, 63, 65, 67, 69, 71, 73, 75, 77, 79, 81, 83, 85, 87, 89, 91, 93, 95, or 97.

Also disclosed herein are microorganisms that can produce an alcohol, such as ethanol, methanol, or isobutanol (or other alcohols such as isopentanol). In these cases, the microorganism can further comprise an alcohol dehydrogenase (ADH) gene. The ADH gene can be from a gram negative or a gram positive bacteria ADH or a yeast. The ADH can be under the control of a rare earth metal switch. In some cases, the rare earth metal switch can be a lanthanum switch. In some cases, the ADH gene can encode for a polynucleotide that comprises at least 60% identical to any one of SEQ ID NOs: 13, 15, or 17. In some cases, the ADH gene encodes for a polypeptide that comprises an amino acid sequence that is at least 90% identical to any one of SEQ ID NOs: 14, 16, or 18. In some cases, the ADH gene comprises a polynucleotide that is substantially similar to any one of SEQ ID NOs: 13, 15, 17, 24, 26, 28, 30, 32, 34, 36, 38, 40, 42, 44, 46, 48, 50, 52, or 54. In some cases, the ADH gene encodes for a polypeptide that comprises an amino acid sequence that is at least 90% identical to the amino acid sequence of any one of SEQ ID NOs: 14, 16, 18, 23, 25, 27, 29, 31, 33, 35, 37, 39, 41, 43, 45, 47, 49, 51, or 53.

In some cases, the ADH gene can be an *E. coli* ADH gene, a *S. cerevisiae* ADH gene, or both. The ADH gene can also be from the genus *Clostridium, Geobacillus,* and/or *Lactococcus*. In some cases, when the ADH gene is an *E. coli* ADH gene, the *E. coli* ADH gene can comprise a polynucleotide that is at least 60% identical to SEQ ID NO: 17. In some cases, when the ADH gene is an *S. cerevisiae* ADH gene, the *S. cerevisiae* ADH gene can comprise a polynucleotide that is at least 60% identical to SEQ ID NO: 13. In some cases, both a *S. cerevisiae* ADH gene and an *E. coli* ADH gene is used, and the *S. cerevisiae* ADH gene can comprise a polynucleotide that is at least 60% identical to SEQ ID NO: 13, whereas the *E. coli* ADH gene can comprise a polynucleotide that is at least 60% identical to SEQ ID NO: 17. Additionally, the genetically modified microorganism can comprise a second ADH gene. The second ADH gene can be from *E. coli, S. cerevisiae,* or both. Additional ADH genes can be used as well (e.g., a third, fourth, or fifth, etc.).

In order to increase the efficiency of aldehyde or alcohol production, the genetically modified microorganism can further comprises a sugar permease gene. The sugar permease gene can be a LacY gene. In some cases, the sugar permease gene is used for gene expression. In some cases, the LacY gene can be under the control of a rare earth metal switch. In some cases, the rare earth metal switch can be a lanthanum switch.

The genetically modified microorganism can use different $C_1$ carbons as a carbon source, such as carbon monoxide (CO), carbon dioxide ($CO_2$), methane ($CH_4$), or any combination thereof. In some cases, the genetically modified microorganism uses $CH_4$ as the $C_1$ carbon source.

In some cases, the genetically modified microorganism can be a methanotroph, for example, from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum,* or *Methyloacidoiphilum*. In particular, methanotrophs that can be used can be from the genera *Methylococcus,* e.g., *Methylococcus capsulatus*.

In some instances, one or more of the acetolactate synthase, ketol-acid reductoisomerase, dihydroxy-acid dehydratase, 2-keto acid decarboxylase (KDC), and alcohol dehydrogenase (ADH) genes can be heterologous to the microorganism. In some cases, one or more of those genes can be endogenous to the microorganism. Further, one or more of the genes can be overexpressed. In some cases, the microorganism can comprise multiple copies of one or more of the genes.

Also disclosed herein is a genetically modified microorganism capable of converting a $C_1$ carbon source to a multicarbon product comprising a sugar permease gene. In some cases, the sugar permease gene can be under the control of rare earth metal switch. In some cases, the rare earth metal switch is a lanthanum switch. The sugar permease genes can be a LacY gene. In some cases, the LacY gene can be a gram negative bacterial LacY gene. In some cases, the LacY gene can comprise a polynucleotide that is at least 80% identical to SEQ ID NO: 19. In some cases, the LacY gene can encode for a polypeptide that comprises an amino acid sequence that is at least 90% identical to SEQ ID NO: 20. In some cases, the genetically modified microorganism can further comprise one or more genes encoding for: (i) acetolactate synthase (AlsS); (ii) ketol-acid reductoisomerase (KARI); (iii) dihydroxy-acid dehydratase (DHAD); (iv) 2-keto acid decarboxylase (KDC); (v) alcohol dehydrogenase (ADH); or (vi) any combination thereof. In some cases, one or more of these additional genes can be under the control of a rare earth metal switch, e.g., a lanthanum switch. One or more of these genes can be heterologous, endogenous, overexpressed, and/or comprise multiple copies (e.g., LacY, AlsS, KARI, DHAD, KDC, and/or ADH).

Further disclosed herein is a vector comprising a polynucleotide that is at least 60% identical to SEQ ID NO: 9. Additionally disclosed is a vector comprising a polynucleotide that is at least 60% identical to SEQ ID NO: 11. Also disclosed is a vector comprising a polynucleotide that is at least 60% identical to SEQ ID NO: 100.

The vector can further comprise an operably linked promoter. The vector can also further comprise one or more genes encoding for: (i) acetolactate synthase (AlsS); (ii) a ketol-acid reductoisomerase (KARI); (iii) a dihydroxy-acid dehydratase (DHAD); (iv) a 2-keto acid decarboxylase (KDC); (v) an alcohol dehydrogenase (ADH); or (vi) any combination thereof. In some cases, the one or more gene encoding for (i) an acetolactate synthase (AlsS); (ii) a ketol-acid reductoisomerase (KARI); (iii) a dihydroxy-acid dehydratase (DHAD) (iv) a 2-keto acid decarboxylase (KDC); (v) an alcohol dehydrogenase (ADH); or (vi) any combination thereof, can be under the control of a rare earth metal switch, e.g., a lanthanum switch. In some cases, the vector can comprise a sugar permease gene. In some instances, the vector can comprise two or more genes encoding for the same enzyme. The two or more genes encoding for the same enzyme can be non-identical genes or in some cases, the two or more gene can be identical genes.

Additionally disclosed herein is a method of making a genetically modified microorganism capable of converting a $C_1$ carbon source to a multicarbon product comprising contacting a microorganism with a polynucleotide encoding for an acetolactate synthase (AlsS); a ketol-acid reductoisomerase (KARI); a dihydroxy-acid dehydratase (DHAD); and/or a 2-keto acid decarboxylase (KDC). In some cases, the 2-keto acid decarboxylase (KDC) can comprise a polynucleotide that is at least 60% identical to SEQ ID NO: 9. In some cases, the microorganism is further contacted with a second polynucleotide encoding for a 2-keto acid decarboxylase (KDC). In some cases, the microorganism is further contacted with a polynucleotide encoding for an alcohol dehydrogenase (ADH). In some cases, the genes can be under the control of a rare earth metal switch, such as a lanthanum switch. One or more of these genes can be heterologous, endogenous, overexpressed, and/or comprise multiple copies (e.g., LacY, AlsS, KARI, DHAD, KDC, and/or ADH). In some cases, the microorganism can be contacted with a sugar permease gene.

In some cases, the microorganism is contacted with a single vector or nucleic acid comprising the acetolactate synthase (AlsS) gene, the ketol-acid reductoisomerase gene, the dihydroxy-acid dehydratase gene, and the 2-keto acid decarboxylase (KDC) gene. In some cases, the microorganism is contacted with the acetolactate synthase (AlsS) gene, the ketol-acid reductoisomerase gene, the dihydroxy-acid dehydratase gene, and the 2-keto acid decarboxylase (KDC) gene using multiple vectors or nucleic acids.

Also described herein is a method of making a genetically modified microorganism capable of converting a $C_1$ carbon source to a multicarbon product comprising contacting a microorganism with a polynucleotide encoding for a sugar permease. The method can further comprise contacting the microorganism with one or more genes encoding for: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof.

Further disclosed herein is a method of making an aldehyde from a $C_1$ carbon comprising: (a) contacting the $C_1$ carbon with a genetically modified microorganism capable of converting the $C_1$ carbon into a multicarbon product, where the genetically modified microorganism comprises a polynucleotide encoding for an acetolactate synthase (AlsS), a ketol-acid reductoisomerase; a dihydroxy-acid dehydratase; and a 2-keto acid decarboxylase (KDC), where the KDC comprises a polynucleotide that is at least 60% identical to SEQ ID NO: 9; and (b) growing the genetically modified microorganism to produce the aldehyde. In some cases, one or more of the genes can be under the control of a rare earth metal switch, such as a lanthanum switch.

This method can also further comprise (c) isolating the aldehyde. In some cases, the aldehyde can be isobutyraldehyde. The method can result in isobutyraldehyde being produced at a level of at least 1 g/L. The isobutyraldehyde can be isolated and can also be substantially pure.

In some cases, the microorganism can further comprise a second gene encoding for a 2-keto acid decarboxylase (KDC). In some cases, the KDC can comprise a polynucleotide that is at least 60% identical to SEQ ID NOs: 9 or 11. In some cases, the KDC can encode for a polypeptide that comprises an amino acid sequence that is at least 90% identical to any one of SEQ ID NOs: 10, 12, 55, 57, 59, 61, 63, 65, 67, 69, 71, 73, 75, 77, 79, 81, 83, 85, 87, 89, 91, 93, 95, or 97.

In some cases, the microorganism used in the method can further comprise a nucleic acid encoding for an ADH. In this case, the genetically modified microorganism can produce an alcohol, such as isobutanol.

In some cases, one or more of the genes can be under the control of a rare earth metal switch, such as a lanthanum switch.

Also disclosed herein is a method of making an alcohol from a $C_1$ carbon comprising: (a) contacting the $C_1$ carbon with a genetically modified microorganism capable of converting the $C_1$ carbon into a multicarbon product, where the genetically modified microorganism comprises a polynucleotide encoding for an acetolactate synthase (AlsS); a ketol-acid reductoisomerase; a dihydroxy-acid dehydratase; a 2-keto acid decarboxylase (KDC); and an alcohol dehydrogenase (ADH), where the KDC is encoded by a nucleotide sequence at least 60% identical to the nucleic acid sequence of SEQ ID NO: 9; and (b) growing the genetically modified microorganism to produce the alcohol. In some cases, the alcohol can be isobutanol.

The method can further comprise (c) isolating the alcohol. In some cases, the alcohol produced can be used as a gasoline additive, a gasoline substitute, or as jetfuel.

Also disclosed herein is an isolated polynucleotide comprising a nucleic acid sequence at least 84% identical to the nucleic acid sequence of SEQ ID NO: 1. Also disclosed herein is an isolated polynucleotide comprising a nucleic acid sequence at least 60% identical to the nucleic acid sequence of SEQ ID NO: 100. These nucleic acid sequences can encode for a protein that has acetolactate synthase activity.

Also disclosed herein is an isolated polynucleotide comprising a nucleic acid sequence at least 88% identical to the nucleic acid sequence of SEQ ID NO: 3. This nucleic acid sequence can encode for a protein that has ketol-acid reductoisomerase activity.

Further disclosed herein is an isolated polynucleotide comprising a nucleic acid sequence at least 88% identical to the nucleic acid sequence of SEQ ID NO: 5 or an isolated polynucleotide comprising a nucleic acid sequence at least 88% identical to the nucleic acid sequence of SEQ ID NO: 7. These nucleic acid sequences can encode for a protein that has dihydroxy-acid dehydratase activity.

Disclosed herein is an isolated polynucleotide comprising a nucleic acid sequence at least 85% identical to the nucleic acid sequence of SEQ ID NO: 9 or an isolated polynucleotide comprising a nucleic acid sequence at least 85% identical to the nucleic acid sequence of SEQ ID NO: 11. These nucleic acid sequences can encode for a protein that has 2-keto acid decarboxylase activity.

Further disclosed herein is an isolated polynucleotide comprising a nucleic acid sequence at least 85% identical to the nucleic acid sequence of SEQ ID NO: 13; an isolated polynucleotide comprising a nucleic acid sequence at least 85% identical to the nucleic acid sequence of SEQ ID NO: 15; and an isolated polynucleotide comprising a nucleic acid sequence at least 85% identical to the nucleic acid sequence of SEQ ID NO: 17. These nucleic acid sequences can encode for a protein that has alcohol dehydrogenase activity.

Also disclosed herein is an isolated polynucleotide comprising a nucleic acid sequence at least 84% identical to the nucleic acid sequence of SEQ ID NO: 19. This nucleic acid sequence can encode for a protein that has sugar permease activity.

Disclosed herein is an isolated polynucleotide comprising a nucleic acid sequence at least 84% identical to the nucleic acid sequence of SEQ ID NO: 21. This nucleic acid sequence can encode for a protein that has arabinose operon regulatory protein activity.

Disclosed herein is also a genetically modified microorganism capable of converting a $C_1$ carbon source to an aldehyde comprising one or more genes encoding for: (i) acetolactate synthase; (ii) ketol-acid reductoisomerase; (iii) dihydroxy-acid dehydratase; (iv) 2-keto acid decarboxylase; or (v) any combination thereof; where (a) the acetolactate synthase gene comprises a polynucleotide that is at least 60% identical to SEQ ID NO: 1 or 100; (b) the ketol-acid reductoisomerase gene comprises a polynucleotide that is at least 85% identical to SEQ ID NO: 3; (c) the dihydroxy-acid dehydratase gene comprises a polynucleotide that is at least 82% identical to SEQ ID NOs: 5 or 7; and/or (d) the 2-keto acid decarboxylase gene comprises a polynucleotide that is at least 60% identical to SEQ ID NOs: 9 or 11. The genetically modified microorganism can further comprise an ADH gene. The ADH gene can comprise (a) a polynucleotide that is at least 60% identical to SEQ ID NO: 13; (b) the nucleic acid sequence of SEQ ID NO: 15; and/or (c) a polynucleotide that is at least 60% identical to SEQ ID NO: 17.

Also described herein is a vector comprising one or more genes encoding for: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof; where (i) the acetolactate synthase gene comprises a polynucleotide that is at least 60% identical to SEQ ID NO: 1 or 100; (ii) the ketol-acid reductoisomerase gene comprises a polynucleotide that is at least 85% identical to SEQ ID NO: 3; (iii) the dihydroxy-acid dehydratase gene comprises a polynucleotide that is at least 82% identical to SEQ ID NO: 5 and/or comprises the a polynucleotide sequence that is SEQ ID NO: 7; (iv) the 2-keto acid decarboxylase gene comprises a polynucleotide that is at least 60% identical to SEQ ID NO: 9 and/or comprises a polynucleotide that is SEQ ID NO: 11; and/or (v) the alcohol dehydrogenase gene comprises (a) a polynucleotide that is at least 60% identical to SEQ ID NO: 13; (b) a polynucleotide that is SEQ ID NO: 15; and/or (c) a polynucleotide that is at least 60% identical to SEQ ID NO: 17.

Further disclosed herein is a method of making a genetically modified microorganism capable of converting a $C_1$ carbon source to an aldehyde or an alcohol comprising contacting a microorganism with one or more genes encoding for: (i) an acetolactate synthase; (ii) a ketol-acid reductoisomerase; (iii) a dihydroxy-acid dehydratase; (iv) a 2-keto acid decarboxylase; (v) an alcohol dehydrogenase; or (vi) any combination thereof; where (i) the acetolactate synthase gene comprises a polynucleotide that is at least 60% identical to SEQ ID NO: 1 or 100; (ii) the ketol-acid reductoisomerase gene comprises a polynucleotide that is at least 85% identical SEQ ID NO: 3; (iii) the dihydroxy-acid dehydratase gene comprises a polynucleotide that is at least 82% identical to SEQ ID NO: 5 and/or comprises a polynucleotide that is SEQ ID NO: 7; (iv) the 2-keto acid decarboxylase gene comprises a polynucleotide that is at least 60% identical to SEQ ID NO: 9 and/or comprises a polynucleotide that is SEQ ID NO: 11; and/or (v) the alcohol dehydrogenase gene comprises (a) a polynucleotide that is at least 60% identical to SEQ ID NO: 13; (b) a polynucleotide that is SEQ ID NO: 15; and/or (c) a polynucleotide that is at least 60% identical to SEQ ID NO: 17.

Also disclosed herein is a method of making a useful product comprising: (a) contacting a genetically modified microorganism with a $C_1$ carbon substrate, where the microorganism comprises at least one heterologous gene encoding for: (i) an acetolactate synthase, (ii) a ketol-acid reductoisomerase, (iii) a dihydroxy-acid dehydratase, (iv) a 2-keto acid decarboxylase, (v) an alcohol dehydrogenase, or (vi) any combination thereof; and (b) growing the microorganism to produce the useful product, where the useful product comprises 2-acetolactate; 2,3-butanediol (2,3-BDO); diacetyl; 2,3-dihydroxy-2-methylbutanoic acid; 2,3-dihydroxyisovalerate; amino acids; ketoisovalerate; isobutyraldehyde; methyl methacrylate (MMA); isovaleraldehyde; isovalerate; isopentanol; isoamyl acetate; pentadecanoic acid; isobutene; or p-xylene.

Further disclosed is a genetically modified microorganism capable of converting a $C_1$ carbon to a multicarbon product, where the genetically modified microorganism comprises an acetolactate synthase gene; a ketol-acid reductoisomerase gene; a dihydroxy-acid dehydratase gene; and a 2-keto acid decarboxylase gene, where the acetolactate synthase gene comprises a polynucleotide that is at least 60% identical to SEQ ID NO: 100. In some cases, the genetically modified microorganism can comprise an alcohol dehydrogenase gene. In other cases, the acetolactate synthase gene, the ketol-acid reductoisomerase gene, the dihydroxy-acid dehydratase gene, the 2-keto acid decarboxylase gene, or the alcohol dehydrogenase gene is heterologous to the microorganism.

Further disclosed is a method of making a genetically modified microorganism capable of converting a $C_1$ carbon source to a multicarbon product, the method comprising contacting a microorganism with an acetolactate synthase gene, a ketol-acid reductoisomerase gene, a dihydroxy-acid dehydratase gene, and a 2-keto acid decarboxylase gene, where the acetolactate synthase gene comprises a polynucleotide that is at least 60% identical to SEQ ID NO: 100.

Also disclosed herein is a method of making 2-acetolactate comprising (a) contacting a $C_1$ carbon with a genetically modified microorganism capable of converting the $C_1$ carbon into a multicarbon product, where the genetically modified microorganism comprises an acetolactate synthase gene comprising a polynucleotide that is at least 60% identical to SEQ ID NO: 100; and (b) growing the genetically modified microorganism to produce the 2-acetolactate.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A shows from left to right, a Kanamycin marker, an arabinose induction machinery (LacY and AraC driven by a J23115 promoter) and a BAD promoter (pBAD) driving the isobutanol pathway ((MCA0996=Kdc), Adh6, AlsS, IlvC and IlvD).

FIG. 4B shows the vector from FIG. 4A with three differences: the KDC here comes from *Carnobacterium divergens* (Cdi), the IlvD comes from *Methylococcus capsulatus*, and an additional ADH gene has been added (YqhD from *E. coli*). FIG. 4C shows a vector that shares a similar architecture to the vector in FIG. 4A with many of the same genes. However, there are several key differences including: 1) two operons, one with pBAD (inducible by arabinose) and the second using pMxaF (strong endogenous promoter) driving the genes; and 2) the addition of a FucO alcohol dehydrogenase from *E. coli*.

DETAILED DESCRIPTION OF THE DISCLOSURE

Figure 1:
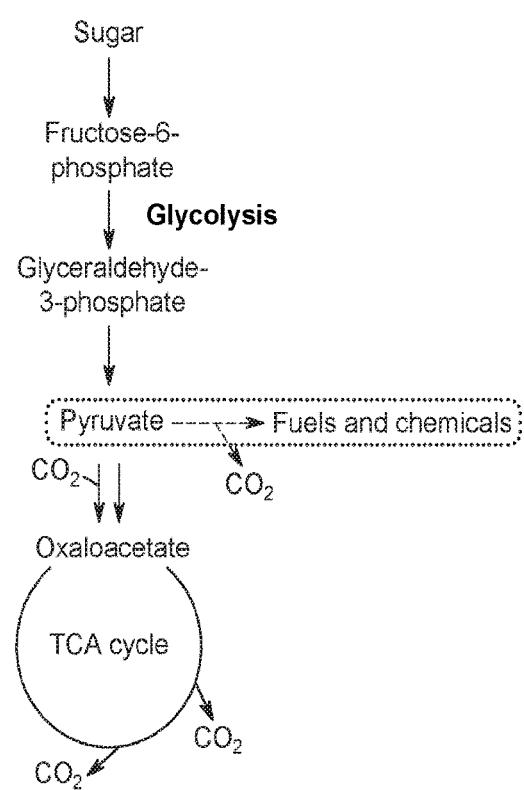
FIG. 1 shows a metabolic pathway from sugar to pyruvate. Pyruvate can then be used to make various products such as fuels and chemicals.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Isobutanol is a high value chemical and fuel that is currently produced from the carbonylation of propylene. Two methods are currently practiced in the industry, including hydroformylation and reppe carbonylation. Hydroformylation is more common and generates a mixture of isobutyraldehydes, which are hydrogenated to the alcohols and then separated. There has been high interest in the biosynthesis of isobutanol. Fermentation typically involves taking a carbon source (usually sugar) and fermenting it using a microorganism that is capable of converting the carbon source into a desired product such as isobutanol.

Costs to produce chemicals, such as isobutanol, by fermentation typically depend on the cost of the carbon source used. Sugars are generally higher cost carbon sources that also result in a decrease of food supply. One carbon source that is currently extremely cost-effective and abundant is natural gas. The primary source of carbon within natural gas is methane. By using cheap carbon sources such as methane, alcohols, such as isobutanol, can be produced economically. However, the challenge lies in engineering fermentation methods and microorganisms to efficiently convert cheap carbon sources, such as methane, into alcohols, such as isobutanol, using a fermentation process.

Only a very few microorganisms are capable of producing isobutanol naturally at very low levels. (Felpeto-Santero, C., et al., "Engineering alternative isobutanol production platforms," *AMB Express*, 5:32 (2015)) At these low titers, the cost of fermentation would be too great to be economically feasible. Thus, genetic engineering is required to produce isobutanol at an economically viable level.

Described herein are genetically modified microorganisms, e.g., methanotrophs, that can convert a carbon substrate, such as methane, into desired products. Some of the genetically modified microorganisms disclosed herein have been designed and altered to efficiently produce alcohols, such as isobutanol, or aldehydes, such as isobutyraldehyde or isovaleraldehyde, multiple folds over what is naturally produced or expected to be produced. Additionally some of the genetically modified microorganisms disclosed herein can be used to convert a carbon substrate (such as methane) into alcohols, such as isobutanol, and subsequently into fuels or other desired products. These genetically modified microorganisms and the novel methods of fermentation and uses thereof are described herein.

Definitions

The term "alcohol" and its grammatical equivalents as used herein can refer to any and all any organic compounds whose molecule contains one or more hydroxyl groups (—OH) attached to a carbon atom. For example, ethanol and isobutanol are alcohols.

The term "aldehyde" and its grammatical equivalents as used herein can refer to any and all organic compounds whose molecule contains a function group with the structure —CHO, which has a carbonyl center (a carbon double-bonded to oxygen) with the carbon atom also bonded to hydrogen and to an R group (which can be any generic alkyl or side chain). For example, isobutyraldehyde and isovaleraldehyde are aldehydes.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

The term "gene" and its grammatical equivalents as used herein can refer to any sequence of DNA or RNA which codes for a molecule that has a function.

The terms "protein", "peptide", "polypeptide", and "amino acid sequence" are used interchangeably herein to refer to polymers of amino acid residues of any length. The polymer can be linear or branched. The polymer can comprise modified amino acids or amino acid analogs, and it can be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

The terms "polynucleotide" and "polynucleic acid" are used interchangeably herein and refer to a polymer of ribonucleic acid (RNA) or deoxyribonucleic acid (DNA). A polynucleotide is made up of four bases: adenine, cytosine, guanine, and thymine/uracil (uracil is used in RNA). A coding sequence from a polynucleotide is indicative of the sequence of the protein encoded by the polynucleotide. The terms include various modifications and analogues.

The terms "nucleotide sequences" and "nucleic acid sequences" are used interchangeably herein and refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double stranded (duplex). Duplex nucleic acids can be homoduplex or heteroduplex.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "substantially pure" and its grammatical equivalents as used herein can mean that a particular substance does not contain a majority of another substance. For example, "substantially pure isobutanol" can mean at least 90% isobutanol. In some instances, "substantially pure isobutanol" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% isobutanol. For example, substantially pure isobutanol can mean at least 70% isobutanol. In some cases, substantially pure isobutanol can mean at least 75% isobutanol. In some cases, substantially pure isobutanol can mean at least 80% isobutanol. In some cases, substantially pure isobutanol can mean at least 85% isobutanol. In some cases, substantially pure isobutanol can mean at least 90% isobutanol. In some cases, substantially pure isobutanol can mean at least 91% isobutanol. In some cases, substantially pure isobutanol can mean at least 92% isobutanol. In some cases, substantially pure isobutanol can mean at least 93% isobutanol. In some cases, substantially pure isobutanol can mean at least 94% isobutanol. In some cases, substantially pure isobutanol can mean at least 95% isobutanol. In some cases, substantially pure isobutanol can mean at least 96% isobutanol. In some cases, substantially pure isobutanol can mean at least 97% isobutanol. In some cases, substantially pure isobutanol can mean at least 98% isobutanol. In some cases, substantially pure isobutanol can mean at least 99% isobutanol.

The terms "heterologous" and "exogenous" and their grammatical equivalents as used herein can mean "from a different species." For example, a "heterologous gene" can mean a gene that is from a different species. In some instances, as "a methanotroph comprising a heterologous gene" can mean that the methanotroph contains a gene that is not from the same methanotroph. The gene can be from a different microorganism such as yeast or from a different species such as a different methanotroph species. In some cases, the terms "heterologous" and "exogenous" and their grammatical equivalents as used herein can refer to polynucleotides and polypeptides.

The term "substantially similar" and its grammatical equivalents in reference to another sequence as used herein can mean at least 50% identical. In some instances, the term substantially similar refers to a sequence that is at least 55% identical. In some instances, the term substantially similar refers to a sequence that is at least 60% identical. In some instances, the term substantially similar refers to a sequence that is at least 65% identical. In some instances, the term substantially similar refers to a sequence that is at least 70% identical. In some instances, the term substantially similar refers to a sequence that is at least 75% identical. In some instances, the term substantially similar refers to a sequence that is at least 80% identical. In other instances, the term substantially similar refers to a sequence that is at least 85% identical. In some instances, the term substantially similar refers to a sequence that is at least 90% identical. In some instances, the term substantially similar refers to a sequence that is at least 91% identical. In some instances, the term substantially similar refers to a sequence that is at least 92% identical. In some instances, the term substantially similar refers to a sequence that is at least 93% identical. In some instances, the term substantially similar refers to a sequence that is at least 94% identical. In some instances, the term substantially similar refers to a sequence that is at least 95% identical. In some instances, the term substantially similar refers to a sequence that is at least 96% identical. In some instances, the term substantially similar refers to a sequence that is at least 97% identical. In some instances, the term substantially similar refers to a sequence that is at least 98% identical. In some instances, the term substantially similar refers to a sequence that is at least 99% identical. In some instances, the term substantially similar refers to a sequence that is 100% identical. In order to determine the percentage of identity between two sequences, the two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. For example, methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that can be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences where at least 50% of the total length of one of the two sequences is involved in the alignment.

The terms "acetolactate synthase" or "AlsS" and their grammatical equivalents as used herein can be interchangeably used with acetohydroxy acid synthase; acetolactate pyruvate-lyase; or acetolactate synthease. The terms "acetolactate synthase" or "AlsS" can include enzymes that are capable of converting pyruvate to 2-acetolactate. For example, the terms "acetolactate synthase" or "AlsS" can include an enzyme having an EC 2.2.1.6.

The terms "ketol acid reductoisomerase" or "IlvC" and their grammatical equivalents as used herein can be used interchangeably with acetohydroxy acid isomeroreductase, ketol acid reductoisomerase, alpha-keto-beta-hydroxylacyl reductoisomerase, acetohydroxy acid reductoisomerase, acetolactate reductoisomerase, dihydroxyisovalerate (isomerizing) dehydrogenase, isomeroreductase, and/or reductoisomerase. The terms "ketol acid reductoisomerase" or "IlvC" can include enzymes that are capable of converting 2-acetolactate into 2,3-dihydroxyisovalerate. For example, the terms "ketol acid reductoisomerase" or "IlvC" can include an enzyme having an EC 1.1.1.86.

The terms "dihydroxy-acid dehydratase" or "IlvD" and their grammatical equivalents as used herein can be used interchangeably with acetohydroxyacid dehydratase, alpha, beta-dihydroxyacid dehydratase, 2,3-dihydroxyisovalerate dehydratase, alpha,beta-dihydroxyisovalerate dehydratase, dihydroxy acid dehydrase, DHAD, or 2,3-dihydroxy-acid hydro-lyase. The terms "dihydroxy-acid dehydratase" or "IlvD" can include enzymes that are capable of converting 2,3-dihydroxyisovalerate into ketoisovalerate. For example, the terms "dihydroxy-acid dehydratase" or "IlvD" can include an enzyme having an EC 4.2.1.9.

The terms "2-keto acid decarboxylase" or "KDC" and their grammatical equivalents as used herein can include enzymes that are capable of converting ketoisovalerate into isobutyraldehyde. For example, the terms "2-keto acid decarboxylase" or "KDC" can include an enzyme having an EC 4.1.1.72.

The terms "alcohol dehydrogenase", "ADH" or "Adh" and their grammatical equivalents as used herein can include enzymes that are capable of converting isobutyraldehyde into an alcohol such as isobutanol. For example, in some instances, the terms "alcohol dehydrogenase" or "Adh" can include an enzyme having an EC 1.1.1.1.

I. Genetically Modified Microorganisms and Methods of Making the Same

Isobutanol and/or isobutyraldehyde is produced by some unmodified microorganisms; however, production levels are extremely low. Disclosed herein are genetically modified microorganisms that have dramatically improved isobutanol and/or isobutyraldehyde biosynthesis rates, and in some cases orders of magnitude higher than what could be naturally produced. For example, disclosed herein are microorganisms that do not normally produce isobutanol and/or isobutyraldehyde that can be genetically modified to synthesize isobutanol and/or isobutyraldehyde, including at significantly high levels.

Microorganisms

The microorganisms described herein can use carbon substrates, such as, but not limited to $CH_4$, as carbon source to produce desired products. This however does not mean that these microorganisms use solely $CH_4$ as a carbon source. Some of the microorganisms disclosed herein can be made to utilize additional carbon substrates, including carbon substrates that the microorganism naturally uses in addition to other carbon substrates. For example, the microorganisms can be made to use two or more carbon substrates, such as $CH_4$ and sugar.

The microorganisms disclosed herein can be a prokaryote or eukaryote. In some cases, other microorganisms such as bacteria, yeast, or algae can be used.

Some microorganisms can use a $C_1$ carbon to generate a desired product. For example, some of the microorganisms that can convert $C_1$ carbon substrates into desired products can be a microorganism that is capable of using natural gas as a carbon substrate. In some cases, the microorganism can use the methane contained within the natural gas as a carbon source to make desired products. One type of microorganism that uses $C_1$ carbon substrates to form desired organic compounds are methanotrophs. The methanotrophs that can be particularly useful include methanotrophs from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum, Methylacidiphilum*, or any combinations thereof. Methanotrophs from the genus *Methylococcus* can be particularly useful. When a methanotroph from the genus *Methylococcus* is used, a methanotroph from the species *Methylococcus capsulatus* can be used.

Some microorganisms disclosed throughout are microorganisms that are capable of using $CO_2$ as a carbon substrate. For instance, the microorganisms can be a methanogen. Microorganisms that are capable of using $CO_2$ as a substrate can contain chlorophyll. One type of microorganism that uses $CO_2$ to form desired organic compounds are algae. Another type of microorganism that can use $CO_2$ as a substrate is a cyanobacterium.

Some microorganisms that can convert $C_1$ carbon substrates into desired products can be a microorganism that is capable of using CO as a carbon substrate. Anaerobic microorganisms can typically process CO and therefore can be used herein. One type of microorganism that naturally uses CO to form desired organic compounds are bacterium such as *Clostridium*. These microorganisms can be genetically modified into making substantial amounts of alcohols, such as isobutanol.

Enzymes

In order to genetically engineer certain microorganisms to produce certain useful products such as isobutanol, microorganisms can be transformed with one or more genes that encode for specific enzymes. The genes encoding for these enzymes can be heterologous to the microorganism.

For example, in order to create a microorganism that can produce an alcohol, such as isobutanol, or an aldehyde, such as isobutyraldehyde, one or more genes (e.g., heterologous genes) can be transformed/transfected (i.e., inserted) into the microorganism (transiently or stably). The microorganism can contain an acetolactate synthase (gene name: AlsS), which is an enzyme that coverts two molecules of pyruvate into 2-acetolactate. The microorganism can in some cases comprise an ketol-acid reductoisomerase (gene name: ilvC) which is an enzyme that converts 2-acetolactate into 2,3-dihydroxy-isovalerate using NADPH as a reduced cofactor. The microorganism can also comprise an dihydroxy-acid dehydratase (gene name: ilvD), which is enzyme that converts 2,3-dihydroxy-isovalerate into 2-ketoisovalerate. The microorganism can in some cases comprise an 2-keto acid decarboxylase (gene name: KDC), which is enzyme that converts 2-ketoisovalerate into isobutyraldehyde. In order to produce isobutanol, the microorganism can in some cases comprise an alcohol dehydrogenase (gene name: ADH), which is enzyme that converts isobutyraldehyde into isobutanol.

Described throughout are microorganisms used to make alcohols, such as isobutanol, or an aldehyde, such as isobutyraldehyde, from a $C_1$ carbon (e.g., methane) or other multi-carbon source. In some cases, the microorganism herein can be transformed with a gene encoding for one or more of the following enzymes: (i) acetolactate synthase; (ii) ketol-acid reductoisomerase; (iii) dihydroxy-acid dehydratase; and/or (iv) 2-keto acid decarboxylase. Should the microorganism be directed to making an alcohol, the microorganism can be transformed with (v) an alcohol dehydrogenase. For example, the microorganism can be transformed with a gene encoding for an acetolactate synthase. The microorganism can be transformed with a gene encoding for a ketol-acid reductoisomerase. The microorganism can be transformed with a gene encoding for a dihydroxy-acid dehydratase. The microorganism can be transformed with a gene encoding for a 2-keto acid decarboxylase. The microorganism can be transformed with a gene encoding for an alcohol dehydrogenase. Any one of or more than one of these genes can be heterologous to the microorganism.

In some instances, the microorganism can be transformed with two or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In one instance, the microorganism can be transformed with at least three or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In other instances, the microorganism can be transformed with at least four or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In some cases, the microorganism can be transformed with at least five or more genes encoding for enzymes such as an acetolactate synthase; ketol-acid reductoisomerase; dihydroxy-acid dehydratase; 2-keto acid decarboxylase; and alcohol dehydrogenase. In this case, the output will be an alcohol, such as isobutanol, unless the alcohol dehydrogenase is non-functional. If the alcohol dehydrogenase is non-functional, then the output will be an aldehyde, such as isobutyraldehyde. One or more of the genes can be heterologous to the microorganism.

In some cases, when an acetolactate synthase is used, the acetolactate synthase can be from a bacteria (e.g., a gram positive bacterium), such as from the genus *Bacillus*. For example, an acetolactate synthase can be from the species *Bacillus subtilis*. In some cases, the acetolactate synthase can be from the species *Bacillus licheniformis*.

The acetolactate synthase can comprise an amino acid sequence that is substantially similar to SEQ ID NO: 2 or 99. For example, the acetolactate synthase can comprise an amino acid sequence that is at least 60% identical to SEQ ID NO: 2 or 99. In some cases, the acetolactate synthase can comprise an amino acid sequence that is at least 65% identical to SEQ ID NO: 2 or 99. In some cases, the acetolactate synthase can comprise an amino acid sequence that is at least 70% identical to SEQ ID NO: 2 or 99. In some cases, the acetolactate synthase can comprise an amino acid sequence that is at least 75% identical to SEQ ID NO: 2 or 99. In some cases, the acetolactate synthase can comprise an amino acid sequence that is at least 80% identical to SEQ ID NO: 2 or 99. In some cases, the acetolactate synthase can comprise an amino acid sequence that is at least 85% identical to SEQ ID NO: 2 or 99. In some cases, the acetolactate synthase can comprise an amino acid sequence that is at least 90% identical to SEQ ID NO: 2 or 99. In some cases, the acetolactate synthase can comprise an amino acid sequence that is at least 91% identical to SEQ ID NO: 2 or 99. In some cases, the acetolactate synthase can comprise an amino acid sequence that is at least 92% identical to SEQ ID NO: 2 or 99. In some cases, the acetolactate synthase can comprise an amino acid sequence that is at least 93% identical to SEQ ID NO: 2 or 99. In some cases, the acetolactate synthase can comprise an amino acid sequence that is at least 94% identical to SEQ ID NO: 2 or 99. In some cases, the acetolactate synthase can comprise an amino acid sequence that is at least 95% identical to SEQ ID NO: 2 or 99. In some cases, the acetolactate synthase can comprise an amino acid sequence that is at least 96% identical to SEQ ID NO: 2 or 99. In some cases, the acetolactate synthase can comprise an amino acid sequence that is at least 97% identical to SEQ ID NO: 2 or 99. In some cases, the acetolactate synthase can comprise an amino acid sequence that is at least 98% identical to SEQ ID NO: 2 or 99. In some cases, the acetolactate synthase can comprise an amino acid sequence that is at least 99% identical to SEQ ID NO: 2 or 99. In some cases, the acetolactate synthase can comprise an amino acid sequence that is SEQ ID NO: 2 or 99.

When a ketol-acid reductoisomerase is used, the ketol-acid reductoisomerase can be from a bacteria (e.g., a gram negative bacterium), such as from the genus *Escherichia*. For example, the ketol-acid reductoisomerase can be from the species *Escherichia coli*.

The ketol-acid reductoisomerase can comprise an amino acid sequence that is substantially similar to SEQ ID NO: 4. For example, the ketol-acid reductoisomerase can comprise an amino acid sequence that is at least 60% identical to SEQ ID NO: 4. In some cases, the ketol-acid reductoisomerase can comprise an amino acid sequence that is at least 65% identical to SEQ ID NO: 4. In some cases, the ketol-acid reductoisomerase can comprise an amino acid sequence that is at least 70% identical to SEQ ID NO: 4. In some cases, the ketol-acid reductoisomerase can comprise an amino acid sequence that is at least 75% identical to SEQ ID NO: 4. In some cases, the ketol-acid reductoisomerase can comprise an amino acid sequence that is at least 80% identical to SEQ ID NO: 4. In some cases, the ketol-acid reductoisomerase can comprise an amino acid sequence that is at least 85% identical to SEQ ID NO: 4. In some cases, the ketol-acid reductoisomerase can comprise an amino acid sequence that is at least 90% identical to SEQ ID NO: 4. In some cases, the ketol-acid reductoisomerase can comprise an amino acid sequence that is at least 91% identical to SEQ ID NO: 4. In some cases, the ketol-acid reductoisomerase can comprise an amino acid sequence that is at least 92% identical to SEQ ID NO: 4. In some cases, the ketol-acid reductoisomerase can comprise an amino acid sequence that is at least 93% identical to SEQ ID NO: 4. In some cases, the ketol-acid reductoisomerase can comprise an amino acid sequence that is at least 94% identical to SEQ ID NO: 4. In some cases, the ketol-acid reductoisomerase can comprise an amino acid sequence that is at least 95% identical to SEQ ID NO: 4. In some cases, the ketol-acid reductoisomerase can comprise an amino acid sequence that is at least 96% identical to SEQ ID NO: 4. In some cases, the ketol-acid reductoisomerase can comprise an amino acid sequence that is at least 97% identical to SEQ ID NO: 4. In some cases, the ketol-acid reductoisomerase can comprise an amino acid sequence that is at least 98% identical to SEQ ID NO: 4. In some cases, the ketol-acid reductoisomerase can comprise an amino acid sequence that is at least 99% identical to SEQ ID NO: 4. In some cases, the ketol-acid reductoisomerase can comprise an amino acid sequence that is SEQ ID NO: 4.

When a dihydroxy-acid dehydratase is used, the dihydroxy-acid dehydratase can be from a bacterium (e.g., from a gram negative bacterium or a methanotroph), such as from the genus *Escherichia* and/or *Methylococcus*. More specifically, the dihydroxy-acid dehydratase can be from the species *Escherichia coli* and/or *Methylococcus capsulatus*.

The dihydroxy-acid dehydratase can comprise an amino acid sequence that is substantially similar to SEQ ID NO: 6 or 8. For example, the dihydroxy-acid dehydratase can comprise an amino acid sequence that is at least 60% identical to SEQ ID NO: 6 or 8. In some cases, the dihydroxy-acid dehydratase can comprise an amino acid sequence that is at least 65% identical to SEQ ID NO: 6 or 8. In some cases, the dihydroxy-acid dehydratase can comprise an amino acid sequence that is at least 70% identical to SEQ ID NO: 6 or 8. In some cases, the dihydroxy-acid dehydratase can comprise an amino acid sequence that is at least 75% identical to SEQ ID NO: 6 or 8. In some cases, the dihydroxy-acid dehydratase can comprise an amino acid sequence that is at least 80% identical to SEQ ID NO: 6 or 8. In some cases, the dihydroxy-acid dehydratase can comprise an amino acid sequence that is at least 85% identical to SEQ ID NO: 6 or 8. In some cases, the dihydroxy-acid dehydratase can comprise an amino acid sequence that is at least 90% identical to SEQ ID NO: 6 or 8. In some cases, the dihydroxy-acid dehydratase can comprise an amino acid sequence that is at least 91% identical to SEQ ID NO: 6 or 8. In some cases, the dihydroxy-acid dehydratase can comprise an amino acid sequence that is at least 92% identical to SEQ ID NO: 6 or 8. In some cases, the dihydroxy-acid dehydratase can comprise an amino acid sequence that is at least 93% identical to SEQ ID NO: 6 or 8. In some cases, the dihydroxy-acid dehydratase can comprise an amino acid sequence that is at least 94% identical to SEQ ID NO: 6 or 8. In some cases, the dihydroxy-acid dehydratase can comprise an amino acid sequence that is at least 95% identical to SEQ ID NO: 6 or 8. In some cases, the dihydroxy-acid dehydratase can comprise an amino acid sequence that is at least 96% identical to SEQ ID NO: 6 or 8. In some cases, the dihydroxy-acid dehydratase can comprise an amino acid sequence that is at least 97% identical to SEQ ID NO: 6 or 8. In some cases, the dihydroxy-acid dehydratase can comprise an amino acid sequence that is at least 98% identical to SEQ ID NO: 6 or 8. In some cases, the dihydroxy-acid dehydratase can comprise an amino acid sequence that is at least 99% identical to SEQ ID NO: 6 or 8. In some cases, the dihydroxy-acid dehydratase can comprise an amino acid sequence that is SEQ ID NO: 6 or 8.

When a 2-keto acid decarboxylase (KDC) is used, the (KDC can be from a bacterium (e.g., a gram positive bacterium) such as from the genus *Carnobacterium* and/or a methanotroph such as from the genus *Methylococcus*. More specifically, the KDC can be from the species *Carnobacterium divergens* and/or *Methylococcus capsulatus*.

The KDC can be from other bacterium, such as those listed in Table 4. For example, the KDC can be from the genus *Methylocaldum, Methylosarcina, Methylomonas, Methylohalobius, Methylobacter, Lamprocystis, Andreprevotia, Lactococcus, Streptococcus, Enterococcus, Brochothrix, Carnobacterium, Helicobacter, Staphylococcus,* and/or *Fictibacillus*. For example, KDC from the following species can be particularly useful: *Methylocaldum szegediense, Methylosarcina lacus, Methylomonas denitrificans, Methylomonas methanica, Methylohalobius crimeensis, Methylobacter marinus, Methylobacter luteus, Lamprocystis purpurea, Andreprevotia chitinilytica, Lactococcus lactis, Streptococcus didelphis, Enterococcus caccae, Enterococcus haemoperoxidus, Enterococcus moraviensis, Carnobacterium maltaromaticum, Brochothrix thermosphacta, Carnobacterium gallinarum, Carnobacterium divergens, Helicobacter bizzozeronii, Staphylococcus aureus* subsp. *aureus* CIG290, and/or *Fictibacillus macauensis*.

The 2-keto acid decarboxylase can comprise an amino acid sequence that is substantially similar to any one of SEQ ID NOs: 10, 12, 55, 57, 59, 61, 63, 65, 67, 69, 71, 73, 75, 77, 79, 81, 83, 85, 87, 89, 91, 93, 95, or 97. For example, the 2-keto acid decarboxylase can comprise an amino acid sequence that is at least 60% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 65% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 70% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 75% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 80% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 85% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 90% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 91% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 92% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 93% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 94% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 95% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 96% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 97% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 98% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 99% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is any one of SEQ ID NOs: 10, 12, 55, 57, 59, 61, 63, 65, 67, 69, 71, 73, 75, 77, 79, 81, 83, 85, 87, 89, 91, 93, 95, or 97.

In some cases, two or more KDCs can be used. In some cases, two KDC genes can be used to increase the production of aldehydes, such as isobutyraldehyde, and/or alcohols, such as isobutanol. In other cases, three KDCs can be used to increase the production of isobutyraldehyde and/or isobutanol. In some cases, four, five, or six KDCs can be used to increase the production of isobutyraldehyde and/or isobutanol.

When an alcohol dehydrogenase is used, the alcohol dehydrogenase can be from a yeast such as from the genus *Saccharomyces* or a bacterium (e.g., a gram negative or gram positive bacterium) such as from the genus *Escherichia*. More specifically, the alcohol dehydrogenase can be from the species *Saccharomyces cerevisiae* and/or *Escherichia coli*.

Other ADHs that can be used can be from the genus *Clostridium, Geobacillus, Lactococcus, Oenococcus, Pectobacterium*, and/or *Psychrobacter*. For example, ADHs from the following species can be particularly useful: *Clostridium acetobutylicum, Geobacillus stearothermophilus, Geobacillus thermoglucosidas, Lactococcus lactis, Oenococcus oeni, Pectobacterium atrosepticum*, and/or *Psychrobacter cryohalolentis*.

The alcohol dehydrogenase can comprise an amino acid sequence that is substantially similar to any one of SEQ ID NOs: 14, 16, 18, 23, 25, 27, 29, 31, 33, 35, 37, 39, 41, 43, 45, 47, 49, 51, or 53. For example, the alcohol dehydrogenase can comprise an amino acid sequence that is at least 60% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 65% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 70% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 75% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 80% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 85% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 90% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 91% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 92% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 93% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 94% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 95% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 96% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 97% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 98% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 99% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is any one of SEQ ID NOs: 14, 16, 18, 23, 25, 27, 29, 31, 33, 35, 37, 39, 41, 43, 45, 47, 49, 51, or 53.

In some cases, two or more ADHs can be used. In some cases, two ADHs can be used to increase the production of alcohols, such as isobutanol. In other cases, three ADHs can be used to increase the production of isobutanol. In some cases, four, five, or six ADHs can be used to increase the production of isobutanol.

Additional enzymes can be placed inside the microorganism in order to make the process more efficient and/or to produce other desired end products.

For example, a sugar permease can be placed within the microorganism in order to increase production of the desired end product, such as an alcohol, e.g., isobutanol, or an aldehyde, e.g., isobutyraldehyde. In some cases, the sugar permease can be from a bacterium (e.g., a gram negative bacterium) such as from the genus *Escherichia*. More specifically, the sugar permease can be from the species *Escherichia coli*.

The sugar permease can comprise an amino acid sequence that is substantially similar to SEQ ID NO: 20. For example, the sugar permease can comprise an amino acid sequence that is at least 60% identical to SEQ ID NO: 20. In some cases, the sugar permease can comprise an amino acid sequence that is at least 65% identical to SEQ ID NO: 20. In some cases, the sugar permease can comprise an amino acid sequence that is at least 70% identical to SEQ ID NO: 20. In some cases, the sugar permease can comprise an amino acid sequence that is at least 75% identical to SEQ ID NO: 20. In some cases, the sugar permease can comprise an amino acid sequence that is at least 80% identical to SEQ ID NO: 20. In some cases, the sugar permease can comprise an amino acid sequence that is at least 85% identical to SEQ ID NO: 20. In some cases, the sugar permease can comprise an amino acid sequence that is at least 90% identical to SEQ ID NO: 20. In some cases, the sugar permease can comprise an amino acid sequence that is at least 91% identical to SEQ ID NO: 20. In some cases, the sugar permease can comprise an amino acid sequence that is at least 92% identical to SEQ ID NO: 20. In some cases, the sugar permease can comprise an amino acid sequence that is at least 93% identical to SEQ ID NO: 20. In some cases, the sugar permease can comprise an amino acid sequence that is at least 94% identical to SEQ ID NO: 20. In some cases, the sugar permease can comprise an amino acid sequence that is at least 95% identical to SEQ ID NO: 20. In some cases, the sugar permease can comprise an amino acid sequence that is at least 96% identical to SEQ ID NO: 20. In some cases, the sugar permease can comprise an amino acid sequence that is at least 97% identical to SEQ ID NO: 20. In some cases, the sugar permease can comprise an amino acid sequence that is at least 98% identical to SEQ ID NO: 20. In some cases, the sugar permease can comprise an amino acid sequence that is at least 99% identical to SEQ ID NO: 20. In some cases, the sugar permease can comprise an amino acid sequence that is SEQ ID NO: 20.

Another peptide that can be placed within the microorganism in order to increase production of the desired end product, such as an alcohol, e.g., isobutanol, or an aldehyde, e.g., isobutyraldehyde, is an arabinose operon regulatory protein (AraC). In some cases, the arabinose operon regulatory protein can be from a bacterium (e.g., a gram negative bacterium) such as from the genus *Escherichia*. More specifically, the arabinose operon regulatory protein can be from the species *Escherichia coli*.

The arabinose operon regulatory protein can comprise an amino acid sequence that is substantially similar to SEQ ID NO: 22. For example, the arabinose operon regulatory protein can comprise an amino acid sequence that is at least 60% identical to SEQ ID NO: 22. In some cases, the arabinose operon regulatory protein can comprise an amino acid sequence that is at least 65% identical to SEQ ID NO: 22. In some cases, the arabinose operon regulatory protein can comprise an amino acid sequence that is at least 70% identical to SEQ ID NO: 22. In some cases, the arabinose operon regulatory protein can comprise an amino acid sequence that is at least 75% identical to SEQ ID NO: 22. In some cases, the arabinose operon regulatory protein can comprise an amino acid sequence that is at least 80% identical to SEQ ID NO: 22. In some cases, the arabinose operon regulatory protein can comprise an amino acid sequence that is at least 85% identical to SEQ ID NO: 22. In some cases, the arabinose operon regulatory protein can comprise an amino acid sequence that is at least 90% identical to SEQ ID NO: 22. In some cases, the arabinose operon regulatory protein can comprise an amino acid sequence that is at least 91% identical to SEQ ID NO: 22. In some cases, the arabinose operon regulatory protein can comprise an amino acid sequence that is at least 92% identical to SEQ ID NO: 22. In some cases, the arabinose operon regulatory protein can comprise an amino acid sequence that is at least 93% identical to SEQ ID NO: 22. In some cases, the arabinose operon regulatory protein can comprise an amino acid sequence that is at least 94% identical to SEQ ID NO: 22. In some cases, the arabinose operon regulatory protein can comprise an amino acid sequence that is at least 95% identical to SEQ ID NO: 22. In some cases, the arabinose operon regulatory protein can comprise an amino acid sequence that is at least 96% identical to SEQ ID NO: 22. In some cases, the arabinose operon regulatory protein can comprise an amino acid sequence that is at least 97% identical to SEQ ID NO: 22. In some cases, the arabinose operon regulatory protein can comprise an amino acid sequence that is at least 98% identical to SEQ ID NO: 22. In some cases, the arabinose operon regulatory protein can comprise an amino acid sequence that is at least 99% identical to SEQ ID NO: 22. In some cases, the arabinose operon regulatory protein can comprise an amino acid sequence that is SEQ ID NO: 22.

The amino acid sequences can also be optimized based on the microorganism in which the enzymes will be expressed. In other words, conservative amino acids substitutions can be made based on whether the respective microorganism typically uses a specific amino acid or how much of that particular amino acid is available for use within the microorganism.

Vectors

Polynucleotide constructs prepared for introduction into a prokaryotic or eukaryotic host can typically, but not always, comprise a replication system (i.e. vector) recognized by the host, including the intended polynucleotide fragment encoding the desired polypeptide, and can, but not necessarily, also include transcription and translational initiation regulatory sequences operably linked to the polypeptide-encoding segment. Expression systems (such as expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides can also be included where appropriate, for example, from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y., 1995).

The manipulation of polynucleotides that encode the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector can be selected to accommodate a polynucleotide encoding a protein of a desired size. Following recombinant modification of a selected vector, a suitable host cell (e.g., the microorganisms described herein) is transfected or transformed with the vector. Each vector contains various functional components, which generally include a cloning site, an origin of replication and at least one selectable marker gene. A vector can additionally possess one or more of the following elements: an enhancer, promoter, and transcription termination and/or other signal sequences. Such sequence elements can be optimized for the selected host species. Such sequence elements can be positioned in the vicinity of the cloning site, such that they are operatively linked to the gene encoding a preselected enzyme.

Vectors, including cloning and expression vectors, can contain nucleic acid sequences that enable the vector to replicate in one or more selected microorganisms. For example, the sequence can be one that enables the vector to replicate independently of the host chromosomal DNA and can include origins of replication or autonomously replicating sequences. Such sequences are known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV40, adenovirus) are useful for cloning vectors.

A cloning or expression vector can contain a selection gene (also referred to as a selectable marker). This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors can be performed in E. coli. An E. coli-selectable marker, for example, the β-lactamase gene that confers resistance to the antibiotic ampicillin, can be of use. These selectable markers can be obtained from E. coli plasmids, such as pBR322 or a pUC plasmid such as pUC18 or pUC19, or pUC119.

Promoters

Vectors can contain a promoter that is recognized by the host microorganism. The promoter can be operably linked to a coding sequence of interest. Such a promoter can be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters. For example, the inducible or repressible promoters that can be used include but are not limited to: (a) sugars such as arabinose and lactose (or non metabolizable analogs, e.g., isopropyl β-D-1-thiogalactopyranoside (IPTG)); (b) metals such as lanthanum, copper, and calcium; (c) temperature; (d) nitrogen-source; (e) oxygen; (f) cell state (growth or stationary); (g) micronutrients such as phosphate, magnesium, and sulfur; (h) CRISPRi; (i) jun; (j) fos; (k) metallothionein and/or (l) heat shock. These promoters can be used in a methanotroph systems. For example, examples of a promoter that can be used within the methanotrophs are a pBAD promoter, a pMxaF promoter, and/or a pTrc promoter.

Constitutively expressed promoters can also be used in the vector systems herein. For example, the promoters that can be used include but are not limited to p.Bba.J23111, p.Bba.J23115, p.Bba.J61111, p.Bba.J61103, p.Bba.J61104, p.Bba.J61105, p.Bba.J61102, p.Bba.J61106, p.Bba.J61107, p.Bba.J61116, p.Bba.J61113, p.Bba.J61101, p.Bba.J61109, p.Bba.J61100, p.Bba.J61114, p.Bba.J61108, p.Bba.J61115, p.Bba.J61110, p.Bba.J61112, uMc.G1gC, uMc IlvC, uGTW0001, uMc.IlvD, uMCA0996, uMc.IlvK, uMc.pmoB, iIlvE, uMc.IlvC, RL122pM, uMc.MCA, or uMc.GrosES promoters. Other promoters that can be used include but are not limited to pXoxF, pMxaF, pTRC, J12100, J23102, pBAD, J23110, lacO, J23116, J23106, J23105, J23108, J23107, J23115, J23114, J23118, J23104, J23101, J23119, and uMCA3034.

Promoters suitable for use with prokaryotic hosts can include, for example, the a-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter can be employed to provide for high level transcription and expression of the desired product.

One or more promoters of a transcription unit can be an inducible promoter. For example, a green fluorescent protein (GFP) can be expressed from a constitutive promoter while an inducible promoter drives transcription of a gene coding for one or more enzymes as disclosed herein and/or the amplifiable selectable marker.

Some vectors can contain prokaryotic sequences that facilitate the propagation of the vector in bacteria. Thus, the vectors can have other components such as an origin of replication (e.g., a nucleic acid sequence that enables the vector to replicate in one or more selected microorganisms), antibiotic resistance genes for selection in bacteria, and/or an amber stop codon which can permit translation to read through the codon. Additional selectable gene(s) can also be incorporated. Generally, in cloning vectors the origin of replication is one that enables the vector to replicate independently of the host chromosomal DNA, and includes origins of replication or autonomously replicating sequences. Such sequences can include the ColEl origin of replication in bacteria or other known sequences.

Rare Earth Metal Molecular Switches

In some cases, the gene expression during the fermentation of high value chemicals (such as those described throughout e.g., isobutyraldehyde and isobutanol), requires precise control/timing of gene expression. In these cases, a molecular switch can be used. Switches that are particularly useful can be a rare earth metal switch. For example, a rare earth metal can be used to control gene expression, including but not limited to cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof. Any of the genes disclosed throughout or any combination thereof, can be controlled by a rare earth metal switch.

Lanthanum

In cases where a switch is used, the media can comprise a molecule that induces or represses the switch. For example, when a lanthanum sensitive switch is used to repress the expression of one or more of the genes described herein, the media can comprise lanthanum, which will repress expression of the one or more genes under the control of the switch. In the case of a lanthanum switch any one of the following concentrations can be used to effectively repress expression of the one or more genes that are under the control of a lanthanum switch: 0.1 µM; 0.5 µM; 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 50 µM; 100 µM or more.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising lanthanum. The media can then be diluted to effectively turn on the expression of the lanthanum repressed genes. The microorganism can be then grown to produce desired products, such as the multicarbon products (or others disclosed throughout).

Cerium, Praseodymium and Neodymium

In certain cases, a cerium, praseodymium, and/or neodymium sensitive switch can be used to repress or induce the expression of one or more of the genes described herein. In some cases, the media can comprise cerium, praseodymium, and/or neodymium, which can in some instances repress expression of the one or more genes under the control of the switch. In the case of cerium, praseodymium, and/or neodymium any one of the following concentrations can effectively repress expression of the one or more genes under the control of the cerium, praseodymium, and/or neodymium switch: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more.

In some cases, the cerium, praseodymium, and/or neodymium in the media can be diluted to turn on expression of the one or more cerium, praseodymium, and/or neodymium repressed genes. For example, in some cases, the dilution of cerium, praseodymium, and/or neodymium containing media can be 1:1 (1 part cerium, praseodymium, and/or neodymium containing media to 1 part non-cerium, praseodymium, and/or neodymium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising cerium, praseodymium, and/or neodymium. The media can then be diluted to effectively turn on the expression of the cerium, praseodymium, and/or neodymium repressed genes. The microorganism can be then grown to produce desired products, such as the multicarbon products (or others disclosed throughout).

Scandium, Yttrium, Samrium, Europium, Gadolinium, Terbium, Dysprosium, Holmium, Erbium, Thulium, and Yterribium In certain cases, a Scandium, Yttrium, Samrium, Europium, Gadolinium, Terbium, Dysprosium, Holmium, Erbium, Thulium, and/or Yterribium switch can be used to repress or induce the expression of one or more of the genes described herein. In some cases, the media can comprise Scandium, Yttrium, Samrium, Europium, Gadolinium, Terbium, Dysprosium, Holmium, Erbium, Thulium, and/or Yterribium, which will repress or induce expression of the one or more genes under the control of the switch. In the case of Scandium, Yttrium, Samrium, Europium, Gadolinium, Terbium, Dysprosium, Holmium, Erbium, Thulium, and/or Yterribium any one of the following concentrations can effectively repress expression of the one or more genes the switch: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more.

In some cases, the Scandium, Yttrium, Samrium, Europium, Gadolinium, Terbium, Dysprosium, Holmium, Erbium, Thulium, and/or Yterribium in the media can be diluted to reverse the effect of Scandium, Yttrium, Samrium, Europium, Gadolinium, Terbium, Dysprosium, Holmium, Erbium, Thulium, and/or Yterribium. For example, in some cases, the dilution of Scandium, Yttrium, Samrium, Europium, Gadolinium, Terbium, Dysprosium, Holmium, Erbium, Thulium, and/or Yterribium containing media can be 1:1 (1 part Scandium, Yttrium, Samrium, Europium, Gadolinium, Terbium, Dysprosium, Holmium, Erbium, Thulium, and/or Yterribium containing media to 1 part non-Scandium, Yttrium, Samrium, Europium, Gadolinium, Terbium, Dysprosium, Holmium, Erbium, Thulium, and/or Yterribium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

After dilution, the microorganism can be then grown to produce desired products, such as the multicarbon products (or others disclosed throughout).

Other Switches

Arabinose

In some cases, an arabinose switch can be used to induce/repress the expression of one or more of the genes described herein. In these cases, the media can comprise arabinose, which will in some cases, induce the expression of the one or more genes under the control of the switch. In the case of arabinose any one of the following concentrations can effectively induce/repress expression of the one or more genes: 0.1 g/L; 0.5 g/L; 1 g/L; 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; g/L; 20 g/L; 25 g/L; 30 g/L; 35 g/L; 40 g/L; 45 g/L; 50 g/L; 55 g/L; 60 g/L; 65 g/L; 70 g/L; 75 g/L; 80 g/L; 85 g/L; 90 g/L; 95 g/L; 100 g/L or more.

In some cases, any one of the following concentrations of arabinose can effectively induce/repress gene expression of the one or more genes controlled by an arabinose switch: 0.1 mM; 0.2 mM; 0.3 mM; 0.4 mM; 0.5 mM; 0.6 mM; 0.7 mM; 0.8 mM; 0.9 mM; 1 mM; 1.5 mM; 2 mM; 2.5 mM; 3 mM; 3.5 mM; 4 mM; 4.5 mM; 5 mM; 5.5 mM; 6 mM; 6.6 mM; 7 mM; 7.5 mM; 8 mM; 8.5 mM; 9 mM; 9.5 mM; 10 mM; 12.5 mM; 15 mM; 17.5 mM; 20 mM; 25 mM; 50 mM; 100 mM or more.

In some cases, the arabinose in the media can be diluted to turn on/off the expression of the one or more arabinose repressed/induced genes. For example, in some cases, the dilution of arabinose containing media can be 1:1 (1 part arabinose containing media to 1 part non-arabinose containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

Isopropyl β-D-1-thiogalactopyranoside

In certain cases, an IPTG sensitive switch can be used to induce or repress the expression of one or more of the genes described herein. In some cases, the media can comprise IPTG, which can in some instances induce expression of the one or more genes under the control of the switch. In the case of IPTG any one of the following concentrations can effectively induce or repress expression of the one or more genes: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more.

In some cases, the IPTG in the media can be diluted to turn on or off expression of the one or more IPTG induced or repressed genes. For example, in some cases, the dilution of IPTG containing media can be 1:1 (1 part IPTG containing media to 1 part non-IPTG containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising IPTG. IPTG can be added to the media to turn on the expression of IPTG induced genes. The microorganism can be then grown to produce desired products, such as the multicarbon products (or others disclosed throughout). The media can then be diluted to effectively turn off the expression of the IPTG induced genes.

Genes

The vectors described throughout can comprise a nucleic acid sequence of one or more of the following genes: (i) acetolactate synthase; (ii) ketol-acid reductoisomerase; (iii) dihydroxy-acid dehydratase; and/or (iv) 2-keto acid decarboxylase. In the case of alcohol production, the vector can also contain a nucleic acid sequence of an (v) alcohol dehydrogenase. For example, the vector can comprise an acetolactate synthase gene. The vector can comprise a ketol-acid reductoisomerase gene. The vector can comprise a dihydroxy-acid dehydratase gene. The vector can comprise an 2-keto acid decarboxylase gene. The vector can comprise an alcohol dehydrogenase gene. These genes can be heterologous to the microorganism in which the vector is contacted with (and eventually transformed with).

In some instances, the vector can comprise two or more of the following genes: (i) acetolactate synthase; (ii) ketol-acid reductoisomerase; (iii) dihydroxy-acid dehydratase; (iv) 2-keto acid decarboxylase; and/or (v) alcohol dehydrogenase. In one situation, the vector can comprise at least three or more of the genes. In another case, the vector can comprise at least four or more of the genes. In another instance, the vector can comprise all five of the genes. The vector with all five genes in most cases, will be used for alcohol (e.g., isobutanol) producing strains, unless the alcohol dehydrogenase gene is non-functional at the genetic or protein level. One or more of the genes can be heterologous to the microorganism in which the vector is contacted with (and eventually transformed with).

In some cases, when an acetolactate synthase is desired, the acetolactate synthase gene can be from a bacteria (e.g., a gram positive bacterium), such as from the genus *Bacillus*, or the species *Bacillus subtilis*.

The acetolactate synthase gene can comprise a nucleotide sequence that is substantially similar to SEQ ID NO: 1 or 100. For example, the acetolactate synthase gene can comprise a nucleotide sequence that is at least 60% identical to SEQ ID NO: 1 or 100. In some cases, the acetolactate synthase gene can comprise a nucleotide sequence that is at least 65% identical to SEQ ID NO: 1 or 100. In some cases, the acetolactate synthase gene can comprise a nucleotide sequence that is at least 70% identical to SEQ ID NO: 1 or 100. In some cases, the acetolactate synthase gene can comprise a nucleotide sequence that is at least 75% identical to SEQ ID NO: 1 or 100. In some cases, the acetolactate synthase gene can comprise a nucleotide sequence that is at least 80% identical to SEQ ID NO: 1 or 100. In some cases, the acetolactate synthase gene can comprise a nucleotide sequence that is at least 85% identical to SEQ ID NO: 1 or 100. In some cases, the acetolactate synthase gene can comprise a nucleotide sequence that is at least 90% identical to SEQ ID NO: 1 or 100. In some cases, the acetolactate synthase gene can comprise a nucleotide sequence that is at least 91% identical to SEQ ID NO: 1 or 100. In some cases, the acetolactate synthase gene can comprise a nucleotide sequence that is at least 92% identical to SEQ ID NO: 1 or 100. In some cases, the acetolactate synthase gene can comprise a nucleotide sequence that is at least 93% identical to SEQ ID NO: 1 or 100. In some cases, the acetolactate synthase gene can comprise a nucleotide sequence that is at least 94% identical to SEQ ID NO: 1 or 100. In some cases, the acetolactate synthase gene can comprise a nucleotide sequence that is at least 95% identical to SEQ ID NO: 1 or 100. In some cases, the acetolactate synthase gene can comprise a nucleotide sequence that is at least 96% identical to SEQ ID NO: 1 or 100. In some cases, the acetolactate synthase gene can comprise a nucleotide sequence that is at least 97% identical to SEQ ID NO: 1 or 100. In some cases, the acetolactate synthase gene can comprise a nucleotide sequence that is at least 98% identical to SEQ ID NO: 1 or 100. In some cases, the acetolactate synthase gene can comprise a nucleotide sequence that is at least 99% identical to SEQ ID NO: 1 or 100. In some cases, the acetolactate synthase gene can comprise a nucleotide sequence that is SEQ ID NO: 1 or 100.

When a ketol-acid reductoisomerase is desired, the ketol-acid reductoisomerase gene can be from a bacteria (e.g., a gram negative bacterium), such as from the genus *Escherichia*, or from the species *Escherichia coli*.

The ketol-acid reductoisomerase gene can comprise a nucleotide sequence that is substantially similar to SEQ ID NO: 3. For example, the ketol-acid reductoisomerase gene can comprise a nucleotide sequence that is at least 60% identical to SEQ ID NO: 3. In some cases, the ketol-acid reductoisomerase gene can comprise a nucleotide sequence that is at least 65% identical to SEQ ID NO: 3. In some cases, the ketol-acid reductoisomerase gene can comprise a nucleotide sequence that is at least 70% identical to SEQ ID NO: 3. In some cases, the ketol-acid reductoisomerase gene can comprise a nucleotide sequence that is at least 75% identical to SEQ ID NO: 3. In some cases, the ketol-acid reductoisomerase gene can comprise a nucleotide sequence that is at least 80% identical to SEQ ID NO: 3. In some cases, the ketol-acid reductoisomerase gene can comprise a nucleotide sequence that is at least 85% identical to SEQ ID NO: 3. In some cases, the ketol-acid reductoisomerase gene can comprise a nucleotide sequence that is at least 90% identical to SEQ ID NO: 3. In some cases, the ketol-acid reductoisomerase gene can comprise a nucleotide sequence that is at least 91% identical to SEQ ID NO: 3. In some cases, the ketol-acid reductoisomerase gene can comprise a nucleotide sequence that is at least 92% identical to SEQ ID NO: 3. In some cases, the ketol-acid reductoisomerase gene can comprise a nucleotide sequence that is at least 93% identical to SEQ ID NO: 3. In some cases, the ketol-acid reductoisomerase gene can comprise a nucleotide sequence that is at least 94% identical to SEQ ID NO: 3. In some cases, the ketol-acid reductoisomerase gene can comprise a nucleotide sequence that is at least 95% identical to SEQ ID NO: 3. In some cases, the ketol-acid reductoisomerase gene can comprise a nucleotide sequence that is at least 96% identical to SEQ ID NO: 3. In some cases, the ketol-acid reductoisomerase gene can comprise a nucleotide sequence that is at least 97% identical to SEQ ID NO: 3. In some cases, the ketol-acid reductoisomerase gene can comprise a nucleotide sequence that is at least 98% identical to SEQ ID NO: 3. In some cases, the ketol-acid reductoisomerase gene can comprise a nucleotide sequence that is at least 99% identical to SEQ ID NO: 3. In some cases, the ketol-acid reductoisomerase gene can comprise a nucleotide sequence that is SEQ ID NO: 3.

When a dihydroxy-acid dehydratase is desired, the dihydroxy-acid dehydratase gene can be a gene from a bacterium (e.g., a gram negative bacterium) or a methanotroph, such as from the genus *Escherichia* and/or *Methylococcus*, or from the species *Escherichia coli* and/or *Methylococcus capsulatus*.

The dihydroxy-acid dehydratase gene can comprise a nucleotide sequence that is substantially similar to SEQ ID NO: 5 or 7. For example, the dihydroxy-acid dehydratase gene can comprise a nucleotide sequence that is at least 60% identical to SEQ ID NO: 5 or 7. In some cases, the dihydroxy-acid dehydratase gene can comprise a nucleotide sequence that is at least 65% identical to SEQ ID NO: 5 or 7. In some cases, the dihydroxy-acid dehydratase gene can comprise a nucleotide sequence that is at least 70% identical to SEQ ID NO: 5 or 7. In some cases, the dihydroxy-acid dehydratase gene can comprise a nucleotide sequence that is at least 75% identical to SEQ ID NO: 5 or 7. In some cases, the dihydroxy-acid dehydratase gene can comprise a nucleotide sequence that is at least 80% identical to SEQ ID NO: 5 or 7. In some cases, the dihydroxy-acid dehydratase gene can comprise a nucleotide sequence that is at least 85% identical to SEQ ID NO: 5 or 7. In some cases, the dihydroxy-acid dehydratase gene can comprise a nucleotide sequence that is at least 90% identical to SEQ ID NO: 5 or 7. In some cases, the dihydroxy-acid dehydratase gene can comprise a nucleotide sequence that is at least 91% identical to SEQ ID NO: 5 or 7. In some cases, the dihydroxy-acid dehydratase gene can comprise a nucleotide sequence that is at least 92% identical to SEQ ID NO: 5 or 7. In some cases, the dihydroxy-acid dehydratase gene can comprise a nucleotide sequence that is at least 93% identical to SEQ ID NO: 5 or 7. In some cases, the dihydroxy-acid dehydratase gene can comprise a nucleotide sequence that is at least 94% identical to SEQ ID NO: 5 or 7. In some cases, the dihydroxy-acid dehydratase gene can comprise a nucleotide sequence that is at least 95% identical to SEQ ID NO: 5 or 7. In some cases, the dihydroxy-acid dehydratase gene can comprise a nucleotide sequence that is at least 96% identical to SEQ ID NO: 5 or 7. In some cases, the dihydroxy-acid dehydratase gene can comprise a nucleotide sequence that is at least 97% identical to SEQ ID NO: 5 or 7. In some cases, the dihydroxy-acid dehydratase gene can comprise a nucleotide sequence that is at least 98% identical to SEQ ID NO: 5 or 7. In some cases, the dihydroxy-acid dehydratase gene can comprise a nucleotide sequence that is at least 99% identical to SEQ ID NO: 5 or 7. In some cases, the dihydroxy-acid dehydratase gene can comprise a nucleotide sequence that is SEQ ID NO: 5 or 7.

When a 2-keto acid decarboxylase (KDC) gene is desired, the KDC can be a gene from a bacterium (e.g., a gram positive bacterium) or a methanotroph, such as from the genus *Carnobacterium* and/or *Methylococcus*, or from the species *Carnobacterium divergens* and/or *Methylococcus capsulatus*.

The KDC gene can be from other bacterium, such as those listed in Table 4. For example, the KDC gene can be from the genus *Methylocaldum, Methylosarcina, Methylomonas, Methylohalobius, Methylobacter, Lamprocystis, Andreprevotia, Lactococcus, Streptococcus, Enterococcus, Brochothrix, Carnobacterium, Helicobacter, Staphylococcus*, and/or *Fictibacillus*. For example, KDCs from the following species can be particularly useful: *Methylocaldum szegediense, Methylosarcina lacus, Methylomonas denitrificans, Methylomonas methanica, Methylohalobius crimeensis, Methylobacter marinus, Methylobacter luteus, Lamprocystis purpurea, Andreprevotia chitinilytica, Lactococcus lactis, Streptococcus didelphis, Enterococcus caccae, Enterococcus haemoperoxidus, Enterococcus moraviensis, Carnobacterium maltaromaticum, Brochothrix thermosphacta, Carnobacterium gallinarum, Carnobacterium divergens, Helicobacter bizzozeronii, Staphylococcus aureus* subsp. *aureus* CIG290, and/or *Fictibacillus macauensis*.

The 2-keto acid decarboxylase gene can comprise a nucleotide sequence that is substantially similar to any one of SEQ ID NOs: 9, 11, 56, 58, 60, 62, 64, 66, 68, 70, 72, 74, 76, 78, 80, 82, 84, 86, 88, 90, 92, 94, 96, or 98. For example, the 2-keto acid decarboxylase gene can comprise a nucleotide sequence that is at least 60% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 65% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 70% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 75% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 80% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 85% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 90% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 91% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 92% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 93% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 94% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 95% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 96% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 97% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 98% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 99% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is any one of SEQ ID NOs: 9, 11, 56, 58, 60, 62, 64, 66, 68, 70, 72, 74, 76, 78, 80, 82, 84, 86, 88, 90, 92, 94, 96, or 98.

In some cases, two or more KDC genes can be used. In some cases, two KDC genes can be used to increase the production of aldehydes, such as isobutyraldehyde, and/or alcohols, such as isobutanol. In other cases, three KDC genes can be used to increase the production of isobutyraldehyde and/or isobutanol. In some cases, four, five, or six KDC genes can be used to increase the production of isobutyraldehyde and/or isobutanol.

When an alcohol dehydrogenase is desired, the alcohol dehydrogenase gene can be from a bacterium (e.g., a gram negative or gram positive bacterium) or a yeast, such as from the genus *Escherichia* or *Saccharomyces*, or from the species *Escherichia coli* or *Saccharomyces cerevisiae*.

Other ADH genes that can be used can be from the genus *Clostridium*, *Geobacillus*, *Lactococcus*, *Oenococcus*, *Pectobacterium*, and/or *Psychrobacter*. For example, ADH genes from the following species can be particularly useful: *Clostridium acetobutylicum*, *Geobacillus stearothermophilus*, *Geobacillus thermoglucosidas*, *Lactococcus lactis*, *Oenococcus oeni*, *Pectobacterium atrosepticum*, and/or *Psychrobacter cryohalolentis*.

The alcohol dehydrogenase gene can comprise a nucleotide sequence that is substantially similar to any one of SEQ ID NOs: 13, 15, 17, 24, 26, 28, 30, 32, 34, 36, 38, 40, 42, 44, 46, 48, 50, 52, or 54. For example, the alcohol dehydrogenase gene can comprise a nucleotide sequence that is at least 60% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 65% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 70% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 75% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 80% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 85% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 90% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 91% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 92% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 93% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 94% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 95% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 96% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 97% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 98% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 99% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is any one of SEQ ID NOs: 13, 15, 17, 24, 26, 28, 30, 32, 34, 36, 38, 40, 42, 44, 46, 48, 50, 52, or 54.

In some cases, two or more ADH genes can be used. In some cases, two ADH genes can be used to increase the production of alcohols, such as isobutanol. In other cases, three ADH genes can be used to increase the production of isobutanol. In some cases, four, five, or six ADH genes can be used to increase the production of isobutanol.

Additional genes can be placed inside the microorganism in order to make other desired end products by fermentation.

For example, a sugar permease gene can be place within the microorganism in order to increase production of the desired end product, such as an aldehyde, e.g., isobutyraldehyde, or an alcohol, e.g., isobutanol. In some cases, the sugar permease gene can be from a bacterium (e.g., a gram negative bacterium) such as from the genus *Escherichia*. More specifically, the sugar permease can be from the species *Escherichia coli*.

The sugar permease gene can comprise a nucleotide sequence that is substantially similar to SEQ ID NO: 19. For example, the sugar permease gene can comprise a nucleotide sequence that is at least 60% identical to SEQ ID NO: 19. In some cases, the sugar permease gene can comprise a nucleotide sequence that is at least 65% identical to SEQ ID NO: 19. In some cases, the sugar permease gene can comprise a nucleotide sequence that is at least 70% identical to SEQ ID NO: 19. In some cases, the sugar permease gene can comprise a nucleotide sequence that is at least 75% identical to SEQ ID NO: 19. In some cases, the sugar permease gene can comprise a nucleotide sequence that is at least 80% identical to SEQ ID NO: 19. In some cases, the sugar permease gene can comprise a nucleotide sequence that is at least 85% identical to SEQ ID NO: 19. In some cases, the sugar permease gene can comprise a nucleotide sequence that is at least 90% identical to SEQ ID NO: 19. In some cases, the sugar permease gene can comprise a nucleotide sequence that is at least 91% identical to SEQ ID NO: 19. In some cases, the sugar permease gene can comprise a nucleotide sequence that is at least 92% identical to SEQ ID NO: 19. In some cases, the sugar permease gene can comprise a nucleotide sequence that is at least 93% identical to SEQ ID NO: 19. In some cases, the sugar permease gene can comprise a nucleotide sequence that is at least 94% identical to SEQ ID NO: 19. In some cases, the sugar permease gene can comprise a nucleotide sequence that is at least 95% identical to SEQ ID NO: 19. In some cases, the sugar permease gene can comprise a nucleotide sequence that is at least 96% identical to SEQ ID NO: 19. In some cases, the sugar permease gene can comprise a nucleotide sequence that is at least 97% identical to SEQ ID NO: 19. In some cases, the sugar permease gene can comprise a nucleotide sequence that is at least 98% identical to SEQ ID NO: 19. In some cases, the sugar permease gene can comprise a nucleotide sequence that is at least 99% identical to SEQ ID NO: 19. In some cases, the sugar permease gene can comprise a nucleotide sequence that is SEQ ID NO: 19.

Another enzyme that can be place within the microorganism in order to increase production of the desired end product, such as an aldehyde, e.g., isobutyraldehyde, or an alcohol, e.g., isobutanol, is an arabinose operon regulatory protein (AraC). In some cases, the arabinose operon regulatory protein gene can be from a bacterium (e.g., a gram negative bacterium) such as from the genus *Escherichia*. More specifically, the arabinose operon regulatory protein gene can be from the species *Escherichia coli*.

The arabinose operon regulatory protein gene can comprise a nucleotide sequence that is substantially similar to SEQ ID NO: 21. For example, the arabinose operon regulatory protein gene can comprise a nucleotide sequence that is at least 60% identical to SEQ ID NO: 21. In some cases, the arabinose operon regulatory protein gene can comprise a nucleotide sequence that is at least 65% identical to SEQ ID NO: 21. In some cases, the arabinose operon regulatory protein gene can comprise a nucleotide sequence that is at least 70% identical to SEQ ID NO: 21. In some cases, the arabinose operon regulatory protein gene can comprise a nucleotide sequence that is at least 75% identical to SEQ ID NO: 21. In some cases, the arabinose operon regulatory protein gene can comprise a nucleotide sequence that is at least 80% identical to SEQ ID NO: 21. In some cases, the arabinose operon regulatory protein gene can comprise a nucleotide sequence that is at least 85% identical to SEQ ID NO: 21. In some cases, the arabinose operon regulatory protein gene can comprise a nucleotide sequence that is at least 90% identical to SEQ ID NO: 21. In some cases, the arabinose operon regulatory protein gene can comprise a nucleotide sequence that is at least 91% identical to SEQ ID NO: 21. In some cases, the arabinose operon regulatory protein gene can comprise a nucleotide sequence that is at least 92% identical to SEQ ID NO: 21. In some cases, the arabinose operon regulatory protein gene can comprise a nucleotide sequence that is at least 93% identical to SEQ ID NO: 21. In some cases, the arabinose operon regulatory protein gene can comprise a nucleotide sequence that is at least 94% identical to SEQ ID NO: 21. In some cases, the arabinose operon regulatory protein gene can comprise a nucleotide sequence that is at least 95% identical to SEQ ID NO: 21. In some cases, the arabinose operon regulatory protein gene can comprise a nucleotide sequence that is at least 96% identical to SEQ ID NO: 21. In some cases, the arabinose operon regulatory protein gene can comprise a nucleotide sequence that is at least 97% identical to SEQ ID NO: 21. In some cases, the arabinose operon regulatory protein gene can comprise a nucleotide sequence that is at least 98% identical to SEQ ID NO: 21. In some cases, the arabinose operon regulatory protein gene can comprise a nucleotide sequence that is at least 99% identical to SEQ ID NO: 21. In some cases, the arabinose operon regulatory protein gene can comprise a nucleotide sequence that is SEQ ID NO: 21.

The amino acid sequences can also be optimized based on the microorganism in which the enzymes will be expressed. In other words, conservative amino acids substitutions can be made based on whether the respective microorganism typically uses a specific amino acid or how much of that particular amino acid is available for use within the microorganism.

The nucleotide sequence (or more specifically the codons that are encoded by the nucleotide sequences) can be optimized based on the microorganism in which the nucleotide sequences will be expressed. The nucleotide sequences can be codon optimized based on the amount of tRNA available within each individual microorganism. In other words, conservative codon substitutions can be made based on whether the respective microorganism typically uses a specific codon or how much of a particular tRNA is available within the microorganism.

In some instances, there can be more than one copy of one of the genes described throughout, for example, one or more copy of the following genes: (i) acetolactate synthase; (ii) ketol-acid reductoisomerase; (iii) dihydroxy-acid dehydratase; (iv) 2-keto acid decarboxylase; (v) alcohol dehydrogenase; (vi) sugar permease (LacY); and/or (vii) arabinose operon regulatory protein (AraC). These copies of the genes can come from a single organism, e.g., an *E. coli*, or from multiple organisms, e.g., one copy from an *E. coli* and one copy from *S. cerevisiae*, etc.

Isolated Nucleic Acids

The genes described herein can be in the form of an isolated polynucleic acid. In other words, the genes can be in forms that do not exist in nature, isolated from a chromosome or other endogenous structure. The isolated polynucleic acids can comprise a nucleic acid sequence of one or more of the following genes: (i) acetolactate synthase; (ii) ketol-acid reductoisomerase; (iii) dihydroxy-acid dehydratase; (iv) 2-keto acid decarboxylase; (v) alcohol dehydrogenase; (vi) sugar permease; and/or (vii) arabinose operon regulatory protein. For example, the isolated polynucleic acid can comprise an acetolactate synthase gene. The isolated polynucleic acid can comprise a ketol-acid reductoisomerase gene. The isolated polynucleic acid can comprise a dihydroxy-acid dehydratase gene. The isolated polynucleic acid can comprise a 2-keto acid decarboxylase gene. The isolated polynucleic acid can comprise an alcohol dehydrogenase gene. The isolated polynucleic acid can comprise a sugar permease gene. The isolated polynucleic acid can comprise an arabinose operon regulatory protein gene.

In some cases, the isolated polynucleic acid can encode for an acetolactate synthase. For example, the isolated polynucleic acid can comprise a nucleotide sequence that is substantially similar to SEQ ID NO: 1 or 100. In some cases, the isolated polynucleic acid can comprise a nucleotide sequence that is at least 60% identical to SEQ ID NO: 1 or 100. In some cases, the isolated polynucleic acid can comprise a nucleotide sequence that is at least 65% identical to SEQ ID NO: 1 or 100. In some cases, the isolated polynucleic acid can comprise a nucleotide sequence that is at least 70% identical to SEQ ID NO: 1 or 100. In some cases, the isolated polynucleic acid can comprise a nucleotide sequence that is at least 75% identical to SEQ ID NO: 1 or 100. In some cases, the isolated polynucleic acid can comprise a nucleotide sequence that is at least 80% identical to SEQ ID NO: 1 or 100. In some cases, the isolated polynucleic acid can comprise a nucleotide sequence that is at least 81% identical to SEQ ID NO: 1 or 100. In some cases, the isolated polynucleic acid can comprise a nucleotide sequence that is at least 82% identical to SEQ ID NO: 1 or 100. In some cases, the isolated polynucleic acid can comprise a nucleotide sequence that is at least 83% identical to SEQ ID NO: 1 or 100. In some cases, the isolated polynucleic acid can comprise a nucleotide sequence that is at least 84% identical to SEQ ID NO: 1 or 100. In some cases, the isolated polynucleic acid can comprise a nucleotide sequence that is at least 85% identical to SEQ ID NO: 1 or 100. In some cases, the isolated polynucleic acid can comprise a nucleotide sequence that is at least 86% identical to SEQ ID NO: 1 or 100. In some cases, the isolated polynucleic acid can comprise a nucleotide sequence that is at least 87% identical to SEQ ID NO: 1 or 100. In some cases, the isolated polynucleic acid can comprise a nucleotide sequence that is at least 88% identical to SEQ ID NO: 1 or 100. In some cases, the isolated polynucleic acid can comprise a nucleotide sequence that is at least 89% identical to SEQ ID NO: 1 or 100. In some cases, the isolated polynucleic acid can comprise a nucleotide sequence that is at least 90% identical to SEQ ID NO: 1 or 100. In some cases, the isolated polynucleic acid can comprise a nucleotide sequence that is at least 91% identical to SEQ ID NO: 1 or 100. In some cases, the isolated polynucleic acid can comprise a nucleotide sequence that is at least 92% identical to SEQ ID NO: 1 or 100. In some cases, the isolated polynucleic acid can comprise a nucleotide sequence that is at least 93% identical to SEQ ID NO: 1 or 100. In some cases, the isolated polynucleic acid can comprise a nucleotide sequence that is at least 94% identical to SEQ ID NO: 1 or 100. In some cases, the isolated polynucleic acid can comprise a nucleotide sequence that is at least 95% identical to SEQ ID NO: 1 or 100. In some cases, the isolated polynucleic acid can comprise a nucleotide sequence that is at least 96% identical to SEQ ID NO: 1 or 100. In some cases, the isolated polynucleic acid can comprise a nucleotide sequence that is at least 97% identical to SEQ ID NO: 1 or 100. In some cases, the isolated polynucleic acid can comprise a nucleotide sequence that is at least 98% identical to SEQ ID NO: 1 or 100. In some cases, the isolated polynucleic acid can comprise a nucleotide sequence that is at least 99% identical to SEQ ID NO: 1 or 100. In some cases, the isolated polynucleic acid can comprise a nucleotide sequence that is SEQ ID NO: 1 or 100.

In some cases, the isolated polynucleic acid can encode for a ketol-acid reductoisomerase. For example, the isolated polynucleic acid can comprise a nucleotide sequence that is substantially similar to SEQ ID NO: 3. In some cases, the isolated polynucleic acid can comprise a nucleotide sequence that is at least 60% identical to SEQ ID NO: 3. In some cases, the isolated polynucleic acid can comprise a nucleotide sequence that is at least 65% identical to SEQ ID NO: 3. In some cases, the isolated polynucleic acid can comprise a nucleotide sequence that is at least 70% identical to SEQ ID NO: 3. In some cases, the isolated polynucleic acid can comprise a nucleotide sequence that is at least 75% identical to SEQ ID NO: 3. In some cases, the isolated polynucleic acid can comprise a nucleotide sequence that is at least 80% identical to SEQ ID NO: 3. In some cases, the isolated polynucleic acid can comprise a nucleotide sequence that is at least 81% identical to SEQ ID NO: 3. In some cases, the isolated polynucleic acid can comprise a nucleotide sequence that is at least 82% identical to SEQ ID NO: 3. In some cases, the isolated polynucleic acid can comprise a nucleotide sequence that is at least 83% identical to SEQ ID NO: 3. In some cases, the isolated polynucleic acid can comprise a nucleotide sequence that is at least 84% identical to SEQ ID NO: 3. In some cases, the isolated polynucleic acid can comprise a nucleotide sequence that is at least 85% identical to SEQ ID NO: 3. In some cases, the isolated polynucleic acid can comprise a nucleotide sequence that is at least 86% identical to SEQ ID NO: 3. In some cases, the isolated polynucleic acid can comprise a nucleotide sequence that is at least 87% identical to SEQ ID NO: 3. In some cases, the isolated polynucleic acid can comprise a nucleotide sequence that is at least 88% identical to SEQ ID NO: 3. In some cases, the isolated polynucleic acid can comprise a nucleotide sequence that is at least 89% identical to SEQ ID NO: 3. In some cases, the isolated polynucleic acid can comprise a nucleotide sequence that is at least 90% identical to SEQ ID NO: 3. In some cases, the isolated polynucleic acid can comprise a nucleotide sequence that is at least 91% identical to SEQ ID NO: 3. In some cases, the isolated polynucleic acid can comprise a nucleotide sequence that is at least 92% identical to SEQ ID NO: 3. In some cases, the isolated polynucleic acid can comprise a nucleotide sequence that is at least 93% identical to SEQ ID NO: 3. In some cases, the isolated polynucleic acid can comprise a nucleotide sequence that is at least 94% identical to SEQ ID NO: 3. In some cases, the isolated polynucleic acid can comprise a nucleotide sequence that is at least 95% identical to SEQ ID NO: 3. In some cases, the isolated polynucleic acid can comprise a nucleotide sequence that is at least 96% identical to SEQ ID NO: 3. In some cases, the isolated polynucleic acid can comprise a nucleotide sequence that is at least 97% identical to SEQ ID NO: 3. In some cases, the isolated polynucleic acid can comprise a nucleotide sequence that is at least 98% identical to SEQ ID NO: 3. In some cases, the isolated polynucleic acid can comprise a nucleotide sequence that is at least 99% identical to SEQ ID NO: 3. In some cases, the isolated polynucleic acid can comprise a nucleotide sequence that is SEQ ID NO: 3.

In some cases, the isolated polynucleic acid can comprise a nucleotide sequence that encodes for a dihydroxy-acid dehydratase. In some cases, the isolated polynucleic acid can comprise a nucleotide sequence that is substantially similar to SEQ ID NO: 5 or 7. For example, the isolated polynucleic acid can comprise a nucleotide sequence that is at least 60% identical to SEQ ID NO: 5 or 7. In some cases, the isolated polynucleic acid can comprise a nucleotide sequence that is at least 65% identical to SEQ ID NO: 5 or 7. In some cases, the isolated polynucleic acid can comprise a nucleotide sequence that is at least 70% identical to SEQ ID NO: 5 or 7. In some cases, the isolated polynucleic acid can comprise a nucleotide sequence that is at least 75% identical to SEQ ID NO: 5 or 7. In some cases, the isolated polynucleic acid can comprise a nucleotide sequence that is at least 80% identical to SEQ ID NO: 5 or 7. In some cases, the isolated polynucleic acid can comprise a nucleotide sequence that is at least 81% identical to SEQ ID NO: 5 or 7. In some cases, the isolated polynucleic acid can comprise a nucleotide sequence that is at least 82% identical to SEQ ID NO: 5 or 7. In some cases, the isolated polynucleic acid can comprise a nucleotide sequence that is at least 83% identical to SEQ ID NO: 5 or 7. In some cases, the isolated polynucleic acid can comprise a nucleotide sequence that is at least 84% identical to SEQ ID NO: 5 or 7. In some cases, the isolated polynucleic acid can comprise a nucleotide sequence that is at least 85% identical to SEQ ID NO: 5 or 7. In some cases, the isolated polynucleic acid can comprise a nucleotide sequence that is at least 86% identical to SEQ ID NO: 5 or 7. In some cases, the isolated polynucleic acid can comprise a nucleotide sequence that is at least 87% identical to SEQ ID NO: 5 or 7. In some cases, the isolated polynucleic acid can comprise a nucleotide sequence that is at least 88% identical to SEQ ID NO: 5 or 7. In some cases, the isolated polynucleic acid can comprise a nucleotide sequence that is at least 89% identical to SEQ ID NO: 5 or 7. In some cases, the isolated polynucleic acid can comprise a nucleotide sequence that is at least 90% identical to SEQ ID NO: 5 or 7. In some cases, the isolated polynucleic acid can comprise a nucleotide sequence that is at least 91% identical to SEQ ID NO: 5 or 7. In some cases, the isolated polynucleic acid can comprise a nucleotide sequence that is at least 92% identical to SEQ ID NO: 5 or 7. In some cases, the isolated polynucleic acid can comprise a nucleotide sequence that is at least 93% identical to SEQ ID NO: 5 or 7. In some cases, the isolated polynucleic acid can comprise a nucleotide sequence that is at least 94% identical to SEQ ID NO: 5 or 7. In some cases, the isolated polynucleic acid can comprise a nucleotide sequence that is at least 95% identical to SEQ ID NO: 5 or 7. In some cases, the isolated polynucleic acid can comprise a nucleotide sequence that is at least 96% identical to SEQ ID NO: 5 or 7. In some cases, the isolated polynucleic acid can comprise a nucleotide sequence that is at least 97% identical to SEQ ID NO: 5 or 7. In some cases, the isolated polynucleic acid can comprise a nucleotide sequence that is at least 98% identical to SEQ ID NO: 5 or 7. In some cases, the isolated polynucleic acid can comprise a nucleotide sequence that is at least 99% identical to SEQ ID NO: 5 or 7. In some cases, the isolated polynucleic acid can comprise a nucleotide sequence that is SEQ ID NO: 5 or 7.

In some cases, the isolated polynucleic acid can comprise a nucleotide sequence that encodes for a 2-keto acid decarboxylase. In some cases, the isolated polynucleic acid can comprise a nucleotide sequence that is substantially similar to any one of SEQ ID NOs: 9, 11, 56, 58, 60, 62, 64, 66, 68, 70, 72, 74, 76, 78, 80, 82, 84, 86, 88, 90, 92, 94, 96, or 98. For example, the isolated polynucleic acid can comprise a nucleotide sequence that is at least 60% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 65% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 70% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 75% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 80% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 81% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 82% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 83% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 84% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 85% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 86% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 87% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 88% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 89% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 90% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 91% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 92% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 93% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 94% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 95% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 96% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 97% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 98% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 99% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is any one of SEQ ID NOs: 9, 11, 56, 58, 60, 62, 64, 66, 68, 70, 72, 74, 76, 78, 80, 82, 84, 86, 88, 90, 92, 94, 96, or 98.

In some cases, the isolated polynucleic acid can comprise a nucleotide sequence that encodes for an alcohol dehydrogenase. In some cases, the isolated polynucleic acid can comprise a nucleotide sequence that is substantially similar to any one of SEQ ID NOs: 13, 15, 17, 24, 26, 28, 30, 32, 34, 36, 38, 40, 42, 44, 46, 48, 50, 52, or 54. For example, the isolated polynucleic acid can comprise a nucleotide sequence that is at least 60% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 65% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 70% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 75% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 80% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 81% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 82% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 83% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 84% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 85% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 86% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 87% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 88% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 89% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 90% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 91% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 92% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 93% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 94% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 95% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 96% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 97% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 98% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 99% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is any one of SEQ ID NOs: 13, 15, 17, 24, 26, 28, 30, 32, 34, 36, 38, 40, 42, 44, 46, 48, 50, 52, or 54.

In some cases, the isolated polynucleic acid can comprise a nucleotide sequence that encodes for a sugar permease. In some cases, the isolated polynucleic acid can comprise a nucleotide sequence that is substantially similar to SEQ ID NO: 19. For example, the isolated polynucleic acid can comprise a nucleotide sequence that is at least 60% identical to SEQ ID NO: 19. In some cases, the isolated polynucleic acid can comprise a nucleotide sequence that is at least 65% identical to SEQ ID NO: 19. In some cases, the isolated polynucleic acid can comprise a nucleotide sequence that is at least 70% identical to SEQ ID NO: 19. In some cases, the isolated polynucleic acid can comprise a nucleotide sequence that is at least 75% identical to SEQ ID NO: 19. In some cases, the isolated polynucleic acid can comprise a nucleotide sequence that is at least 80% identical to SEQ ID NO: 19. In some cases, the isolated polynucleic acid can comprise a nucleotide sequence that is at least 81% identical to SEQ ID NO: 19. In some cases, the isolated polynucleic acid can comprise a nucleotide sequence that is at least 82% identical to SEQ ID NO: 19. In some cases, the isolated polynucleic acid can comprise a nucleotide sequence that is at least 83% identical to SEQ ID NO: 19. In some cases, the isolated polynucleic acid can comprise a nucleotide sequence that is at least 84% identical to SEQ ID NO: 19. In some cases, the isolated polynucleic acid can comprise a nucleotide sequence that is at least 85% identical to SEQ ID NO: 19. In some cases, the isolated polynucleic acid can comprise a nucleotide sequence that is at least 86% identical to SEQ ID NO: 19. In some cases, the isolated polynucleic acid can comprise a nucleotide sequence that is at least 87% identical to SEQ ID NO: 19. In some cases, the isolated polynucleic acid can comprise a nucleotide sequence that is at least 88% identical to SEQ ID NO: 19. In some cases, the isolated polynucleic acid can comprise a nucleotide sequence that is at least 89% identical to SEQ ID NO: 19. In some cases, the isolated polynucleic acid can comprise a nucleotide sequence that is at least 90% identical to SEQ ID NO: 19. In some cases, the isolated polynucleic acid can comprise a nucleotide sequence that is at least 91% identical to SEQ ID NO: 19. In some cases, the isolated polynucleic acid can comprise a nucleotide sequence that is at least 92% identical to SEQ ID NO: 19. In some cases, the isolated polynucleic acid can comprise a nucleotide sequence that is at least 93% identical to SEQ ID NO: 19. In some cases, the isolated polynucleic acid can comprise a nucleotide sequence that is at least 94% identical to SEQ ID NO: 19. In some cases, the isolated polynucleic acid can comprise a nucleotide sequence that is at least 95% identical to SEQ ID NO: 19. In some cases, the isolated polynucleic acid can comprise a nucleotide sequence that is at least 96% identical to SEQ ID NO: 19. In some cases, the isolated polynucleic acid can comprise a nucleotide sequence that is at least 97% identical to SEQ ID NO: 19. In some cases, the isolated polynucleic acid can comprise a nucleotide sequence that is at least 98% identical to SEQ ID NO: 19. In some cases, the isolated polynucleic acid can comprise a nucleotide sequence that is at least 99% identical to SEQ ID NO: 19. In some cases, the isolated polynucleic acid can comprise a nucleotide sequence that is SEQ ID NO: 19.

In some cases, the isolated polynucleic acid can comprise a nucleotide sequence that encodes for an arabinose operon regulatory protein. In some cases, the isolated polynucleic acid can comprise a nucleotide sequence that is substantially similar to SEQ ID NO: 21. For example, the isolated polynucleic acid can comprise a nucleotide sequence that is at least 60% identical to SEQ ID NO: 21. In some cases, the isolated polynucleic acid can comprise a nucleotide sequence that is at least 65% identical to SEQ ID NO: 21. In some cases, the isolated polynucleic acid can comprise a nucleotide sequence that is at least 70% identical to SEQ ID NO: 21. In some cases, the isolated polynucleic acid can comprise a nucleotide sequence that is at least 75% identical to SEQ ID NO: 21. In some cases, the isolated polynucleic acid can comprise a nucleotide sequence that is at least 80% identical to SEQ ID NO: 21. In some cases, the isolated polynucleic acid can comprise a nucleotide sequence that is at least 81% identical to SEQ ID NO: 21. In some cases, the isolated polynucleic acid can comprise a nucleotide sequence that is at least 82% identical to SEQ ID NO: 21. In some cases, the isolated polynucleic acid can comprise a nucleotide sequence that is at least 83% identical to SEQ ID NO: 21. In some cases, the isolated polynucleic acid can comprise a nucleotide sequence that is at least 84% identical to SEQ ID NO: 21. In some cases, the isolated polynucleic acid can comprise a nucleotide sequence that is at least 85% identical to SEQ ID NO: 21. In some cases, the isolated polynucleic acid can comprise a nucleotide sequence that is at least 86% identical to SEQ ID NO: 21. In some cases, the isolated polynucleic acid can comprise a nucleotide sequence that is at least 87% identical to SEQ ID NO: 21. In some cases, the isolated polynucleic acid can comprise a nucleotide sequence that is at least 88% identical to SEQ ID NO: 21. In some cases, the isolated polynucleic acid can comprise a nucleotide sequence that is at least 89% identical to SEQ ID NO: 21. In some cases, the isolated polynucleic acid can comprise a nucleotide sequence that is at least 90% identical to SEQ ID NO: 21. In some cases, the isolated polynucleic acid can comprise a nucleotide sequence that is at least 91% identical to SEQ ID NO: 21. In some cases, the isolated polynucleic acid can comprise a nucleotide sequence that is at least 92% identical to SEQ ID NO: 21. In some cases, the isolated polynucleic acid can comprise a nucleotide sequence that is at least 93% identical to SEQ ID NO: 21. In some cases, the isolated polynucleic acid can comprise a nucleotide sequence that is at least 94% identical to SEQ ID NO: 21. In some cases, the isolated polynucleic acid can comprise a nucleotide sequence that is at least 95% identical to SEQ ID NO: 21. In some cases, the isolated polynucleic acid can comprise a nucleotide sequence that is at least 96% identical to SEQ ID NO: 21. In some cases, the isolated polynucleic acid can comprise a nucleotide sequence that is at least 97% identical to SEQ ID NO: 21. In some cases, the isolated polynucleic acid can comprise a nucleotide sequence that is at least 98% identical to SEQ ID NO: 21. In some cases, the isolated polynucleic acid can comprise a nucleotide sequence that is at least 99% identical to SEQ ID NO: 21. In some cases, the isolated polynucleic acid can comprise a nucleotide sequence that is SEQ ID NO: 21.

Exemplary Vector Sequences

Vectors that can be integrated into various microorganisms, such as methanotrophs, are disclosed herein (see e.g., FIGS. 4A-4C, 5, and 6). In some cases, minor changes can be made to the vectors without significant changes in the effectiveness of the vectors or the amount of enzymes the vectors are able to produce.

Figures 4A, 4B:
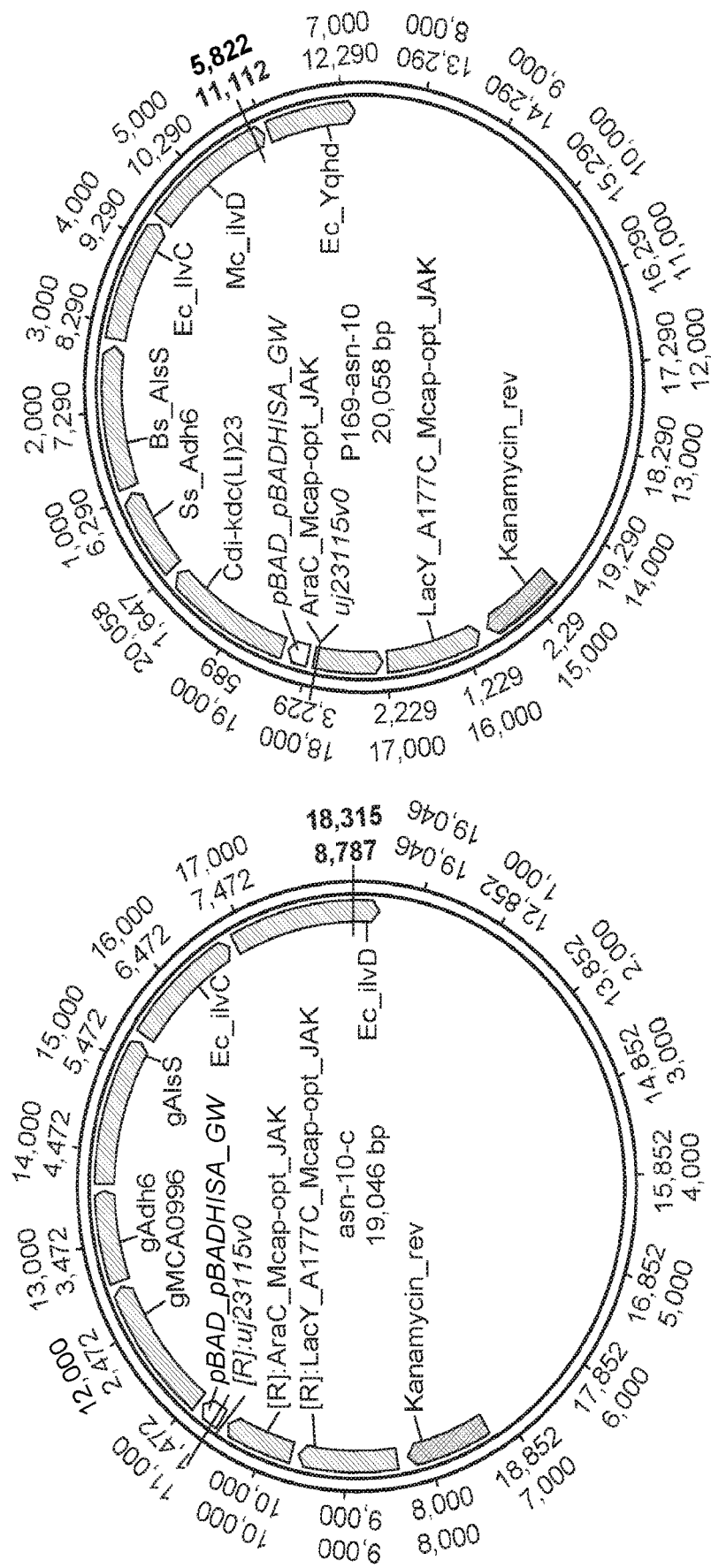
FIGS. 4A-4C show inducible expression vectors useful to express isobutanol pathway enzymes in microorganisms such as methanotrophs.

In some cases, the expression plasmid as disclosed in FIG. 4A or 4B, can be contacted with (and inserted into) a microorganism. These expression plasmids comprise a Kanamycin marker, an arabinose induction machinery (LacY and AraC driven by a J23115 promoter) and a BAD promoter (e.g., a pBAD promoter) driving the expression of enzymes useful in the isobutanol pathway ((MCA0996=Kdc), Adh6, AlsS, IlvC and IlvD).

Figure 4C:
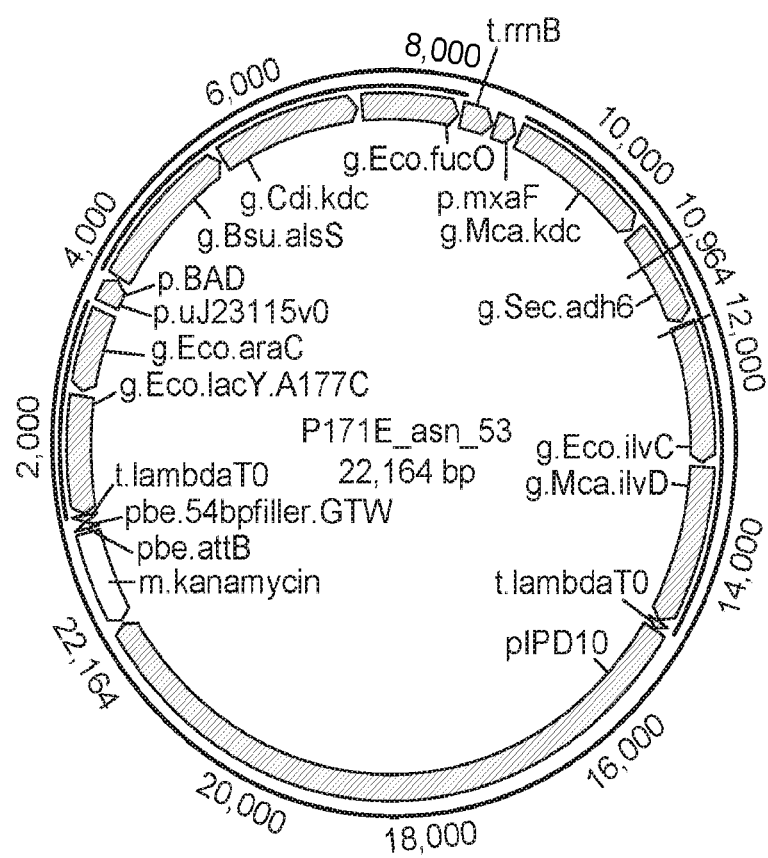
Figure 5:
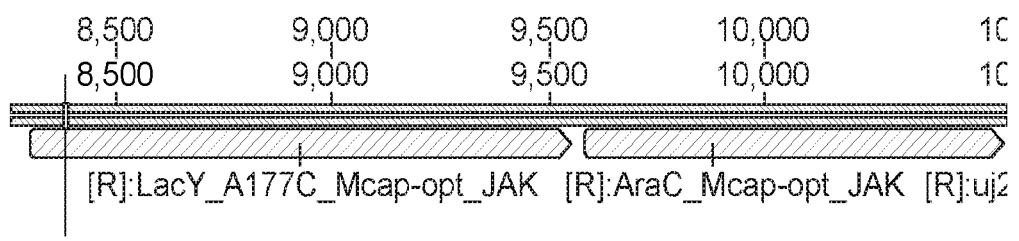
FIG. 5 shows the arabinose induction machinery: LacY and AraC.
Figure 6:
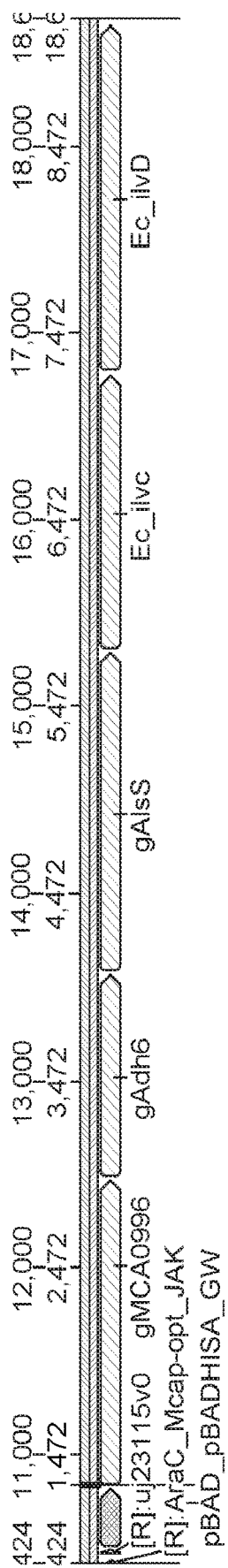
FIG. 6 shows the isobutanol operon expressed from the pBAD promoter. The pBAD promoter uses the pBAD ribosome binding site. In between each of the genes that follow MCA0996, the same RBS GTW0001 is used.

In other cases, the expression plasmid as disclosed in FIG. 4C can be contacted with (and inserted into) a microorganism. This expression plasmid comprises a Kanamycin marker, an arabinose induction machinery (LacY and AraC driven by a J23115 promoter) and two operons with two different promoters (a BAD promoter (pBAD) and a pMxaF promoter) driving the expression of enzymes useful in the isobutanol pathway Kdc, Adh, AlsS, IlvC and IlvD.

II. Method of Making the Genetically Modified Microorganisms

Figure 2:
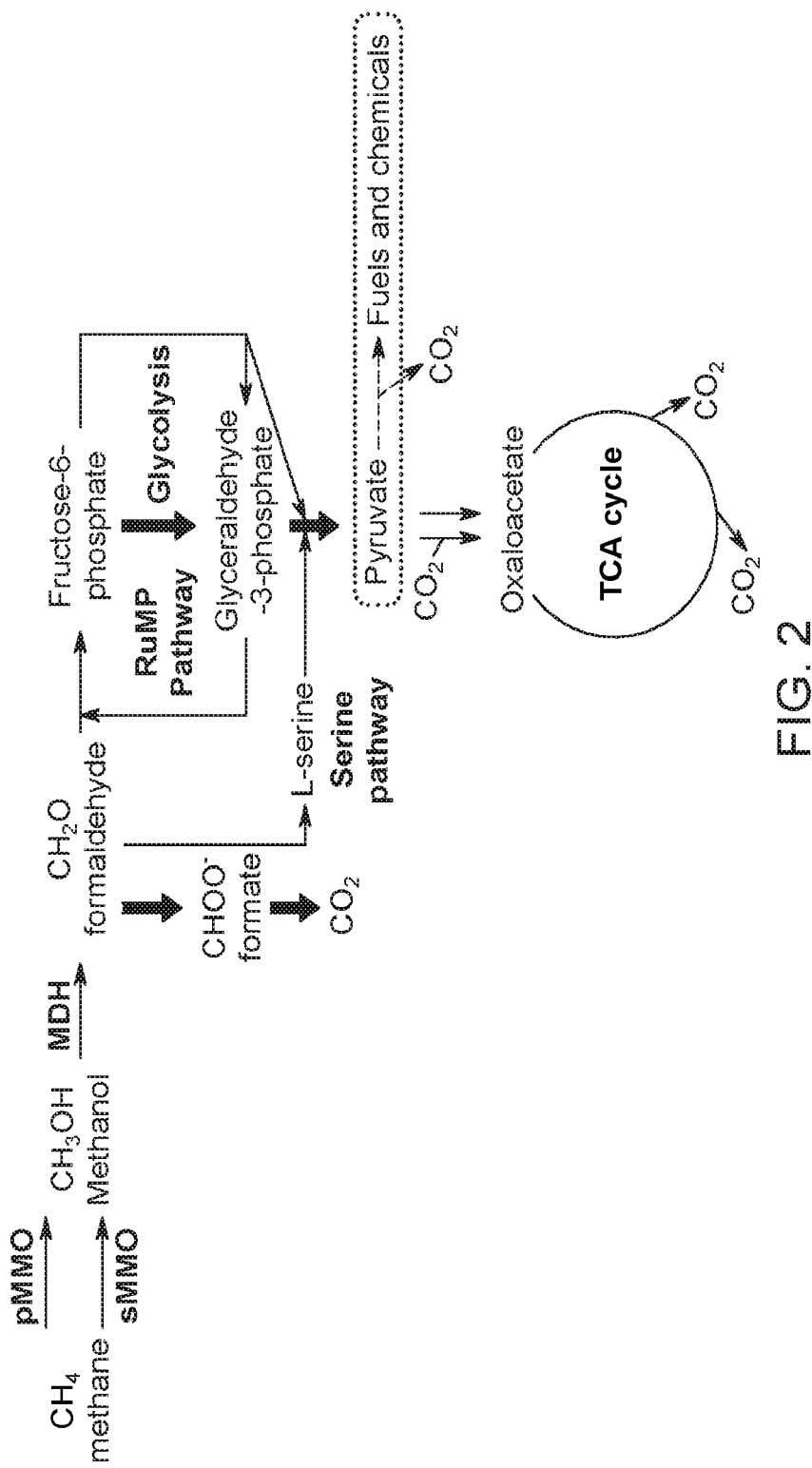
FIG. 2 shows a metabolic pathway from methane ($CH_4$) to pyruvate. Pyruvate can then be used to make various products such as fuels and chemicals.
Figure 3:
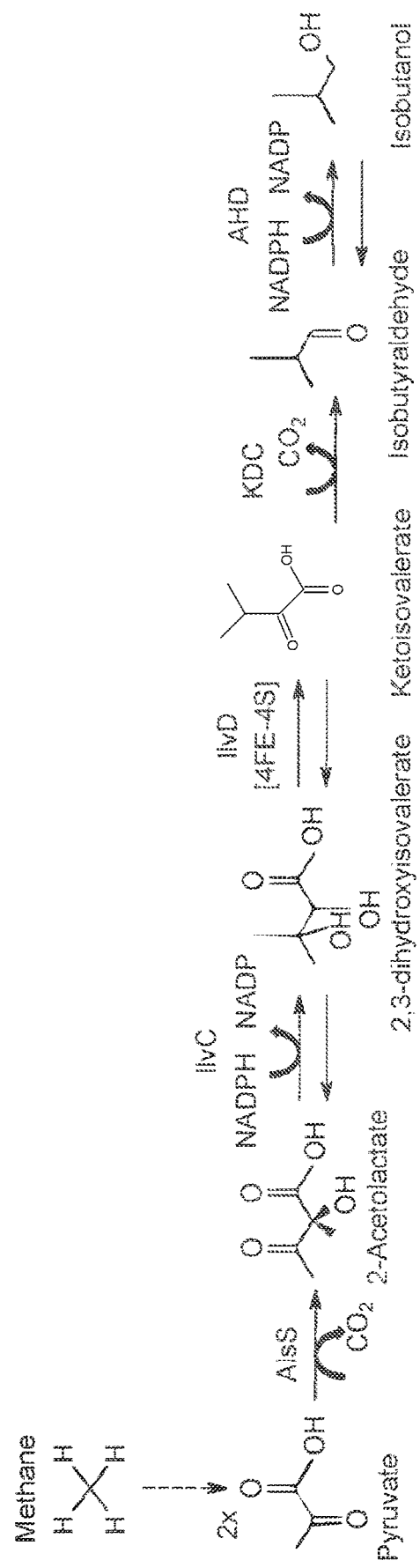
FIG. 3 shows a metabolic pathway from methane ($CH_4$) to isobutanol. Methane is converted to pyruvate by the pathway shown in FIG. 2, and pyruvate is converted into isobutanol through the action of at least five enzymes which include acetolactate synthase (gene name: AlsS); ketol-acid reductoisomerase (enzyme abbreviation: KARI; gene name: IlvC); dihydroxy-acid dehydratase (enzyme abbreviation: DHAD; gene name: IlvD); 2-keto acid decarboxylase (gene name: KDC); and alcohol dehydrogenase (gene name: ADH).

The genetically modified microorganisms above can be made by a variety of ways. A microorganism can be modified (e.g., genetically engineered) by any method to comprise and/or express one or more polynucleotides encoding for enzymes in a pathway that catalyze a conversion of a fermentable carbon source to one or more intermediates in a pathway for the production of a desired product, such as isobutanol. For example, the genetically modified microorganism can comprise one or more nucleic acids encoding for an enzyme capable of catalyzing one or more of the reactions: i) methane to methanol; ii) methanol to formaldehyde; and/or iii) formaldehyde to pyruvate. For example, the genetically modified microorganism can comprise one or more genes including but not limited to pMMO; sMMO; and/or methanol dehydrogenase (MDH). Such enzymes can include any of those enzymes as set forth in FIG. 2 or 3. For example, one or more of any of the genes above can be inserted into a microorganism. The genes can be inserted by an expression vector. The one or more genes can also be stably integrated into the genome of the microorganism.

The microorganism used in this method can be any described above, including but not limited to a prokaryote. Other microorganisms such as bacteria, yeast, or algae can be used. One microorganism of particular interest is a methanotroph, such as a methanotroph from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum,* or *Methyloacidoiphilum*. One desired species can include a *Methylococcus capsulatus*.

An exemplary method of making a genetically modified microorganism disclosed herein is contacting (or transforming) a microorganism with a nucleic acid that expresses at least one heterologous gene from: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof. For example, in order to make a microorganism that produces an aldehyde, e.g., isobutyraldehyde, (i) acetolactate synthase; (ii) ketol-acid reductoisomerase; (iii) dihydroxy-acid dehydratase; and/or (iv) 2-keto acid decarboxylase can be transformed into a microorganism. Additionally, should a microorganism that produces an alcohol be desired, an additional gene encoding for an (v) alcohol dehydrogenase can be transformed into the microorganism. One or more of these enzymes can be heterologous to the microorganism. Additionally, one or more of these enzymes can be endogenous to the microorganism. Further, one or more of these enzymes can be overexpressed in the microorganism. The microorganism can be any microorganism that is capable of converting a carbon source into a desired product. In some cases, the product is isobutanol. In some cases, the product is isobutyraldehyde.

The acetolactate synthase; ketol-acid reductoisomerase; dihydroxy-acid dehydratase; 2-keto acid decarboxylase; and/or alcohol dehydrogenase, used in the method can be any of the variations described throughout. For example, the alcohol dehydrogenase can be from yeast such as from the genus *Saccharomyces* or a bacterium (e.g., a gram negative or gram positive bacterium) such as from the genus *Escherichia*. Other bacterial genera that can be used include *Clostridium, Escherichia, Geobacillus, Lactococcus, Oenococcus, Pectobacterium,* and/or *Psychrobacter*. More specifically, the alcohol dehydrogenase can be from the species *Saccharomyces cerevisiae, Escherichia coli, Clostridium acetobutylicum, Escherichia coli, Geobacillus stearothermophilus, Geobacillus thermoglucosidas, Lactococcus lactis, Oenococcus oeni, Pectobacterium atrosepticum,* and/or *Psychrobacter cryohalolentis*. Further, multiple alcohol dehydrogenases can be used. For example, one or more bacterial alcohol dehydrogenases and one or more yeast alcohol dehydrogenases can be expressed within a microorganism.

The one or more genes that are inserted into a microorganism can be heterologous to the microorganism itself. For example, if the microorganism is a methanotroph, the one or more genes that are inserted can be from yeast, a bacterium, or a different species of methanotroph. Further, the one or more genes can be endogenously part of the genome of the microorganism. When endogenous genes are used, they can be overexpressed or they can be modified so that expression is altered compared to the unmodified endogenous gene. For example, the endogenous gene can be made to be under the control of a different promoter, such as an inducible promoter.

Techniques for Genetic Modification

The microorganisms disclosed herein can be genetically engineered by using classic microbiological techniques. Some of such techniques are generally disclosed, for example, in Sambrook et al., 1989, Molecular Cloning: A Laboratory Manual, Cold Spring Harbor Labs Press.

The genetically modified microorganisms disclosed herein can include a polynucleotide that has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase gene expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements.

Where desired, the expression of one or more of the enzymes provided herein is under the control of a regulatory sequence that controls directly or indirectly the enzyme expression in a time-dependent fashion during the fermentation. Inducible promoters can be used to achieve this.

In some cases, a microorganism is transformed or transfected with a genetic vehicle, such as an expression vector comprising a heterologous polynucleotide sequence coding for the enzymes are provided herein.

To facilitate insertion and expression of different genes coding for the enzymes as disclosed herein from the constructs and expression vectors, the constructs can be designed with at least one cloning site for insertion of any gene coding for any enzyme disclosed herein. The cloning site can be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide can be maintained as a non-integrated vector, for example, a plasmid, or alternatively, can be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextranmediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the transfection is a stable transfection.

Transformation

Expression vectors or other nucleic acids can be introduced to selected microorganisms by any of a number of suitable methods. For example, vector constructs can be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation can also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods can be used (e.g., Rose et al, 1990, Methods in Yeast Genetics, Cold Spring Harbor Laboratory Press, Cold Spring Harbor, N.Y.). Transformed cells can be isolated on selective media appropriate to the selectable marker used. Alternatively, or in addition, plates or filters lifted from plates can be scanned for GFP fluorescence to identify transformed clones.

For the introduction of vectors comprising differentially expressed sequences to certain types of cells, the method used can depend upon the form of the vector. Plasmid vectors can be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., N.Y., N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell can be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression or vectors for production of one or more enzymes as disclosed herein or with polynucleotides coding for one or more enzymes as disclosed herein and cultured in nutrient media modified as appropriate for the specific microorganism, inducing promoters, selecting transformants, or amplifying the genes encoding the desired sequences.

For example, within the context of a methanotroph, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas System

Methods that require any of the genes described herein can take advantage of pinpoint insertion of genes or the deletion of genes (or parts of genes). Methods described herein can take advantage of a CRISPR/Cas system. For example, double-strand breaks (DSBs) can be generated using a CRISPR/Cas system, e.g., a type II CRISPR/Cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used include class 1 and class 2. Non-limiting examples of Cas proteins include Cas1, Cas1B, Cas2, Cas3, Cas4, Cas5, Cas5d, Cas5t, Cas5h, Cas5a, Cash, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated with respect to a corresponding wild-type enzyme such that the mutated CRISPR enzyme lacks the ability to cleave one or both strands of a target polynucleotide containing a target sequence can be used.

A vector that encodes a CRISPR enzyme comprising one or more nuclear localization sequences (NLSs) can be used. For example, there can be 1, 2, 3, 4, 5, 6, 7, 8, 9, or 10 NLSs used. A CRISPR enzyme can comprise the NLSs at or near the amino-terminus, e.g., 1, 2, 3, 4, 5, 6, 7, 8, 9, or 10 NLSs at or near the carboxy-terminus, or any combination of these (e.g., one or more NLS at the amino-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with an RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or microorganism by transfecting the cell or microorganism with an isolated guide RNA or plasmid DNA comprising a sequence coding for the guide RNA and a promoter. A guide RNA can also be transferred into a cell or microorganism in other way, such as using virus-mediated gene delivery.

A guide RNA can be isolated. For example, a guide RNA can be transfected in the form of an isolated RNA into a cell or microorganism. A guide RNA can be prepared by in vitro transcription using any in vitro transcription system known in the art. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (e.g., from 10 nts to 25 nts; or from 15 nts to 25 nts; or from 10 nts to 20 nts; or from 15 nts to 20 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a cell or embryo as an RNA molecule. For example, an RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. An RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Site Specific Insertion

Inserting one or more genes in any microorganisms used in the of the methods disclosed throughout can be site-specific. For example, one or more genes can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, Φ31 integrase (a serine recombinase derived from *Streptomyces* phage Φ31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/Cas to facilitate the insertion of a transgene at the insertion site.

The techniques which can be used to allow a DNA or RNA construct entry into a host cell in the methods described herein include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods herein. Vectors that can be used include, but are not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene or a portion of a gene can be inserted by using known methods, such as restriction enzyme-based techniques.

III. Other Methods
Making Useful Chemicals

The genetically modified microorganisms described herein can be used to make chemicals that are useful, including but not limited to 2-acetolactate; 2,3-dihydroxy-isovalerate; ketoisovalerate; isobutyraldehyde; and isobutanol. Other useful products or chemicals that can be made with the methods and microorganisms described throughout can include amino acids such as lysine and isoleucine, sugar/glycogen, acetate, pyruvate, lactate, citrate, isovaleraldehyde, isopentanol, acetylated isobutanol or acetylated isopentanol (isobutrylacetate and isoamylacetate), and pentadecanoic acid (rare odd chain fatty acid over produced by the genetically modified microorganisms disclosed throughout but not produced at high level in wild-type strains).

Further, some of these chemicals can be used to produce other useful products including but not limited, to isobutyl acetate, isobutyl esters such as diisobutyl phthalate (DIBP), methyl methacrylate (MMA), isobutene, para-xylene, paint solvents, varnish remover, ink ingredients, paint additives, gasoline additives, gasoline alternatives, automotive polish additives, automotive paint cleaner additives, and chemical extractants in the production of organic compounds.

The microorganism can be any of the microorganisms discussed throughout including but not limited to a prokaryote, such as a methanotroph.

The carbon substrate can be any carbon substrate discussed throughout including but not limited to methane.

2-acetolactate

With regards to 2-acetolactate, one method disclosed herein is a method of making 2-acetolactate comprising: (a) contacting a genetically modified microorganism with a carbon substrate, where the microorganism comprises a heterologous gene encoding for acetolactate synthase; and (b) growing the microorganism to produce 2-acteolactate. In some cases, the acetolactate synthase gene can be from the genus *Bacillus*, such as the species *Bacillus subtilis* and/or *Bacillus licheniformis*. For example, an acetolactate synthase that can be used can be encoded by a nucleic acid having substantial similarity to SEQ ID NO: 1 or 100. The microorganisms that can be used in this method are described throughout (such as a methanotroph). Additionally, the microorganism can be transformed with or made to express one or more of the genes to make other products such as 2,3-butanediol ("2,3-BDO") and/or isobutanol and/or isobutyraldehyde (such as the genes that are described throughout). Further, the carbon sources can be any carbon source described throughout, such as a $C_1$ carbon source. The 2-acetolactate produced can be substantially pure. The 2-acetolactate produced can be recovered.

The 2-acetolactate can be further processed through the use of one or more enzymatic reactions. For example, 2-acetolactate can be processed into 2,3-BDO by contacting it with alpha-acetolactate (budA) or acetoin reductase (butA). In some cases, the 2-acetolactate can be contacted with a 2,3-butanediol dehydrogenase.

2,3-Butanediol ("2,3-BDO")

With regards to 2,3-BDO, one method disclosed herein is a method of making 2,3-BDO comprising: (a) contacting a genetically modified microorganism with a carbon substrate, where the microorganism comprises a heterologous gene encoding for acetolactate synthase; and (b) growing the microorganism to produce 2,3-BDO. The microorganisms that can be used in this method are described throughout (such as a methanotroph). Additionally, the microorganism can be transformed with or made to express one or more of the genes (such as a gene encoding for an alpha-acetolactate (budA) or acetoin reductase (butA)) or other genes as disclosed throughout. Further, the carbon sources can be any carbon source described throughout, such as a $C_1$ carbon source. The 2,3-BDO produced can be substantially pure. The 2,3-BDO produced can be recovered.

The 2,3-BDO can be further processed through the use of one or more catalysts. For example, 2,3-BDO can be processed into methyl ethyl ketone (MEK) by contacting the 2,3-BDO with a dehydrating catalyst (such as alumina, direct reaction with sulfuric acid, Cu, $AlO_3$, and/or zeolite (or other solid acid catalysts)). 2,3-BDO can also be processed into 1,3-butadiene by contacting the 2,3-BDO with a catalyst capable of producing a hydride shift, such as alumina or sulfuric acid. 2,3-BDO can also be processed into butene by contacting the 2,3-BDO with a HBr following by Zn. MEK, 1,3-butadiene and butene can be converted into a variety of different products such as synthetic rubbers or solvents.

The 2,3-BDO can also be further processed by a diol dehydratase (B12). This enzymatic reaction can produce butan-2-one (also known as methyl ethyl ketone or MEK). Thus, disclosed is a method of making butan-2-one comprising: (a) contacting a genetically modified microorganism with a carbon substrate, where the microorganism comprises a heterologous gene encoding for diol dehydratase; and (b) growing the microorganism to produce butan-2-one. The microorganism can also comprise an acetolactate synthase (AlsS), alpha-acetolactate (budA), and/or acetoin reductase (butA).

In some cases, the butan-2-one can be further processed by an alcohol dehydrogenase. This enzymatic reaction can produce butan-2-ol (also known as 2-butanol). Thus, disclosed is a method of making butan-2-ol comprising: (a) contacting a genetically modified microorganism with a carbon substrate, where the microorganism comprises a heterologous gene encoding for an alcohol dehydrogenase; and (b) growing the microorganism to produce butan-2-ol. The microorganism can also comprise an acetolactate synthase (AlsS), alpha-acetolactate (budA), acetoin reductase (butA), and/or diol dehydratase (B12).

Diacetyl

Diacetyl (also known as butanedione) can also be produced from 2-acetolactate. Disclosed herein is a method of making 2-acetolactate comprising: (a) contacting a genetically modified microorganism with a carbon substrate, where the microorganism comprises a heterologous gene encoding for acetolactate synthase; (b) growing the microorganism to produce 2-acetolactate; and (c) further processing 2-acetolactate into diacetyl. In general, diacetyl can be made by the spontaneous oxidative decarboxylation of acetolactate. Milne, N., et al., "Excessive by-product formation: A key contributor to low isobutanol yields of engineered Saccharomyces cerevisiae strains," Metabolic Engineering Communications 3:39-51 (2016). Diacetyl can be produced during fermentation as a byproduct of valine synthesis, when 2-acetolactate escapes the cell and is spontaneously decarboxylated into diacetyl.

The microorganisms that can be used in this method are described throughout (such as a methanotroph). Additionally, the microorganism can be transformed with or made to express one or more of the genes as disclosed throughout. Further the carbon sources can be any carbon source described throughout, such as a $C_1$ carbon source. The diacetyl produced can be substantially pure. The diacetyl that is produced can be recovered.

Diacetyl can be used in food products as it has buttery characteristics. Therefore, diacetyl can be used in the manufacture of foods in which a buttery taste is desired, such as artificial butter flavoring, margarines or similar oil-based products (along with acetoin and beta-carotene) to make the final product butter-flavored. Diacetyl can also be used in electronic cigarette liquids for flavoring.

Diacetyl can also be used in alcoholic beverages. At low levels, diacetyl provides a slipperiness to the feel of the alcoholic beverage in the mouth. As diacetyl levels increase, it imparts a buttery or butterscotch flavor. For example, diacetyl can be contained in beer and wines. For example, concentrations from 0.005 mg/L to 1.7 mg/L were measured in chardonnay wines, and the amount needed for the flavor to be noticed is at least 0.2 mg/L.

2,3-dihydroxy-2-methylbutanoic Acid 2,3-dihydroxy-2-methylbutanoic acid can be produced from the methods and microorganisms discussed herein. For example, disclosed is a method of making 2,3-dihydroxy-2-methylbutanoic acid comprising: (a) contacting a genetically modified microorganism with a carbon substrate, where the microorganism comprises a heterologous gene encoding for acetolactate synthase; (b) growing the microorganism to produce 2-acetolactate; and (c) contacting the 2-acetolactate with an enzyme that is capable of converting 2-acetolactate to 2,3-dihydroxy-2-methylbutanoic acid. In some cases the enzyme has an EC number 1.1.1.86. In some cases, the enzyme is a ketol-acid reductoisomerase.

The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The 2,3-dihydroxy-2-methylbutanoic acid produced can be substantially pure. The 2,3-dihydroxy-2-methylbutanoic acid that is produced can be recovered.

2,3-dihydroxy-2-methylbutanoic acid can also be used in alcoholic beverages. 2,3-dihydroxy-2-methylbutanoic acid can be contained in alcoholic beverages such as beer and wines. For example, concentrations from 0.26 ppm were measured in some German beers.

2,3-dihydroxyisovalerate

With regards to 2,3-dihydroxyisovalerate, one method disclosed herein is a method of making 2,3-dihydroxyisovalerate comprising (a) contacting a genetically modified microorganism with a carbon substrate, where the microorganism comprises at least one heterologous gene encoding for: (i) acetolactate synthase and/or (ii) ketol-acid reductoisomerase; and (b) growing the microorganism to produce 2,3-dihydroxyisovalerate. The microorganisms that can be used in this method are described throughout (such as a methanotroph). Additionally, the microorganisms can be transformed with or made to express one or more of the genes as disclosed throughout. Further the carbon sources can be any carbon source described throughout, such as a $C_1$ carbon source. The 2,3-dihydroxyisovalerate produced can be substantially pure. The 2,3-dihydroxyisovalerate that is produced can be recovered.

The 2,3-dihydroxyisovalerate can be further processed by the same microorganism, a different microorganism, or outside a microorganism (i.e., in vitro) through the use of additional enzymes such as a dihydroxy-acid dehydratase. The same microorganism can comprise a dihydroxy-acid dehydratase. In other instances, a different microorganism can comprise a dihydroxy-acid dehydratase or a dihydroxy-acid dehydratase is isolated from a cell and used in vitro. If the dihydroxy-acid dehydratase is in a different microorganism or is isolated from a cell, the microorganism/isolated enzyme can convert 2,3-dihydroxyisovalerate that is in the culture media (either by supplemental addition or by secretion by 2,3-dihydroxyisovalerate producing microorganism). The conversion of 2,3-dihydroxyisovalerate by dihydroxy-acid dehydratase can produce some desired products such as ketoisovalerate or isobutanol.

Amino Acids

Amino acids can be made using the methods and microorganisms disclosed throughout. For example, disclosed herein is a method of making amino acids comprising (a) contacting a genetically modified microorganism with a carbon substrate, where the microorganism comprises at least one heterologous gene encoding for: (i) acetolactate synthase and/or (ii) ketol-acid reductoisomerase; (b) growing the microorganism to produce 2,3-dihydroxyisovalerate; and (c) contacting the 2,3-dihydroxyisovalerate with one or more enzymes that are capable of converting 2,3-dihydroxyisovalerate into an amino acid. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The amino acids produced can be substantially pure. The amino acids that are produced can be recovered. The amino acids can be any one of valine, leucine, isoleucine, or any combination thereof.

The one or more enzymes that are capable of converting 2,3-dihydroxyisovalerate into an amino acid can be one or more of the following: dihydroxy-acid dehydratase; branched-chain amino acid transaminase (BAT2); branched-chain amino acid aminotransferase (BAT1); alpha-isopropylmalate synthase (LEU9, LEU4), isopropylmalate isomerase (LEU1), and/or beta-IPM dehydrogenase (LEU2).

For example, biosynthesis of valine includes steps of converting 2,3-dihydroxyisovalerate to 2-keto-isovalerate by dihydroxy-acid dehydratase, and conversion of 2-keto-isovalerate to valine by branched-chain amino acid transaminase (BAT2) and branched-chain amino acid aminotransferase (BAT1). Further, biosynthesis of leucine includes the same steps to 2-keto-isovalerate, followed by conversion of 2-keto-isovalerate to alpha-isopropylmalate by alpha-isopropylmalate synthase (LEU9, LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1).

Ketoisovalerate

With regards to ketoisovalerate, one method disclosed herein is a method of making ketoisovalerate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce ketoisovalerate. The microorganisms that can be used in this method are described throughout (such as a methanotroph). Additionally, the microorganisms can be transformed with or made to express one or more of the genes as disclosed throughout. Further the carbon sources can be any carbon source described throughout, such as a $C_1$ carbon source. The ketoisovalerate produced can be substantially pure. The ketoisovalerate that is produced can be recovered.

The ketoisovalerate can be further processed by the same microorganism, a different microorganism, or outside a microorganism (i.e., in vitro) through the use of additional enzymes such as a 2-keto acid decarboxylase. The same microorganism can comprise a 2-keto acid decarboxylase. In other instances, a different microorganism can comprise a 2-keto acid decarboxylase or a 2-keto acid decarboxylase is isolated from a cell and used in vitro. If the 2-keto acid decarboxylase is in a different microorganism or is isolated from a cell, the microorganism/isolated enzyme can convert ketoisovalerate that is in the culture media (either by supplemental addition or by secretion by ketoisovalerate producing microorganism). The conversion of ketoisovalerate by 2-keto acid decarboxylase can produce some desired products such as isobutyraldehyde or isobutanol.

Isobutyraldehyde

With regards to isobutyraldehyde, one method disclosed herein is a method of making isobutyraldehyde comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isobutyraldehyde. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a C1 carbon source. The isobutyraldehyde produced can be substantially pure. The isobutyraldehyde that is produced can be recovered.

The isobutyraldehyde can be further processed by the same microorganism, a different microorganism, or outside a microorganism (i.e., in vitro) through the use of additional enzymes such as an alcohol dehydrogenase. The same microorganism can comprise an alcohol dehydrogenase. In other instances, a different microorganism can comprise an alcohol dehydrogenase or an alcohol dehydrogenase is isolated from a cell and used in vitro. If the alcohol dehydrogenase is in a different microorganism or is isolated from a cell, the microorganism/isolated enzyme can convert isobutyraldehyde that is in the culture media (either by supplemental addition or by secretion by isobutyraldehyde producing microorganism). The conversion of isobutyraldehyde by alcohol dehydrogenase can produce some desired products such as isobutanol or other products such as methyl methacrylate.

Isobutyrate

With regards to isobutyrate, one method disclosed herein is a method of making isobutyrate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isobutyrate. In some cases, isobutyraldehyde produced by the microorganism can be oxidized. This oxidization can produce isobutyrate. The oxidization can be performed by catalysts or an enzyme. In some cases, when enzymatic oxidization is required, a promiscuous phenylacetaldehyde dehydrogenase (PadA) can be used (e.g., an enzyme having an EC number of 1.2.1.39). The PadA can be from a microorganism such as E. coli. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutyrate produced can be substantially pure. The isobutyrate that is produced can be recovered.

The isobutyrate produced can be made into other products such as methyl methacrylate (MMA). Isobutyrate can also be combined with many other chemicals, which can in turn be used for a variety of purposes. For example, phenoxy ethyl isobutyrate or styralyl isobutyrate have pleasant scents and can be used in a variety of perfumes.

Methyl Methacrylate (MMA)

With regards to methyl methacrylate (MMA), disclosed herein is a method of making MMA comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; (b) growing the microorganism to produce isobutyraldehyde; and (c) contacting the isobutyraldehyde with one or more catalysts capable of converting isobutyraldehyde to MMA. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The MMA from this method can be substantially pure. The MMA produced can be recovered. The MMA can be converted into polymethyl methacrylate acrylic plastics.

Isobutyraldehyde can be oxidized (sometimes in liquid phase) to form isobutyric acid. The isobutyric acid can be dehydrogenated (e.g., in a gas phase) into methacrylic acid. The catalyst that can be used for dehydrogenation can be a heteropoly acid catalyst (e.g., 12-tungstosilicate and 12-molybdophosphate). The methacrylic acid can be then esterified to form methacrylates. Otake, M., and Onoda, T., "A New Route to Methacrylates from Isobutyraldehyde," *Studies in Surface Science and Catalysis*, Vol. 7, Part B: 780-791 (1981).

MMA is used primarily for the manufacture of polymethyl methacrylate acrylic plastics (PMMA). Methyl methacrylate can also be used for the production of the copolymer methyl methacrylate-butadiene-styrene (MBS), which is used as a modifier for PVC. Another application of MMA is as cement used in total hip replacements as well as total knee replacements. MMA is also a raw material for the manufacture of other methacrylates. These derivatives include ethyl methacrylate (EMA), butyl methacrylate (BMA) and 2-ethyl hexyl methacrylate (2-EHMA). Methacrylic acid (MAA) is used as a chemical intermediate as well as in the manufacture of coating polymers, construction chemicals and textile applications.

Isovaleraldehyde

With regards to isovaleraldehyde, disclosed herein is a method of making isovaleraldehyde comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isovaleraldehyde. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isovaleraldehyde from this method can be substantially pure. The isovaleraldehyde produce can be recovered. Isovaleraldehyde can be produced as a significant product during the fermentation of pyruvate to isobutyraldehyde.

The amino acids produced by the methods and microorganisms described throughout can be converted into isovaleraldehyde. Isovaleraldehyde can be made when leucine is broken down. However, isovaleraldehyde can also be made by the hydroformylation of isobutene.

The isovaleraldehyde made by the methods and microorganisms described herein can be converted into different products. Isovaleraldehyde can be used as a flavoring in many different types of foods, such as beer, cheese, coffee, chicken, fish, chocolate, olive oil, and tea.

Isovaleraldehyde can also be used as a reactant in the synthesis of a number of compounds. For example, isovaleraldehyde can be used to synthesize 2,3-dimethyl-2-butene. 2,3-dimethyl-2-butene can then be converted to 2,3-dimethylbutane-2,3-diol and methyltert-butylketone, better known as pinacolone. Pinacolone can then be used in the synthesis of pesticides. Additionally, a range of pharmaceuticals, such as butizide, are synthesized from isovaleraldehyde and its corresponding acid.

Isovalerate

With regards to isovalerate, disclosed herein is a method of making isovalerate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isovalerate. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isovalerate from this method can be substantially pure. The isovalerate produced can be recovered. Isovalerate can be produced as a significant product during the fermentation of pyruvate to isobutyraldehyde. The amino acids produced by the methods and microorganisms described throughout can be converted into isovalerate. Isovalerate can be made when leucine is broken down.

The isovalerate made by the methods and microorganisms described herein can be converted into different products. Isovalerate esters can be used in perfumes as it has a pleasing scent. Isovaleric acid has also been used to synthesize β-hydroxyisovaleric acid.

Isopentanol

With regards to isopentanol (also known as isoamyl alcohol or isopentyl alcohol), one method disclosed herein is a method of making isopentanol comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce isopentanol. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isopentanol produced can be substantially pure. The isopentanol that is produced can be recovered. The isopentanol can also be acetylated. Therefore, the microorganism can produce acetylated isopentanol.

Isopentanol is a main ingredient in the production of banana oil, an ester found in nature. Isopentanol is also produced as a flavoring for the food industry. Isopentanol is also one of the components of the aroma produced by black truffles. Isopentanol is also the main ingredient of Kovac's reagent, used for the bacterial diagnostic indole test. Isopentanol can also be used as an antifoaming agent in a Chloroform:Isomyl Alcohol reagent. Isopentanol is used in a phenol-chloroform extraction mixed with the chloroform to further inhibit RNase activity and prevent solubility of RNAs with long tracts of poly-adenine.

Isoamyl Acetate

With regards to isoamyl acetate, one method disclosed herein is a method of making isoamyl acetate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce isoamyl acetate. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isoamyl acetate produced can be substantially pure. The isoamyl acetate that is produced can be recovered.

Isoamyl acetate can be formed by contact of isoamyl alcohol (e.g., isopentanol) and an acid catalyst (e.g., a lacial acetic acid or sulfuric acid). Sulfuric acid or an acidic ion exchange resin can be used as a catalyst.

Isoamyl acetate is used to confer banana flavor in foods. Pear oil commonly refers to a solution of isoamyl acetate in ethanol that is used as an artificial flavor. Isoamyl acetate can be used as a solvent for some varnishes and nitrocellulose lacquers. Isoamyl acetate can also be used in thermometers.

Pentadecanoic Acid

With regards to pentadecanoic acid, one method disclosed herein is a method of making pentadecanoic acid comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; and (b) growing the microorganism to produce pentadecanoic acid. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source.

The starter unit (propionyl-CoA) for pentadecanoic acid biosynthesis can be produced through amino acid degradation, such as isoleucine. The pentadecanoic acid that is produced can be recovered. The pentadecanoic acid produced can be substantially pure.

Pentadecanoic acid is rare in nature. It is a fatty acid of exogenous (primarily ruminant) origin. Many "odd" length long chain amino acids are derived from the consumption of dairy fats (milk and meat). The butterfat in cow's milk is its major dietary source and it is used as a marker for butterfat consumption. Pentadecanoic acid can decrease mother-to-child transmission of HEV through breastfeeding.

Isobutanol

With regards to isobutanol, one method disclosed herein is a method of making isobutanol comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; and (b) growing the microorganism to produce isobutanol. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutanol produced can be substantially pure. The isobutanol that is produced can be recovered.

The isobutanol can be further processed by the same microorganism, a different microorganism, or outside a microorganism (i.e., in vitro) through the use of additional enzymes or catalysts. The isobutanol can be made into different products such as isobutene.

Isobutene (Aka Isobutylene)

With regards to isobutene, one method disclosed herein is a method of making isobutene comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; (b) growing the microorganism to produce isobutanol; and (c) dehydrating the isobutanol to form isobutene. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutene produced can be substantially pure. The isobutene that is produced can be recovered.

In some instances, the dehydration of isobutanol can occur enzymatically. For example, an oleate hydratase can be used to convert the isobutanol produced herein to make isobutene. Should an enzymatic dehydration be desired, the genetically modified can comprises one or more oleate hydratases.

Isobutene can be further converted into different products. For example, isobutene can be used as an intermediate in the production of a variety of products. It is reacted with methanol and ethanol in the manufacture of the gasoline oxygenates methyl tert-butyl ether (MTBE) and ethyl tert-butyl ether (ETBE), respectively. Alkylation with butane produces isooctane, another fuel additive. Isobutene is also used in the production of methacrolein. Polymerization of isobutene produces butyl rubber (polyisobutylene). Antioxidants such as butylated hydroxytoluene (BHT) and butylated hydroxyanisole (BHA) are produced by Friedel-Crafts alkylation of phenols using isobutene.

Para-Xylene (p-xylene)

With regards to para-xylene (p-xylene), one method disclosed herein is a method of making p-xylene comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; (b) growing the microorganism to produce isobutanol; and (c) contacting the isobutanol with a catalyst capable of converting isobutanol into p-xylene. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The catalyst of (c) can be a catalyst that is capable of dehydrating isobutanol. The dehydration of isobutanol can form a $C_4$ alkene, such as isobutene. The $C_4$ alkene can subsequently be dimerized by an oligomerization catalyst to form a $C_8$ alkene, such as 2,4,4-trimethylpentenes or 2,5-dimethylhexene. The $C_8$ alkene can be dehydrocyclized by a dehydrocyclization catalyst to form p-xylene. The p-xylene that is produced can be recovered. The p-xylene produced can be substantially pure.

In some cases, the dehydration catalyst can be an organic or inorganic acid, or a metal salt, for example, an acidic γ-alumina catalyst. In some cases, the oligomerization catalyst can be a heterogeneous acidic catalyst. For example, the oligomerization catalyst can be an acidic zeolite, solid phosphoric acid, or a sulfonic acid resin. In some cases, the dehydrocyclization catalyst is a heterogeneous metal-containing dehydrogenation catalyst. In some cases, the dehydrocyclization catalyst is a supported chromium-containing compound. The dehydrocyclization catalyst can also be a chromium-oxide treated alumina; platinum- and tin-containing zeolites; or alumina, cobalt- or molybdenum-containing alumina.

p-xylene is an important chemical feedstock. Among other industrial applications, it is a raw material in the large scale synthesis of various polymers, such as for the production of terephthalic acid to make polyesters such as polyethylene terephthalate. It also can be polymerized directly to produce parylene. p-xylene is converted into either TPA or TPA esters by oxidation over a transition metal-containing catalyst. For example, p-xylene can be oxidized in air or oxygen (or air or oxygen diluted with other gases) over a catalyst containing nickel, manganese, and cobalt. p-xylene produced can be made into a renewable polyester by contacting TPA with ethylene glycol, propylene glycol, or butylene glycol in the presence of an acidic polymerization catalyst, such as antimony (III) oxide.

IV. Fermentation

In general, the microorganisms disclosed herein should be used in fermentation conditions that are appropriate to convert a carbon (such as methane) to isobutanol (or other desired product). Reaction conditions that should be considered include, but are not limited to, temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of carbon transfer (e.g., methane) from the gas phase to the liquid phase where it can be taken up by the microorganism as a carbon source for the production of isobutanol (or other desired products). This in turn means that the retention time (defined as the liquid volume in the bioreactor divided by the input gas flow rate) can be reduced when bioreactors are maintained at elevated pressure rather than atmospheric pressure.

The use of pressurized systems can greatly reduce the volume of the bioreactor required, and consequently the capital cost of the fermentation equipment. In some cases, reactor volume can be reduced in linear proportion to increases in reactor operating pressure, i.e., bioreactors operated at 10 atmospheres of pressure need only be one tenth the volume of those operated at 1 atmosphere of pressure.

It is also desirable that the rate of introduction of the gaseous carbon substrate (such as methane) is such as to ensure that the concentration of gaseous carbon substrate (such as methane) in the liquid phase does not become limiting. This is because a consequence of carbon substrate (e.g., methane) limited conditions can be that the isobutanol (or other desired product) is consumed by the culture.

Fermentation Conditions pH can be optimized based on the microorganism used. For example, the pH used during the methanotroph fermentation of methane to a desired product can be from 4 to 10. In other instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some cases, the pH can be from 5 to 9. In some cases, the pH can be from 6 to 8. In some cases, the pH can be from 6.1 to 7.9. In some cases, the pH can be from 6.2 to 7.8. In some cases, the pH can be from 6.3 to 7.7. In some cases, the pH can be from 6.4 to 7.6. In some cases, the pH can be from 6.5 to 7.5. In some cases, the pH used for the fermentation of methanotrophs can be greater than 6.

[[Do You Know if Higher Temperatures Work Better in this Strain?]]

Temperature can also be adjusted based on the microorganism used. For example, the temperature used during the methanotroph fermentation of methane to a desired product can be from 30° C. to 45° C. In other instances, the temperature of the fermentation can be from 30° C. to 45° C.; 31° C. to 44° C.; 32° C. to 43° C.; 33° C. to 42° C.; 34° C. to 41° C.; 35° C. to 40° C. For example, the temperature can be from 36° C. to 39° C. (e.g., 36° C., 37° C., 38° C., or 39° C.). In some cases, the temperature can be from 30° C. to 45° C. (e.g., 30° C., 31° C., 32° C., 33° C., 34° C., 35° C., 36° C., 37° C., 38° C., 39° C., 40° C., 41° C., 42° C., 43° C., 44° C., or 45° C.). In some cases, the temperature can be from 31° C. to 44° C. (e.g., 31° C., 32° C., 33° C., 34° C., 35° C., 36° C., 37° C., 38° C., 39° C., 40° C., 41° C., 42° C., 43° C., or 44° C.). In some cases, the temperature can be from 32° C. to 43° C. In some cases, the temperature can be from 33° C. to 42° C. (e.g., 33° C., 34° C., 35° C., 36° C., 37° C., 38° C., 39° C., 40° C., 41° C., or 42° C.). In some cases, the temperature can be from 34° C. to 41° C. (e.g., 34° C., 35° C., 36° C., 37° C., 38° C., 39° C., 40° C., or 41° C.). In some cases, the temperature can be from 35° C. to 40° C. (e.g., 35° C., 36° C., 37° C., 38° C., 39° C., or 40° C.).

In some cases, the temperatures can be within one tenth of a degree. For example, in some cases, the temperature of fermentation can be 37.0° C., 37.1° C., 37.2° C., 37.3° C., 37.4° C., 37.5° C., 37.6° C., 37.7° C., 37.8° C., 37.9° C., 38.0° C., 38.1° C., 38.2° C., 38.3° C., 38.4° C., 38.5° C., 38.6° C., 38.7° C., 38.8° C., 38.9° C., 39.0° C., 39.1° C., 39.2° C., 39.3° C., 39.4° C., 39.5° C., 39.6° C., 39.7° C., 39.8° C., 39.9° C., 40.0° C., 40.1° C., 40.2° C., 40.3° C., 40.4° C., 40.5° C., 40.6° C., 40.7° C., 40.8° C., 40.9° C., 41.0° C., 41.1° C., 41.2° C., 41.3° C., 41.4° C., 41.5° C., 41.6° C., 41.7° C., 41.8° C., 41.9° C., 42.0° C., 42.1° C., 42.2° C., 42.3° C., 42.4° C., 42.5° C., 42.6° C., 42.7° C., 42.8° C., 42.9° C., 43.0° C., 43.1° C., 43.2° C., 43.3° C., 43.4° C., 43.5° C., 43.6° C., 43.7° C., 43.8° C., 43.9° C., 44.0° C., 44.1° C., 44.2° C., 44.3° C., 44.4° C., 44.5° C., 44.6° C., 44.7° C., 44.8° C., 44.9° C., 45.0° C., 45.1° C., 45.2° C., 45.3° C., 45.4° C., 45.5° C., 45.6° C., 45.7° C., 45.8° C., 45.9° C., 46.0° C., 46.1° C., 46.2° C., 46.3° C., 46.4° C., 46.5° C., 46.6° C., 46.7° C., 46.8° C., 46.9° C., 47.0° C., 47.1° C., 47.2° C., 47.3° C., 47.4° C., 47.5° C., 47.6° C., 47.7° C., 47.8° C., or 47.9° C.

In some cases, the temperature of fermentation can be from 37.0° C. to 47.9° C. In some cases, the temperature of fermentation can be from 37.1° C. to 47.8° C. In some cases, the temperature of fermentation can be from 37.2° C. to 47.7° C. In some cases, the temperature of fermentation can be from 37.3° C. to 47.6° C. In some cases, the temperature of fermentation can be from 37.4° C. to 47.5° C. In some cases, the temperature of fermentation can be from 37.5° C. to 47.4° C. In some cases, the temperature of fermentation can be from 37.6° C. to 47.3° C. In some cases, the temperature of fermentation can be from 37.7° C. to 47.2° C. In some cases, the temperature of fermentation can be from 37.8° C. to 47.1° C. In some cases, the temperature of fermentation can be from 37.9° C. to 47.0° C. In some cases, the temperature of fermentation can be from 38.0° C. to 46.9° C. In some cases, the temperature of fermentation can be from 38.1° C. to 46.8° C. In some cases, the temperature of fermentation can be from 38.2° C. to 46.7° C. In some cases, the temperature of fermentation can be from 38.3° C. to 46.6° C. In some cases, the temperature of fermentation can be from 38.4° C. to 46.5° C. In some cases, the temperature of fermentation can be from 38.5° C. to 46.4° C. In some cases, the temperature of fermentation can be from 38.6° C. to 46.3° C. In some cases, the temperature of fermentation can be from 38.7° C. to 46.2° C. In some cases, the temperature of fermentation can be from 38.8° C. to 46.1° C. In some cases, the temperature of fermentation can be from 38.9° C. to 46.0° C. In some cases, the temperature of fermentation can be from 39.0° C. to 45.9° C. In some cases, the temperature of fermentation can be from 39.1° C. to 45.8° C. In some cases, the temperature of fermentation can be from 39.2° C. to 45.7° C. In some cases, the temperature of fermentation can be from 39.3° C. to 45.6° C. In some cases, the temperature of fermentation can be from 39.4° C. to 45.5° C. In some cases, the temperature of fermentation can be from 39.5° C. to 45.4° C. In some cases, the temperature of fermentation can be from 39.6° C. to 45.3° C. In some cases, the temperature of fermentation can be from 39.7° C. to 45.2° C. In some cases, the temperature of fermentation can be from 39.8° C. to 45.1° C. In some cases, the temperature of fermentation can be from 39.9° C. to 45.0° C. In some cases, the temperature of fermentation can be from 40.0° C. to 44.9° C. In some cases, the temperature of fermentation can be from 40.1° C. to 44.8° C. In some cases, the temperature of fermentation can be from 40.2° C. to 44.7° C. In some cases, the temperature of fermentation can be from 40.3° C. to 44.6° C. In some cases, the temperature of fermentation can be from 40.4° C. to 44.5° C. In some cases, the temperature of fermentation can be from 40.5° C. to 44.4° C. In some cases, the temperature of fermentation can be from 40.6° C. to 44.3° C. In some cases, the temperature of fermentation can be from 40.7° C. to 44.2° C. In some cases, the temperature of fermentation can be from 40.8° C. to 44.1° C. In some cases, the temperature of fermentation can be from 40.9° C. to 44.0° C. In some cases, the temperature of fermentation can be from 41.0° C. to 43.9° C. In some cases, the temperature of fermentation can be from 41.1° C. to 43.8° C. In some cases, the temperature of fermentation can be from 41.2° C. to 43.7° C. In some cases, the temperature of fermentation can be from 41.3° C. to 43.6° C. In some cases, the temperature of fermentation can be from 41.4° C. to 43.5° C. In some cases, the temperature of fermentation can be from 41.5° C. to 43.4° C. In some cases, the temperature of fermentation can be from 41.6° C. to 43.3° C. In some cases, the temperature of fermentation can be from 41.7° C. to 43.2° C. In some cases, the temperature of fermentation can be from 41.8° C. to 43.1° C. In some cases, the temperature of fermentation can be from 41.9° C. to 43.0° C. In some cases, the temperature of fermentation can be from 42.0° C. to 42.9° C. In some cases, the temperature of fermentation can be from 42.1° C. to 42.8° C. In some cases, the temperature of fermentation can be from 42.2° C. to 42.7° C. In some cases, the temperature of fermentation can be from 42.3° C. to 42.6° C. In some cases, the temperature of fermentation can be from 42.4° C. to 42.5° C.

Availability of oxygen and other gases such as gaseous $C_1$ carbon substrates (such as methane) can affect overall microorganism biomass accumulation. For example, when considering oxygen availability, the percent of dissolved oxygen (DO) within the media can be from 10% to 40%. In certain instances, the DO concentration can be from 10% to 20%; 15% to 25%; 17% to 30%; 20% to 35%; 25% to 40%. For example, in some cases the DO concentration can be from 10% to 20%. In other cases, the DO can be from 15% to 25%. In some instances, the DO can be from 17% to 30%. In some cases, the DO can be from 20% to 35%. In some cases, the DO can be from 25% to 40%. In some cases, the DO can be 15%. In some cases, the DO can be 20%. In some cases, the DO can be 25%. In some cases, these DO concentrations can be used to grow the number of methanotrophs, e.g., increase overall biomass.

When using a methanotroph, the type of methane substances can have an effect on yield and fermentation rates. For example, natural gas can be used, which typically has a methane content of above 85% (e.g., above 90%) methane. Other components within natural gas can include but are not limited to, ethane, propane, iso-butane, normal-butane, iso-pentane, normal pentane, hexanes plus, nitrogen, carbon dioxide, oxygen, hydrogen, and hydrogen sulfides.

"Pure" methane can be used as well. In these cases, the methane typically comes from a tank. The methane contained within these tanks can range from 90% or greater methane content and the remaining gas are other gases (such as carbon dioxide). For example, gas having a methane content, of greater than 90% can be used during the fermentation process. In certain instances, the methane concentration can be greater than 90%; 91%; 92%; 93%; 94%; 95%; 96%; 97%; 98%; 99%; or 99.9%. In some instances, the methane concentration can be 90% methane and 10% are other gases (such as carbon dioxide). In other instances, the methane concentration can be 91% methane and 9% are other gases (such as carbon dioxide). In some instances, the methane concentration can be 92% methane and 8% are other gases (such as carbon dioxide). In some instances, the methane concentration can be 93% methane and 7% are other gases (such as carbon dioxide). In some instances, the methane concentration can be 94% methane and 6% are other gases (such as carbon dioxide). In some instances, the methane concentration can be 95% methane and 5% are other gases (such as carbon dioxide). In other instances, the methane concentration can be 96% methane and 4% are other gases (such as carbon dioxide). In some instances, the methane concentration can be 97% methane and 3% are other gases (such as carbon dioxide). In some instances, the methane concentration can be 98% methane and 2% are other gases (such as carbon dioxide). In some instances, the methane concentration can be 99% methane and 1% is other gases (such as carbon dioxide). In some instances, the methane concentration can be 99.9% methane and 0.1% is other gases (such as carbon dioxide).

In cases where a switch is used, the media can comprise the molecule that induces or represses the switch. For example, when a lanthanum switch is used to repress the expression of one or more of the genes described herein, the media can comprise lanthanum, which will repress expression of the one or more genes under the control of the switch. In the case of lanthanum any one of the following concentrations can effectively repress expression of the one or more genes: 0.1 µM; 0.5 µM; 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 50 µM; 100 µM or more. In one case, 0.1 µM lanthanum can be used to repression expression of the one or more genes under the control of a lanthanum switch. In other cases, at least 0.5 µM lanthanum can be used. In other cases, at least 1 µM lanthanum can be used. In other cases, at least 2 µM lanthanum can be used. In other cases, at least 3 µM lanthanum can be used. In other cases, at least 4 µM lanthanum can be used. In other cases, at least 5 µM lanthanum can be used. In other cases, at least 6 µM lanthanum can be used. In other cases, at least 7 µM lanthanum can be used. In other cases, at least 8 µM lanthanum can be used. In other cases, at least 9 µM lanthanum can be used. In other cases, at least 10 µM lanthanum can be used. In other cases, at least 12.5 µM lanthanum can be used. In other cases, at least 15 µM lanthanum can be used. In other cases, at least 17.5 µM lanthanum can be used. In other cases, at least 20 µM lanthanum can be used. In other cases, at least 25 µM lanthanum can be used. In other cases, at least 50 µM lanthanum can be used. In other cases, at least 100 µM lanthanum can be used. In some cases, a range of 0.5 µM lanthanum to 100 µM lanthanum will effectively repress gene expression. In some cases, a range of 0.5 µM lanthanum to 50 µM lanthanum will repress gene expression. In other cases, a range of 1 µM lanthanum to 20 µM lanthanum will repress gene expression. In some cases, a range of 2 µM lanthanum to 15 µM lanthanum will repress gene expression. In some cases, a range of 3 µM lanthanum to 12.5 µM lanthanum will repress gene expression. In some cases, a range of 4 µM lanthanum to 12 µM lanthanum will repress gene expression. In some cases, a range of 5 µM lanthanum to 11.5 µM lanthanum will repress gene expression. In some cases, a range of 6 µM lanthanum to 11 µM lanthanum will repress gene expression. In some cases, a range of 7 µM lanthanum to 10.5 µM lanthanum will repress gene expression. In some cases, a range of 8 µM lanthanum to 10 µM lanthanum will repress gene expression.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising lanthanum. The media can then be diluted to effectively turn on the expression of the lanthanum repressed genes. The microorganism can be then grown in conditions to promote the production of desired products, such as 2,3-BDO and acetoin (or others disclosed throughout).

In some cases, other rare earth metals can be used. For example, other rare earth metals such as cerium (Ce), dysprosium (Dy), erbium (Er), europium (Eu), gadolinium (Gd), holmium (Ho), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof, can be used to repress or activate a molecular switch.

Bioreactor

Fermentation reactions can be carried out in any suitable bioreactor. In some embodiments of the invention, the bioreactor can comprise a first, growth reactor in which the microorganisms are cultured, and a second, fermentation reactor, to which broth from the growth reactor is fed and in which most of the fermentation product (isobutyraldehyde and/or isobutanol, for example) is produced.

Product Recovery

The fermentation of the microorganisms disclosed herein can produce a fermentation broth comprising a desired product (e.g., isobutyraldehyde and/or isobutanol) and/or one or more by-products as well as the microorganisms (e.g., a genetically modified methanotroph), in the growth/fermentation medium.

The microorganisms and the methods herein can produce isobutyraldehyde and/or isobutanol at surprisingly high efficiency, more so than other known fermentation processes. For example, the microorganisms and the methods disclosed herein can convert a carbon substrate (such as methane) at a rate of greater than 40% of the theoretical maximum. This means that at least 40% of the available carbon within the system is converted into product, such as isobutyraldehyde and/or isobutanol. In some cases, the conversion of a carbon substrate into isobutyraldehyde and/or isobutanol can be at least 41%, 42%, 43%, 44%, 45%, 46%, 47%, 48%, 49%, 50%, 51%, 52%, 53%, 54%, 55%, 56%, 57%, 58%, 59%, or 60%. In some cases, the conversion of a $C_1$ carbon substrate into isobutyraldehyde and/or isobutanol can be at least 40% of the theoretical maximum. In some cases, the conversion of a $C_1$ carbon substrate into isobutyraldehyde and/or isobutanol can be at least 41% of the theoretical maximum. In some cases, the conversion of a $C_1$ carbon substrate into isobutyraldehyde and/or isobutanol can be at least 42% of the theoretical maximum. In some cases, the conversion of a $C_1$ carbon substrate into isobutyraldehyde and/or isobutanol can be at least 43% of the theoretical maximum. In some cases, the conversion of a $C_1$ carbon substrate into isobutyraldehyde and/or isobutanol can be at least 43% of the theoretical maximum. In some cases, the conversion of a $C_1$ carbon substrate into isobutyraldehyde and/or isobutanol can be at least 44% of the theoretical maximum. In some cases, the conversion of a $C_1$ carbon substrate into isobutyraldehyde and/or isobutanol can be at least 45% of the theoretical maximum. In some cases, the conversion of a $C_1$ carbon substrate into isobutyraldehyde and/or isobutanol can be at least 46% of the theoretical maximum. In some cases, the conversion of a $C_1$ carbon substrate into isobutyraldehyde and/or isobutanol can be at least 47% of the theoretical maximum. In some cases, the conversion of a $C_1$ carbon substrate into isobutyraldehyde and/or isobutanol can be at least 48% of the theoretical maximum. In some cases, the conversion of a $C_1$ carbon substrate into isobutyraldehyde and/or isobutanol can be at least 49% of the theoretical maximum. In some cases, the conversion of a $C_1$ carbon substrate into isobutyraldehyde and/or isobutanol can be at least 50% of the theoretical maximum. In some cases, the conversion of a $C_1$ carbon substrate into isobutyraldehyde and/or isobutanol can be at least 51% of the theoretical maximum. In some cases, the conversion of a $C_1$ carbon substrate into isobutyraldehyde and/or isobutanol can be at least 52% of the theoretical maximum. In some cases, the conversion of a $C_1$ carbon substrate into isobutyraldehyde and/or isobutanol can be at least 53% of the theoretical maximum. In some cases, the conversion of a $C_1$ carbon substrate into isobutyraldehyde and/or isobutanol can be at least 54% of the theoretical maximum. In some cases, the conversion of a $C_1$ carbon substrate into isobutyraldehyde and/or isobutanol can be at least 55% of the theoretical maximum. In some cases, the conversion of a $C_1$ carbon substrate into isobutyraldehyde and/or isobutanol can be at least 56% of the theoretical maximum. In some cases, the conversion of a $C_1$ carbon substrate into isobutyraldehyde and/or isobutanol can be at least 57% of the theoretical maximum. In some cases, the conversion of a $C_1$ carbon substrate into isobutyraldehyde and/or isobutanol can be at least 58% of the theoretical maximum. In some cases, the conversion of a $C_1$ carbon substrate into isobutyraldehyde and/or isobutanol can be at least 59% of the theoretical maximum. In some cases, the conversion of a $C_1$ carbon substrate into isobutyraldehyde and/or isobutanol can be at least 60% of the theoretical maximum.

In certain methods when producing isobutyraldehyde, the overall amount isobutyraldehyde produced can be at least 1 g/L after 72 hours (or other time frame such as 48, 60, 84, 96, 108, or 120 hours). For example, the overall amount of isobutyraldehyde after 72 hours (or other time frame) produced can be at least 3 g/L to 7 g/L, 4 g/L to 8 g/L, 5 g/L to 9 g/L, 6 g/L to 10 g/L, 7 g/L to 11 g/L, 8 g/L to 12 g/L, 9 g/L to 13 g/L, 10 g/L to 14 g/L, 11 g/L to 15 g/L, 12 g/L to 16 g/L, 13 g/L to 17 g/L, 14 g/L to 18 g/L, 15 g/L to 19 g/L, 16 g/L to 20 g/L, 17 g/L to 21 g/L, or 18 g/L to 22 g/L. In some cases, the overall amount of isobutyraldehyde produced can be at least 7 g/L after 72 hours (or other time frame). In some cases, the overall amount of isobutyraldehyde produced can be at least 9 g/L after 72 hours (or other time frame). In some cases, the overall amount of isobutyraldehyde produced can be at least 12 g/L after 72 hours (or other time frame). In some cases, the overall amount of isobutyraldehyde produced can be at least 15 g/L after 72 hours (or other time frame). In some cases, the overall amount of isobutyraldehyde produced can be at least 18 g/L after 72 hours (or other time frame). In some cases, the overall amount of isobutyraldehyde produced can be at least 20 g/L after 72 hours (or other time frame).

In certain methods when producing isobutanol, the amount of isobutanol produced can be at least 1 g/L after 72 hours (or other time frame). For example, the amount of isobutanol produced can be at least 1 g/L to 5 g/L, 2 g/L to 6 g/L, 3 g/L to 7 g/L, or 4 g/L to 8 g/L, 5 g/L to 9 g/L, 6 g/L to 10 g/L, 7 g/L to 11 g/L, 8 g/L to 12 g/L, 9 g/L to 13 g/L, 10 g/L to 14 g/L, 11 g/L to 15 g/L, 12 g/L to 16 g/L, 13 g/L to 17 g/L, 14 g/L to 18 g/L, 15 g/L to 19 g/L, 16 g/L to 20 g/L, 17 g/L to 21 g/L, or 18 g/L to 22 g/L after 72 hours (or other time frame). In some cases, the amount of isobutanol produced can be at least 8 g/L after 72 hours (or other time frame). In some cases, the amount of isobutanol produced can be at least 7 g/L after 72 hours (or other time frame). In some cases, the amount of isobutanol produced can be at least 6 g/L after 72 hours (or other time frame). In some cases, the amount of isobutanol produced can be from 1 g/L to 5 g/L after 72 hours (or other time frame). In some cases, the amount of isobutanol produced can be from 2 g/L to 6 g/L after 72 hours (or other time frame). In some cases, the amount of isobutanol produced can be from 3 g/L to 7 g/L after 72 hours (or other time frame). In some cases, the amount of isobutanol produced can be from 4 g/L to 8 g/L after 72 hours (or other time frame). In some cases, the amount of isobutanol produced can be from 5 g/L to 9 g/L after 72 hours (or other time frame). In some cases, the amount of isobutanol produced can be from 6 g/L to 10 g/L after 72 hours (or other time frame). In some cases, the amount of isobutanol produced can be from 7 g/L to 11 g/L after 72 hours (or other time frame). In some cases, the amount of isobutanol produced can be from 8 g/L to 12 g/L after 72 hours (or other time frame). In some cases, the amount of isobutanol produced can be from 9 g/L to 13 g/L after 72 hours (or other time frame). In some cases, the amount of isobutanol produced can be from 10 g/L to 14 g/L after 72 hours (or other time frame). In some cases, the amount of isobutanol produced can be from 11 g/L to 15 g/L after 72 hours (or other time frame). In some cases, the amount of isobutanol produced can be from 12 g/L to 16 g/L after 72 hours (or other time frame). In some cases, the amount of isobutanol produced can be from 13 g/L to 17 g/L after 72 hours (or other time frame). In some cases, the amount of isobutanol produced can be from 14 g/L to 18 g/L after 72 hours (or other time frame). In some cases, the amount of isobutanol produced can be from 15 g/L to 19 g/L after 72 hours (or other time frame). In some cases, the amount of isobutanol produced can be from 16 g/L to 20 g/L after 72 hours (or other time frame). In some cases, the amount of isobutanol produced can be from 17 g/L to 21 g/L after 72 hours (or other time frame). In some cases, the amount of isobutanol produced can be from 18 g/L to 22 g/L after 72 hours (or other time frame).

In some cases, when methods such as "stripping" are used to isolate isobutanol (or isobutyraldehyde) continuously during fermentation, the amount of isobutanol (or isobutyraldehyde) present in the fermentation broth can be less than 10 g/L. For example, in some cases, the fermentation broth can comprise less than 9 g/L, 8 g/L, 7 g/L, 6 g/L, 5, g/L, 4 g/L, 3 g/L, 2 g/L, or 1 g/L of isobutanol (or isobutyraldehyde) during continuous fermentation. In some cases the fermentation broth titer can be less than 1 g/L of isobutanol (or isobutyraldehyde) during continuous fermentation.

In other cases, when microorganisms are used that normally produce at least some isobutyraldehyde and/or isobutanol, after genetic modification and fermentation, the genetically modified microorganism can produce isobutyraldehyde and/or isobutanol in concentrations that are at least 1.1× the amount that is normally produced. In some cases, the genetically modified microorganism can produce at least 2×, 3×, 4×, 5×, 10×, 25×, 50×, and or 100× the amount that is normally produced. In some cases, the genetically modified microorganism can produce at least 2× the amount that is normally produced. In some cases, the genetically modified microorganism can produce at least 3× the amount that is normally produced. In some cases, the genetically modified microorganism can produce at least 4× the amount that is normally produced. In some cases, the genetically modified microorganism can produce at least 5× the amount that is normally produced. In some cases, the genetically modified microorganism can produce at least 10× the amount that is normally produced. In some cases, the genetically modified microorganism can produce at least 25× the amount that is normally produced. In some cases, the genetically modified microorganism can produce at least 50× the amount that is normally produced. In some cases, the genetically modified microorganism can produce at least 100× the amount that is normally produced.

As discussed above, in certain embodiments the isobutyraldehyde and/or isobutanol produced in the fermentation reaction is converted to other desired products directly from the fermentation broth. In other embodiments, the isobutyraldehyde and/or isobutanol is first recovered from the fermentation broth before conversion to other desired products.

In some cases, isobutyraldehyde and/or isobutanol can be continuously removed from a portion of broth and recovered as purified isobutyraldehyde and/or isobutanol. In particular embodiments, the recovery of isobutyraldehyde and/or isobutanol includes passing the removed portion of the broth containing isobutyraldehyde and/or isobutanol through a separation unit to separate the microorganisms (e.g., genetically modified methanotroph) from the broth, to produce a cell-free isobutyraldehyde and/or isobutanol containing permeate, and returning the microorganisms to the bioreactor. The cell-free isobutyraldehyde and/or isobutanol-containing permeate can then can be stored or be used for subsequent conversion to other desired products.

The recovering of isobutyraldehyde and/or isobutanol and/or one or more other products or by-products produced in the fermentation reaction can comprise continuously removing a portion of the broth and recovering separately isobutyraldehyde and/or isobutanol and one or more other products from the removed portion of the broth. In some embodiments the recovery of isobutyraldehyde and/or isobutanol and/or one or more other products includes passing the removed portion of the broth containing isobutyraldehyde and/or isobutanol and/or one or more other products through a separation unit to separate microorganisms from the isobutyraldehyde and/or isobutanol and/or one or more other products, to produce cell-free isobutyraldehyde and/or isobutanol and one or more other product-containing permeate, and returning the microorganisms to the bioreactor.

In the above embodiments, the recovery of isobutyraldehyde and/or isobutanol and one or more other products can include first removing isobutyraldehyde and/or isobutanol from the cell-free permeate followed by removing the one or more other products from the cell-free permeate. The cell-free permeate can then be returned to the bioreactor.

Isobutyraldehyde and/or isobutanol, or a mixed product stream containing isobutyraldehyde and/or isobutanol, can be recovered from the fermentation broth. For example, methods that can be used can include but are not limited to, fractional distillation or evaporation, pervaporation, and extractive fermentation. For example, stripping, adsorption, pervaporation, membrane solvent extraction, and liquid-liquid extraction can be used.

In liquid-liquid extraction, an extractant is contacted with the fermentation broth to partition the isobutyraldehyde and/or isobutanol between the fermentation broth and the extractant phase. The isobutyraldehyde and/or isobutanol and the extractant are recovered by a separation process, for example by distillation. In the recovery process, the isobutyraldehyde and/or isobutanol can also be separated from any water, non-condensable gas, and/or fermentation by-products which can have been removed from the fermentation broth through use of the extractant.

Pervaporation or vacuum membrane distillation can be used to concentrate isobutyraldehyde and/or isobutanol (Qureshi, N., et al., "Recovery of 2,3-Butanediol by Vacuum Membrane Distillation," *Separation Science and Technology* 29:13 (1994)) in water as an extract from the fermentation broth. A microporous polytetrafluoroethylene (PTFE) membrane is used in the integrated process, while a silicone membrane is usually used in pervaporative ethanol or butanol fermentations.

In certain cases, isobutyraldehyde and/or isobutanol and by-products are recovered from the fermentation broth by continuously removing a portion of the broth from the bioreactor, separating microbial cells from the broth (conveniently by filtration, for example), and recovering isobutyraldehyde and/or isobutanol and optionally other alcohols and acids from the broth. Alcohols can conveniently be recovered for example by distillation, and acids can be recovered for example by adsorption on activated charcoal. The separated microbial cells can be returned to the fermentation bioreactor. The cell free permeate remaining after the isobutyraldehyde and/or isobutanol have been removed is returned to the fermentation bioreactor. Additional nutrients can be added to the cell free permeate to replenish the nutrient medium before it is returned to the bioreactor.

Also, if the pH of the broth was adjusted during recovery of isobutyraldehyde and/or isobutanol and/or by-products, the pH should be re-adjusted to a similar pH to that of the broth in the fermentation bioreactor, before being returned to the bioreactor.

In certain embodiments, the isobutyraldehyde and/or isobutanol is continuously recovered from the fermentation broth or bioreactor and fed directly for chemical conversion to one or more desired products, such as gasoline additive or polymers. For example, the isobutyraldehyde and/or isobutanol can be fed directly through a conduit to one or more vessel suitable for chemical synthesis of one or more of the desired products.

Biomass

After the product is recovered from fermentation media, the remaining material can be spun down and harvested as biomass. This biomass can be cleaned in some cases, and then can be dried. The biomass can then be used as feed for fish, pigs, cows, and other animals. In some instances, the biomass is not dried, and can be used as a wetcake. The wetcake can also be used as animal feed.

In some cases, the biomass can comprises one or more of the microorganisms that are disclosed throughout. In some cases, the biomass can comprise homogeneous microorganisms. In some cases, the biomass can comprise a heterogeneous mix of microorganisms.

In some cases, the microorganism used in the biomass can comprise a methanotroph. In some cases, the methanotroph can be a *Methylococcus*. In some cases, the *Methylococcus* can be a *Methylococcus capsulatus*.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein will be employed in practicing the invention.

EXAMPLES

Example 1: Genetic Engineering of Methanotrophs

To engineer a methanotroph to produce isobutyraldehyde or isobutanol, *M. capsulatus* was used as a starting point several isobutanol biosynthetic genes from a variety of sources. The various plasmids used are disclosed throughout. Generally however, the genes of the isobutanol pathway were expressed or overexpressed within a methanotroph. For example, various different combinations of α-acetolactate synthase (AlsS); ketol-acid reductoisomerase (IlvC); dihydroxy-acid dehydratase (IlvD); 2-keto acid decarboxylase (KDC); and alcohol dehydrogenase (ADH) were transformed into a methanotroph.

In order to produce methanotroph strains that can make isobutyraldehyde from methane, various different combinations of AlsS, ilvCs, ilvDs, and KDCs were transformed into a methanotroph and tested under conditions that promote isobutyraldehyde fermentation. In order to produce methanotroph strains that can produce isobutanol, the isobutyraldehyde strains were additionally transformed with various combinations of ADHs.

Example 2: Isobutanol Productivity

The various plasmids were transformed into transformation competent methanotroph strains, and the resulting strains (including biological replicate strains) were evaluated for isobutanol production in small scale microtiter plate fermentation or 1 L or 2 L fermentations, using methane as the carbon source. The various strains that were tested are found below.

Example 3: 2-Keto Acid Decarboxylase (KDCs)

Figure 7:
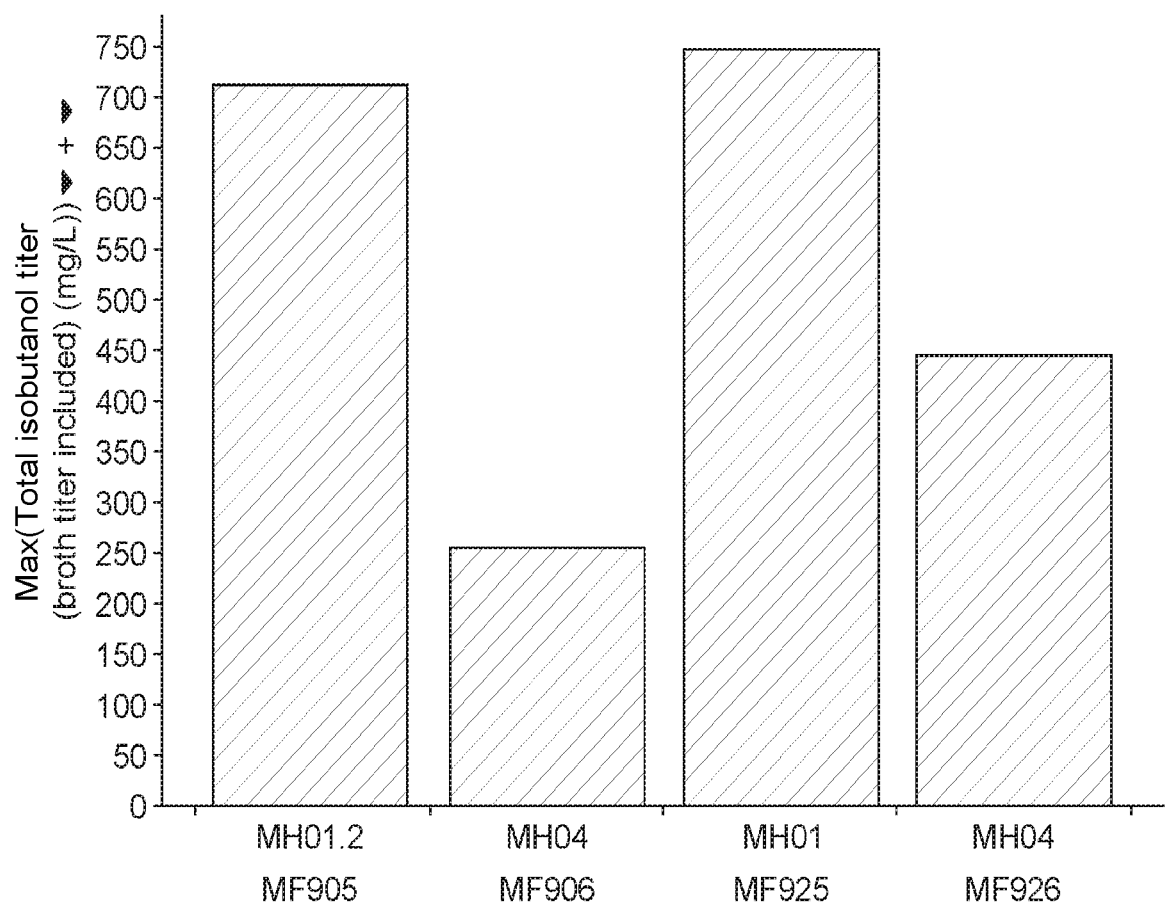
FIG. 7 shows a comparison of the isobutanol pathway in *E. coli* (see e.g., Atsumi., S., et al., "Non-fermentative pathways for synthesis of branch-chain higher alcohol as biofuels," *Nature*, 451(7174); 86-9 (2008) and Atsumi, S., et al., "Engineering the isobutanol biosynthetic pathway in *Escherichia coli* by comparison of three aldehyde reductase/alcohol dehydrogenase genes," *Appl. Microbiol. Biotechnol.*, 85(3): 651-7 (2010)) versus the isobutanol pathway designed herein using an *M. capsulatus* KDC. The data shows that KivD (used in the *E. coli* pathway by Atsumi et al.) does not produce nearly as much isobutanol compared to the *M. capsulatus* KDC when expressed in a methanotroph. *M. capsulatus* KDC is better in the context of the full pathway from pyruvate to isobutanol. MH04 comprises KivD, and MH01 comprises *M. capsulatus* KDC.

In order to improve isobutanol production, the effects of different KDCs on isobutanol production were compared using the methanotroph system disclosed herein. The isobutanol pathway in *E. coli* (see e.g., Atsumi et al. 2008 and Atsumi et al. 2010) was compared with the isobutanol pathway designed herein using an *M. capsulatus* KDC. The data in FIG. 7 shows that KivD (used in the *E. coli* pathway by Atsumi et al.) does not produce nearly as much isobutanol compared to the *M. capsulatus* KDC when expressed in a methanotroph. *M. capsulatus* KDC was found to be better in the context of the full pathway from pyruvate to isobutanol. For reference, MH04 comprises KivD, and MH01 comprises *M. capsulatus* KDC.

In order to test the effect different KDCs (e.g., *Carnobacterium divergens* v. *Methylococcus capsulatus*) have on the production of isobutanol in our strains, several different plasmids (Table 1, below) were transformed into a competent methanotroph strain and the resulting isobutanol production levels were evaluated.

TABLE 1

| | |
|---|---|
| JB140 | p.BAD > g.Cdi.kdc-g.Sce.adh6-Bsu.alsS-g.Eco.ilvC-g.Mca.ilvD-g.Eco.yqhD |
| SW1357 | p.BAD > Cdi.kdc__Sc.Adh6__Bs.AlsS-Mc.ilvC__Mc__ilvD |
| SW351 | p.BAD > g.Mca.kdc-g.Sce.adh6__g.Bsu.alsS__Ec.ilvC__Ec.ilvD |

Figure 8:
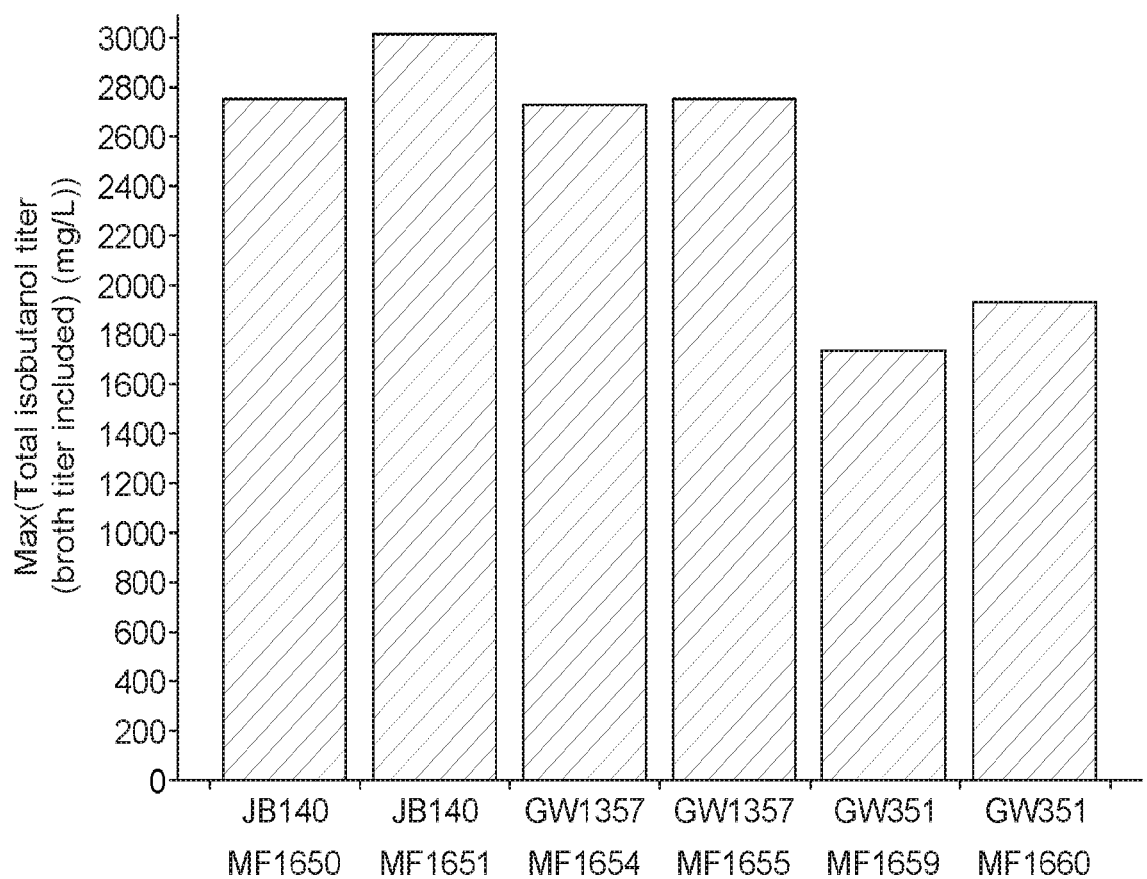
FIG. 8 shows isobutanol titers when methanotrophs are transformed with plasmids expressing a KDC from *Carnobacterium divergens* (CDI) (MF1650, MF1651; MF 1654; MF1655). Methanotrophs that were not transformed (MF1659, MF1660) with plasmids expressing *Carnobacterium divergens* (CDI) showed an approximate 40% decrease of isobutanol production.

As shown in FIG. 8, methanotrophs transformed with plasmids expressing a KDC from *Carnobacterium divergens* resulted in an approximate 40% increase over methanotrophs that expressed an endogenous *Methylococcus capsulatus* KDC.

The difference of overexpression of KDC from *Methylococcus capsulatus* and *Lactococcus lactis* was tested. Plasmids comprising isobutanol pathway genes, and KDCs from *Methylococcus capsulatus* or *Lactococcus lactis* were constructed and expressed. See Table 2. *Methylococcus capsulatus* transformants were produced with these plasmids and tested for the ability of the transformants to produce isobutanol.

TABLE 2

| | |
|---|---|
| MH01 | p.BAD > g.Mca.kdc__g.Sce.adh6__g.Bsu.alsS__g.Eco.ilvC__g.Eco.ilvD |
| MH04 | p.BAD > g.Lla.kivD__g.Sce.adh6__g.Bsu.alsS__g.Eco.ilvC__g.Eco.ilvD |

Figure 9:
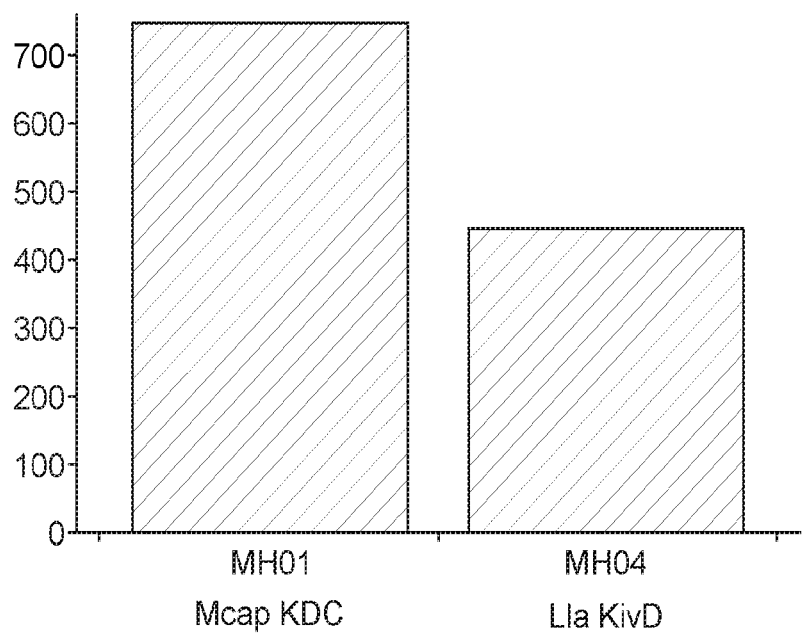
FIG. 9 shows the isobutanol production titer of methanotrophs that are transformed with *Methylococcus capsulatus* KDC or *Lactococcus lactis* KDC. KDC from *Methylococcus capsulatus* showed a vast improvement of isobutanol production (approximately 40%) compared to *Lactococcus lactis* KDC.

As seen in FIG. 9, KDC from *Methylococcus capsulatus* showed a vast improvement of isobutanol production compared to *Lactococcus lactis* KDC. The improvement was approximately a 40% increase.

Example 4: Alcohol Dehydrogenases (ADHs)

It was determined that not all the aldehydes produced by the genetically modified methanotrophs were converted into alcohols. In order to efficiently produce more alcohols such as isobutanol, different alcohol dehydrogenases were tested in the methanotroph model disclosed herein.

In order to test the effect alcohol dehydrogenases had on the production of isobutanol, several different plasmids were transformed into competent methanotroph strains and the resulting isobutanol production levels were evaluated.

Figure 10:
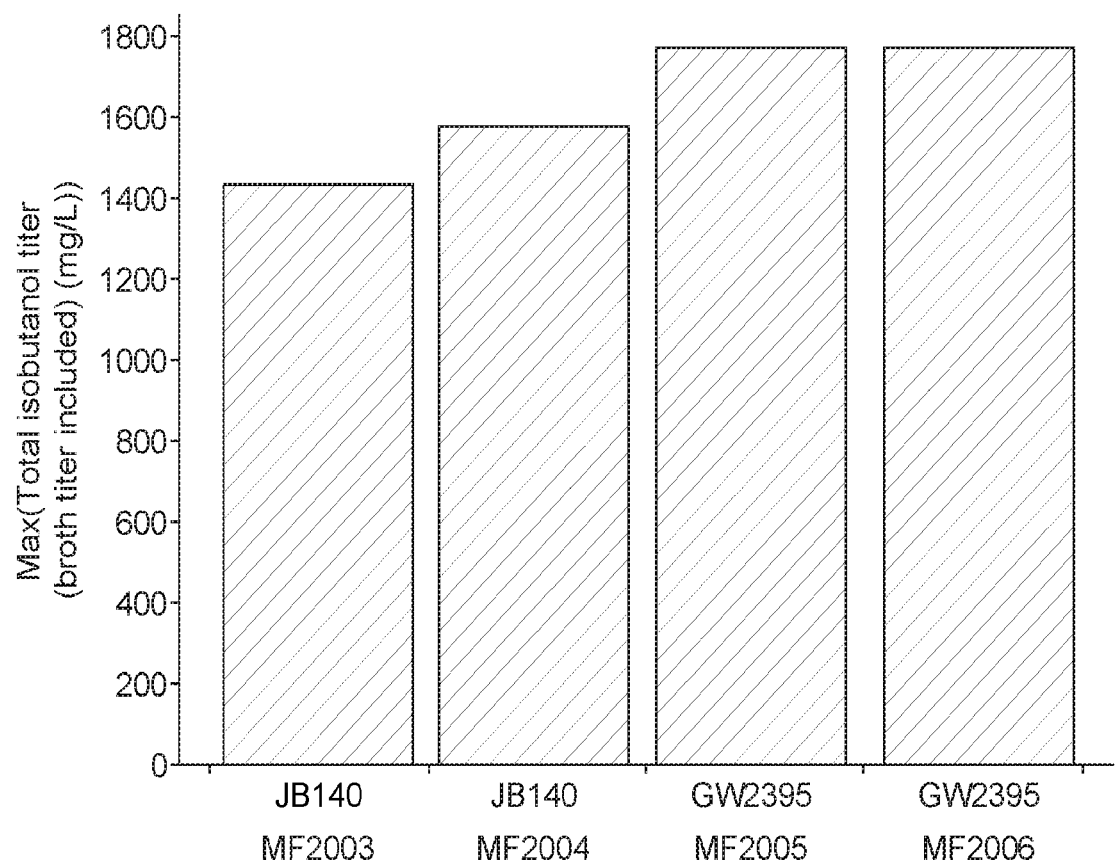
FIG. 10 shows isobutanol titers when methanotrophs are transformed with plasmids expressing either an Eco.fucO (MR2005; MF2006) or an Ec.YqdD (MF2003; MF2004) alcohol dehydrogenase. The methanotrophs expressing the Eco.fucO ADH showed increased isobutanol titers.

FIG. 10 shows isobutanol titers when methanotrophs are transformed with plasmids expressing either an Ec.fucO (MR2005; MF2006) or an Ec.YqdD (MF2003; MF2004) alcohol dehydrogenase. The methanotrophs expressing the Ec.fucO ADH showed increased isobutanol titers.

Another set of experiments testing different ADHs was performed. Constructs expressing different types of ADHs were created (Table 3, below). All methanotrophs expressed p.BAD>g.Mca.kdc variable ADH_g.Bsu.alsS_g.Eco.ilvC_g.Eco.ilvD. The ADH genes listed in Table 3 below were substituted into the plasmid listed as "variable ADH." The methanotrophs were then grown up in fermenters (2 L) and isobutanol production was tested.

TABLE 3

| Ref. # | SEQ ID NO: (Amino Acid) | SEQ ID NO: (Nucleotide) | ADH gene | Species |
|---|---|---|---|---|
| 1 | 23 | 24 | Ca_BdhA | C. acetobutylicum |
| 2 | 25 | 26 | Ca_BdhB | C. acetobutylicum |
| 3 | 27 | 28 | Ec_AdhP | E. coli |
| 4 | 29 | 30 | Ec_ahr | E. coli |
| 5 | 31 | 32 | Ec_FucO | E. coli |
| 6 | 33 | 34 | Ec_YjgB | E. coli |
| 7 | 35 | 36 | Ec_YqhD | E. coli |
| 8 | 37 | 38 | Gs_adh | G. stearothermophilus |
| 9 | 39 | 40 | Gs_adh2 | G. stearothermophilus |
| 10 | 41 | 42 | Gt_3237 | G. thermoglucosidas |
| 11 | 43 | 44 | Gt_3823 | G. thermoglucosidas |
| 12 | 45 | 46 | Ll_AdhA.29CB | L. lactis |
| 13 | 47 | 48 | Ll_AdhA | L. lactis |
| 14 | 49 | 50 | Oo_Adh3 | O. oeni |
| 15 | 51 | 52 | Pa_YqhD | P. atrosepticum |
| 16 | 53 | 54 | Psy_MadH | P. cryohalolentis |

Four of the top isobutanol producing plasmids were used that comprised: SL324 (p.BAD>g.Mca.kdc_g.Sce.adh6_g.Bsu.alsS_g.Eco.ilvC_g.Eco.ilvD); JB03 (p.BAD>g.Mca.kdc_g.Cac.BdhB_g.Bsu.alsS_g.Eco.ilvC_g.Eco.ilvD); JB07 (p.BAD>g.Mca.kdc_g.Eco.FucO_g.Bsu.alsS_g.Eco.ilvC_g.Eco.ilvD); and JB09 (p.BAD>g.Mca.kdc_g.Eco.YqhD_g.Bsu.alsS_g.Eco.ilvC_g.Eco.ilvD).

Figure 11:
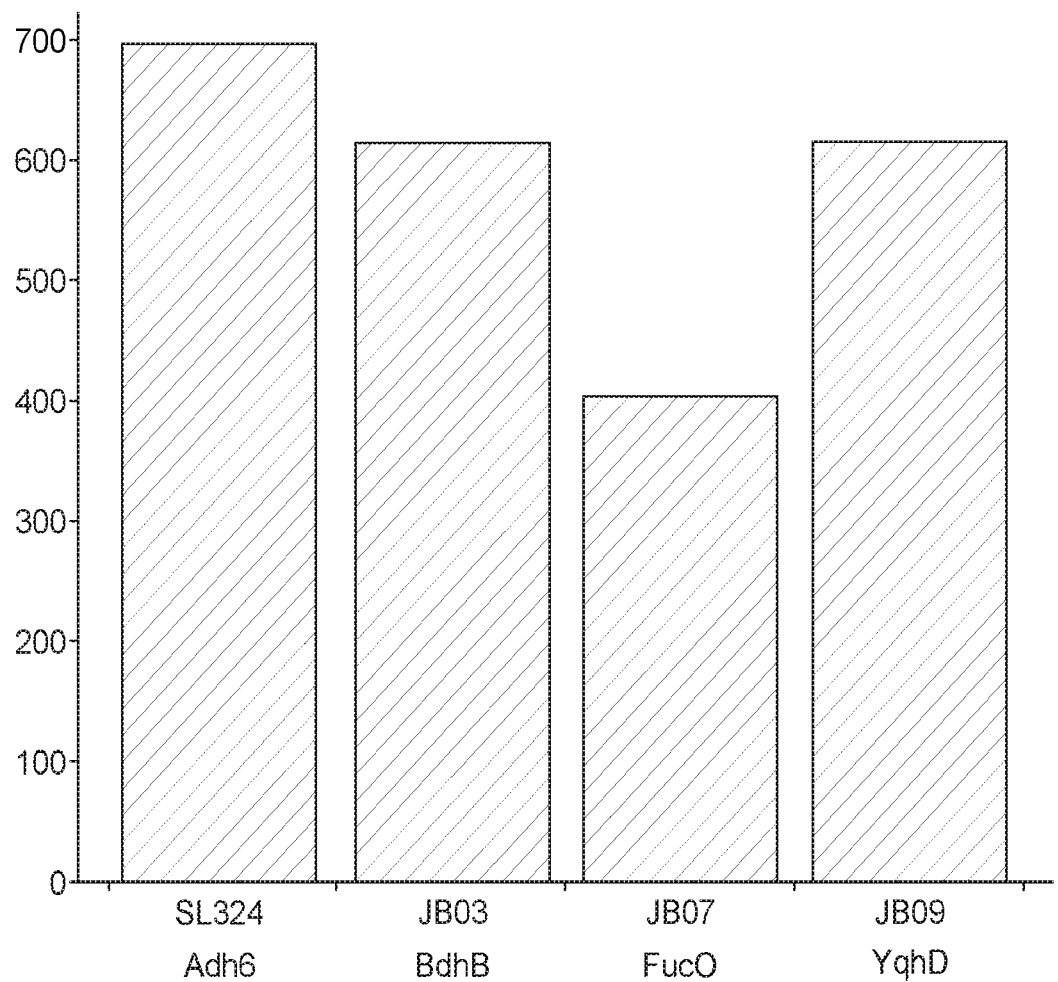
FIG. 11 shows isobutanol titers when methanotrophs are transformed with plasmids expressing different alcohol dehydrogenases and tested in a fermenter. Plasmids expressing Adh6, BdhB, FucO, and YqhD are represented. Methanotrophs expressing Adh6 produced the most isobutanol. BdhB and YqhD produced similar amounts of isobutanol.

As shown in FIG. 11, Adh6 produced the most isobutanol when testing in a fermenter (2 L). BdhB and YqhD produced similar amounts of isobutanol.

Example 5: Additional KDCs

Even with the optimization of ADHs, side products from the branch chain amino acid pathway were observed. Therefore, 21 additional KDCs listed in Table 4 were tested.

The following constructs in Table 5 were made and tested in 2 L fermenters:

TABLE 5

| Name | Genes |
|---|---|
| GW1035 | pBAD > Ach.KDC-Sc_Adh6-Bs_AlsS-Mc_IlvC-Mc_IlvD |
| GW1049 | pBAD > Cdi.KDC-Sc_Adh6-Bs_AlsS-Mc_IlvC-Mc_IlvD |
| GW1137 | pBAD > Mc.KDC-Adh6-Bs_AlsS-Mc_IlvC-Mc_IlvD |
| GW1145 | pBAD > Mde.KDC-Sc_Adh6-Bs_AlsS-Mc_IlvC-Mc_IlvD |
| GW1151 | pBAD > Mma-KDC-Sc_Adh6-Bs_AlsS-Mc_IlvC-Mc_IlvD |

Figure 12:
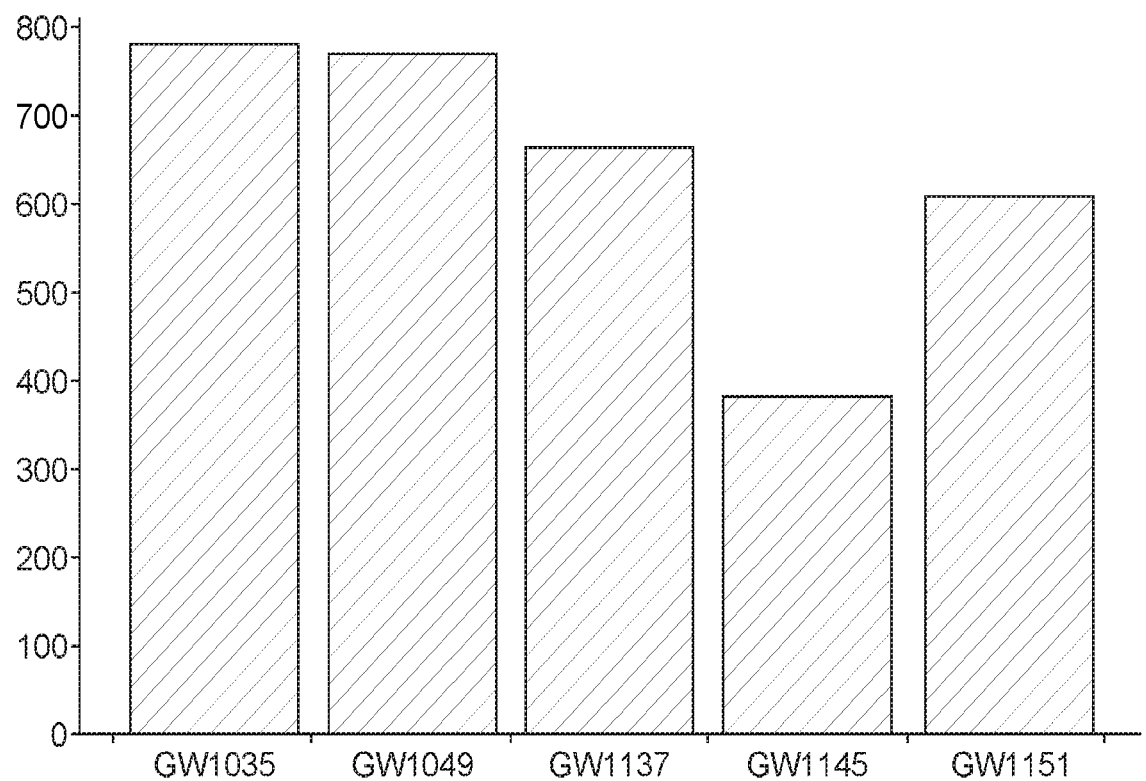
FIG. 12 shows isobutanol production levels using KDCs from *Andreprevotia chitinilytica* (GW1035), *Carnobacterium divergens* (GW1049), *Methylococcus capsulatus* (GW1137), *Methylomonas denitrificans* (GW1145), and *Methylobacter marinus* (GW1151). KDCs from *Andreprevotia chitinilytica* or *Carnobacterium divergens* showed increased ability to produce isobutanol titers at high titers, approximately 0.8 g/L of isobutanol. *Andreprevotia chitinilytica* or *Carnobacterium divergens* KDCs produced approximately double that of *Methylomonas denitrificans* KDC.

As shown in FIG. 12 KDCs from *Andreprevotia chitinilytica* or *Carnobacterium divergens* showed increased ability to produce isobutanol titers at high titers, approximately 0.8 g/L of isobutanol. *Andreprevotia chitinilytica* or *Carnobacterium divergens* KDCs produced approximately double that of *Methylomonas denitrificans* KDC.

TABLE 4

| Ref. No | SEQ ID NO: (Amino Acid) | SEQ ID NO: (Nucleotide) | KDC gene | Species |
|---|---|---|---|---|
| 1 | 55 | 56 | Msz.KDC | Methylocaldum szegediense |
| 2 | 57 | 58 | Mla.KDC | Methylosarcina lacus |
| 3 | 59 | 60 | Mde.KDC | Methylomonas denitrificans |
| 4 | 61 | 62 | Mme.KDC | Methylomonas methanica |
| 5 | 63 | 64 | Mcr.KDC | Methylohalobius crimeensis |
| 6 | 65 | 66 | Mma.KDC | Methylobacter marinus |
| 7 | 67 | 68 | Mlu.KDC | Methylobacter luteus |
| 8 | 69 | 70 | Lpu.KDC | Lamprocystis purpurea |
| 9 | 71 | 72 | Ach.KDC | Andreprevotia chitinilytica |
| 10 | 73 | 74 | Lla.KDC2 | Lactococcus lactis |
| 11 | 75 | 76 | Lla2.KDC2 | Lactococcus lactis |
| 12 | 77 | 78 | Sdi.KDC | Streptococcus didelphis |
| 13 | 79 | 80 | Eca.KDC | Enterococcus caccae |
| 14 | 81 | 82 | Eha.KDC | Enterococcus haemoperoxidus |
| 15 | 83 | 84 | Emo.KDC | Enterococcus moraviensis |
| 16 | 85 | 86 | Cma.KDC | Carnobacterium maltaromaticum |
| 17 | 87 | 88 | Bth.KDC | Brochothrix thermosphacta |
| 18 | 89 | 90 | Cga.KDC | Carnobacterium gallinarum |
| 19 | 91 | 92 | Cdi.KDC | Carnobacterium divergens |
| 20 | 93 | 94 | Hbi.KDC | Helicobacter bizzozeronii |
| 21 | 95 | 96 | Sau.KDC | Staphylococcus aureus subsp. aureus CIG290 |
| 22 | 97 | 98 | Fma.KDC | Fictibacillus macauensis |

Example 6: Isobutyraldehyde Productivity

In order to increase isobutyraldehyde, strains that did not have any heterologous alcohol dehydrogenases were designed. The same combinations of acetolactate synthase; ketol-acid reductoisomerase; dihydroxy-acid dehydratase; and 2-keto acid decarboxylase were generated and tested for isobutyraldehyde production. Data from two of the following strains are shown: GW692 (pBAD>Mc.KDC_Bs.AlsS_Ec.ILVC_Ec.ILVD); and SL691 (pBAD>Bsu.alsS-g.Cdi.kdc; p.mxaF>g.Mca.kdc-g.Eco.ilvC-g.Mca.ilvD).

Figure 13:
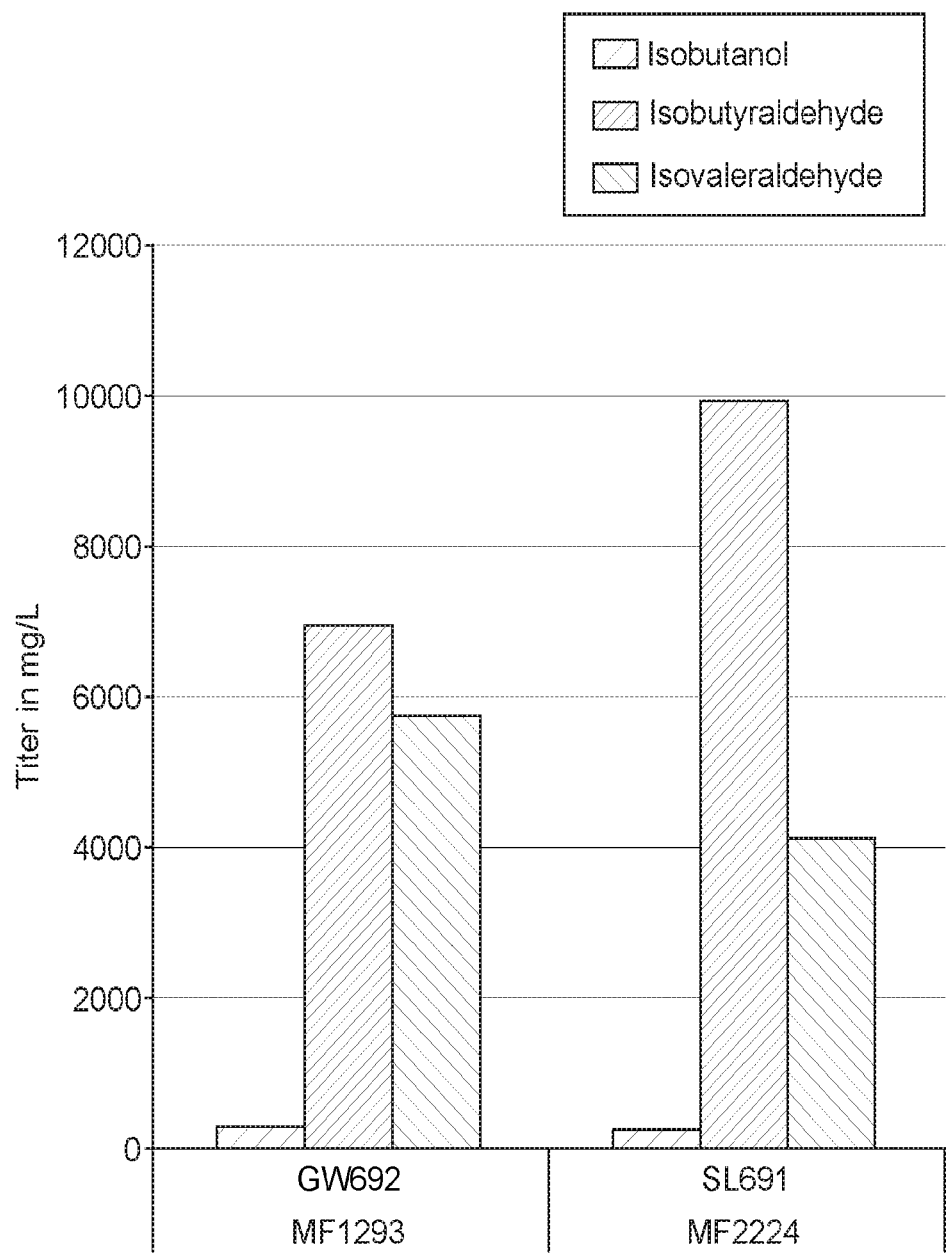
FIG. 13 shows production titers of isobutyraldehyde, isovaleraldehyde, and isobutanol of two strains that do not express heterologous alcohol dehydrogenase. The strains expressed acetolactate synthase; ketol-acid reductoisomerase; dihydroxy-acid dehydratase; and 2-keto acid decarboxylase; and are designated GW692 (pBAD>Mc.KDC_Bs.AlsS_Ec.ILVC_Ec.ILVD) and SL691 (pBAD>Bsu.alsS-g.Cdi.kdc; p.mxaF>g.Mca.kdc-g.Eco.ilvC-g.Mca.ilvD). Strain GW692 produced approximately 7 g/L of isobutyraldehyde, whereas strain SL691 produced close to 10 g/L. Strain GW692 also produced approximately 5.8 g/L of isovaleraldehyde, whereas strain SL691 produced approximately 4.1 g/L.

As shown in FIG. 13, the production titers of isobutyraldehyde from the two strains were increased significantly. For example, strain GW692 produced approximately 7 g/L of isobutyraldehyde, whereas strain SL691 produced close to 10 g/L. Strain GW692 also produced approximately 5.8 g/L of isovaleraldehyde, whereas strain SL691 produced approximately 4.1 g/L. Negligible amounts of isobutanol were produced by both strains.

Example 7: Acetolactate Synthase

In order to increase the levels of 2-acteolactate, several strains were generated in which the acetolactate synthase were optimized. The plasmids described in Table 6 (below), were transformed into a methanotroph. The resulting strains were tested for the ability to utilize any increases of 2-acteolactate. Since 2,3-butanediol titers directly correlate to increases in 2-acetolactate in these strains, 2,3-BDO titers were measured as an indicator of increased 2-acteolactate production. Thus, if additional 2-acetolactate were produced by the differences in acetolactate synthase, there would be a correlating difference in 2,3-BDO titers.

2,3-BDO titers compared with strain XZ58. However, remarkably, a strain that contained rbs.Mca.MxaF for the Kpn.BudA, instead of a rbs.GTW0001 and expressed a *Bacillus licheniformis* AlsS gene (e.g., strain XZ562), exhibited a significant increase in 2,3-BDO titers, up to 44.6% compared to strain XZ58. This data indicates that methanotroph strains expressing *Bacillus licheniformis* AlsS, produce greatly increased levels of 2-acetolactate compared to those expressing *Bacillus subtilis* AlsS.

Example 8: Regulating Gene Expression by Using Rare Earth Metals

Figure 15:
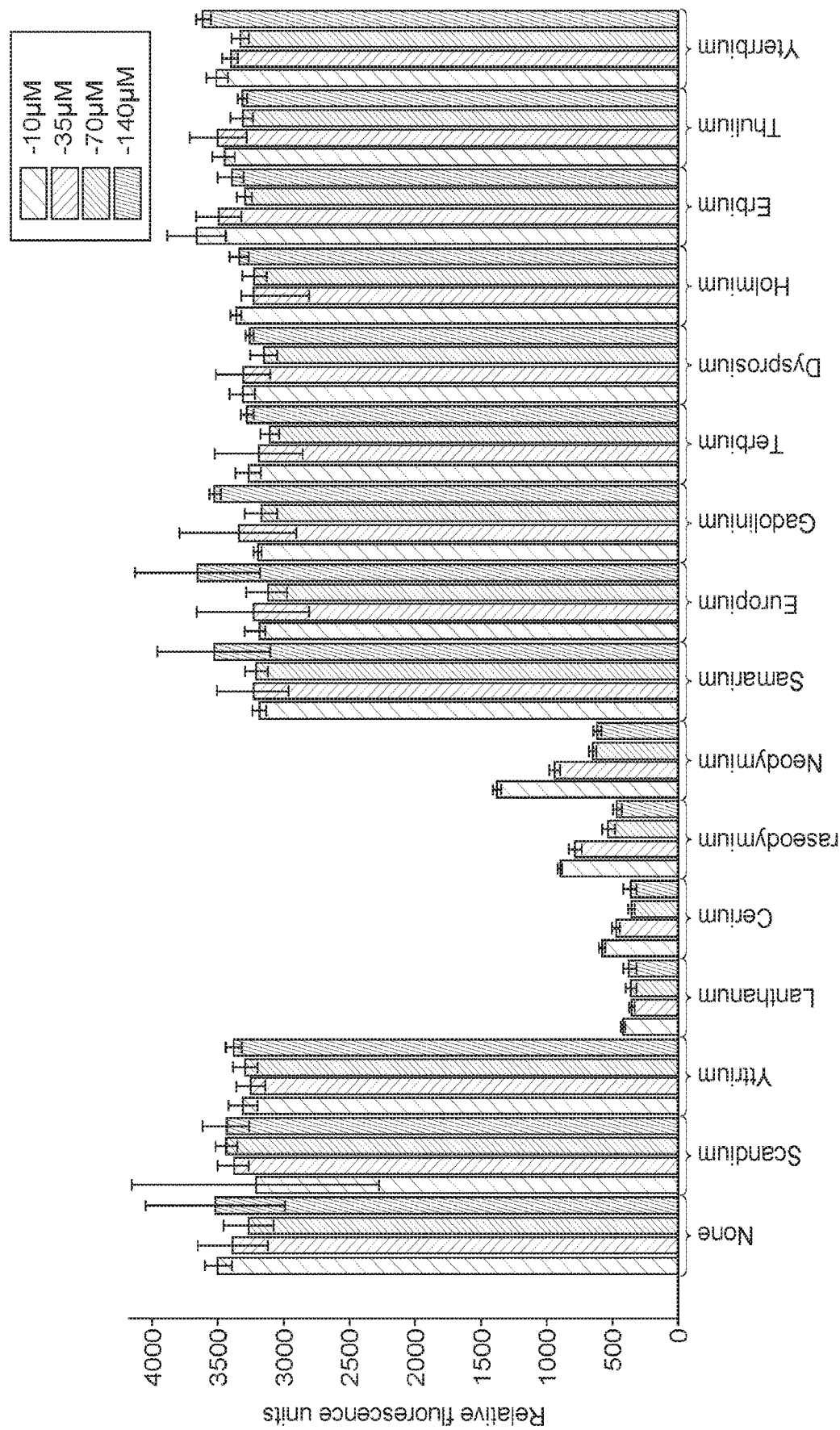
FIG. 15 shows the ability of various rare earth metals at a concentration of 10 µM, 35 µM, 70 µM, or 140 µM to activate or repress the pMxaF promoter as measured by mCherry. Scandium (Sc), yttrium (Y), samarium (Sm), europium (Eu), gadolinium (Gd), terbium (Tb), dysprosium (Dy), holmium (Ho), erbium (Er), thulium (Tm), and ytterbium (Yb) minimally activated or repressed the pMxaF promoter at 10 µM, 35 µM, 70 µM, or 140 µM. However, lanthanum (La), cerium (Ce), praseodymium (Pr), and neodymium (Nd) significantly repressed the expression of the pMxaF promoter at all concentrations. Maximal repression was observed starting at 35 µM for lanthanum, 70 µM for cerium, and 140 µM for praseodymium and neodymium.

In order to determine whether rare earth metals can be used to modify the expression of genes of the isobutyraldehyde and/or isobutanol pathways, different rare earth metals (at four different concentrations: 10, 35, 70, and 140 µM) were placed into the media in the presence of a *Methylococcus capsulatus* having a pMxaF promoter driving mCherry expression. The cultures were treated with for 24 hours with the respective rare earth metal. As seen in FIG. 15, lanthanum (La), cerium (Ce), praseodymium (Pr), and neodymium (Nd), repressed the pMxaF promoter. The other rare earth metals did not have an observable repressive effect on the pMxaF promoter.

Figure 16:
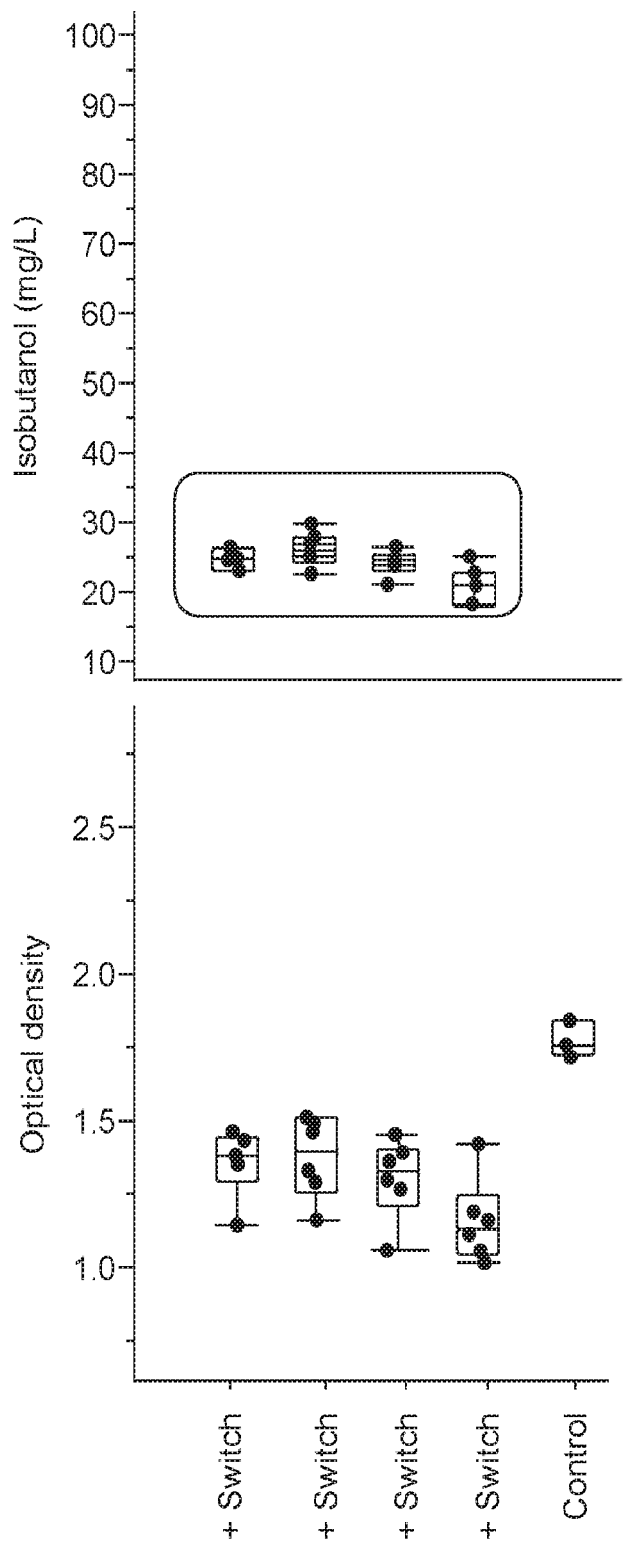
FIG. 16 shows the ability of a *M. capsulatus* strain expressing isobutanol pathway genes under the control of a rare earth metal switch to produce isobutanol. The strains were grown up in the presence of 35 µM lanthanum in shake bottles. After 24 hours, lanthanum was diluted out and the strain was allowed to produce isobutanol. Strains expressing isobutanol pathway genes under the control of a rare earth metal switch were able to produce isobutanol while the control strain did not. Optical density was highest in control strains.

*Methylococcus capsulatus* expressing isobutanol pathway genes under the control of a rare earth metal switch were grown up in the presence of 35 µM lanthanum in shake bottles. After 24 hours, lanthanum was diluted out and the strain was allowed to ferment isobutanol. As shown in FIG. 16, the strains expressing isobutanol pathway genes under the control of a rare earth metal switch were able to produce isobutanol. The control strain without isobutanol gene did not produce any isobutanol.

Example 9: Integration of Alcohol Dehydrogenase

In order to examine whether an integrated alcohol dehydrogenase gene could be used to produce isobutanol, a single

TABLE 6

| Strain | Strain Genotype | Average Titer (mg/L) | % diff. vs. XZ58 |
|---|---|---|---|
| XZ58 | p.BAD > g.Bsu.alsS > (rbs.GTW0001)g.Kpn.BudA > p.mxaF > g.Cau.ButA | 372 | 0.0% |
| XZ557 | p.BAD > g.Blic.alsS –> (rbs.GTW0001)g.Kpn.BudA-p.mxaF > g.Cau.ButA | 421 | 16.1% |
| XZ546 | p.BAD > g.Bsu.alsS-(rbs.Mca.MxaF)g.Kpn.BudA-p.mxaF > g.Cau.ButA | 373 | 0.3% |
| XZ562 | p.BAD > g.Blic.alsS-(rbs.Mca.MxaF)g.Kpn.BudA-p.mxaF > g.Cau.ButA | 538 | 44.6% |

Figure 14:
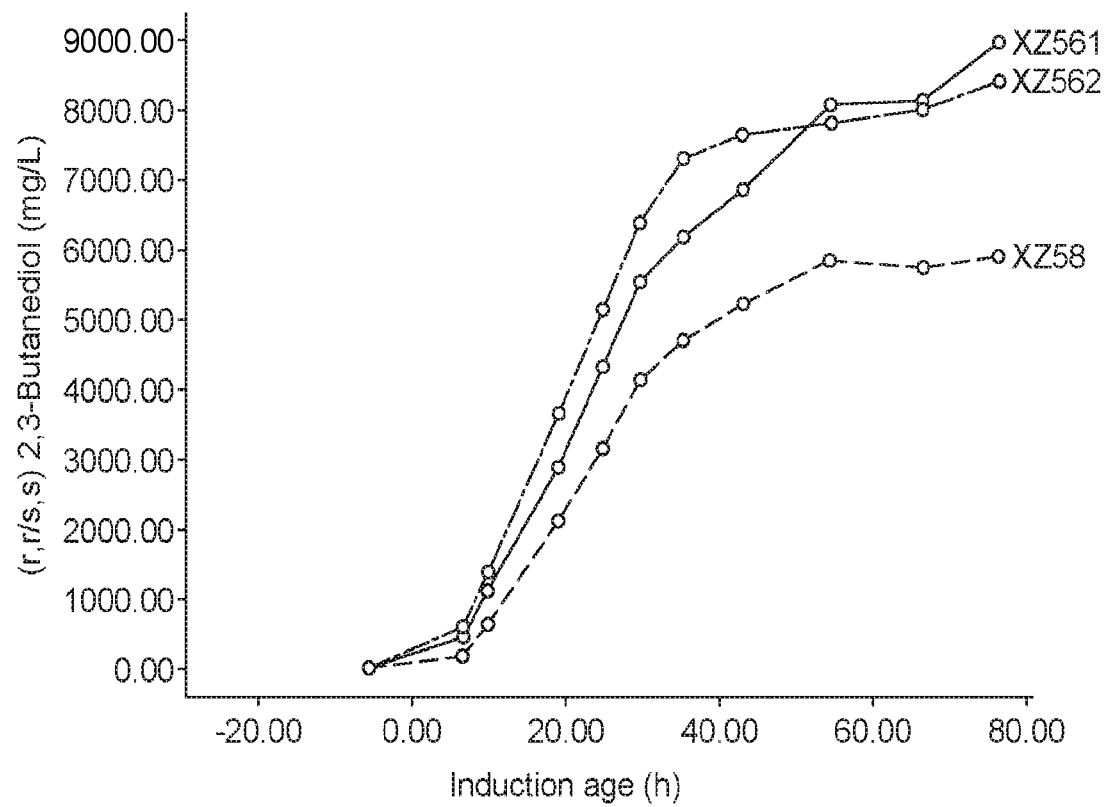
FIG. 14 shows that strains expressing a *Bacillus licheniformis* AlsS exhibited significantly improved 2-acetolate production, as indicated by measuring 2,3-BDO titers. In one strain expressing *Bacillus licheniformis* AlsS (XZ562), the 2,3-BDO titers increased an average of 44.6% over the XZ58 strain over the course of the fermentation run. Another biological replicate (XZ561), produced also significantly higher average 2,3-BDO titers compared to the XZ58 strain. This data indicates that methanotrophs expressing *Bacillus licheniformis* AlsS produce significantly higher levels of 2-acetolactate compared to methanotrophs expressing other AlsS, including the *Bacillus subtilis* AlsS.

The resulting strains from Table 6 were grown in a small scale microtiter plate fermentation using methane as the carbon source. As shown in Table 6 and in FIG. 14, the strains that expressed *Bacillus licheniformis* AlsS gene, showed better 2,3-BDO production titers than the strains that expressed *Bacillus subtilis* AlsS. In one example, a strain that has a substitution of only the AlsS gene (e.g., strains XZ557) exhibited an increase of 2,3-BDO production titer of up to 16.1% compared to strain XZ58. Strain XZ546, a strain having a substitution of only the ribosome binding site for the Kpn.BudA gene, showed virtually no increase of copy of ADH6 was integrated into a *Methylococcus capsulatus* strain. Further, a strain expressing an ADH on a plasmid as well as having an integrated ADH was made. The strains were tested for their ability to form isobutanol.

Figure 17:
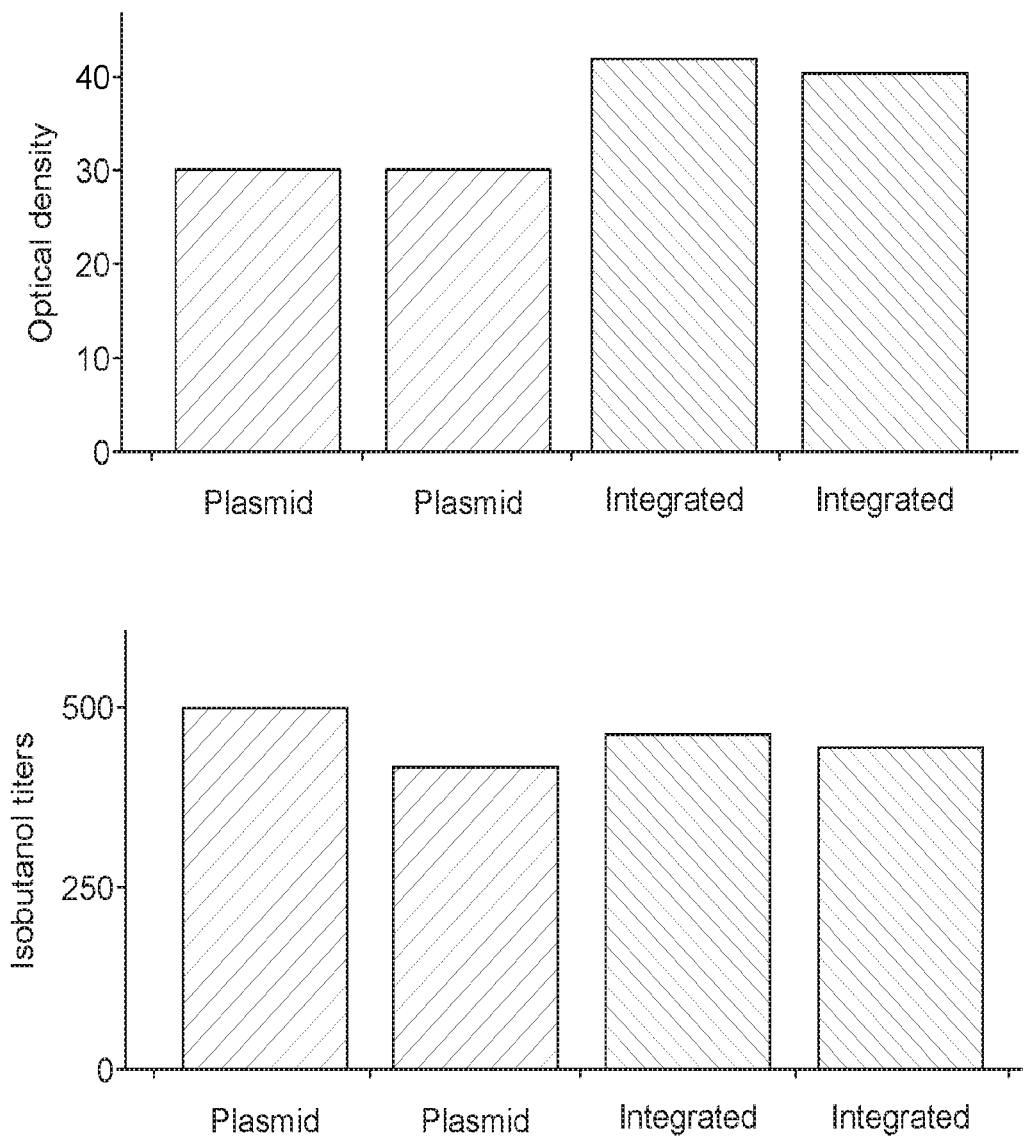
FIG. 17 shows the ability of *M. capsulatus* strain with an integrated copy of ADH6 to produce isobutanol. A significant amount of alcohol dehydrogenase activity from the integrated ADH was observed. Compared with the non-integrated ADH strains, there was no observable difference in total carbon, alcohol and aldehyde. Optimal density fared better with in strains with integrated copies of ADH6.

We observed a significant amount of alcohol dehydrogenase activity from the integrated ADH. The integrated ADH functioned as well as non-integrated ADH, as there was no difference in total carbon, alcohol and aldehyde in these strains. (See FIG. 17) Strains expressing both integrated ADH and a plasmid expressing ADH resulted in a better conversion of aldehydes to alcohols.

What is claimed is:

1. A genetically modified microorganism capable of converting a $C_1$ carbon to a multicarbon product, wherein the microorganism is *Methylococcus capsulatus* and comprises:
   (a) a heterologous gene encoding an acetolactate synthase (AlsS) comprising the amino acid sequence of SEQ ID NO: 99; and
   (b) a heterologous gene encoding a ketol-acid reductoisomerase (KARI) comprising the amino acid sequence of SEQ ID NO: 4;
   (c) a heterologous gene encoding a dihydroxy-acid dehydratase (DHAD) comprising the amino acid sequence of SEQ ID NO: 6;
   (d) a heterologous gene encoding a 2-keto acid decarboxylase (KDC) comprising the amino acid sequence of SEQ ID NO: 10; and
   (e) a heterologous gene encoding an ADH comprising the amino acid sequence of SEQ ID NO: 14.

2. The genetically modified microorganism of claim 1, further comprising a sugar permease gene.

3. The genetically modified microorganism of claim 1, wherein at least one of the gene(s) encoding the AlsS, the KARI, the DHAD, the KDC, or the ADH is overexpressed.

4. The genetically modified microorganism of claim 1, comprising multiple copies of at least one of the gene(s) encoding the AlsS, the KARI, the DHAD, the KDC, and/or the ADH.

5. The genetically modified microorganism of claim 1, wherein at least one of the gene(s) encoding the AlsS, the KARI, the DHAD, the KDC, or the ADH is under the control of a rare earth metal switch.

6. The genetically modified microorganism of claim 5, wherein the rare earth metal switch is a lanthanum switch.

7. A method of making the genetically modified microorganism of claim 1 comprising contacting a microorganism with a polynucleotide encoding the AlsS and at least one polynucleotide encoding the KARI, the DHAD, the KDC, and/or the ADH.

8. A method of making the genetically modified microorganism of claim 2, comprising contacting a microorganism with a polynucleotide encoding a sugar permease.

9. A method of making an alcohol or an aldehyde from a $C_1$ carbon comprising:
   (a) contacting a $C_1$ carbon with the genetically modified microorganism of claim 1; and
   (b) growing the genetically modified microorganism to produce the aldehyde or alcohol.

10. A method of making a useful product comprising:
    contacting the genetically modified microorganism of claim 1 with a $C_1$ carbon substrate; and
    (b) growing the genetically modified microorganism to produce the useful product, wherein the useful product comprises 2-acetolactate, 2,3-butanediol (2,3-BDO), diacetyl, 2,3-dihydroxy-2-methylbutanoic acid, 2,3-dihydroxyisovalerate, amino acids, ketoisovalerate, isobutyraldehyde, isobutyrate, methyl methacrylate (MMA), isovaleraldehyde, isovalerate, isopentanol, isoamyl acetate, pentadecanoic acid, isobutene, and/or p-xylene.

11. The genetically modified microorganism of claim 1, wherein:
    (a) the heterologous gene encoding the AlsS comprises the nucleic acid sequence of SEQ ID NO: 100;
    (b) the heterologous gene encoding the KARI comprises the nucleic acid sequence of SEQ ID NO: 3;
    (c) the heterologous gene encoding the DHAD comprises the nucleic acid sequence of SEQ ID NO: 5;
    (d) the heterologous gene encoding the KDC comprises the nucleic acid sequence of SEQ ID NO: 9; and
    (e) the heterologous gene encoding the ADH comprises the nucleic acid sequence of SEQ ID NO: 13.

* * * * *